(12) United States Patent
Frattini et al.

(10) Patent No.: US 10,640,486 B2
(45) Date of Patent: *May 5, 2020

(54) HETEROARYLCARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Sara Frattini, Castelleone (IT); Remko Bakker, Biberach an der Riss (DE); Riccardo Giovannini, Biberach an der Riss (DE); Giacomo Fossati, Lissone (IT); Dieter Hamprecht, Frenchs Forest (AU); Iain Lingard, Monza (IT); Alexander Pautsch, Biberach an der Riss (DE); Bernd Wellenzohn, Friedrichshafen (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/770,763

(22) PCT Filed: Oct. 20, 2016

(86) PCT No.: PCT/EP2016/075222
§ 371 (c)(1),
(2) Date: Apr. 25, 2018

(87) PCT Pub. No.: WO2017/072021
PCT Pub. Date: May 4, 2017

(65) Prior Publication Data
US 2018/0319771 A1    Nov. 8, 2018

(30) Foreign Application Priority Data
Oct. 27, 2015  (EP) .................. 15191759

(51) Int. Cl.
| | | |
|---|---|---|
| *C07D 401/14* | (2006.01) |
| *C07D 498/10* | (2006.01) |
| *C07D 471/04* | (2006.01) |
| *C07D 487/04* | (2006.01) |
| *C07D 405/14* | (2006.01) |
| *C07D 491/052* | (2006.01) |
| *C07D 498/04* | (2006.01) |
| *A61P 3/10* | (2006.01) |
| *A61K 45/06* | (2006.01) |

(52) U.S. Cl.
CPC .............. *C07D 401/14* (2013.01); *A61P 3/10* (2018.01); *C07D 405/14* (2013.01); *C07D 471/04* (2013.01); *C07D 487/04* (2013.01); *C07D 491/052* (2013.01); *C07D 498/04* (2013.01); *C07D 498/10* (2013.01); *A61K 45/06* (2013.01); *A61K 2300/00* (2013.01)

(58) Field of Classification Search
CPC ....... A61K 2300/00; A61K 45/06; A61P 3/10; C07D 471/04; C07D 487/052; C07D 98/04; C07D 98/10; C07D 401/14; C07D 405/14; C07D 487/04; C07D 498/10
See application file for complete search history.

(56) References Cited

FOREIGN PATENT DOCUMENTS

| WO | 2009097141 A1 | 8/2009 |
| WO | 2013111107 A1 | 8/2013 |
| WO | 2013111108 A1 | 8/2013 |
| WO | 2014188211 A1 | 11/2014 |
| WO | WO-2014188211 A1 * | 11/2014 |
| WO | 2017072020 A1 | 5/2017 |
| WO | 2017072021 A1 | 5/2017 |

OTHER PUBLICATIONS

Feener,E.P., "Plasma Kallikrein and Diabetic Macular Edema", Current Diabetes Reports, 2010, vol. 10, issue 4, pp. 270-275. (Year: 2010).*
Keener, Plasma Kallikrein and Diabetic Macular Edema, Curr. Diab. Rep. 2010.
International Search Report for PCT/EP2016/075222 dated Oct. 25, 2016.
Written Opinion for PCT/EP2016/075222 dated Oct. 26, 2016.
International Search Report for PCT/EP2016/075221 dated Jan. 18, 2017.
Written Opinion for PCT/EP2016/075221 dated Jan. 18, 2017.
International Search Report and Written Opinion for PCT/EP2018059633 dated Jul. 6, 2018.
Japtap, Heck Reaction, Catalysts, 2017.
Hashiguchi, Asymmetric Transfer Hrydogenation of Aromatic Ketones Catalyzed by Chiral Ruthenium (II) Complexes, J. Am. Chem. Soc, 1995, vol. 117, p. 7562-7563.
(Continued)

*Primary Examiner* — Samira J Jean-Louis
(74) *Attorney, Agent, or Firm* — David L. Kershner

(57) ABSTRACT

The present invention relates to compounds of general formula (I), wherein $D^1$ to $D^3$, -A-, n, $R^1$, $R^2$, $Y^1$, L and $y^2$ are defined as in claim 1, which have valuable pharmacological properties, in particular are inhibitors of plasma kallikrein. The compounds are suitable for treatment and prevention of diseases which can be influenced by inhibition of plasma kallikrein, such as diabetic complications, particularly in the treatment of retinal vascular permeability associated with diabetic retinopathy and diabetic macular edema.

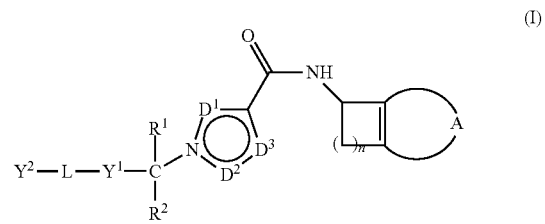

13 Claims, No Drawings

(56) References Cited

OTHER PUBLICATIONS

Li, Enantioselective, Organocataltyic Reduction of Ketones using Bifunctional Thiorea-Amine Catalysts, Organic Letters, 2010, vol. 12, p. 1756-1759.
Kim, Asymmetric Reductions involving Borohydrides, Organic Research and Development, 2006, vol. 10, p. 949-958.
Nakamura, Recent Developments in asymmetric reduction of ketones with biocatalysts, Tetrahedron: Asymmetry, 2003, vol. 14, p. 2659-2681.
Yoshimura, Recent topics in catalytic asymmetric hydrogenation of ketones, Tetrahedron Letters, 2014, vol. 55, p. 3635-3640.
Biagetti, Synthesis and structure-activity relationship of N-(3-azabicyclo[3.1.0]hex-6-ylmethyl)-5-(2-pyridinyl)-1,3-thiazol-2-amines derivatives as NPY Y5 antagonists, Bioorganic & Medicinal Chem Letters, 2010, vol. 20, p. 4741-4744.

\* cited by examiner

HETEROARYLCARBOXAMIDE DERIVATIVES AS PLASMA KALLIKREIN INHIBITORS

FIELD OF THE INVENTION

The present invention relates to novel 5-membered heteroarylcarboxamide derivatives, that are plasma kallikrein inhibitors, to processes for their preparation, to pharmaceutical compositions containing these compounds and to their medical use for the prophylaxis and/or treatment of diseases which can be influenced by the inhibition of plasma kallikrein. Particularly, the pharmaceutical compositions of the invention are suitable for the prophylaxis and/or therapy of diabetic complications, particularly in the treatment of retinal vascular permeability associated with diabetic retinopathy and diabetic macular edema.

BACKGROUND OF THE INVENTION

Plasma kallikrein is a trypsin-like serine protease secreted by hepatocytes in the liver as an inactive plasma prekallikrein that circulates in plasma either as a free zymogen or as a heterodimer complex bound to high molecular weight kininogen which is activated to give the active plasma kallikrein that can liberate kinins from kininogens in addition to processing other substrates. Kinins are potent mediators of inflammation that act through G protein-coupled receptors such as bradykinin receptors.

Plasma kallikrein is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), polypoidal choroidal vasculopathy (PCV), choroidal neovascularization, posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS) and other diseases.

Plasma kallikrein inhibitors are considered to be useful in the treatment of a wide range of disorders, particularly in the treatment of edema formation in diseases, e.g. edema formation related to ischemic reperfusion injuries, retinopathy or edema-associated diseases, such as hereditary angioedema, macular edema and brain edema. Plasma kallikrein inhibitors are considered to be especially useful in the treatment of retinopathy, e.g. retinopathy associated with diabetes and/or hypertension, and in the treatment of macular edema, e.g. macular edema associated with diabetes and/or hypertension.

Plasma kallikrein inhibitors suitable for therapeutic use should bind potently and with high selectivity to plasma kallikrein. They should be well absorbed from the gastrointestinal tract, be sufficiently metabolically stable and possess favorable pharmacokinetic properties. They should be non-toxic and demonstrate few side-effects.

The compounds of the invention are plasma kallikrein inhibitors and are therefore potentially useful in the treatment of disorders mentioned hereinbefore, particularly should have utility as a treatment to reduce retinal vascular permeability associated with diabetic retinopathy and diabetic macular edema retinopathy or edema-associated diseases.

Other complications of diabetes such as cerebral haemorrhage, nephropathy, cardiomyopathy and neuropathy, all of which have associations with plasma kallikrein may also be considered as targets for a plasma kallikrein inhibitor.

Low molecular weight plasma kallikrein inhibitors are known in the art, for example, the compounds disclosed in WO2013/111108, WO2013/11107 and WO2014/188211.

OBJECT OF THE PRESENT INVENTION

The object of the present invention is to provide new compounds, hereinafter described as compounds of formula I, in particular new 5-membered heteroarylcarboxamide derivatives, which are plasma kallikrein inhibitors and possess suitable pharmacological and pharmacokinetic properties to use them as medicaments.

A further object of the present invention is to provide effective plasma kallikrein inhibitors, in particular for the treatment of diabetic complications, for example diabetic retinopathy and diabetic macular edema, retinopathy, or edema-associated diseases.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

The 5-membered heteroarylcarboxamide derivatives of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

SUMMARY OF THE INVENTION

The extension -Gn used hereinafter within the definitions is meant to identify genus n of the respective substituent. For example, $R^1$-G1 defines genus 1 of the substituent $R^1$.

In a first aspect the invention relates to a compound of formula

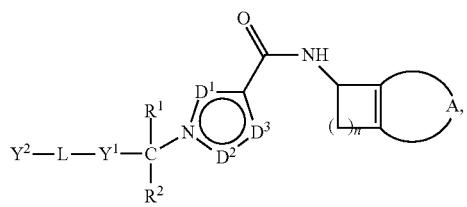

I wherein according to embodiment D-G1
of $D^1$ to $D^3$
(i) each denote N, or
(ii) 2 denote N and 1 denotes CH, or
(iii) 1 denotes N, 2 denote CH, or
(iv) each denote CH
and one or two H-atoms attached to C optionally are replaced by a substituent selected from the group consisting of $C_{1-4}$-alkyl, —$CF_3$, —$CHF_2$, —CN and —$OCH_3$;
n is 1, 2 or 3;

according to embodiment A-G1 denotes a 4-membered bridge composed of a —C(NH$_2$)=N— unit and a second unit of —CH=CH—, including both orientations for unsymmetric units, wherein a H-atom attached to a C-atom optionally is replaced by a substituent selected from the group consisting of F, Cl, $CH_3$, $CF_3$ and $CHF_2$;
$R^1$ according to embodiment $R^1$-G1 denotes H, F, CN, $C_{1-3}$-alkyl, $CF_3$, OH, or —$OCH_3$;
$R^2$ according to embodiment $R^2$-G1 denotes H, F, CN, $CF_3$, $CHF_2$, —$OCH_3$ or a $C_{1-3}$-alkyl group optionally substituted by —OH;
or $R^1$ and $R^2$ according to embodiment $R^{1/2}$-G1 together denote =O or together with the carbon atom they are attached to form a 3-7 membered saturated ring system wherein 1 —$CH_2$— group optionally is replaced by O, S or NH;
$Y^1$ according to embodiment $Y^1$-G1 denotes a divalent phenyl ring or a divalent 6-membered heteroaromatic ring containing 1 or 2 =N— ring members, wherein both ring systems are optionally substituted at one or two carbon atoms by a halogen atom, $C_{1-3}$-alkyl, —$C_{1-4}$-cycloalkyl, —$CF_3$, —CN, —OH, HO—$C_{1-3}$-alkyl- or $C_{1-3}$-alkyloxy-;
L according to embodiment L-G1 denotes a bond or a linker selected from —C($R_3R_4$)— and —O—, wherein
$R^3$ denotes H, F, CN, $C_{1-3}$-alkyl, $CF_3$, $CHF_2$, —OH, —$CH_2$—OH or —$OCH_3$,
$R^4$ denotes H, F, CN, $C_{1-3}$-alkyl, $CF_3$, CH $F_2$, —$CH_2$—OH or —$OCH_3$; and
$Y^2$ according to embodiment $Y^2$-G1 denotes a fused or spiro polycyclic ring system attached to L via a C-atom or, where applicable, via a N-atom, containing 6 to 12 ring members in total, wherein
0 to 3 ring members are heteroatoms selected from —N<, —NH—, —N=, —O—, —S— with the proviso that one ring does not contain more than one heteroatom selected from —O— and —S—,
the polycyclic ring system is saturated, or
one ring is saturated and a second ring is partially unsaturated, or
one ring is saturated and a second ring is aromatic or heteroaromatic, or
one ring is partially unsaturated and a second ring is aromatic or heteroaromatic, or
a first and a second ring of the polycyclic ring system are partially unsaturated
one —$CH_2$— ring member linked to a N-atom optionally is replaced by —C(O)—,
and wherein the polycyclic ring system is optionally substituted at one or two carbon atoms by one or two groups independently selected from halogen atoms, $C_{1-3}$-alkyl, —$CF_3$, —CN, —OH, HO—$C_{1-3}$-alkyl- and $C_{1-3}$-alkyloxy-, with the proviso that two substituents containing an O-atom cannot be attached to the same carbon atom, and wherein the H-atom in one or more NH groups present in $Y^2$ optionally is replaced by $C_{1-4}$-alkyl or —$CH_2$—$C_{1-4}$-cycloalkyl;
wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which can be influenced by the inhibition of plasma kallikrein in a patient in need thereof characterized in that a compound of general formula I or a pharmaceutically acceptable salt thereof is administered to the patient.

According to another aspect of the invention, there is provided a method for treating diabetic complications, particularly in the treatment of retinal vascular permeability associated with diabetic retinopathy and diabetic macular edema, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition which can be influenced by the inhibition of plasma kallikrein in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which which can be influenced by the inhibition of plasma kallikrein in a patient in need thereof.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $D^1$ to $D^3$, -A-, n, $R^1$, $R^2$, $Y^1$, L and $Y^2$ are defined as above and hereinafter. If residues, substituents, or groups occur several times in a compound, they may have the same or different meanings. Some preferred meanings of individual groups and substituents of the compounds according to the invention will be given hereinafter as embodiments of the invention. Any and each of the embodiments D-G1 to D-G3, A-G1 to A-G2, $R^1$-G1 to $R^1$-G4, $R^2$-G1 to $R^2$-G4, $R^{1/2}$-G1 to $R^{1/2}$-G2, $Y^1$-G1 to $Y^1$-G3, L-G1 to L-G4, and $Y^2$-G1 to $Y^2$-G4, embodiments of n hereinafter may be combined with each other.

$D^1$ to $D^3$:

D-G2:

According to another embodiment D-G2 of the invention of $D^1$ to $D^3$
(i) 2 denote N and 1 denotes CH, or
(ii) 1 denotes N, and 2 denote CH,
and one or two H-atoms attached to C optionally are replaced by a substituent selected from the group consisting of $C_{1-3}$-alkyl, —$CF_3$, —CN and —$OCH_3$.

D-G3:

According to another embodiment D-G3 of the invention $D^1$ denotes CH,
$D^2$ denotes N,
$D^3$ denotes N or CH,
and one or two H-atoms attached to C optionally are replaced by a substituent selected from the group consisting of $C_{1-3}$-alkyl and —$CF_3$.

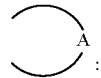:

A-G2:

According to another embodiment A-G2 of the invention A is selected from the group consisting of —C($NH_2$)=N—CH=CH—, —N=C($NH_2$)—CH=CH— and —CH=C($NH_2$)—N=CH—, including both orientations regarding the attachment points, wherein a H-atom attached to a C-atom optionally is replaced by a substituent selected from the group consisting of F, $CH_3$ and $CF_3$.

$R^1$:

$R^1$-G2:

$R^1$ according to embodiment $R^1$-G2 denotes H, F, CN, $CH_3$ or $CF_3$.

$R^1$-G3:

$R^1$ according to embodiment $R^1$-G3 denotes H, F or $CH_3$.

$R^1$-G4:

$R^1$ according to embodiment $R^1$-G4 denotes H or $CH_3$.

$R^2$:

$R^2$-G2:

$R^2$ according to embodiment $R^2$-G2 denotes H, F, CN, $CF_3$ or a $C_{1-3}$-alkyl group optionally substituted by —OH.

$R^2$-G3:

$R^2$ according to embodiment $R^2$-G3 denotes H, F, $CF_3$ or $CH_3$.

$R^2$-G4:

$R^2$ according to embodiment $R^2$-G4 denotes H.

$R^{1/2}$-G2:

$R^1$ and $R^2$ according to embodiment $R^{1/2}$-G2 together with the carbon atom they are attached to form a 3-5 membered saturated ring system, preferably a cyclopropyl ring.

$Y^1$-G2:

$Y^1$ according to embodiment $Y^1$-G2 denotes a divalent phenyl ring, optionally mono- or disubstituted independently by a F or Cl atom, by $C_{1-3}$-alkyl or —$CF_3$.

$Y^1$-G3:

$Y^1$ according to embodiment Y1-G3 denotes a divalent 6-membered heteroaromatic ring containing 1 or 2 =N— ring members, optionally substituted by a F or Cl atom, by $C_{1-3}$-alkyl or —$CF_3$.

L-G2:

L according to embodiment L-G2 denotes a bond.

L-G3:

L according to embodiment L-G3 denotes a —C($R_3R_4$)— linker, wherein
$R^3$ denotes H, F, $CH_3$ or $CF_3$, preferably H, and
$R^4$ denotes H.

L-G4:

L according to embodiment L-G4 denotes —O—.

$Y^2$-G2:

$Y^2$ according to embodiment $Y^2$-G2 denotes a fused or spiro bicyclic ring system attached to L via a C-atom or, preferably, via a N-atom, containing 6 to 10 ring members in total, wherein
1 to 3 ring members are heteroatoms selected from —N<, —NH—, —O—, with the proviso that one ring does not contain more than one —O— ring member,
the bicyclic ring system is saturated,
one —$CH_2$— ring member linked to a N-atom optionally is replaced by —C(O)—,
and wherein the bicyclic ring system is optionally substituted at one or two carbon atoms by one or two groups independently selected from F, $C_{1-3}$-alkyl and —$CF_3$.

$Y^2$-G3:

$Y^2$ according to embodiment $Y^2$-G3 denotes a fused or spiro bicyclic ring system attached to L via a N-atom, containing 6 to 8 ring members in total, wherein 1 or 2 ring members are —N< atoms,
the bicyclic ring system is saturated,
one —CH$_2$— ring member linked to a N-atom optionally is replaced by —C(O)—,
and wherein the bicyclic ring system is optionally substituted at one or two carbon atoms by one or two groups independently selected from F, methyl and —CF$_3$.

Y$^2$-G4:

Y$^2$ according to embodiment Y$^2$-G4 denotes a fused or spiro bicyclic ring system attached to L via a C-atom or, where applicable, via a N-atom, containing 6 to 8 ring members in total, wherein
1 to 3 ring members are heteroatoms selected from —N<, —NH—, —N=, —O—, with the proviso that one ring does not contain more than one —O— ring member,
one ring is saturated and the second ring is partially unsaturated, or
one ring is saturated and the second ring is aromatic or heteroaromatic,
one —CH$_2$— ring member linked to a N-atom optionally is replaced by —C(O)—,
and wherein the bicyclic ring system is optionally substituted at one or two carbon atoms by one or two groups independently selected from F, methyl and —CF$_3$.

According to one embodiment n denotes 2.

According to another embodiment n denotes 3.

Examples of preferred subgeneric embodiments (E) according to the present invention are set forth in the following table 1, wherein each substituent group of each embodiment is defined according to the definitions set forth hereinbefore. For example, the entry -G1 in the column under R$^1$—and the line of E1 means that in embodiment E1 substituent R$^1$ is selected from the definition designated R$^1$-G1. The same applies analogously to the other variables incorporated in the general formulas.

TABLE 1

| E | D$^1$ to D$^3$ | A | R$^1$- | R$^2$- | Y$^1$ | L | Y$^2$ | n |
|---|---|---|---|---|---|---|---|---|
| E1 | D-G1 | A-G1 | R$^1$-G1 | R$^2$-G1 | Y$^1$-G1 | L-G1 | Y$^2$-G1 | 1, 2 or 3 |
| E2 | D-G1 | A-G1 | R$^{1/2}$-G1 | | Y$^1$-G1 | L-G1 | Y$^2$-G1 | 1, 2 or 3 |
| E3 | D-G2 | A-G2 | R$^1$-G2 | R$^2$-G2 | Y$^1$-G2 | L-G2 or L-G3 | Y$^2$-G2 | 2 or 3 |
| E4 | D-G2 | A-G2 | R$^1$-G2 | R$^2$-G2 | Y$^1$-G3 | L-G2 or L-G3 | Y$^2$-G2 | 2 or 3 |

Stereochemistry

In one embodiment the compounds have the stereochemistry depicted in formula I.1 in a second embodiment the compounds have the stereochemistry depicted in formula I.2

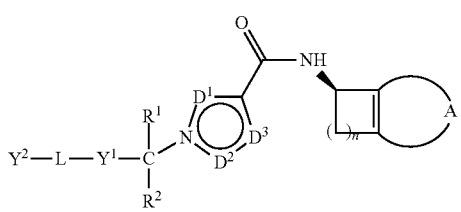

I.1

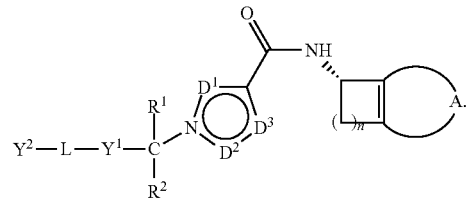

I.2

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds according to the invention and their intermediates may be obtained using methods of synthesis which are known to the one skilled in the art and described in the literature of organic synthesis for example using methods described in "Comprehensive Organic Transformations, 2$^{nd}$ edition", Richard C. Larock, Wiley-VCH, 2009., and "March's Advanced Organic Chemistry, 6$^{th}$ edition", Michael B. Smith, Jerry March, Wiley Interscience, 2007. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man and described in the literature for example in "Protecting Groups, 3$^{rd}$ Edition", Philip J. Kocienski, Thieme, 2005 or "Greene's Protective Groups in Organic Synthesis, 4th Edition", Peter G. M. Wuts, Theadora W. Greene, John Wiley and Sons, 2007.

Scheme 1:

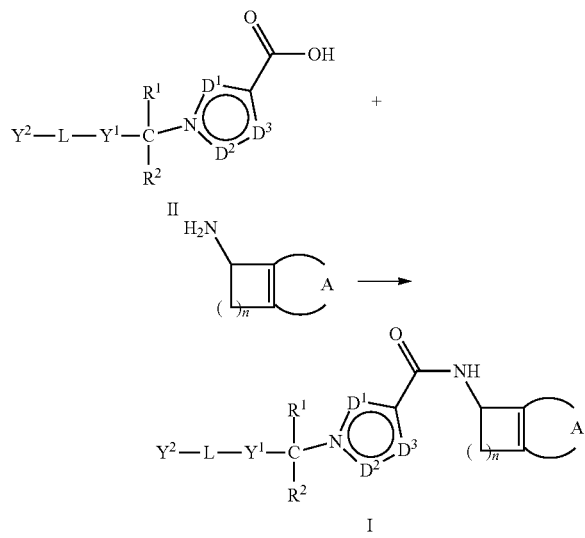

Scheme 1:

Compounds of formula I can be prepared by the reaction of a suitable acid of formula II (either as a free acid or as a salt with a suitable metal cation such as Li+, Na+, K+ etc.) and a suitable amine of formula III (either as a free amine or as a salt such as a hydrochloride, hydrobromide etc.), wherein $R^1$, $R^2$, $Y^1$, $Y^2$, L, $D^1$ to $D^3$, n and A have the meanings as defined hereinbefore, in a suitable solvent (e.g. dichloromethane, tetrahydrofuran, 1,4-dioxane, N,N-dimethylformamide, N,N-dimethylacetamide, 1-methyl-2-pyrrolidinone etc.) in the presence of a suitable coupling agent (e.g. O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents etc.) and a base (e.g. triethylamine, N,N-diisopropylamine, pyridine etc.) to form an amide bond.

Scheme 2:

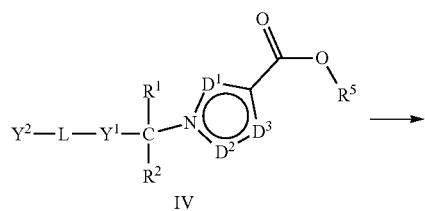

-continued

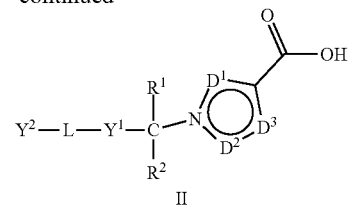

Scheme 2:

Acids of formula II, wherein $R^1$, $R^2$, $Y^1$, $Y^2$, L and $D^1$ to $D^3$ have the meanings as defined hereinbefore, can be prepared from the corresponding ester IV through the removal of cleavable group $R^5$, typically by hydrolysis or hydrogenolysis. Suitable $R^5$ groups include lower alkyl such as ethyl or methyl esters, in these cases $R^5$ can be removed by hydrolysis with a hydroxide base such as NaOH, LiOH, KOH in a mixture of water and a suitable miscible solvent (e.g. tetrahydrofuran, methanol, ethanol, 1,4-dioxane etc. or mixtures of these), with heating if necessary. The acid may be isolated either as a salt with the metal cation or as a free acid. An alternative $R^5$ group is tert-butyl, which can be removed by treatment with an acid (e.g. hydrochloric acid) in a suitable solvent (e.g. dichloromethane, 1,4-dioxane, methanol, ethanol, tetrahydrofuran, water or mixtures of these). Another $R^5$ group is benzyl, which can be removed by hydrogenation with a suitable catalyst (e.g. palladium on carbon, platinum oxide etc.) in a suitable solvent (e.g. ethanol, methanol, tetrahydrofuran, dichloromethane, ethyl acetate etc.) under an atmosphere of hydrogen.

Scheme 3

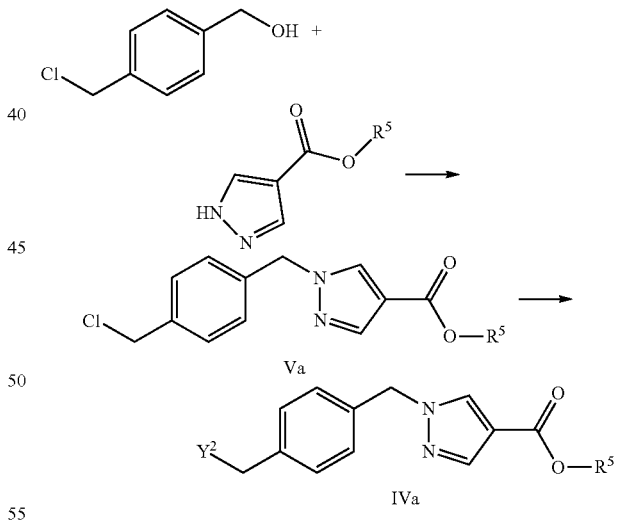

Scheme 3:

Some esters of formula IVa, wherein (referring to formula IV) $R^1$ and $R^2$ denote H, $R^5$ denotes a cleavable group, $D^1$ and $D^3$ denote CH, $D^2$ denotes N, $Y^1$ denotes a phenyl ring, L denotes —CH$_2$— and $Y^2$ is as defined hereinbefore, can be prepared by reaction of 4-chloromethyl benzylalcohol with an ester of 1H-pyrazole-4-carboxylic acid in a Mitsonobu reaction with suitable reagents (e.g. triphenylphosphine plus diethylazodicarboxylate (DEAD) or diisopropyl azodicarboxylate (DIAD) etc.) in a suitable solvent (e.g. tetrahydrofuran, 1,4-dioxane, diethylether etc). The resulting intermediate Va can then be reacted with a suitable polycyclic nucleophile in the presence of a suitable base (e.g. sodium hydride, cesium carbonate, potassium carbonate etc.) in a suitable solvent (e.g. tetrahydrofuran, N,N-dimethylformamide etc.) to give intermediates of formula IVa.

Scheme 4

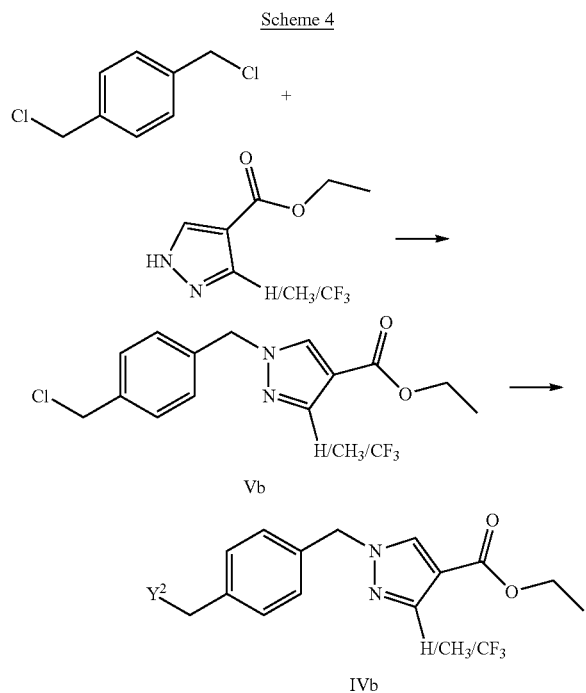

Scheme 4:

Some esters of formula IVb, which is defined as formula IVa except for $D^3$ denoting CH, C(CH$_3$) or C(CF$_3$), (referring to formula IV) can be prepared by reaction of 1,4-bis chloromethylbenzene with 1H-pyrazole-4-carboxylic acid ethyl ester or 3-trifluoromethyl-1H-pyrazole-4-carboxylic acid ethyl ester or 3-methyl-1H-pyrazole-4-carboxylic acid ethyl ester in the presence of a suitable base (e.g. sodium hydride, cesium carbonate, potassium carbonate etc.) in a suitable solvent (e.g. tetrahydrofuran, N,N-dimethylformamide etc.). The resulting intermediate Vb can be further reacted as described in Scheme 3 to give intermediates of formula IVb.

Scheme 5

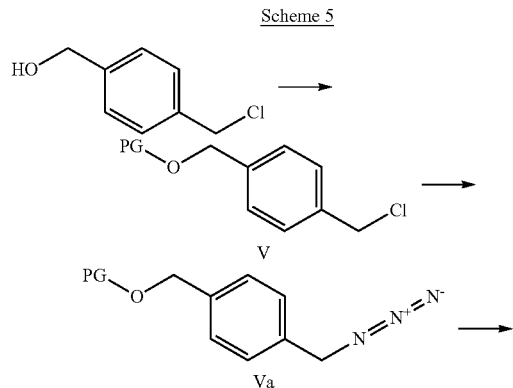

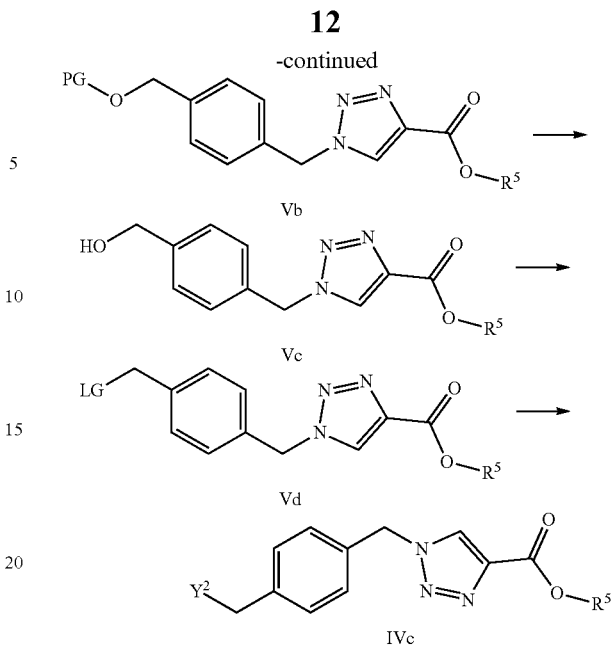

Scheme 5:

Some esters of formula IVc, which is defined as formula IVa except for $D^3$ denoting N, (referring to formula IV) can be prepared by the protection of the hydroxyl group of 4-chloromethylbenzylalcohol with a suitable protecting group PG, e.g. tert-butyldimethylsilyl ether, tert-butyl ether, tetrahydropyran etc., to give an intermediate of formula V. This can then be reacted with sodium azide in N,N-dimethylformamide or another suitable solvent to give an intermediate of formula Va which can be reacted with a suitable propiolic acid ester under copper mediated catalytic conditions (e.g. ethyl propiolate, tert-butyl propiolate etc with catalytic copper sulfate and sodium ascorbate in water/tert-butanol) to give a triazole intermediate of formula Vb. The protecting group can then be removed under conditions appropriate for the group chosen and the hydroxyl group liberated in intermediate Vc converted into a suitable leaving group LG, e.g. Br, Cl, mesylate, through the use of a suitable reagent (e.g. PBr$_3$, SOCl$_2$, methanesulfonyl chloride) in the presence of a suitable base (e.g. triethylamine, N,N-diisopropylamine, pyridine etc) if required. The resulting intermediate Vd can be further reacted as described in Scheme 3 to give intermediates of formula IVc.

Scheme 6

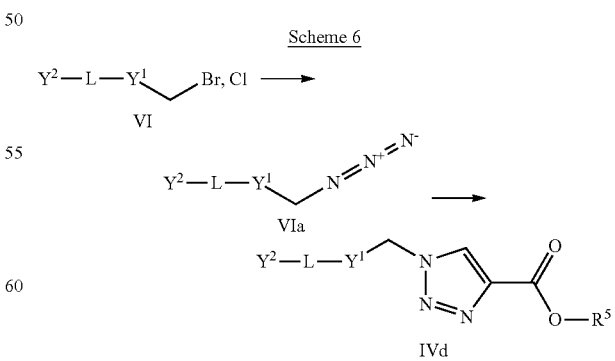

Scheme 6:

Some esters of formula IVd, wherein $R^1$ and $R^2$ denote H, $D^1$ denotes CH, $D^2$ and $D^3$ denote N (referring to formula IV), $Y^1$, $Y^2$ and L have the meanings defined hereinbefore, and $R^5$ denotes a cleavable group, can be prepared by the treatment of a corresponding alkyl bromide or chloride of formula VI with sodium azide in N,N-dimethylformamide or another suitable solvent to give an intermediate of formula VIa which can be reacted with a suitable propiolic acid ester under copper mediated catalytic conditions (e.g. ethyl propiolate, tert-butyl propilate etc with catalytic copper sulfate and sodium ascorbate in water/tert-butanol) to give a triazole intermediate of formula IVd.

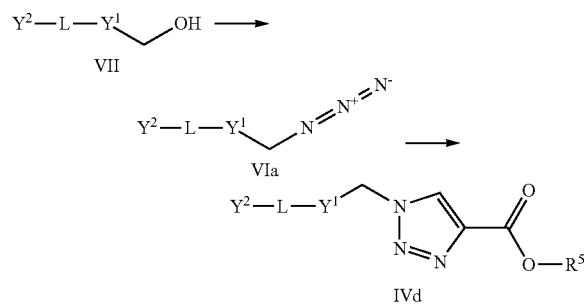

Scheme 7:

Some esters of formula IVd, wherein $R^1$ and $R^2$ denote H, $D^1$ denotes CH, $D^2$ and $D^3$ denote N (referring to formula IV), $Y^1$, $Y^2$ and L have the meanings defined hereinbefore, and $R^5$ denotes a cleavable group, can also be prepared by the treatment of a corresponding alcohol of formula VII with diphenylphosphoryl azide in the presence of a suitable base such as DBU in N,N-dimethylformamide or another suitable solvent to give an intermediate of formula VIa which can be further reacted as described in Scheme 6 to give an intermediate of formula IVd.

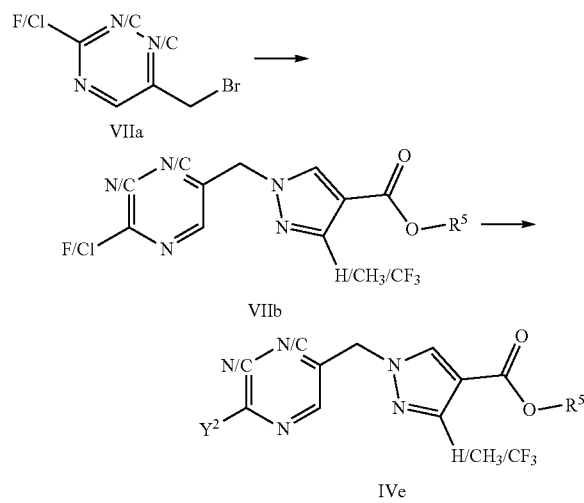

Scheme 7:

Some esters of formula IVe, wherein $R^1$ and $R^2$ denote H, $D^1$ denotes CH, $D^2$ denotes N, $D^3$ denotes CH or $C(CF_3)$, $Y^1$ denotes a 6 membered heteroaromatic ring containing at least 1 =N— ring member, L denotes a bond (referring to formula IV), $R^5$ denotes a cleavable group, and $Y^2$ is as defined hereinbefore, can be prepared by the treatment of a bromomethyl substituted heteroaromatic molecule of formula VIIa with an ester of 1H-pyrazole-4-carboxylic acid, 3-methyl-1H-pyrazole-4-carboxylic acid or 3-trifluoromethyl-1H-pyrazole-4-carboxylic acid in the presence of a suitable base (e.g. sodium hydride, cesium carbonate, potassium carbonate etc.) in a suitable solvent (e.g. tetrahydrofuran, N,N-dimethylformamide etc.) to give an intermediate of formula VIIb. Reaction with a suitable polycyclic nucleophile in the presence of a suitable base (e.g. sodium hydride, cesium carbonate, potassium carbonate etc.) in a suitable solvent (e.g. tetrahydrofuran, N,N-dimethylformamide etc.) leads to intermediates of formula IVe.

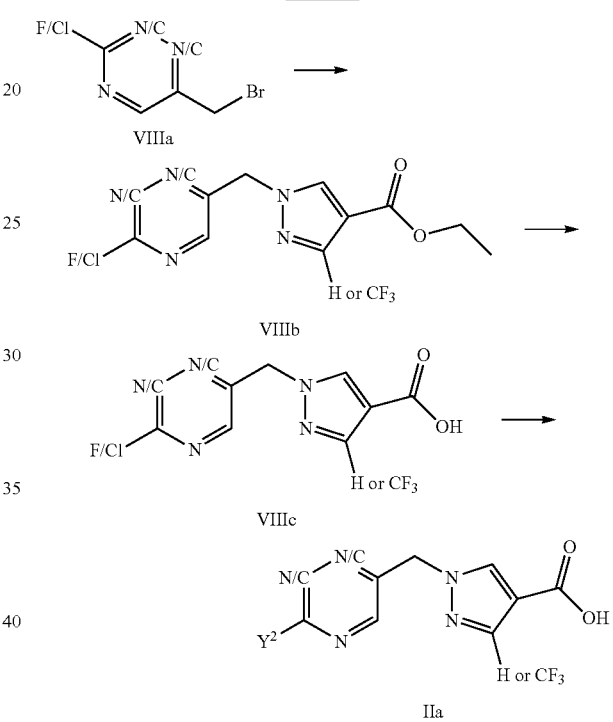

Scheme 8:

Some acids of formula IIa, wherein $R^1$ and $R^2$ denote H, $D^1$ denotes CH, $D^2$ denotes N, $D^3$ denotes CH or $C(CF_3)$, $Y^1$ denotes a 6 membered heteroaromatic ring containing at least 1 =N— ring member, L denotes a bond (referring to formula IV) and $Y^2$ is as defined hereinbefore, can be prepared by the treatment of a bromomethyl substituted heteroaromatic molecule of formula VIIIa with 1H-pyrazole-4-carboxylic acid ethyl ester or 3-trifluoromethyl-1H-pyrazole-4-carboxylic acid ethyl ester in the presence of a suitable base (e.g. sodium hydride, cesium carbonate, potassium carbonate etc.) in a suitable solvent (e.g. tetrahydrofuran, N,N-dimethylformamide etc.) to give an intermediate of formula VIIIb. Hydrolysis with a suitable hydroxide base (e.g. LiOH, NaOH, KOH) in a suitable solvent (e.g. tetrahydrofuran, methanol, ethanol, 1,4.dioxane, water or a mixture of these etc) gives Intermediated VIIIc. Reaction with a suitable polycyclic nucleophile in the presence of a suitable base (e.g. sodium hydride, cesium carbonate, potassium carbonate etc.) in a suitable solvent (e.g. tetrahydrofuran, N,N-dimethylformamide etc.) leads to intermediates of formula IIa.

Scheme 9

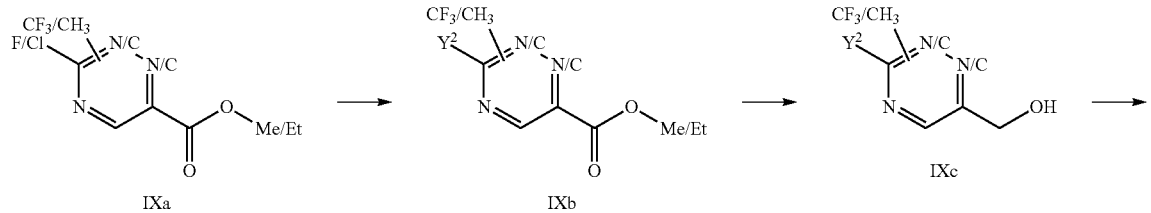

Scheme 9:
Some esters of formula IVf and IVg, wherein R[1] and R[2] denote H, D[1], D[2] and D[3] are as defined hereinbefore, Y[1] denotes a 6 membered heteroaromatic ring containing at least 1 =N— ring member and is optionally substituted with CH$_3$ or CF$_3$, L denotes a bond (referring to formula IV), R[5] denotes a cleavable group, and Y[2] is as defined hereinbefore, can be prepared by the treatment of a ester containing heteroaromatic molecule of formula IXa with a suitable polycyclic nucleophile in the presence of a suitable base (e.g. sodium hydride, cesium carbonate, potassium carbonate etc.) in a suitable solvent (e.g. tetrahydrofuran, N,N-dimethylformamide etc.) to give an intermediate of formula IXb. Reduction of the ester functionality be treatment with a suitable reducing agent such as LiBH4, LiAlH4, DIBAL etc gives an alcohol intermediate of formula IXc which can be converted into an alkyl bromide of formula IXd by treatment with for example PBr3 or triphenylphosphine and carbon tetrabromide. This intermediate and/or intermediate IXc can be further reacted as described in schemes 6, 7 and 8 to give intermediates of formula IVf and IVg.

Scheme 10

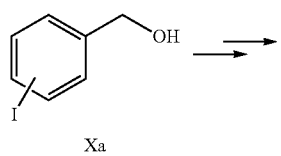

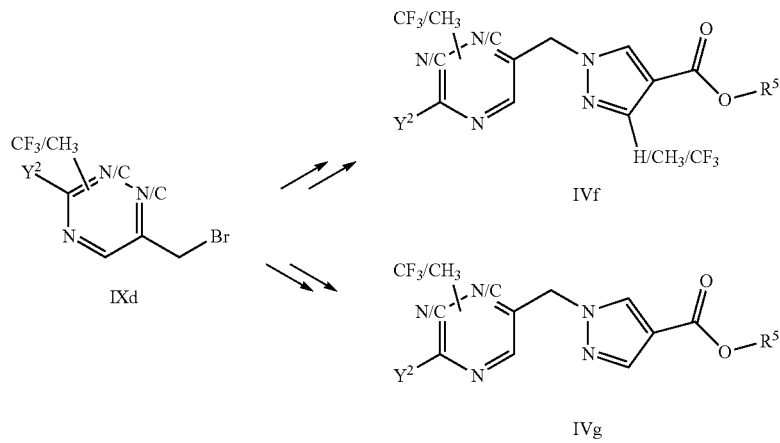

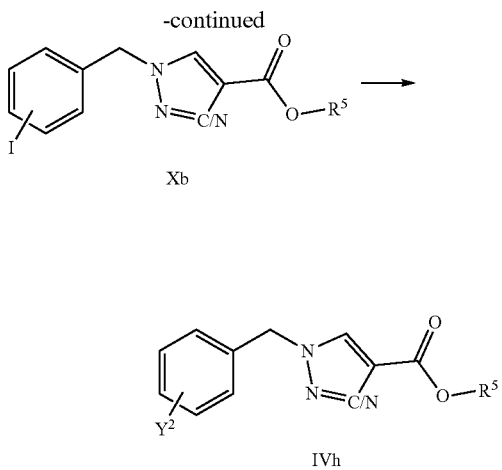

Scheme 10:
Some esters of formula IVh, wherein R[1] and R[2] denote H, D[1], D[2] and D[3] are as defined hereinbefore, Y[1] denotes a phenyl ring, L denotes a bond (referring to formula IV), R[5] denotes a cleavable group, and Y[2] is as defined hereinbefore, can be prepared by the treatment of an iodo benzyl alcohol or formula Xa using the methods described in schemes 3, 7 or 9 to give an intermediate of formula Xb. Reaction with a polycyclic nucleophile under palladium or copper catalysis using suitable ligands, bases and solvents under Ullman, Buckwald and Hartwig or similar methodologies leads to intermediates of formula IVh.

Scheme 11

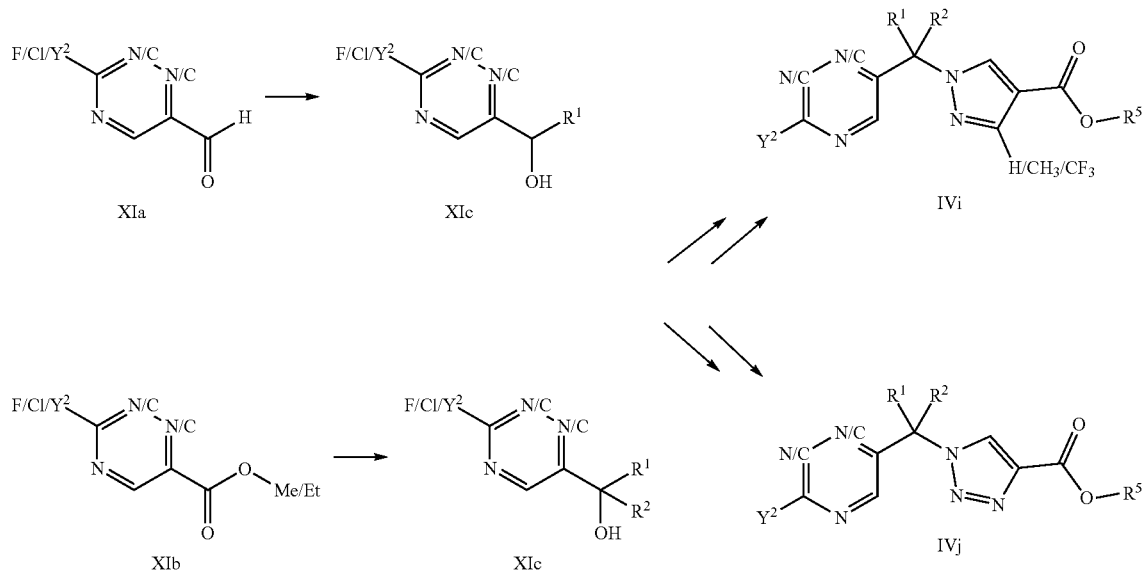

Scheme 11:

Some esters of formula IVi or IVj, wherein $R^1$ or both $R^1$ and $R^2$ denote a small alkyl group, $D^1$, $D^2$ and $D^3$ are as defined hereinbefore, $Y^1$ denotes a 6 membered heteroaromatic ring containing at least 1 =N— ring member, L denotes a bond (referring to formula IV), $R^5$ denotes a cleavable group, and $Y^2$ is as defined hereinbefore, can be prepared by the treatment of an aldehyde of formula XIa or an ester of formula XIb with a suitable organometallic nucleophile (e.g. a Grignard reagent, organozinc reagent, organolithium reagenst etc) to give a substituted benzyl alcohol of formula XIc or XId These intermediates can be further reacted as described in schemes 6, 7, 8 and 9 to give intermediates of formula IVi and IVj.

Scheme 12

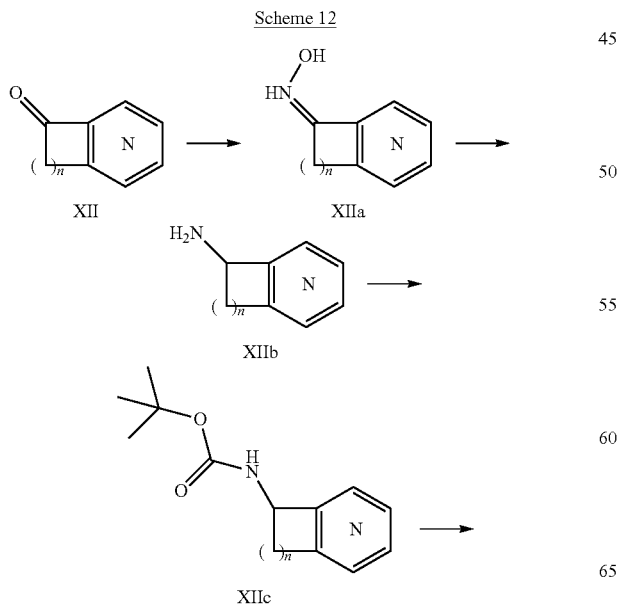

-continued

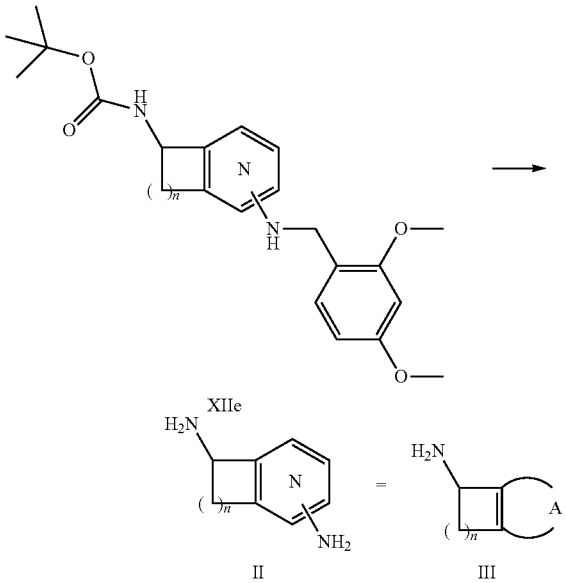

Scheme 10:

Amines of formula III can be prepared as follows:

A ketone of formula XII, wherein the N-tagged phenyl ring means that one CH ring member is replaced by N, is treated with hydroxylamine in a suitable solvent (e.g. ethanol, methanol, water, tetrahydrofuran or a mixture of these etc.) with heating if necessary to give an oxime of formula XIIa. This can then be reduced to an amine of formula XIIb by treatment with zinc in an appropriate acid (e.g. acetic acid, dilute hydrochloric acid etc) or by hydrogenation using a suitable catalyst (e.g. Raney Nickel, platinum oxide) under an atmosphere of hydrogen. The resulting amine can be protected as a Boc derivative by treatment with e.g. di-tert-butyl dicarbonate in a suitable solvent (e.g. tetrahydrofuran, methanol, ethanol, water etc or a mixture of these) to give an intermediate of formula XIIc. Reaction with a suitable oxidising agent (e.g. 3-chloroperbenzoic acid, oxone, hydrogen peroxide etc.) gives the N-oxide intermediate of formula XIId. This can be reacted with PyBrop in the presence of 2,4-dimethoxybenzylamine to give an intermediate of formula XIIe in which the dimethoxybenzylamine moiety is attached to a carbon adjacent to the ring nitrogen. Treatment with acid such as hydrochloric acid, with heating if required removes the protecting groups to give an amine intermediate of formula III.

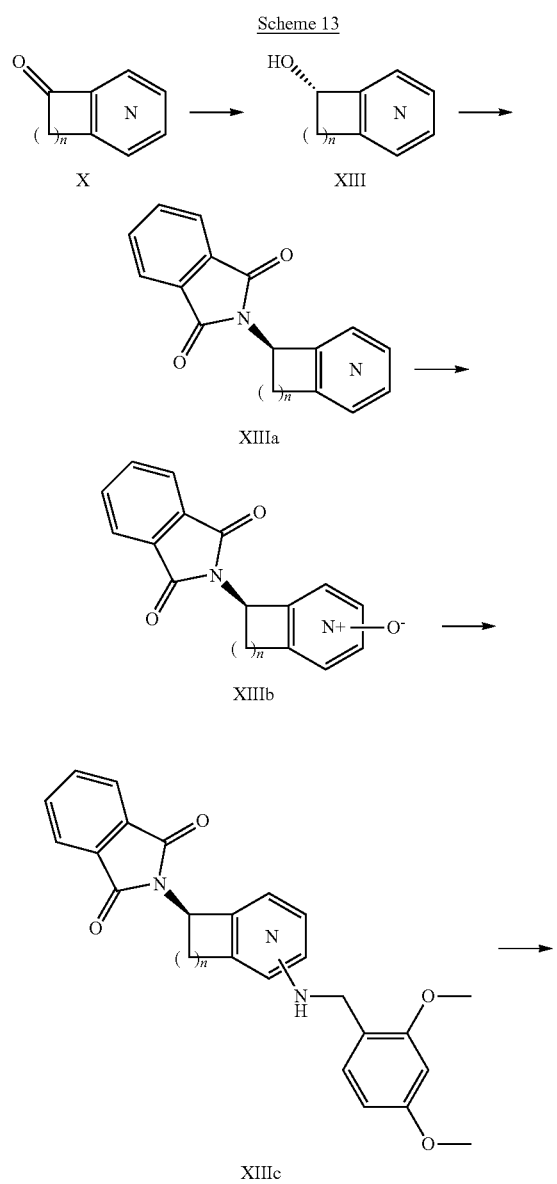

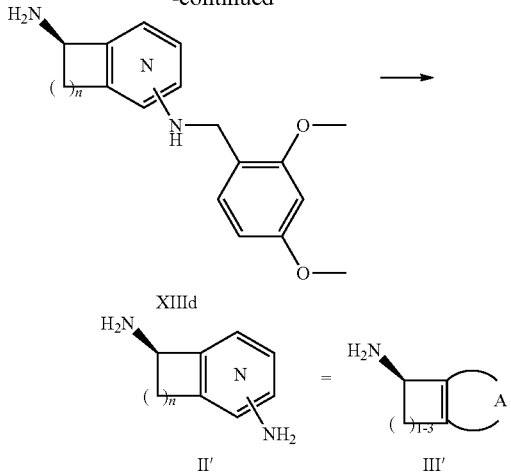

Scheme 11:

Enantiopure amines of formula III' can be prepared as follows:

A ketone of formula XII, wherein the N-tagged phenyl ring means that one CH ring member is replaced by N, is reduced under enantioselective conditions (e.g. those described by Noyori et. al., J. Am. Chem. Soc., 1995, 117 (28), pp 7562-7563.) to give a enantiopure alcohol of formula XIII. This can then be reacted with phthalimide in a Mitsonobu reaction with suitable reagents (e.g. triphenylphosphine plus diethylazodicarboxylate (DEAD) or diisopropyl azodicarboxylate (DIAD) etc.) in a suitable solvent (e.g. tetrahydrofuran, 1,4-dioxane, diethylether etc) leading to the inversion of the stereocenter and an intermediate of formula XIIIa. Treatment as described in Scheme 9 leads to the intermediate XIIIb. The phthalimide group can be removed by treatment with e.g. hydrazine or ethanolamine in a suitable solvent (e.g. ethanol, methanol, tetrahydrofuran, water etc or a mixture of these) with heating if necessary to give an intermediate of formula XIIIc. Treatment with acid such as hydrochloric acid, with heating if required removes the protecting group to give a chiral amine intermediate of formula III'.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

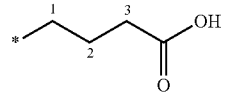

wherein the carboxy group is attached to the third carbon atom of the propyl group. The terms "1-methylpropyl-", "2,2-dimethylpropyl-" or "cyclopropylmethyl-" group represent the following groups:

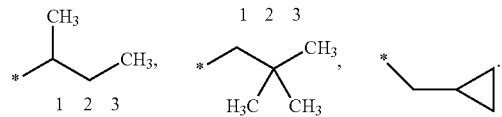

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

The activity of the compounds of the invention may be demonstrated using the following assay:

Biological Methods

The ability of compounds of Formula I to inhibit plasma kallikrein (KLKB1), Factor XIIa (FXIIa), Factor XIa (FXIa), Factor Xa (FXa), Factor IIa (alpha-thrombin; FIIa), plasmin, trypsin, tissue kallikrein 1 (KLK1), Factor VIIa (FVIIa), or FVIIa complexed with Tissue Factor, phospholipids and $CaCl_2$ ($FVIIa/TF/PL/CaCl_2$) was determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO:

Evaluation of the Inhibition of KLKB1 Using an Endpoint Assay

Human KLKB1 (0.01 U/mL; Enzyme Research Laboratories) or rat KLKB1 (0.625 nM; produced in-house) was incubated for 1 hr at Room Temperature with 0.10 µM fluorogenic substrate H-Pro-Phe-Arg-AMC (11295 from Bachem) and various concentrations of the test compound in assay buffer. Subsequently, PPACK II (Calbiochem) was added as a stop solution to achieve a final concentration of 1 µM and fluorescence was measured using an Envision Reader (PerkinElmer) with the wavelength excitation setting of 355 nm and the wavelength emission setting of 460 nm.

Evaluation of the Inhibition of Human KLKB1 in Dextransulfat Activated Human PPP.

Platelet poor plasma (PPP) obtained from human whole-blood, anticoagulated with EDTA, was activated with 12.5 µg/mL dextransulfate for 7 min on ice. The activated PPP was incubated with various concentrations of the test compound in assay buffer. Afterwards the mixture was incubated at 24° C. with 0.25 mM fluorogenic substrate H-Pro-Phe-Arg-AMC (11295 from Bachem) and measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of KLKB1 ($K_i$)

Human KLKB1 (1.78 nM or 0.025 U/mL; Enzyme Research Laboratories) was incubated at 24° C. with 0.25 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXIIa ($K_i$)

Human FXIIa (47.5 nM or 1.1 U/mL; Enzyme Research Laboratories) was incubated at 24° C. with 0.5 mM chromogenic Substrate S2302 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the inhibition of FXIa ($K_i$)

Human FXIa (0.5 nM or 0.016 U/mL; Enzyme Research Laboratories) was incubated at 24° C. with 0.25 mM fluorogenic substrate Boc-Glu(OBzl)-Ala-Arg-AMC.HCl (I1575 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$)

Human FXa (0.86 nM or 0.01 U/mL; Enzyme Research Laboratories) was incubated at 24° C. with 0.5 mM chromogenic Substrate S2765 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) was incubated at 24° C. with 0.5 mM chromogenic Substrate S2238 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) was incubated at 24° C. with 0.3 mM chromogenic Substrate S2251 (Chromogenix) and various concentrations of the test compound in assay buffer.

Measurements were performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) was incubated at 24° C. with 0.5 mM chromogenic Substrate S2222 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of KLK1 ($K_i$)

Prior to the assay, human KLK1 (R&D Systems) was activated by incubation with human trypsin (Calbiochem) in a 1:10,000 ratio for 15 min at 37° C. For assaying KLK1 inhibitory activity, activated KLK1 (31.25 nM or 1 U/mL) was incubated at 24° C. with 0.1 mM fluorogenic substrate H-Pro-Phe-Arg-AMC (I1295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FVIIa ($K_i$)

Human FVIIa (0.86 nM or 0.01 U/mL; Enzyme Research Laboratories) was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FVIIa/TF/PL/$CaCl_2$($K_i$)

Human FVIIa (300 nM or 585 U/mL; Enzyme Research Laboratories) together with mM $CaCl_2 \cdot 2H_2O$ and 13.3% (v/v) Dade® Innovin® (Siemens; OQUMI94E0002(5534), which contains recombinant human tissue factor synthetic phospholipids (thromboplastin), was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Calculation of $pIC_{50}$ and $pK_i$ values

The average $V_{max}$ values for the time interval from 2 to 12 min after initiation of the assay (expressed as either delta OD/min for assays using a chromogenic substrate or delta RFU/min for assays using a fluorigenic substrate, respectively) were plotted versus the Log of the concentration in molar of the evaluated inhibitor compound. The $pIC_{50}$ values were then fitted using a four-parametric fitting procedure using using GraphPad Prism (version 6; GraphPad Software, Inc.). Respective K values were obtained by correction of the $IC_{50}$ values for the respective $K_M$ value of the used substrate (see Table X for the obtained $K_M$ values of the used substrates) using the following formula:

$$K_i = \frac{IC_{50}}{1 + \frac{[\text{Substrate}, mM]}{K_M}}$$

Where the $IC_{50}$ is in molar and the $K_M$ value in mM.

TABLE X $K_M$ values obtained for the substrates used in the enzymatic assays.

| Enzyme | Substrate | $K_M$ (mM) |
|---|---|---|
| KLKB1 | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| KLK1 | I1295 | 0.07 |
| FVIIa | Pefachrome ® FVIIa | 0.42 |
| FVIIa/TF/PL/$CaCl_2$ | Pefachrome ® FVIIa | 3.92 |

Evaluation of Permeability

Caco-2 cells (1-2×$10^5$ cells/1 $cm^2$ area) are seeded on filter inserts (Costar transwell polycarbonate or PET filters, 0.4 µm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, pH 7.2) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 µl per time point contains TRIS buffer pH 7.6 at RT (0.1 M), magnesium chloride (5 mM), microsomal protein (1 mg/ml) and the test compound at a final concentration of 1 µM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum.

Following a (typically) 30 min preincubation in an incubator (37° C., 10% CO2) 5 µl of test compound solution (80 µM; from 2 mM in DMSO stock solution diluted 1:25 with medium) are added into 395 µl hepatocyte suspension (cell density in the range 0.25-5 Mio cells/mL, typically 1 Mio cells/mL; final concentration of test compound 1 µM, final DMSO concentration 0.05%).

The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [µM], CD: cell density of vital cells [10e6 cells/mL], AUD: area under the data [µM×h], clast: concentration of last data point [µM], k: slope of the regression line for parent decline [h−1].

Evaluation of Plasma Protein Binding.

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 ml Acetonitril/water (80/20). Aliquots of 25 µL of the plasma dialysate are transferred into deep well plates and mixed with 25 µl Acetonitril/water (80/20), 25 µl buffer, 25 µL calibration solution and 25 µl Internal Standard solution. Protein prezipitation is done by adding 200 µl Acetonitrile.

Aliquots of 50 µl of the buffer dialysate are transferred into deep well plates and mixed with 25 µl blank plasma, 25 µl Internal Standard solution and 200 µl Acetonitrile.

Samples are measured on HPLC-MS/MS-Systems and evaluated with Analyst-Software.

Percent bound is calculated with the formula: % bound=(plasma concentration−buffer concentration/plasma concentration)×100

Evaluation of Solubility

The aqueous solubility of the test compound is determined by comparing the amount dissolved in buffer to the amount in an acetonitrile/water (1/1) solution. Starting from a 10 mM DMSO stock solution aliquots are diluted with acetonitril/water (1/1) or buffer resp. After 24 h of shaking, the solutions are filtrated and analyzed by LC-UV. The amount dissolved in buffer is compared to the amount in the acetonitrile solution. Solubility will usually be measured from 0.001 to 0.125 mg/ml at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples.

PK parameters are calculated using non compartment methods. AUC and Cmax are normalized to a dose of 1 µmol/kg.

Biological Activity:

The inhibitory activity of compounds of the invention is demonstrated by the data in Table XX. The $IC_{50}$ values were obtained with the aid of the inhibition of KLKB1 endpoint assay described above.

TABLE XX $IC_{50}$ measurements for the inhibition of human Plasma Kallikrein (KLKB1)

| Example | $IC_{50}$ (nM) |
| --- | --- |
| 1 | 530 |
| 2 | 2100 |
| 3 | 17 |
| 4 | 63 |
| 5 | 10 |
| 6 | 71 |
| 7 | 420 |
| 8 | 14 |
| 9 | 3200 |
| 10 | 560 |
| 11 | >10000 |
| 12 | >10000 |
| 13 | >10000 |
| 14 | 5900 |
| 15 | 81 |
| 16 | 85 |
| 17 | 42 |
| 18 | 1200 |
| 19 | 2600 |
| 20 | 4 |
| 22 | 19 |
| 23 | 2 |
| 24 | 3300 |
| 27 | >10000 |
| 29 | 2200 |
| 32 | 24 |
| 33 | 2 |
| 34 | 390 |
| 35 | 600 |
| 36 | 1 |
| 37 | 8 |
| 38 | 1 |
| 39 | 14 |
| 40 | 9 |
| 41 | 1 |
| 42 | 1 |
| 43 | 13 |
| 44 | 30 |
| 45 | 4 |
| 46 | 38 |
| 47 | 4 |
| 48 | 69 |
| 49 | 2 |
| 50 | 1 |
| 51 | 89 |
| 52 | 41 |
| 53 | 1 |
| 54 | 46 |
| 55 | 490 |
| 56 | 1200 |
| 57 | 6200 |
| 58 | 1600 |
| 59 | 2200 |
| 60 | 7500 |
| 61 | 340 |
| 62 | 410 |
| 63 | 3000 |
| 64 | 580 |
| 65 | 1100 |
| 66 | 18 |

TABLE XX-continued

IC$_{50}$ measurements for the inhibition of human Plasma Kallikrein (KLKB1)

| Example | IC$_{50}$ (nM) |
| --- | --- |
| 67 | 470 |
| 68 | 10 |
| 69 | 55 |
| 70 | >10000 |
| 71 | 9 |
| 72 | 10 |
| 73 | 6 |
| 74 | 41 |
| 75 | 1 |
| 76 | 8 |
| 77 | 2 |
| 78 | 21 |
| 79 | 8 |
| 80 | 3 |
| 81 | 19 |
| 82 | 7 |
| 83 | 73 |
| 84 | 1 |
| 85 | 4 |
| 86 | 34 |
| 87 | 3200 |
| 88 | 3 |
| 89 | 5 |
| 90 | 78 |
| 91 | 38 |
| 92 | 23 |

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by unwanted plasma kallikrein activity in a patient, preferably in a human.

In yet another aspect the present invention relates to a method for treating a disease or condition mediated by unwanted plasma kallikrein activity in a mammal that includes the step of administering to a patient, preferably a human, in need of such treatment a therapeutically effective amount of a compound or a pharmaceutical composition of the present invention.

Diseases and conditions mediated by unwanted plasma kallikrein activity embrace diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), polypoidal choroidal vasculopathy (PCV), hereditary angioedema and acute respiratory distress syndrome (ARDS). According to one aspect the compounds and pharmaceutical compositions of the present invention are particularly suitable for treating ocular diseases including diabetic retinopathy, proliferative and non-proliferative retinopathy, diabetic macular edema (DME), retinal vein occlusion, aged-related macular degeneration (AMD), polypoidal choroidal vasculopathy (PCV) as well as hereditary angioedema.

Therefore according to another aspect the invention relates to compounds of formula I and pharmaceutical compositions according to the invention for use in in ophthalmic indications such as diabetic retinopathy, proliferative and non-proliferative retinopathy, diabetic macular edema (DME), age-related macular degeneration (AMD and polypoidal choroidal vasculopathy (PCV).

In addition the compounds and pharmaceutical compositions according to the invention are suitable for use in one or more of the following therapeutic processes: Treatment of edema, particularly hereditary angioedema.

In particular, the compounds and pharmaceutical compositions according to the invention are suitable for the treatment of of diabetic retinopathy, proliferative and non-proliferative retinopathy, diabetic macular edema (DME), age-related macular degeneration (AMD and polypoidal choroidal vasculopathy (PCV).

The compounds according to the invention are most particularly suitable for treating diabetic retinopathy, proliferative and non-proliferative retinopathy, diabetic macular edema (DME).

The dose range of the compounds of general formula I applicable per day is usually from 0.01 to 10 mg per kg body weight.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by unwanted plasma kallikrein activity, in particular diseases or conditions as described hereinbefore and hereinafter.

In yet another aspect the present invention relates a method for treating a disease or condition mediated by unwanted plasma kallikrein activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES/PRELIMINARY REMARKS

The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of use of a chiral starting material of known stereochemistry or by stereoselective synthesis of known stereochemistry.

Abbreviations

Ac acetyl
ACN acetonitrile
APCI atmospheric pressure chemical ionization
Boc tert-butyloxycarbonyl CU 1,1'-carbonyldiimidazole
d day
dba dibenzylideneacetone
DCM dichloromethane
DIPEA N,N-diisopropylethylamine
DME 1,2-dimethoxyethane
DMF N,N-dimethylformamide
DMSO dimethyl sulfoxide
dppf 1,1'-Bis(diphenylphosphino)ferrocene
ESI electrospray ionization (in MS)
EtOAc ethylacetate
EtOH ethanol
Ex. example
h hour(s)
HATU O-(7-azabenzotriazol-1-yl)-N,N,N',N'-tetramethyl-uronium-hexafluorophosphate
HPLC high performance liquid chromatography
HPLC-MS coupled high performance liquid chromatography-mass spectrometry
LC liquid chromatography
LC-MS coupled liquid chromatography—mass spectrometry
M molar (mol/L)
MeOH methanol
min minute(s)
MS mass spectrometry
NMP 1-methyl-2-pyrrolidinone
PyBop (benzotriazol-1-yloxy)tripyrrolidinophosphonium hexafluorophosphate
PyBrop bromotripyrrolidinophosphonium hexafluorophosphate
RP reverse phase
rt room temperature
$t_R$ retention time (in HPLC/LC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography—mass spectrometry Analytical Methods
UPLC-MS and HPLC-MS methods:
Method 1
Instrument: LC/MS Waters Acquity UPLC System DAD, SQD single quadrupole
Column: BEH C18 1.7 µm 2.1×50 mm, Temp 35° C.
Mobile phase: A=$H_2O$ 90%+$CH_3CN$ 10%+$NH_4COOH$ 5 mM
B=$CH_3CN$ 90%+$H_2O$ 10%

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu
Method 2
Instrument: LC/MS ThermoFinnigan HPLC Surveyor DAD, MSQ single quadrupole
Column: Synergi Hydro RP100A, 2.5 µm, 3×50 mm
Mobile phase: A=$H_2O$ 90%+10% $CH_3CN$+$NH_4COOH$ 10 mM
B=$CH_3CN$ 90%+$H_2O$ 10%+$NH_4COOH$ 10 mM

| Time in min: | % A | % B | Flow rate in mL/min |
|---|---|---|---|
| 0.00 | 100 | 0 | 1.2 |
| 0.50 | 100 | 0 | 1.2 |
| 6.50 | 0 | 100 | 1.2 |
| 7.50 | 0 | 100 | 1.2 |
| 8.00 | 100 | 0 | 1.2 |
| 9.00 | 100 | 0 | 1.2 |

Detection: UV 254 nm
Detection: Finnigan MSQ, single quadrupole
Ion source: APCI+/APCI−
Scan range: 100-900 amu
Method 3
Instrument: LC/MS ThermoFinnigan HPLC Surveyor DAD, LCQFleet Ion Trap
Column: Xselect CSH, 2.5 µm, 4.6×50 mm
Mobile phase: A=$H_2O$ 90%+10% $CH_3CN$+HCOOH 0.1%
B=$CH_3CN$ 90%+$H_2O$ 10%+HCOOH 0.1%

| Time in min: | % A | % B | Flow rate in mL/min |
|---|---|---|---|
| 0.00 | 100 | 0 | 1.4 |
| 4.00 | 0 | 100 | 1.4 |
| 5.30 | 0 | 100 | 1.4 |
| 5.50 | 100 | 0 | 1.4 |
| 6.00 | 100 | 0 | 1.4 |

Detection: UV 254 nm
Detection: Finnigan Fleet, Ion Trap
Ion source: ES+
Scan range: 100-900 amu
Method 4
Instrument: LC/MS Waters Acquity UPLC System DAD, SQD single quadrupole
Column: BEH C18 1.7 µm 2.1×50 mm, Temp 35° C.
Mobile phase: A=$H_2O$ 90%+$CH_3CN$ 10%+$CF_3COOH$ 0.1%
B=$CH_3CN$ 90%+$H_2O$ 10%

| Time in min | % A | % B | flow rate in mL/min |
|---|---|---|---|
| 0.00 | 100 | 0 | 0.70 |
| 0.70 | 0 | 100 | 0.70 |
| 2.30 | 0 | 100 | 0.70 |
| 2.40 | 100 | 0 | 0.70 |
| 2.60 | 100 | 0 | 0.70 |

Detection: UV 254 nm
Detection: SQD, single quadrupole
Ion source: ES+/ES−
Scan range: 90-900 amu
Method 5
Instrument: LC/MS Waters Acquity UPLC System DAD, SQD single quadrupole
Column: BEH C18 1.7 µm 2.1×50 mm, Temp 35° C.
Mobile phase: A=$H_2O$ 90%+$CH_3CN$ 10%+$NH_4HCO3$ 5 mM
B=$CH_3CN$ 90%+$H_2O$ 10%

| Time in min | % A | % B | flow rate in mL/min |
| --- | --- | --- | --- |
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

Detection: UV 254 nm
Detection: SQD, single quadrupole
Ion source: ES+/ES−
Scan range: 90-900 amu
Method 6
Instrument: LC/MS Waters Alliance 2695 HPLC System DAD, Quattro Micro Triple quadrupole
Column: Atlantis dC18 5 □m 4.6×50 mm, Temp 35° C.
Mobile phase: A=$H_2O$ 90%+10% $CH_3CN$+$CF_3COOH$ 0.05%
B=$CH_3CN$ 90%+10% $H_2O$

| Time in min | % A | % B | flow rate in ml/min |
| --- | --- | --- | --- |
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
Method 7
Instrument: LC/MS Waters Alliance 2695 HPLC System DAD, Quattro Micro Triple quadrupole
Column: Zorbax Eclipse XDB-C18 3.5 □m 4.6×50 mm, Temp 35° C.
Mobile phase: A=$H_2O$ 90%+10% $CH_3CN$+$NH_4COOH$ 5 mM
B=$CH_3CN$ 90%+10% $H_2O$

| Time in min | % A | % B | flow rate in ml/min |
| --- | --- | --- | --- |
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+/−
Scan range: 90-1000 amu
Method 8
Instrument: LC/MS Waters Alliance 2695 HPLC System DAD, Quattro Micro Triple quadrupole
Column: Xbridge Phenyl 3.5 □m 3×30 mm, Temp 35° C.
Mobile phase: A=$H_2O$ 90%+10% $CH_3CN$+$NH_4HCO_3$ 5 mM
B=$CH_3CN$ 90%+10% $H_2O$

| Time in min | % A | % B | flow rate in ml/min |
| --- | --- | --- | --- |
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+/−
Scan range: 90-1000 amu
GC-MS Methods:
Method 9
Instrument: GC/MS Thermo Scientific TRACE GC ULTRA, DSQ II MS single quadrupole
Column: Agilent DB-5MS, 25 m×0.25 mm×0.25 um
Carrier gas: Helium, 1 mL/min constant flow
Oven Program: 50° C., to 100° C. in 10° C./min, to 200° C. in 20° C./min, to 320° C. in 30° C./min (hold 10 min).
Detection: DSQ II MS single quadrupole
Ion source: EI
Scan range: 50-450 amu
Microwave Heating:
Discover® CEM instruments, equipped with 10 and 35 mL vessels
NMR Equipment:
The 1H NMR spectra were recorded on a Bruker Avance III (500 MHz) or a Varian 400 (400 MHz) instrument using deuterated dimethylsulfoxide (DMSO-d6) as the solvent with tetramethylsilane (TMS) or the residual solvent peak as an internal standard. Chemical shifts are reported in δ values (ppm) relative to TMS.

SYNTHESIS OF INTERMEDIATES

Intermediate 1

3-Aza-bicyclo[4.1.0]heptan-4-one

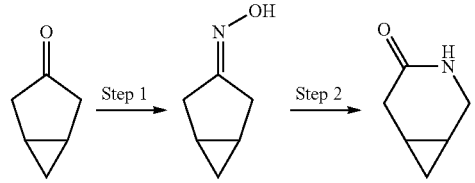 [SMILES: O=C1CC2CC2C1 ; ON=C1CC2CC2C1 ; O=C1CC2CC2CN1]

Step 1: Bicyclo[3.1.0]hexan-3-one oxime

Bicyclo[3.1.0]hexan-3-one (commercially available from FCHgroup, FCH1584334, 3 g, 31.2 mmol) and hydroxylamine (1.91 ml, 50% aq. solution, 31.2 mmol) are dissolved in ethanol (30 ml). The solution is stirred at 50° C. for 5 hours, then the reaction mixture is concentrated and water (10 ml) is added. The precipitate is collected and washed with diethyl ether to give the title compound (yield 3.2 g).
GC-MS (Method 9): $t_R$=4.39 min; Mass spectrum (ES+): m/z=111 [M]+.

Step 2: 3-Aza-bicyclo[4.1.0]heptan-4-one

Bicyclo[3.1.0]hexan-3-one oxime (3 g, 27.0 mmol) is dissolved in diethyl ether (30 ml), the solution is cooled to 0° C. and thionyl chloride (6 g, 50.4 mmol) is added, the mixture is warmed to 20° C. and stirred for 3 hours. The mixture is concentrated and water (30 ml) is added, the solution is stirred for 30 minutes, then Na2CO3 is added until pH 8 is reached. The mixture is extracted with dichloromethane (150 ml), the organic layer is collected, filtered over a pad of celite, dried over sodium sulfate and concentrated under vacuum. The residue is purified by reverse phase flash chromatography (C18, 0 to 50% acetonitrile in water) to give the title compound (yield 1.1 g).

LC (Method 3): $t_R$=0.50 min; Mass spectrum (ES+): m/z=112 [M+H]+.

Intermediate 2

3-(4-Chloromethyl-benzyl)-3-aza-bicyclo[4.1.0]heptan-4-one

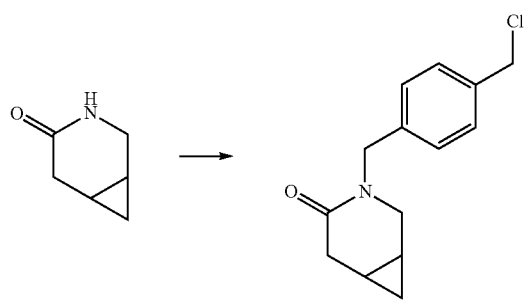 [SMILES: O=C1CC2CC2CN1 ; O=C1CC2CC2CN1Cc1ccc(CCl)cc1]

3-Aza-bicyclo[4.1.0]heptan-4-one (Intermediate 1, 250 mg, 2.25 mmol,) and sodium hydride (179 mg, 60% in oil dispersion, 4.50 mmol) are dissolved in N,N-dimethylformamide (15 ml), the mixture is stirred at room temperature for 15 minutes, then 1,4-bis-chloromethyl-benzene (984 mg, 5.62 mmol) is added. The mixture is heated to 100° C. and stirred for 3 hours. The reaction mixture is concentrated under reduced pressure, dichloromethane (80 ml) and water (80 ml) are added, phases are separated and the organic layer is collected, dried over sodium sulfate and concentrated under vacuum. The residue obtained is purified by flash chromatography (20-100% ethyl acetate in cyclohexane) to give the title compound (yield 200 mg).

LC (Method 1): $t_R$=1.03 min; Mass spectrum (ES+): m/z=250 [M+H]$^+$.

Intermediate 3

1-(4-Chloromethyl-benzyl)-3-trifluoromethyl-1H-pyrazole-4-carboxylic acid ethyl ester

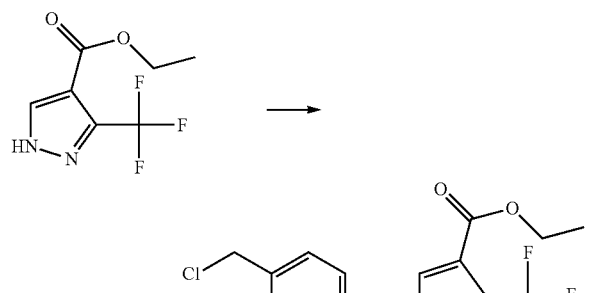

1,4-Bis-chloromethyl-benzene (4.2 g, 24.0 mmol), 3-trifluoromethyl-1H-pyrazole-4-carboxylic acid ethyl ester (2.5 g, 12.0 mmol) and cesium carbonate (5.87 g, 18.0 mmol) are dissolved in N,N-dimethylformamide (10 ml), the mixture is stirred at room temperature overnight. The solution is concentrated under reduced pressure, dichloromethane (100 ml) and water (100 ml) are added, phases are separated and the organic layer is collected, dried over sodium sulfate and concentrated. The residue obtained is purified by reverse phase flash chromatography (C18, 60 to 100% acetonitrile in water) to give the title compound (yield 1.3 g).

LC (Method 3): $t_R$=1.32 min; Mass spectrum (ES+): m/z=347 [M+H]$^+$.

Intermediate 4

1-(4-Chloromethyl-benzyl)-3-methyl-1H-pyrazole-4-carboxylic acid ethyl ester

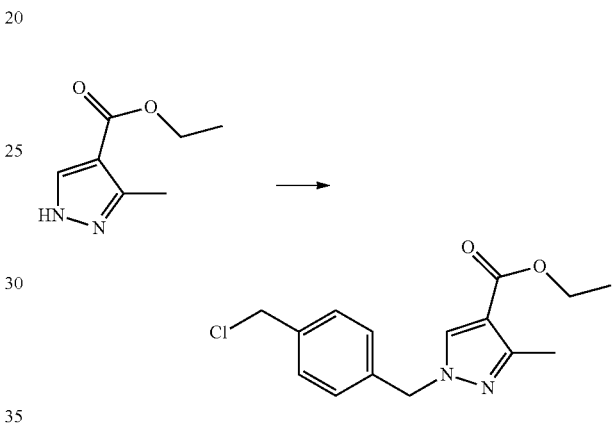

The title compound is prepared from 1,4-bis-chloromethyl-benzene (6.0 g, 34.27 mmol) and ethyl-3-methyl-1-H-pyrazole-4-carboxylate (3.5 g 22.7 mmol) in analogy to the method used for the preparation of Intermediate 3 after purification by flash chromatography (20-100% ethyl acetate in cyclohexane). Product obtained as major component in mixture with the regioisomer (Yield 5.0 g).

LC (Method 3): $t_R$=1.21 min; Mass spectrum (ES+): m/z=293 [M+H]+.

Intermediate 5

1-(4-Hydroxymethyl-benzyl)-1H-[1,2,3]triazole-4-carboxylic acid ethyl ester

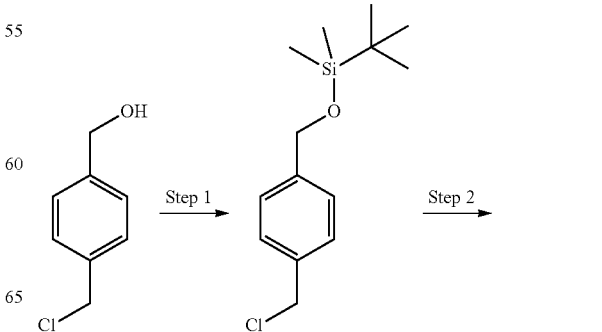

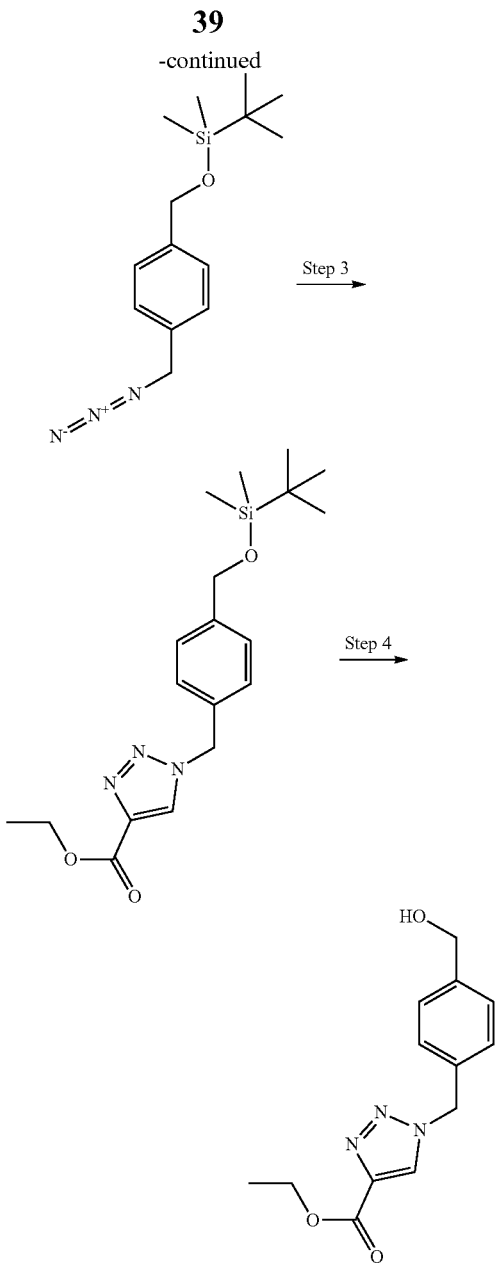

dissolved in anhydrous DMF (50 ml) and the reaction mixture is stirred at 25° C. for 24 hours. The reaction mixture is concentrated, dichloromethane (50 ml) and water (50 ml) are added, the organic layer is collected, dried over sodium sulfate and concentrated under vacuum to give the title compound. (yield 4.6 g)

GC-MS (Method 9): $t_R$=10.36 min; Mass spectrum (ES+): m/z=220, [M–tBu]+.

Step 3: 1-[4-(tert-Butyl-dimethyl-silanyloxymethyl)-benzyl]-1H-[1,2,3]triazole-4-carboxylic acid ethyl ester (4-Azidomethyl-benzyloxy)-tert-butyl-dimethyl-silane (4.6 g, 14.9 mmol) and ethyl propiolate (1.52 ml, 14.9 mmol) are dissolved in tert-butanol (20 ml) and water (20 ml). Sodium ascorbate (2.95 g, 14.9 mmol) and cupric sulfate pentahydrate (745 mg, 2.98 mmol) are added and the reaction mixture is stirred at room temperature for 6 hours.

The reaction mixture is concentrated, water (80 ml) was added and the reaction mixture is extracted with dichloromethane (80 ml). The organic phase is collected, dried over sodium sulfate and concentrated under vacuum. The residue obtained is purified by flash chromatography (20-50% ethyl acetate in cyclohexane) to give the title compound (yield 1.98 g).

LC (Method 1): $t_R$=1.53 min; Mass spectrum (ES+): m/z=376 [M+H]+.

Step 4: 1-(4-Hydroxymethyl-benzyl)-1H-[1,2,3] triazole-4-carboxylic acid ethyl ester 1-[4-(tert-Butyl-dimethyl-silanyloxymethyl)-benzyl]-1H-[1,2,3]triazole-4-carboxylic acid ethyl ester (1.98 g, 5.16 mmol) is dissolved in anhydrous tetrahydrofuran (20 ml), tetrabutylammonium fluoride (7.75 mL of a 1M solution in THF, 7.75 mmol) is added and the reaction mixture is stirred at room temperature for 2 hours. The mixture is concentrated, water is added and the reaction mixture is extracted with dichloromethane. The organic phase is collected, dried over sodium sulfate and concentrated under vacuum. The residue is purified by flash chromatography (20-60% ethyl acetate in cyclohexane) to give the title compound (yield 1.05 g).

LC (Method 1): $t_R$=0.74 min; Mass spectrum (ES+): m/z=262 [M+H]+.

Intermediate 6

1-(4-Methanesulfonyloxymethyl-benzyl)-1H-[1,2,3] triazole-4-carboxylic acid ethyl ester

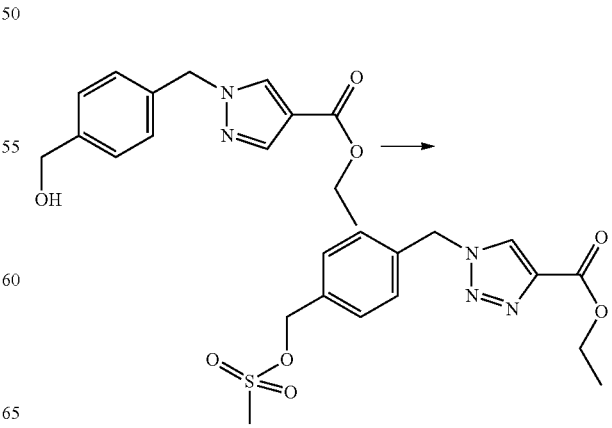

Step 1: tert-Butyl-(4-chloromethyl-benzyloxy)-dimethyl-silane 4-(Chloromethyl)benzylalcohol (4.0 g, 25.5 mmol) is dissolved in anhydrous dichloromethane (120 ml), tert-butyldimethylchlorosilane (4.81 g, 31.9 mmol) and imidazole (2.6 g, 38.3 mmol) are added at room temperature and the reaction mixture is stirred for 5 hours. The reaction mixture is washed with water, the organic layer is separated, dried over sodium sulfate and concentrated under reduced pressure to give the title compound. (Yield 6.0 g)

GC-MS (Method 9): $t_R$=9.88 min; Mass spectrum (ES+): m/z=213 [M–tBu]+.

Step 2: (4-Azidomethyl-benzyloxy)-tert-butyl-dimethyl-silane tert-Butyl-(4-chloromethyl-benzyloxy)-dimethyl-silane (5 g, 18.5 mmol) and sodium azide (4.8 g, 73.8 mmol) are 1-(4-hydroxymethyl-benzyl)-1H-[1,2,3]triazole-4-carboxylic acid ethyl ester (Intermediate 5, 550 mg, 2.06 mmol) and N,N-diisopropylethylamine (0.898 ml, 5.15 mmol) are dissolved in anhydrous dichloromethane (15 ml). the reaction mixture is stirred at 0° C. and methanesulfonyl chloride (0.239 ml, 3.1 mmol) is added. The reaction mixture is allowed to reach 20° C. and stirred for 1 hour. Dichloromethane (30 ml) is added and the organic solution is washed with water (50 ml), the organic layer is collected, dried over sodium sulfate and concentrated under vacuum. The residue obtained is purified by flash chromatography (10-80% ethyl acetate in cyclohexane) to give the title compound (yield 410 mg).

LC (Method 2): $t_R$=3.37 min; Mass spectrum (ES+): m/z=340 [M+H]$^+$.

Intermediate 7

1-[4-((1R,6R)-4-Oxo-3-aza-bicyclo[4.1.0]hept-3-ylmethyl)-benzyl]-1H-pyrazole-4-carboxylic acid ethyl ester

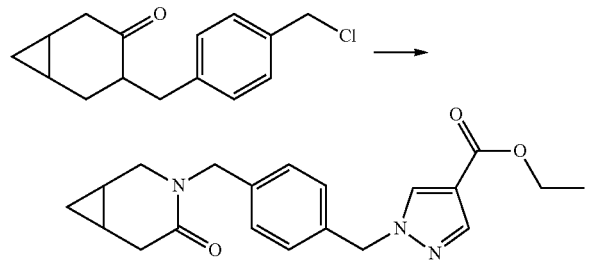

3-(4-Chloromethyl-benzyl)-3-aza-bicyclo[4.1.0]heptan-4-one (Intermediate 2, 200 mg, 0.72 mmol), 1H-pyrazole-4-carboxylic acid ethyl ester (141 mg, 1.00 mmol) and cesium carbonate (470 mg, 1.44 mmol) are dissolved in N,N-dimethylformamide (5 ml), the reaction mixture is stirred at 90° C. for 2 hours, then dichloromethane (25 ml) is added. The reaction mixture is filtered, the solution is concentrated under reduced pressure and the crude obtained is purified by flash chromatography (20-80% ethyl acetate in cyclohexane) to give the title compound. (yield 250 mg)

LC (Method 3): $t_R$=0.98 min; Mass spectrum (ES+): m/z=354 [M+H]+

Intermediate 8

3-(5-Bromomethyl-6-trifluoromethyl-pyridin-2-yl)-3-aza-bicyclo[3.1.0]hexane

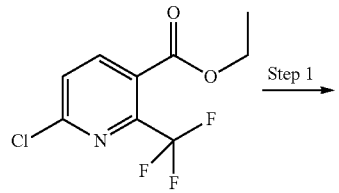

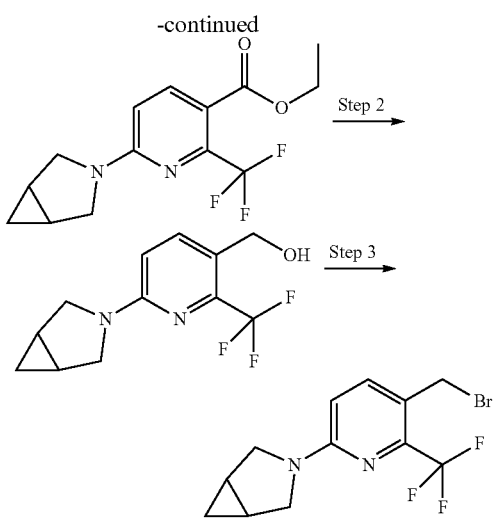

Step 1: 6-(3-Aza-bicyclo[3.1.0]hex-3-yl)-2-trifluoromethyl-nicotinic acid ethyl ester 6-Chloro-2-trifluoromethyl-nicotinic acid ethyl ester (synthesis described in patent application WO2004/29026 A1, 2.8 g 11.0 mmol), 3-azabicyclo[3.1.0]hexane hydrochloride (3.96 g, 33.1 mmol) and potassium carbonate (5.34 g, 38.6 mmol) are dissolved in 1-methyl-2-pyrrolidinone (5 ml). The reaction mixture is warmed to 95° C. and stirred for 30 minutes. Water (30 ml) and ethyl acetate (50 ml) are added, the organic layer is collected, dried over sodium sulfate and concentrated under vacuum. The residue obtained is purified by flash chromatography (10-90% ethyl acetate in cyclohexane) to give the title compound (yield 3.0 g).

LC (Method 2): $t_R$=5.82 min; Mass spectrum (ES+): m/z=301 [M+H]+

Step 2: [6-(3-Aza-bicyclo[3.1.0]hex-3-yl)-2-trifluoromethyl-pyridin-3-yl]-methanol 6-(3-Aza-bicyclo[3.1.0]hex-3-yl)-2-trifluoromethyl-nicotinic acid ethyl ester (3.0 g, 9.99 mmol) is dissolved in anhydrous tetrahydrofuran (20 ml). Lithium borohydride (5.49 mL of a 2M solution in THF, 10.99 mmol) is added, the reaction mixture is stirred for 2 hours at 25° C., then methanol (2 ml) is added. The reaction mixture is warmed to 65° C. and stirred for 5 hours. The reaction mixture is concentrated, water is added and the mixture is extracted with dichloromethane. The organic phase is collected, dried over sodium sulfate and concentrated under vacuum. The residue obtained is purified by flash chromatography (30-100% ethyl acetate in cyclohexane) to give the title compound (yield 2.6 g).

LC (Method 2): $t_R$=4.65 min; Mass spectrum (ES+): m/z=259 [M+H]$^+$.

Step 3: 3-(5-Bromomethyl-6-trifluoromethyl-pyridin-2-yl)-3-aza-bicyclo[3.1.0]hexane

[6-(3-Aza-bicyclo[3.1.0]hex-3-yl)-2-trifluoromethyl-pyridin-3-yl]-methanol (2.6 g, 10.1 mmol) is dissolved in anhydrous dichloromethane (80 ml). The solution is cooled to 0° C. and phosphorus tribromide (15.1 mL of a 1 M solution in dichloromethane, 15.1 mmol) is added. The reaction mixture is warmed to room temperature and stirred for 30 min; diisopropylethylamine (5 ml) is added, then the reaction mixture is concentrated under vacuum. The crude obtained is used in the next step without purification (8.7 g).

LC (Method 1): $t_R$=1.39 min;

Mass spectrum (ES+): m/z=273 [M+H]$^+$ (sample from the crude quenched with methanol).

Intermediate 9

3-(5-Bromomethyl-4-trifluoromethyl-pyridin-2-yl)-3-aza-bicyclo[3.1.0]hexane

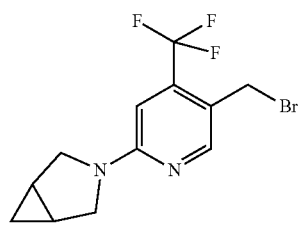 [SMILES: FC(F)(F)c1cc(N2CC3CC3C2)ncc1CBr]

The title compound is prepared in analogy to Intermediate 8 starting from 6-chloro-4-trifluoromethyl-nicotinic acid ethyl ester (commercially available from ACC CN DSH047816, 1.6 g, 6.3 mmol) (yield 3 g).

LC (Method 1): $t_R$=1.26 min;

Mass spectrum (ES+): m/z=273 [M+H]$^+$ (sample from the crude quenched with methanol).

Intermediate 10

[6-(3-Aza-bicyclo[3.1.0]hex-3-yl)-4-methyl-pyridin-3-yl]-methanol

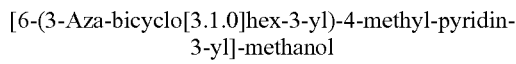

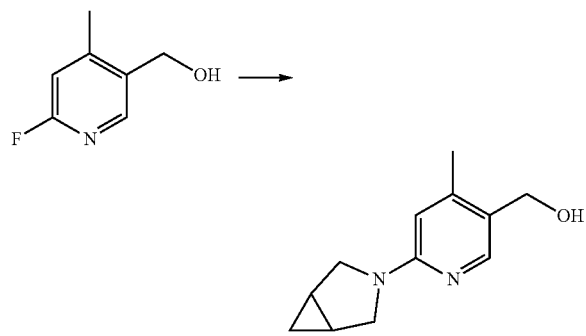

(6-Fluoro-4-methyl-pyridin-3-yl)-methanol (commercially available from AOB CHEM, 24860, 1 g, 7.08 mmol)), 3-azabicyclo[3.1.0]hexane hydrochloride (2.11 g, 17.7 mmol) and potassium carbonate (1.95 g, 14.2 mmol) are dissolved in 1-methyl-2-pyrrolidinone (1 ml). The reaction mixture is warmed to 95° C. and stirred for 60 minutes. Water (30 ml) and ethyl acetate (50 ml) are added, the organic layer is collected, dried over sodium sulfate and concentrated under vacuum. The residue obtained is purified by flash chromatography (10-90% ethyl acetate in cyclohexane) to give the title compound (yield 1.3 g).

LC (Method 2): $t_R$=2.92 min; Mass spectrum (ES+): m/z=205 [M+H]+

Intermediate 11

3-(5-Bromomethyl-4-methyl-pyridin-2-yl)-3-azabicyclo[3.1.0]hexane

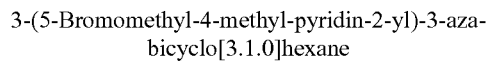

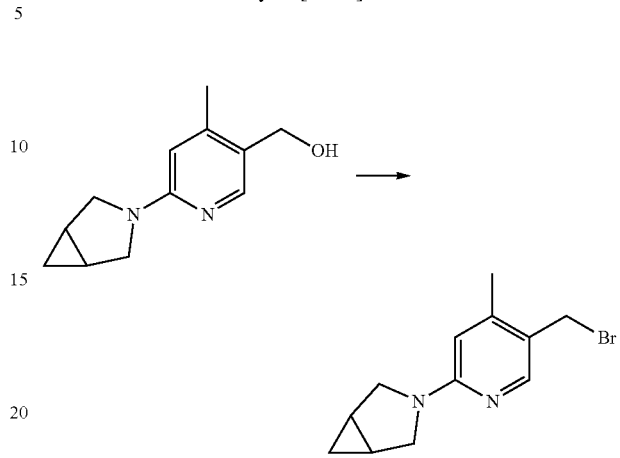

[6-(3-Aza-bicyclo[3.1.0]hex-3-yl)-4-methyl-pyridin-3-yl]-methanol (Intermediate 10, 1.3 g, 6.3 mmol) is dissolved in anhydrous dichloromethane (80 ml). The solution is cooled to 0° C. and phosphorus tribromide (9.54 mL of a 1 M solution in dichloromethane, 9.54 mmol) is added. The reaction mixture is warmed to room temperature and stirred for 30 min; diisopropylethylamine (2 ml) is added, then the reaction mixture is concentrated under vacuum. The crude obtained is used in the next step without purification (Yield 2.8 g).

LC (Method 1): $t_R$=1.00 min; Mass spectrum (ES+): m/z=219 [M+H]$^+$ (sample from the crude quenched with methanol).

Intermediate 12

1-[6-(3-Aza-bicyclo[3.1.0]hex-3-yl)-2-trifluoromethyl-pyridin-3-ylmethyl]-1H-pyrazole-4-carboxylic acid ethyl ester

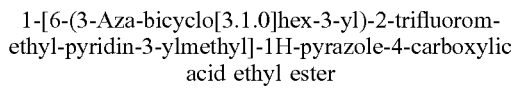

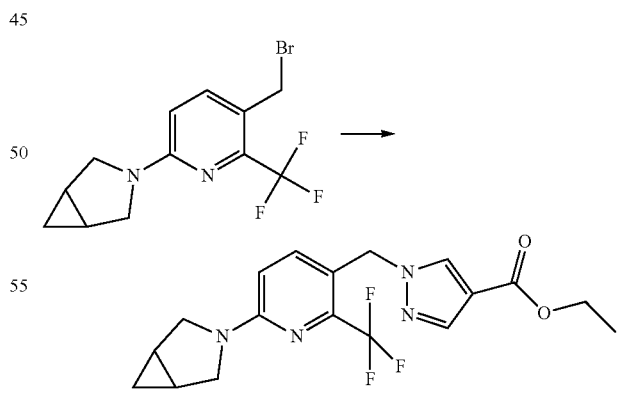

Crude 3-(5-Bromomethyl-6-trifluoromethyl-pyridin-2-yl)-3-aza-bicyclo[3.1.0]hexane (Intermediate 8, 4.0 g,) and 1H-pyrazole-4-carboxylic acid ethyl ester (0.873 g, 6.23 mmol) are dissolved in anhydrous DMF (5 ml). The reaction mixture is heated at 70° C. and stirred for 12 hours. The reaction mixture is partitioned between water and ethyl acetate, the organic layer is collected, dried over sodium sulfate and concentrated under vacuum. The residue is purified by flash chromatography (10-90% ethyl acetate in cyclohexane) to give the title compound (yield 1.1 g).

LC (Method 2): $t_R$=5.73 min; Mass spectrum (ES+): m/z=381 [M+H]+

Intermediate 13

1-[6-(3-Aza-bicyclo[3.1.0]hex-3-yl)-4-trifluoromethyl-pyridin-3-ylmethyl]-1H-pyrazole-4-carboxylic acid ethyl ester

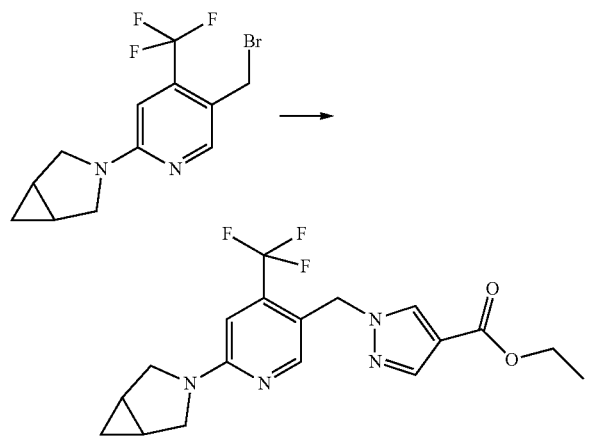

The title compound is prepared from crude 3-(5-Bromomethyl-4-trifluoromethyl-pyridin-2-yl)-3-aza-bicyclo[3.1.0]hexane (Intermediate 9, 2.0 g,) in analogy to the method used for the preparation of Intermediate 12 (yield 2.0 g)

LC (Method 2): $t_R$=5.12 min Mass spectrum (ES+): m/z=381 [M+H]+.

Intermediate 14

1-[6-(3-Aza-bicyclo[3.1.0]hex-3-yl)-4-methyl-pyridin-3-ylmethyl]-1H-pyrazole-4-carboxylic acid ethyl ester

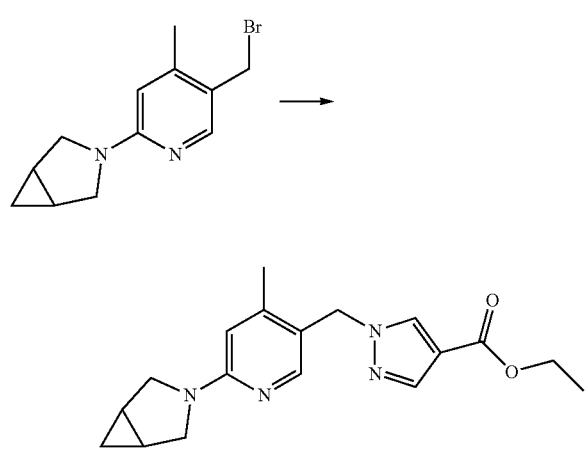

The title compound is prepared from crude 3-(5-Bromomethyl-4-methyl-pyridin-2-yl)-3-aza-bicyclo[3.1.0]hexane (Intermediate 11, 2.0 g,) in analogy to the method used for the preparation of Intermediate 12 (yield 400 mg)

LC (Method 1): $t_R$=1.32 min Mass spectrum (ES+): m/z=327 [M+H]+.

Intermediate 15

1-[4-(6,7-Dihydro-4H-pyrano[4,3-c]pyrazol-2-ylmethyl)-benzyl]-1H-[1,2,3]triazole-4-carboxylic acid ethyl ester

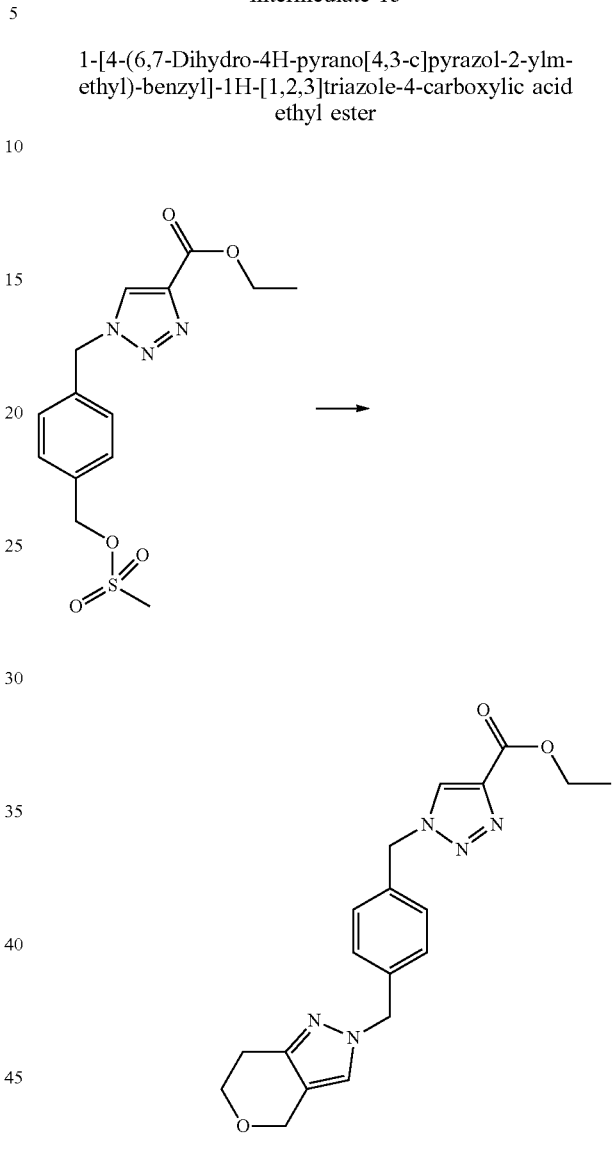

1-(4-Methanesulfonyloxymethyl-benzyl)-1H-[1,2,3]triazole-4-carboxylic acid ethyl ester (Intermediate 6, 200 mg, 0.59 mmol), 2,4,6,7-tetrahydro-pyrano[4,3-c]pyrazole, (commercially available from Anichem K10970, 73 mg, 0.59 mmol) and cesium carbonate (192 mg, 0.59 mmol) are dissolved in N,N-dimethylformamide (15 ml) and the reaction mixture is stirred at 85° C. for 2 hours. The reaction mixture is concentrated, then dichloromethane (15 ml) and water (15 ml) are added, the organic layer is collected, dried over sodium sulfate and concentrated under reduced pressure. The residue obtained is purified by flash chromatography (0-10% methanol in dichloromethane) to give the title compound. (yield 130 mg)

LC (Method 1): $t_R$=0.85 min; Mass spectrum (ES+): m/z=368 [M+H]+

The following intermediate is prepared in analogy to Intermediate 15, from the corresponding starting intermediates:

| Intermediate | Structure | Starting intermediates | Yield | Analysis |
|---|---|---|---|---|
| 16 | (structure shown) | Intermediate 6 (150 mg) and octahydro-pyrido[1,2-a]pyrazin-6-one (commercially available from Emolecule, 44693496, 85 mg). | 80 mg | LC (Method 1): $t_R$ = 0.84 min; Mass spectrum (ES+): m/z = 398 [M + H]$^+$. |

Intermediate 17

1-(6-Fluoro-pyridin-3-ylmethyl)-1H-[1,2,3]triazole-4-carboxylic acid

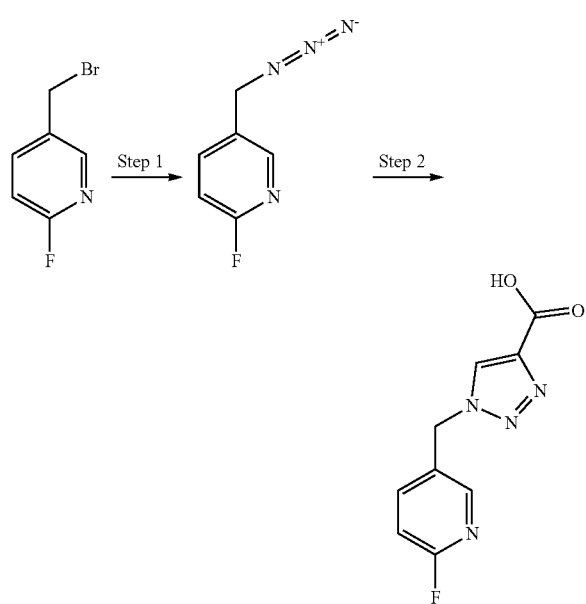

Step 1: 5-Azidomethyl-2-fluoro-pyridine

5-Bromomethyl-2-fluoro-pyridine (available from Apollo Scientific, PC5845; 7.0 g, 22.1 mmol) and sodium azide (4.31 g, 66.3 mmol) are dissolved in anhydrous DMF (5 ml) and the reaction mixture is stirred at 20° C. for 24 hours. The reaction mixture is concentrated and the residue obtained is purified by flash chromatography (0-15% methanol in dichloromethane) to give the title compound. (yield 2.5 g)

LC (Method 1): $t_R$=0.85 min; Mass spectrum (ES+): m/z=154 [M+H]$^+$.

Step 2: 1-(6-Fluoro-pyridin-3-ylmethyl)-1H-[1,2,3]triazole-4-carboxylic acid

5-Azidomethyl-2-fluoro-pyridine (2.5 g, 13.9 mmol) and propiolic acid (0.99 g, 13.9 mmol) are dissolved in tert-butanol (25 ml) and water (25 ml), then sodium ascorbate (2.76 g, 13.9 mmol) and cupric sulfate pentahydrate (698 mg, 2.79 mmol) are added and the reaction mixture is stirred at room temperature for 6 hours.

The reaction mixture is concentrated, Na$_2$CO$_3$ 5% aq. solution is added and the reaction mixture is washed with dichloromethane (100 ml). The aqueous phase is collected and HCl conc aq. solution is added until pH 2 is reached. The precipitate formed is separated and the aqueous phase solution is extracted with dichloromethane. The precipitate and the organic phase are collected together, dried over sodium sulfate and concentrated under vacuum to give the title compound (yield 1.5 g).

LC (Method 1): $t_R$=0.27 min; Mass spectrum (ES+): m/z=223 [M+H]$^+$.

Intermediate 18

1-(4-Iodo-benzyl)-1H-[1,2,3]triazole-4-carboxylic acid ethyl ester

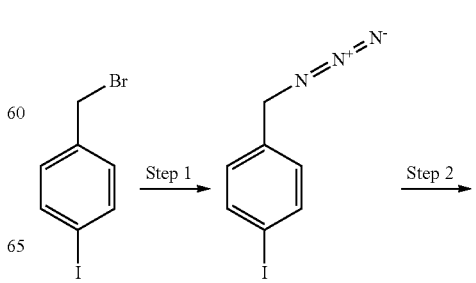

49
-continued

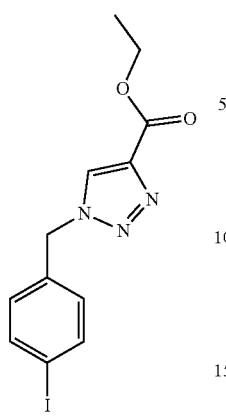

Step 1: 1-Azidomethyl-4-iodo-benzene

1-Bromomethyl-4-iodo-benzene (35 g, 117.8 mmol) and sodium azide (30.6 g, 471.5 mmol) are dissolved in anhydrous DMF (150 ml) and the reaction mixture is stirred at 20° C. for 24 hours. The reaction mixture is concentrated, then dichloromethane (130 ml) and water (40 ml) are added The organic layer is collected, dried over sodium sulfate and concentrated under vacuum to give the title compound. (yield 24.0 g)

GC-MS (Method 9): $t_R$=8.61 min; Mass spectrum (ES+): m/z=259 [M]⁺.

Step 2: 1-(4-Iodo-benzyl)-1H-[1,2,3]triazole-4-carboxylic acid ethyl ester

1-Azidomethyl-4-iodo-benzene (3.20 g, 10.5 mmol) and ethyl propiolate (1.13 g, 11.5 mmol) are dissolved in tert-butanol (8 ml) and water (8 ml), then sodium ascorbate (2.08 g, 10.5 mmol) and cupric sulfate pentahydrate (524 mg, 2.10 mmol) are added and the reaction mixture is stirred at room temperature for 1 hour.

The reaction mixture is concentrated, then water is added and the reaction mixture is extracted with dichloromethane (100 ml). The organic phase is collected, dried over sodium sulfate and concentrated under vacuum. The residue obtained is purified by flash chromatography (0-100% ethyl acetate in cyclohexane) to give the title compound (yield 2 g).

LC (Method 2): $t_R$=4.37 min; Mass spectrum (ES+): m/z=358 [M+H]⁺.

The following intermediate is prepared in two steps in analogy to Intermediate 18, from the corresponding starting material:

50

Intermediate 20

1-(4-Bromomethyl-benzyl)-1H-[1,2,3]triazole-4-carboxylic acid tert-butyl ester

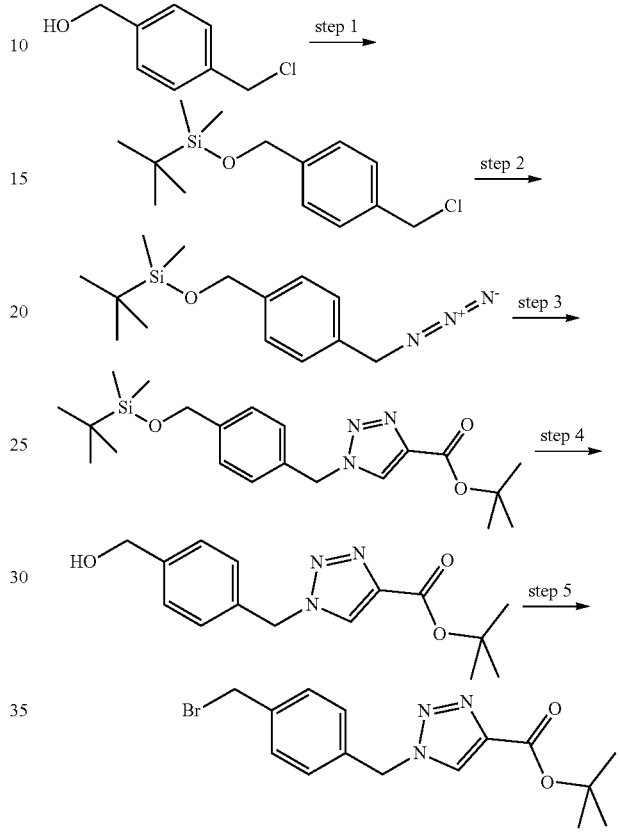

Step 1: tert-Butyl-(4-chloromethyl-benzyloxy)-dimethethyl-silane

Tert-butyldimethylchlorosilane (26.5 g, 176 mmol) and imidazole (14.1 g, 68.1 mmol) are added to a stirred solution of 4-(chloromethyl)benzyl alcohol (25 g, 160 mmol) dissolved in 300 mL of dry DCM and the reaction mixture is stirred at room temperature for 2 hours. Water is added, the organic layer is separated and concentrated under reduced pressure to obtain the crude title compound (yield 42.5 g).

GC (Method 9): $t_R$=9.96 min; Mass spectrum (EI+): m/z=270 [M]⁺

| Intermediate | Structure | Starting material | Yield | Analysis |
|---|---|---|---|---|
| 19 | ![structure] | 4-Chloromethyl-1-iodo-2-methyl-benzene (3.0 g) commercially available from Aldlab A129581 | 1.6 g | LC (Method 1): $t_R$ = 1.22 min; Mass spectrum (ES+): m/z = 372 [M + H]⁺. |

Step 2: (4-Azidomethyl-benzyloxy)-tert-butyl-dimethy-silane tert-Butyl-(4-chloromethyl-benzyloxy)-dimethethyl-silane (42.5 g) and sodium azide (14.5 g, 223 mmol) are dissolved in 150 mL of dry N,N-dimethylformamide and the reaction mixture is stirred at room temperature for 24 hours. The mixture is concentrated and the residue is partitioned between water and DCM; the organic layer is separated and concentrated under reduced pressure to obtain the crude title compound (yield 41.4 g).

GC (Method 9): $t_R$=10.36 min; Mass spectrum (EI+): m/z=220 [M–tBu]$^+$

Step 3: 1-[4-(tert-Butyl-dimethyl-silanyloxymethyl)-benzyl]-1H-[1,2,3]triazole-4-carboxylic acid tert-butyl ester Cupric sulfate pentahydrate (1.03 g, 4.11 mmol) and sodium ascorbate (4.07 g, 20.6 mmol) are added to a stirred solution of (4-Azidomethyl-benzyloxy)-tert-butyl-dimethysilane (6.0 g, 20.6 mmol) and tert-butyl propiolate (3.10 ml, 22.6 mmol) dissolved in a mixture of 50 mL of tert-butanol and 50 ml of water. The reaction mixture is stirred at room temperature for 2 hours. The solvent is removed under reduced pressure and the residue is partitioned between water and DCM. The organic layer is separated and concentrated under reduced pressure to obtain the crude title compound (yield 8.3 g).

LC (Method 4): $t_R$=0.73 min; Mass spectrum (ES+): m/z=404 [M+H]$^+$.

Step 4: 1-(4-Hydroxymethyl-benzyl)-1H-[1,2,3]triazole-4-carboxylic acid tert-butyl ester 1-[4-(tert-Butyl-dimethyl-silanyloxymethyl)-benzyl]-1H-[1,2,3]triazole-4-carboxylic acid tert-butyl ester (5.95 g) is dissolved in 50 mL of dry THF and the solution is cooled with an ice/water bath. After 15 minutes stirring, tetrabutylammonium fluoride solution (1M in THF, 15 ml, 15 mmol) is added and the reaction mixture is stirred at room temperature for 3 hours. The solvent is removed under reduced pressure and the residue is partitioned between water and a mixture of diethylether/cyclohexane 9:1. The organic layer is separated, dried over sodium sulfate, filtered and concentrated under reduced pressure to obtain the crude title compound (3.8 g).

LC (Method 1): $t_R$=0.89 min; Mass spectrum (ES+): m/z=290 [M+H]$^+$.

Step 5: 1-(4-Bromomethyl-benzyl)-1H-[1,2,3]triazole-4-carboxylic acid tert-butyl ester Carbon tetrabromide (3.5 g 10.5 mmol) is added to a stirred solution of 1-(4-Hydroxymethyl-benzyl)-1H-[1,2,3]triazole-4-carboxylic acid tert-butyl ester (2.6 g) dissolved in 50 mL of DCM. The reaction mixture is cooled to 0° C., triphenylphosphine (2.8 g, 10.5 mmol) is added portion-wise and the reaction mixture is stirred at room temperature overnight. The solvent is removed under reduced pressure and the crude is purified by flash chromatography (10-30% EtOAc in cyclohexane) to give the title compound (yield 3.2 g).

LC (Method 1): $t_R$=1.21 min; Mass spectrum (ES+): m/z=352-354 [M+H]$^+$.

Intermediate 21

1-[4-(3-Aza-bicyclo[3.1.0]hex-3-ylmethyl)-benzyl]-1H-[1,2,3]triazole-4-carboxylic acid tert-butyl ester

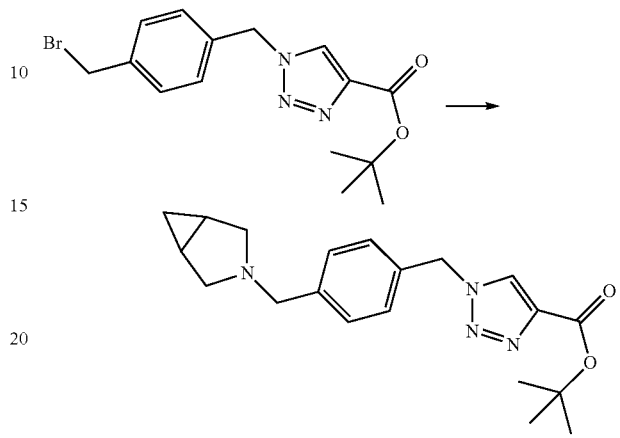

1-(4-Bromomethyl-benzyl)-1H-[1,2,3]triazole-4-carboxylic acid tert-butyl ester (Intermediate 20, 350 mg, 0.99 mmol), azabicyclo[3.1.0]hexane hydrochloride (119 mg, 0.99 mmol) and N,N-diisopropylethylamine (510 μL, 2.98 mmol) are dissolved in 3 mL of dry DMF and the reaction mixture is stirred for 3 hours. The solvent is removed under reduced pressure and the residue is partitioned between DCM and water. The organic layer is separated, washed with brine, dried over sodium sulfate, filtered and concentrated under reduced pressure to obtain the crude title compound (yield 343 mg).

LC (Method 1): $t_R$=0.96 min; Mass spectrum (ES+): m/z=355 [M+H]$^+$.

Intermediate 22

1-[4-(3-Aza-bicyclo[3.1.0]hex-3-ylmethyl)-benzyl]-1H-[1,2,3]triazole-4-carboxylic acid

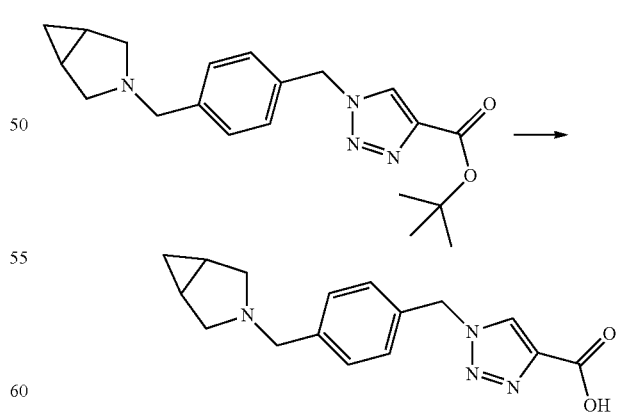

Trifluoroacetic acid (670 μL, 8.7 mmol) is added to a stirred solution of 1-[4-(3-Aza-bicyclo[3.1.0]hex-3-ylmethyl)-benzyl]-1H-[1,2,3]triazole-4-carboxylic acid tert-butyl ester (Intermediate 21, 343 mg, 0.87 mmol) dissolved in 10 mL of DCM and the reaction mixture is stirred 2 hours.

The solvent is removed under reduced pressure, the residue is suspended in diethylether, HCl (2N diethylether solution, 2.2 ml, 4.4 mmol) is added and the mixture is stirred 1 hour. The precipitate is filtered to obtain the title compound as crude hydrochloride salt (yield 321 mg).

LC (Method 1): $t_R$=0.30 min; Mass spectrum (ES+): m/z=299 [M+H]$^+$.

Intermediate 23

Hexahydro-pyrrolo[1,2-c]imidazol-3-one

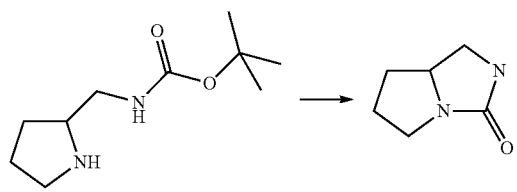

Boc-Aminomethylpyrrolidine (270 mg, 1.35 mmol) is loaded in a microwave vial and heated in a microwave reactor at 200° C. for 1 hour. DCM is added, the organic layer is washed with brine and concentrated under reduced pressure to give the crude title compound (yield 148 mg).

LC (Method 1): $t_R$=0.48 min; Mass spectrum (ES+): m/z=127 [M+H]$^+$.

Intermediate 24

1-[4-(3-Oxo-tetrahydro-pyrrolo[1,2-c]imidazol-2-ylmethyl)-benzyl]-1H-[1,2,3]triazole-4-carboxylic acid tert-butyl ester

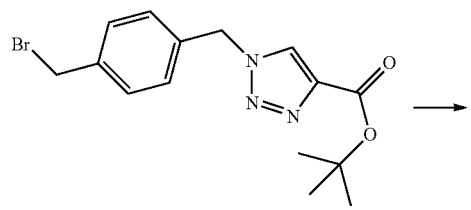

Sodium hydride (60% oil suspension, 37.5 mg, 0.94 mmol) is added portion-wise to a stirred solution of hexahydro-pyrrolo[1,2-c]imidazol-3-one (Intermediate 23, 107.4 mg, 0.85 mmol) dissolved in 5 mL of dry DMF under nitrogen atmosphere and the reaction mixture is stirred 20 minutes. 1-(4-Bromomethyl-benzyl)-1H-[1,2,3]triazole-4-carboxylic acid tert-butyl ester (Intermediate 20, 300 mg, 0.85 mmol) is added and the reaction mixture is further stirred 3 hours. The solvent is removed under reduced pressure and the residue is partitioned between water and DCM. The organic layer is separated, washed with brine, dried and concentrated under reduced pressure. The crude is suspended in diethylether, triturated and filtered to give the crude title compound (yield 287 mg).

LC (Method 1): $t_R$=1.01 min; Mass spectrum (ES+): m/z=398 [M+H]+.

Intermediate 25

1-[4-(3-Oxo-tetrahydro-pyrrolo[1,2-c]imidazol-2-ylmethyl)-benzyl]-1H-[1,2,3]triazole-4-carboxylic acid

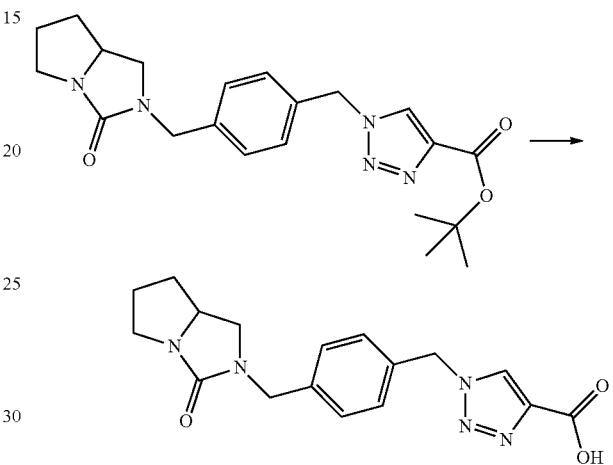

The title compound is prepared from 1-[4-(3-Oxo-tetrahydro-pyrrolo[1,2-c]imidazol-2-ylmethyl)-benzyl]-1H-[1,2,3]triazole-4-carboxylic acid tert-butyl ester (Intermediate 24, 226 mg, 0.51 mmol) in a manner analogous to that described for Intermediate 22 (yield 170 mg).

LC (Method 1): $t_R$=0.56 min; Mass spectrum (ES+): m/z=342 [M+H]$^+$.

Intermediate 26

1-[4-(2-Oxo-3-aza-bicyclo[3.1.0]hex-3-ylmethyl)-benzyl]-1H-[1,2,3]triazole-4-carboxylic acid tert-butyl ester

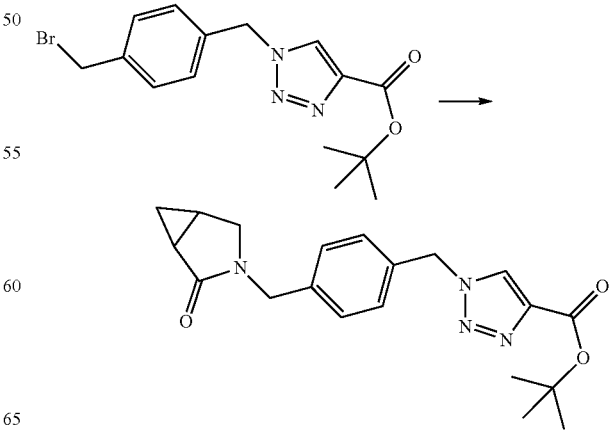

The title compound is prepared from 1-(4-Bromomethyl-benzyl)-1H-[1,2,3]triazole-4-carboxylic acid tert-butyl ester (Intermediate 20, 350 mg, 0.99 mmol) and 3-azabicyclo[3.1.0]hexan-2-one (diverchim DIV02536, 96 mg, 0.99 mmol) in a manner analogous to that described for Intermediate 24 (yield 180 mg).

LC (Method 1): $t_R$=0.96 min; Mass spectrum (ES+): m/z=369 [M+H]⁺.

Intermediate 27

1-[4-(2-Oxo-3-aza-bicyclo[3.1.0]hex-3-ylmethyl)-benzyl]-1H-[1,2,3]triazole-4-carboxylic acid

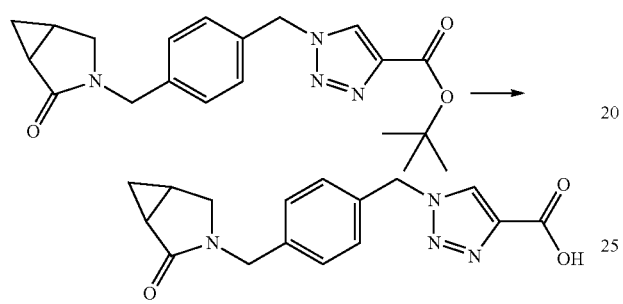

The title compound is prepared from 1-[4-(2-Oxo-3-aza-bicyclo[3.1.0]hex-3-ylmethyl)-benzyl]-1H-[1,2,3]triazole-4-carboxylic acid tert-butyl ester (Intermediate 26, 180 mg, 0.49 mmol) in a manner analogous to that described for Intermediate 22 (yield 150 mg).

LC (Method 1): $t_R$=0.58 min; Mass spectrum (ES+): m/z=313 [M+H]⁺.

Intermediate 28

1-[4-(3-Oxo-tetrahydro-pyrrolo[1,2-c]imidazol-2-yl)-benzyl]-1H-[1,2,3]triazole-4-carboxylic acid ethyl ester

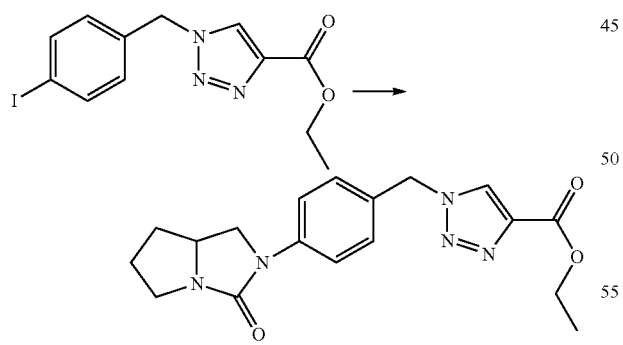

Trans N,N'-dimethylcyclohexane-1,2-diamine (50.3 µL, 0.32 mmol) is added to a stirred suspension of 1-(4-Iodo-benzyl)-1H-[1,2,3]triazole-4-carboxylic acid ethyl ester (Intermediate 18, 400 mg, 1.06 mmol), hexahydro-pyrrolo[1,2-c]imidazol-3-one (Intermediate 23, 148 mg, 1.17 mmol), copper(I) iodide (202 mg, 1.06 mmol) and potassium carbonate (294 mg, 2.13 mmol) in 5 mL of dry DMSO under nitrogen atmosphere and the reaction mixture is stirred at 110° C. for 3 hours. Water is added and the reaction mixture is extracted with DCM, the organic layer is separated, washed with brine, dried and concentrated under reduced pressure. The residue is triturated in diethylether and filtered to give the crude title compound (yield 328 mg).

LC (Method 1): $t_R$=0.93 min; Mass spectrum (ES+): m/z=356 [M+H]⁺.

Intermediate 29

1-[4-(3-Oxo-tetrahydro-pyrrolo[1,2-c]imidazol-2-yl)-benzyl]-1H-[1,2,3]triazole-4-carboxylic acid

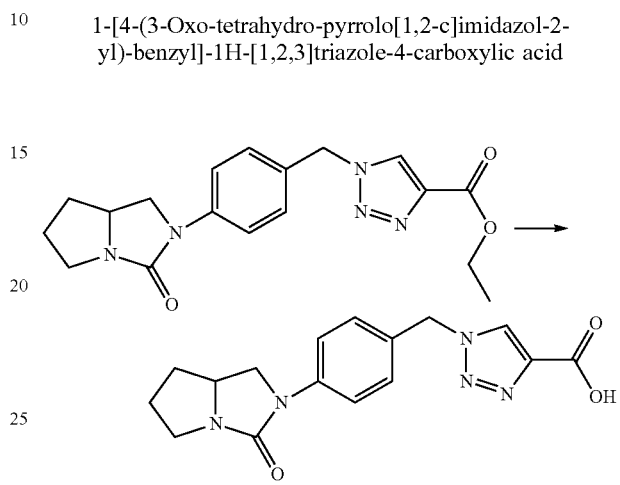

Lithium hydroxide monohydrate (142 mg, 3.40 mmol) is added to a stirred solution of 1-[4-(3-Oxo-tetrahydro-pyrrolo[1,2-c]imidazol-2-yl)-benzyl]-1H-[1,2,3]triazole-4-carboxylic acid ethyl ester (Intermediate 28, 127 mg, 0.34 mmol) dissolved in 9 mL of water and 1 mL of THF and the reaction mixture is stirred for 2 hours. The solvents are removed under reduced pressure, the residue is suspended in water and the aqueous layer is acidified to pH=3 by addition of 1M HCl solution. EtOAc is added, the organic layer is separated, washed with brine and concentrated under reduced pressure to obtain the crude title compound (yield 61 mg).

LC (Method 1): $t_R$=0.59 min; Mass spectrum (ES+): m/z=328 [M+H]⁺.

Intermediate 30

1-[4-(4-Oxo-5-aza-spiro[2.4]hept-5-ylmethyl)-benzyl]-1H-[1,2,3]triazole-4-carboxylic acid tert-butyl ester

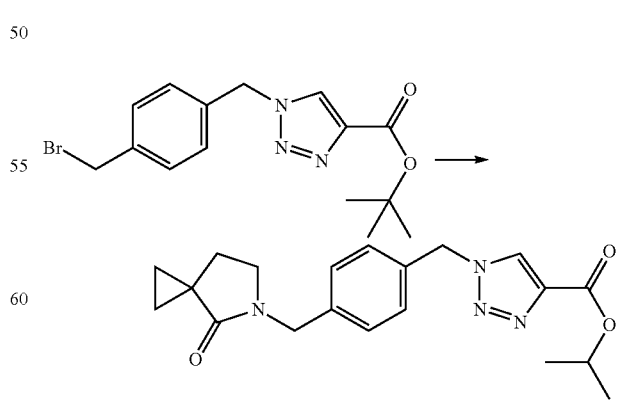

The title compound is prepared from 1-(4-Bromomethyl-benzyl)-1H-[1,2,3]triazole-4-carboxylic acid tert-butyl ester (Intermediate 20, 400 mg, 1.08 mmol) and 5-azaspiro[2.4]heptan-4-one (Zerenex ZXH004127HCl, 120 mg, 1.08 mmol) in a manner analogous to that described for Intermediate 24 (yield 226 mg).

LC (Method 1): $t_R$=1.05 min; Mass spectrum (ES+): m/z=383 [M+H]$^+$.

Intermediate 31

1-[4-(4-Oxo-5-aza-spiro[2.4]hept-5-ylmethyl)-benzyl]-1H-[1,2,3]triazole-4-carboxylic acid

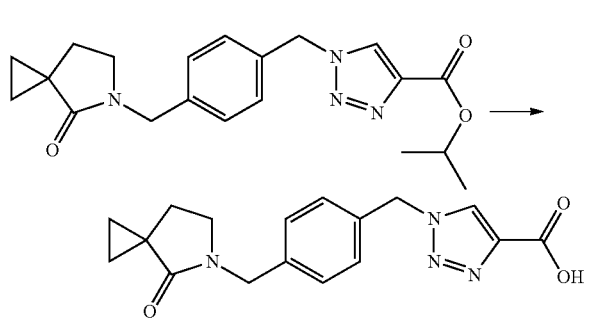

The title compound is prepared from 1-[4-(4-Oxo-5-aza-spiro[2.4]hept-5-ylmethyl)-benzyl]-1H-[1,2,3]triazole-4-carboxylic acid tert-butyl ester (Intermediate 30, 226 mg, 0.53 mmol) in a manner analogous to that described for Intermediate 22 (yield 174 mg).

LC (Method 1): $t_R$=0.60 min; Mass spectrum (ES+): m/z=327 [M+H]+.

Intermediate 32

1-[4-(2-Oxo-3-aza-bicyclo[3.1.0]hex-3-yl)-benzyl]-1H-[1,2,3]triazole-4-carboxylic acid ethyl ester

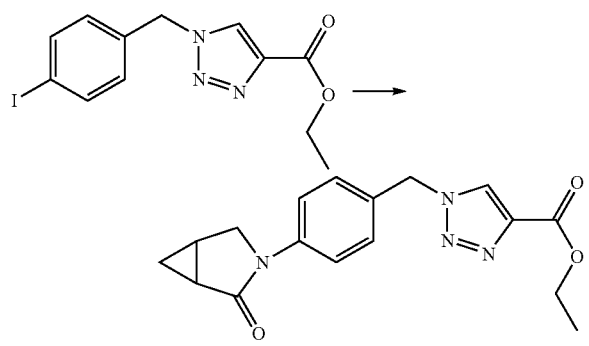

Trans N,N'-dimethylcyclohexane-1,2-diamine (38 μL, 0.30 mmol) is added to a stirred suspension of 1-(4-Iodobenzyl)-1H-[1,2,3]triazole-4-carboxylic acid ethyl ester (Intermediate 18, 300 mg, 0.80 mmol), 3-azabicyclo[3.1.0]hexan-2-one (diverchim DIV02536, 78 mg, 0.80 mmol), copper(I) iodide (152 mg, 0.80 mmol) and potassium carbonate (220 mg, 1.60 mmol) in 5 mL of dry DMSO under nitrogen atmosphere and the reaction mixture is stirred at 110° C. for 3 hours. Water is added and the reaction mixture is extracted with DCM, the organic layer is separated, washed with brine, dried and concentrated under reduced pressure. The crude is purified by flash chromatography (10-80% EtOAc in cyclohexane) to give the title compound (yield 153 mg).

LC (Method 2): $t_R$=3.32 min; Mass spectrum (ES+): m/z=327 [M+H]$^+$.

Intermediate 33

1-[4-(2-Oxo-3-aza-bicyclo[3.1.0]hex-3-yl)-benzyl]-1H-[1,2,3]triazole-4-carboxylic acid

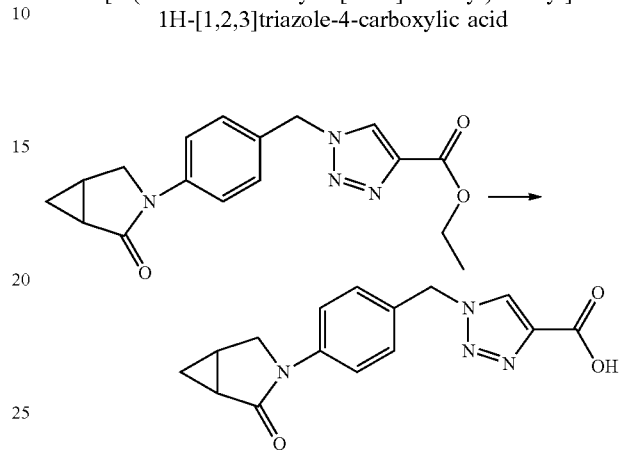

The title compound is prepared from 1-[4-(2-Oxo-3-aza-bicyclo[3.1.0]hex-3-yl)-benzyl]-1H-[1,2,3]triazole-4-carboxylic acid ethyl ester (Intermediate 32, 170 mg, 0.49 mmol), in a mixture of 15 mL of THF and 5 mL of water, in a manner analogous to that described for Intermediate 29 (yield 97 mg).

LC (Method 6): $t_R$=2.97 min; Mass spectrum (ES+): m/z=299 [M+H]$^+$.

Intermediate 34

4-tert-Butoxymethyl-3-methyl-benzoic acid methyl ester

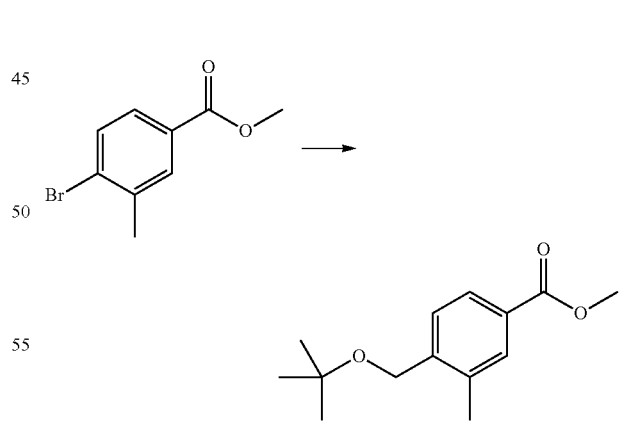

Methyl 4-Bromo-3-Methylbenzoate (3.0 g, 13.1 mmol), Potassium Tert-butoximethyltrifluoroborate (5.1 g, 26.2 mmol), cesium carbonate (6.4 g, 19.6 mmol), 2'-cyclohexylphosphino-2,6-dimethoxy-3-sulfonato-1,1'-biphenyl hydrate sodium salt (347 mg, 0.65 mmol), allylpalladium chloride dimer (480 mg, 1.3 mmol) are suspended under argon atmosphere in a mixture of 5 mL of water and 50 mL of cyclopentyl methyl ether, previously degassed with argon, and heated in a sealed flask at 120° C. for 4 hours. Water is added and the product is extracted with EtOAc. The organic layer is separated, dried over sodium sulfate and concentrated under reduced pressure. The crude is purified by flash chromatography (25-75% EtOAc in cyclohexane) to give the title compound (yield 1.43 g).

LC (Method 1): $t_R$=1.43 min; Mass spectrum (ES+): m/z=237 [M+H]$^+$.

Intermediate 35

4-Hydroxymethyl-3-methyl-benzoic acid methyl ester

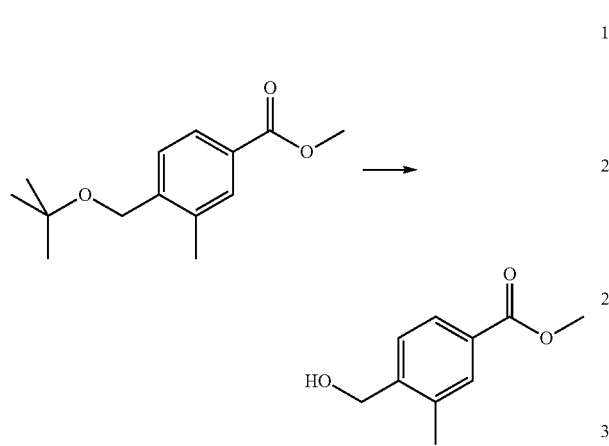

4-tert-Butoxymethyl-3-methyl-benzoic acid methyl ester (Intermediate 34, 1.8 g, 7.6 mmol) is dissolved in 4M dioxane HCl solution (30 ml, 120 mmol) and the reaction mixture is stirred overnight. The solvent is removed under reduced pressure to obtain the crude title compound (yield 1.2 g).

LC (Method 5): $t_R$=0.85 min; Mass spectrum (ES+): m/z=181 [M+H]$^+$.

Intermediate 36

4-Bromomethyl-3-methyl-benzoic acid methyl ester

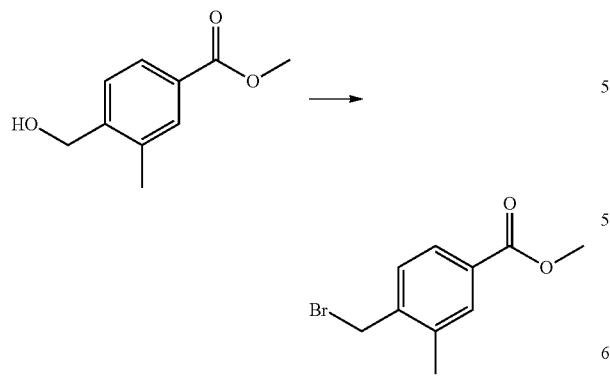

Carbon tetrabromide (2.3 g, 7.0 mmol) is added to a stirred solution of 4-hydroxymethyl-3-methyl-benzoic acid methyl ester (Intermediate 35, 1.1 g, 6.1 mmol) dissolved in 50 mL of DCM, the solution is cooled to 0° C. and triphenylphosphine (1.8 g, 7.0 mmol) is added. The reaction mixture is stirred overnight at room temperature then the solvent is removed under reduced pressure. The crude is purified by flash chromatography (10-40% EtOAc in cyclohexane) to give the title compound (yield 1.0 g).

LC (Method 1): $t_R$=1.25 min.

Intermediate 37

3-Methyl-4-(2-oxo-3-aza-bicyclo[3.1.0]hex-3-ylmethyl)-benzoic acid methyl ester

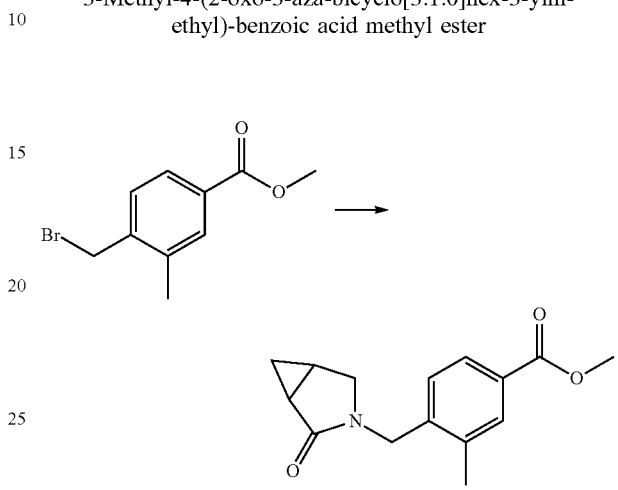

Sodium hydride (60% oil suspension, 136 mg, 3.4 mmol) is added to a stirred solution of 3-azabicyclo[3.1.0]hexan-2-one (diverchim DIV02536, 300 mg, 3.1 mmol) under nitrogen atmosphere in 5 mL of anhydrous DMF. After stirring for 20 minutes, 4-Bromomethyl-3-methyl-benzoic acid methyl ester (Intermediate 36, 1.0 g, 3.3 mmol) is added and the reaction mixture is stirred for 3 hours. The solvent is removed under reduced pressure and the residue is partitioned between water and DCM. The organic layer is washed with brine, dried over sodium sulfate and concentrated under reduced pressure. The crude is purified by flash chromatography (50-80% EtOAc in cyclohexane) to give the title compound (yield 707 mg).

LC (Method 1): $t_R$=0.87 min; Mass spectrum (ES+): m/z=260 [M+H]$^+$.

Intermediate 38

3-(4-Hydroxymethyl-2-methyl-benzyl)-3-aza-bicyclo[3.1.0]hexan-2-one

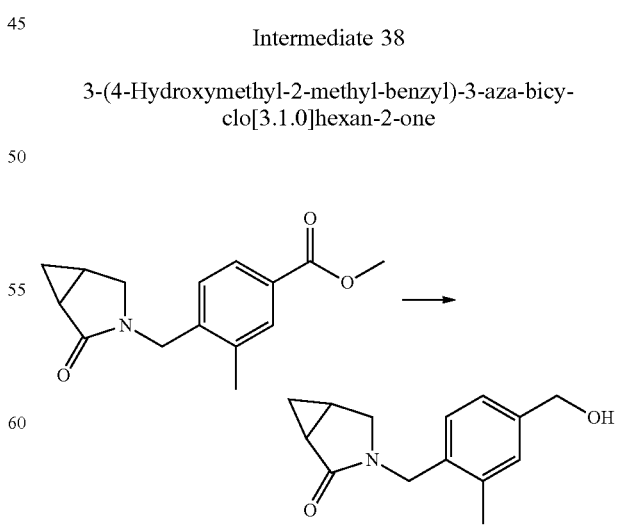

Calcium chloride dehydrated (2.1 g, 18.8 mmol) followed by sodium borohydride (1.4 g, 37.6 mmol) is added to a stirred solution of 3-Methyl-4-(2-oxo-3-aza-bicyclo[3.1.0]hex-3-ylmethyl)-benzoic acid methyl ester (Intermediate 37, 1.1 g, 3.7 mmol) dissolved in 10 mL of dry THF under nitrogen atmosphere. 10 mL of dry methanol are added and the reaction mixture is stirred overnight at room temperature then at 50° C. for 3 hours. The mixture is diluted with water at room temperature and stirred for 3 hours. The organic layer is separated, washed with brine, dried over sodium sulfate and concentrated under reduced pressure to obtain the crude title compound (yield 490 mg).

LC (Method 1): $t_R$=0.64 min; Mass spectrum (ES+): m/z=232 [M+H]$^+$.

Intermediate 39

3-(4-Bromomethyl-2-methyl-benzyl)-3-aza-bicyclo[3.1.0]hexan-2-one

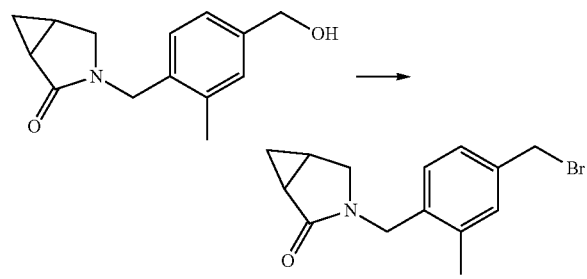

The title impure compound is prepared from 3-(4-Hydroxymethyl-2-methyl-benzyl)-3-aza-bicyclo[3.1.0]hexan-2-one (Intermediate 38, 300 mg, 1.2 mmol) in a manner analogous to that described for Intermediate 36 (yield 477 mg).

LC (Method 1): $t_R$=1.01 min; Mass spectrum (ES+): m/z=294-296 [M+H]$^+$.

Intermediate 40

1-[3-Methyl-4-(2-oxo-3-aza-bicyclo[3.1.0]hex-3-ylmethyl)-benzyl]-1H-pyrazole-4-carboxylic acid ethyl ester

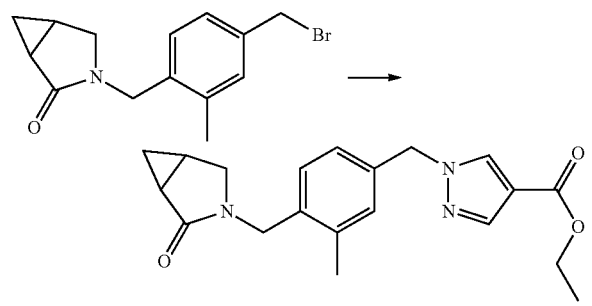

3-(4-Bromomethyl-2-methyl-benzyl)-3-aza-bicyclo[3.1.0]hexan-2-one (Intermediate 39, 477 mg) dissolved in 1 mL of DMF is added to a stirred suspension of ethyl-4-pyrazolecarboxylate (200 mg, 1.4 mmol) and potassium carbonate (781 mg, 5.6 mmol) in 3 mL of DMF and the reaction mixture is stirred overnight. Water and EtOAc are added, the organic layer is separated, dried over sodium sulfate and concentrated under reduced pressure. The crude is purified by flash chromatography (10-90% EtOAc in cyclohexane) to give the title compound (yield 170 mg).

LC (Method 1): $t_R$=0.92 min; Mass spectrum (ES+): m/z=354 [M+H]$^+$.

Intermediate 41

1-[3-Methyl-4-(2-oxo-3-aza-bicyclo[3.1.0]hex-3-ylmethyl)-benzyl]-1H-pyrazole-4-carboxylic acid

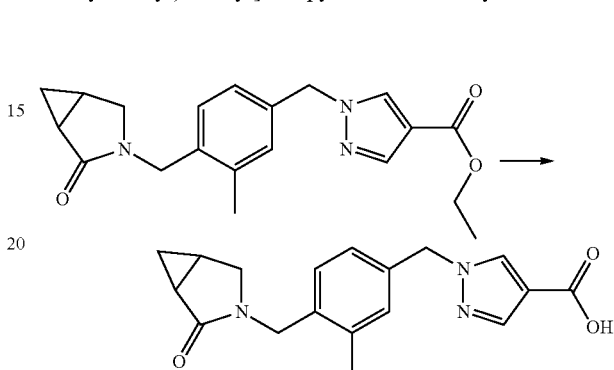

Lithium hydroxide monohydrate (96 mg, 2.3 mmol) is added to a stirred solution of 1-[3-methyl-4-(2-oxo-3-aza-bicyclo[3.1.0]hex-3-ylmethyl)-benzyl]-1H-pyrazole-4-carboxylic acid ethyl ester (Intermediate 40, 170 mg, 0.5 mmol) dissolved in 2 mL of water and 20 mL of THF and the reaction mixture is stirred overnight. Water is added and the pH is adjusted to 5 by addition of 1M HCl solution. EtOAc is added, the organic layer is separated, washed with brine and concentrated under reduced pressure to obtain the crude title compound (yield 143 mg).

LC (Method 1): $t_R$=0.60 min; Mass spectrum (ES+): m/z=326 [M+H]$^+$.

Intermediate 42

2-Bromo-4-(2-oxo-3-aza-bicyclo[3.1.0]hex-3-ylmethyl)-benzoic acid methyl ester

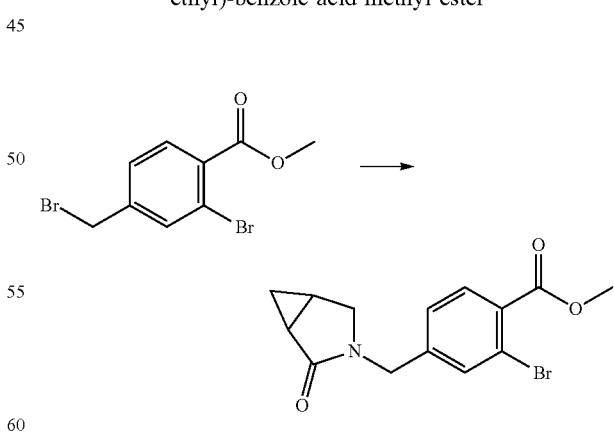

The title compound is prepared as a crude from methyl-2-bromo-4-bromomethylbenzoate (2.62 g, 8.5 mmol) in a manner analogous to that described for Intermediate 37 (yield 2.4 g).

LC (Method 1): $t_R$=0.95 min; Mass spectrum (ES+): m/z=324-326 [M+H]$^+$.

Intermediate 43

2-Methyl-4-(2-oxo-3-aza-bicyclo[3.1.0]hex-3-ylmethyl)-benzoic acid methyl ester

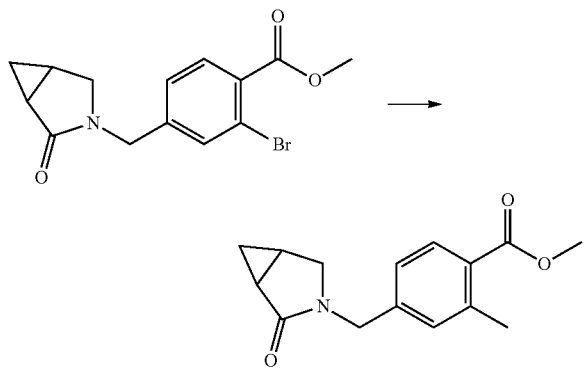

A mixture of 2-bromo-4-(2-oxo-3-aza-bicyclo[3.1.0]hex-3-ylmethyl)-benzoic acid methyl ester (Intermediate 42, 2.4 g), trimethylboroxine (965 µL, 6.9 mmol), potassium carbonate (1.9 g, 13.8 mmol) and 1,1'-bis(diphenylphosphino)ferrocenepalldium (II) dichloride, DCM (1.1 g, 1.4 mmol) in 15 mL of anhydrous DMF is heated in a sealed flask, under nitrogen atmosphere, at 100° C. for 4 hours. The solvent is removed under reduced pressure and the product is partitioned between water and DCM. The organic layer is separated, washed with brine and dried over anhydrous sodium sulfate. The solvent is removed and the crude is purified by flash chromatography (50-75% EtOAc in cyclohexane) to give the title compound (yield 935 mg).

LC (Method 1): $t_R$=0.94 min; Mass spectrum (ES+): m/z=260 [M+H]$^+$.

Intermediate 44

3-(4-Hydroxymethyl-3-methyl-benzyl)-3-aza-bicyclo[3.1.0]hexan-2-one

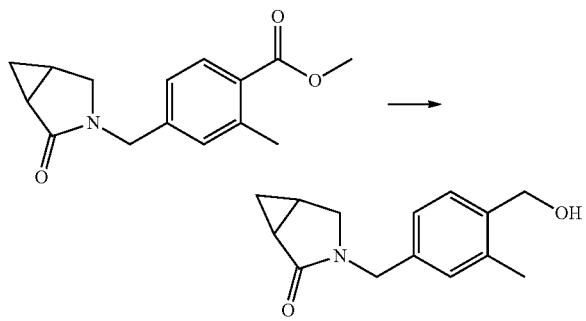

The title compound is prepared as a crude from 2-Methyl-4-(2-oxo-3-aza-bicyclo[3.1.0]hex-3-ylmethyl)-benzoic acid methyl ester (Intermediate 43, 935 mg, 3.3 mmol) in a manner analogous to that described for Intermediate 38 (yield 167 mg).

LC (Method 1): $t_R$=0.71 min; Mass spectrum (ES+): m/z=232 [M+H]$^+$.

Intermediate 45

3-(4-Bromomethyl-3-methyl-benzyl)-3-aza-bicyclo[3.1.0]hexan-2-one

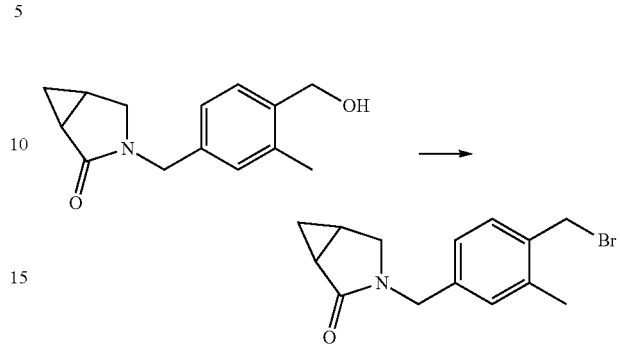

The title impure compound is prepared from 3-(4-Hydroxymethyl-3-methyl-benzyl)-3-aza-bicyclo[3.1.0]hexan-2-one (Intermediate 44, 396 mg, 1.6 mmol) in a manner analogous to that described for Intermediate 36 (yield 772 mg).

LC (Method 1): $t_R$=1.01 min; Mass spectrum (ES+): m/z=294-296 [M+H]$^+$.

Intermediate 46

1-[2-Methyl-4-(2-oxo-3-aza-bicyclo[3.1.0]hex-3-ylmethyl)-benzyl]-1H-pyrazole-4-carboxylic acid ethyl ester

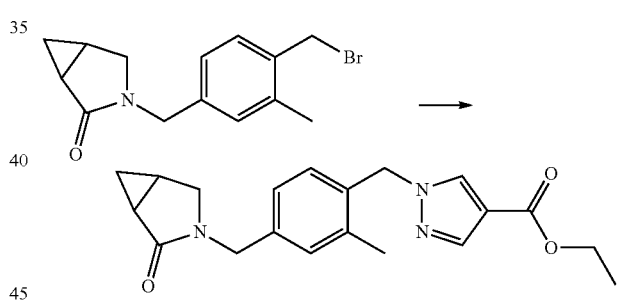

The title impure compound is prepared from 3-(4-Bromomethyl-3-methyl-benzyl)-3-aza-bicyclo[3.1.0]hexan-2-one (Intermediate 45, 770 mg) and ethyl-4-pyrazolecarboxylate (200 mg, 1.4 mmol) in a manner analogous to that described for Intermediate 40 (yield 325 mg).

LC (Method 1): $t_R$=0.93 min; Mass spectrum (ES+): m/z=354 [M+H]$^+$.

Intermediate 47

1-[2-Methyl-4-(2-oxo-3-aza-bicyclo[3.1.0]hex-3-ylmethyl)-benzyl]-1H-pyrazole-4-carboxylic acid

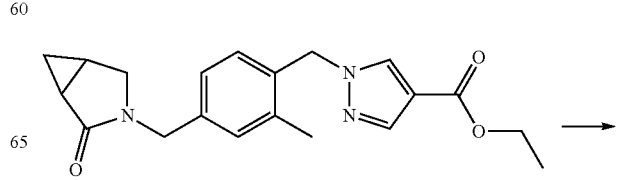

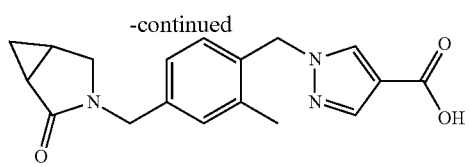

The title compound is prepared from 1-[2-Methyl-4-(2-oxo-3-aza-bicyclo[3.1.0]hex-3-ylmethyl)-benzyl]-1H-pyrazole-4-carboxylic acid ethyl ester (Intermediate 46, 325 mg) in a manner analogous to that described for Intermediate 41 (yield 80 mg).

LC (Method 1): $t_R$=0.53 min; Mass spectrum (ES+): m/z=326 [M+H]$^+$.

Intermediate 48

1-(3-Iodo-benzyl)-1H-[1,2,3]triazole-4-carboxylic acid ethyl ester

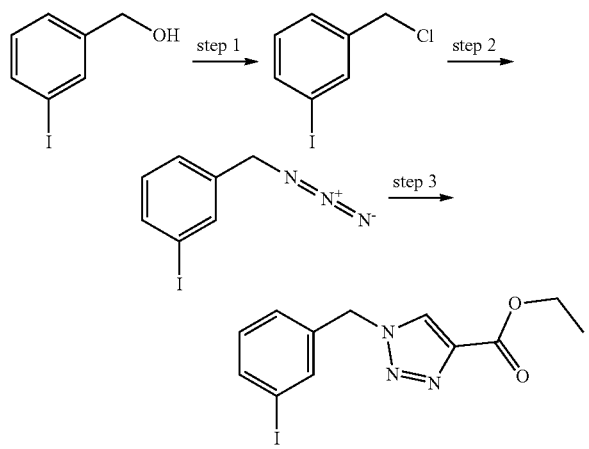

Step 1: 1-Chloromethyl-3-iodo-benzene

Methanesulfonylchloride (868 µL, 10.7 mmol) is added to a stirred solution of 3-Iodo-benzyl alcohol (2.5 g, 11.2 mmol) and triethylamine (3.7 ml, 26.7 mmol) dissolved in dry DCM and the reaction mixture is stirred at room temperature for 2 hours. Water is added, the organic layer is separated and concentrated under reduced pressure to obtain the crude title compound (yield 2.5 g).

GC (Method 9): $t_R$=7.91 min; Mass spectrum (EI+): m/z=252 [M]$^+$

Step 2: 1-Azidomethyl-3-iodo-benzene

1-Chloromethyl-3-iodo-benzene (2.5 g) and sodium azide (3.2 g, 49.5 mmol) are dissolved in 5 mL of dry N,N-dimethylformamide and the reaction mixture is stirred at room temperature for 2 hours. Water and DCM are added and the organic layer is separated and concentrated under reduced pressure to obtain the crude title compound (yield 1.64 g).

GC (Method 9): $t_R$=8.53 min; Mass spectrum (EI+): m/z=259 [M]$^+$

Step 3: 1-(3-Iodo-benzyl)-1H-[1,2,3]triazole-4-carboxylic acid ethyl ester

Cupric sulfate pentahydrate (132 mg, 0.53 mmol) and sodium ascorbate (525 mg, 2.65 mmol) are added to a stirred solution of 1-Azidomethyl-3-iodo-benzene (1.6 g, 5.70 mmol) and ethyl propiolate (271 µL, 2.65 mmol) dissolved in a mixture of 5 mL of tert-butanol and 5 mL of water. The reaction mixture is stirred at room temperature for 2 hours. The solvent is removed under reduced pressure and the residue is partitioned between water and DCM. The organic layer is separated, dried over anhydrous sodium sulfate and concentrated under reduced pressure. The crude is purified by flash chromatography (0-20% Methanol in DCM) to obtain the title compound (yield 868 mg).

LC (Method 1): $t_R$=1.11 min; Mass spectrum (ES+): m/z=358 [M+H]$^+$.

Intermediate 49

1-[3-(1-Oxo-octahydro-pyrido[1,2-a]pyrazin-2-yl)-benzyl]-1H-[1,2,3]triazole-4-carboxylic acid ethyl ester

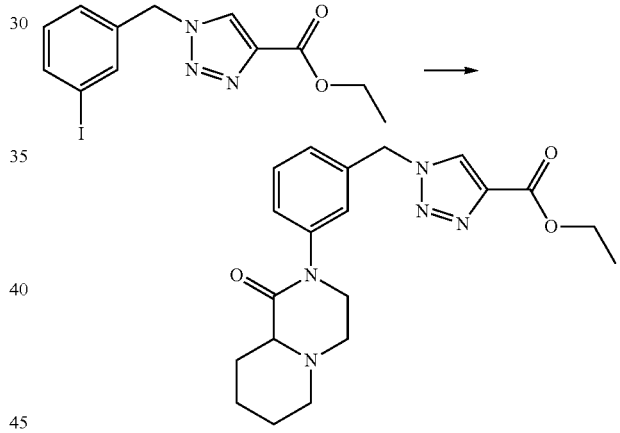

Trans N,N'-dimethylcyclohexane-1,2-diamine (50 µL, 0.32 mmol) is added to a stirred suspension of 1-(3-Iodo-benzyl)-1H-[1,2,3]triazole-4-carboxylic acid ethyl ester (Intermediate 48, 400 mg, 1.06 mmol), hexahydro-pyrido[1,2-A]pyrazin-1-one (fluorochem 026340, 197 mg, 1.28 mmol), copper(I) iodide (61 mg, 0.32 mmol) and potassium carbonate (294 mg, 2.13 mmol) in 5 mL of dry DMSO under nitrogen atmosphere and the reaction mixture is stirred at 110° C. for 3 hours. Further hexahydro-pyrido[1,2-A]pyrazin-1-one (fluorochem 026340, 197 mg, 1.28 mmol) and copper(I) iodide (61 mg, 0.32 mmol) are added and the reaction mixture is further stirred at 110° C. for 16 hours. The solvent is removed under reduced pressure and the residue is partitioned between water and DCM; the organic layer is separated, dried over anhydrous sodium sulfate and concentrated under reduced pressure. The crude is purified by flash chromatography (0-20% Methanol in DCM) to give the title compound (yield 94 mg).

LC (Method 1): $t_R$=0.84 min; Mass spectrum (ES+): m/z=384 [M+H]$^+$.

Intermediate 50

1-[3-(1-Oxo-octahydro-pyrido[1,2-a]pyrazin-2-yl)-benzyl]-1H-[1,2,3]triazole-4-carboxylic acid sodium salt

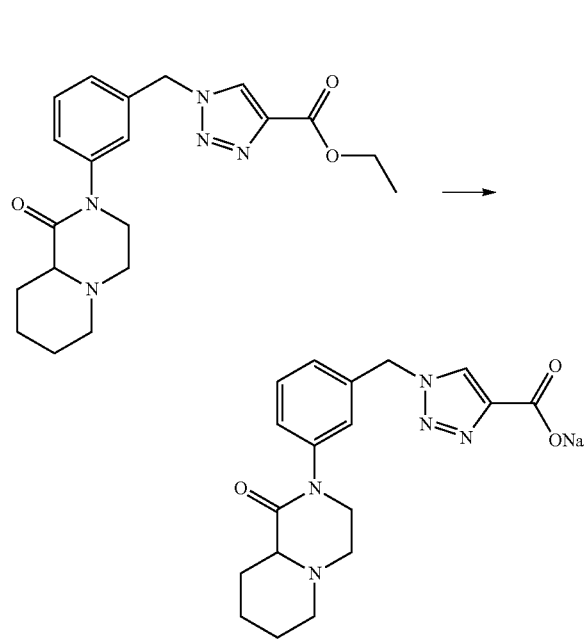

1-[3-(1-Oxo-octahydro-pyrido[1,2-a]pyrazin-2-yl)-benzyl]-1H-[1,2,3]triazole-4-carboxylic acid ethyl ester (Intermediate 49, 94 mg, 0.23 mmol) and NaOH (aqueous 32% solution, 224 ul, 2.33 mmol) are dissolved in 5 mL of THF and the reaction mixture is stirred for 2 hours. The solvents are removed, the residue is suspended in diethylether and filtered to obtain the crude title compound (yield 87 mg).

LC (Method 1): $t_R$=0.56 min; Mass spectrum (ES+): m/z=356 [M+H]$^+$.

Intermediate 51

1-(6-Chloro-pyridin-3-yl)-ethanol

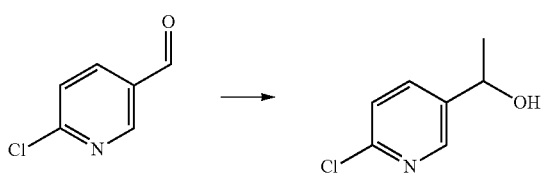

Methylmagnesium chloride (3 M solution in THF, 647 μL, 1.94 mmol) is added dropwise to a stirred solution of 6-Chloropyridine-3-carboxaldehyde (250 mg, 1.77 mmol) dissolved in 20 mL of anhydrous THF, under nitrogen atmosphere, cooled with an ice/water bath and the reaction mixture is stirred 30 minutes. Aqueous saturated NH$_4$Cl solution is added and the ice bath is removed. EtOAc is added to the reaction mixture and the organic phase is separated and concentrated under reduced pressure to obtain the crude title compound (yield 271 mg).

LC (Method 1): $t_R$=0.65 min; Mass spectrum (ES+): m/z=158 [M+H]$^+$.

Intermediate 52

2-Chloro-5-(1-chloro-ethyl)-pyridine

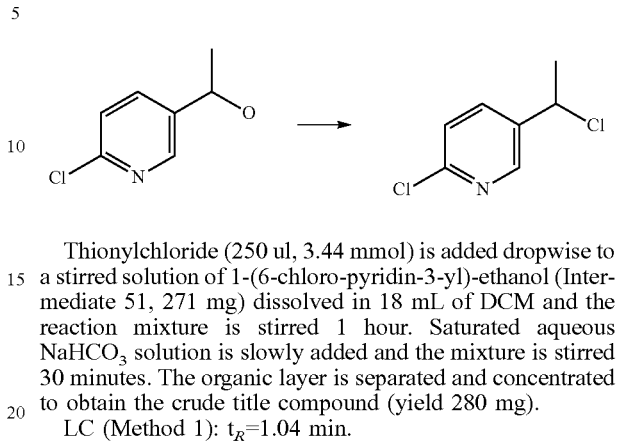

Thionylchloride (250 ul, 3.44 mmol) is added dropwise to a stirred solution of 1-(6-chloro-pyridin-3-yl)-ethanol (Intermediate 51, 271 mg) dissolved in 18 mL of DCM and the reaction mixture is stirred 1 hour. Saturated aqueous NaHCO$_3$ solution is slowly added and the mixture is stirred 30 minutes. The organic layer is separated and concentrated to obtain the crude title compound (yield 280 mg).

LC (Method 1): $t_R$=1.04 min.

Intermediate 53

1-[1-(6-Chloro-pyridin-3-yl)-ethyl]-1H-pyrazole-4-carboxylic acid ethyl ester

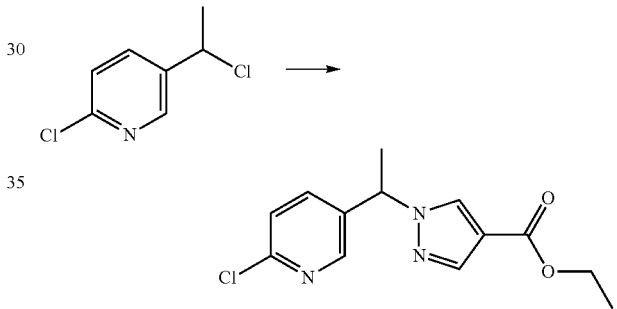

Cesium carbonate (1.4 g, 4.30 mmol) is added to a stirred solution of 2-Chloro-5-(1-chloro-ethyl)-pyridine (Intermediate 52, 280 mg) and ethyl-4-pyrazolecarboxylate (216 mg, 1.54 mmol) dissolved in 5 mL of DMF and the reaction mixture is stirred in a sealed vial at 50° C. for 2.5 hours. Water and EtOAc are added and the phases are separated. The organic layer is washed with diluted HCl solution and concentrated under reduced pressure. The residue is purified by flash chromatography (0-50% EtOAc in cyclohexane) to obtain the title compound (yield 342 mg).

LC (Method 1): $t_R$=1.01 min; Mass spectrum (ES+): m/z=280 [M+H]$^+$.

Intermediate 54

1-{1-[6-(3-Aza-bicyclo[3.1.0]hex-3-yl)-pyridin-3-yl]-ethyl}-1H-pyrazole-4-carboxylic acid ethyl ester

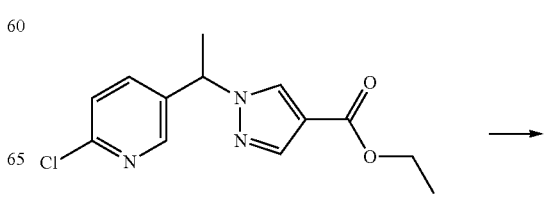

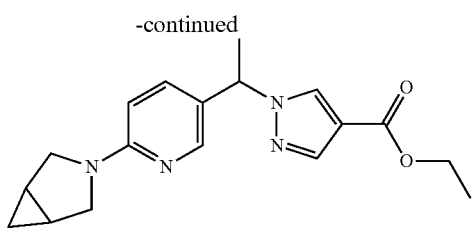

1-[1-(6-Chloro-pyridin-3-yl)ethyl]-1H-pyrazole-4-carboxylic acid ethyl ester (Intermediate 53, 342 mg, 1.22 mmol), 3-azabicyclo[3.1.0]hexane hydrochloride (175 mg, 1.47 mmol) and cesium carbonate (597 mg, 1.83 mmol) are mixed in 5 mL of dry NMP and the reaction mixture is heated in a microwave reactor at 110° C. for 3 hours. Further 3-azabicyclo[3.1.0]hexane hydrochloride (85 mg, 0.71 mmol) is added and the reaction mixture is further heated in a microwave reactor at 120° C. for 3 hours. Water and EtOAc are added, the organic phase is separated, washed with water and concentrated under reduced pressure. The residue is purified by flash chromatography (20 to 40% EtOAc in cyclohexane) to obtain the title compound (yield 170 mg).

LC (Method 1): $t_R$=1.13 min; Mass spectrum (ES+): m/z=327 [M+H]$^+$.

Intermediate 55

1-{1-[6-(3-Aza-bicyclo[3.1.0]hex-3-yl)-pyridin-3-yl]-ethyl}-1H-pyrazole-4-carboxylic acid lithium salt

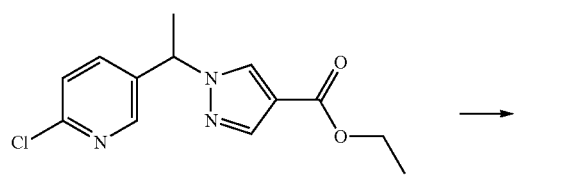

Lithium hydroxide monohydrate (24 mg, 0.57 mmol) is added to a stirred solution of 1-{1-[6-(3-Aza-bicyclo[3.1.0]hex-3-yl)-pyridin-3-yl]-ethyl}-1H-pyrazole-4-carboxylic acid ethyl ester (Intermediate 54, 170 mg, 0.52 mmol) dissolved in 4 mL of THF and 0.4 mL of water and the reaction mixture is stirred at 50° C. for 16 hours. The solvents are removed to obtain the crude title compound (yield 165 mg).

LC (Method 1): $t_R$=0.62 min; Mass spectrum (ES+): m/z=299 [M+H]$^+$.

Intermediate 56

{1-[6-(3-Aza-bicyclo[3.1.0]hex-3-yl)-pyridin-3-yl]-cyclopropyl}-hydrazine hydrochloride

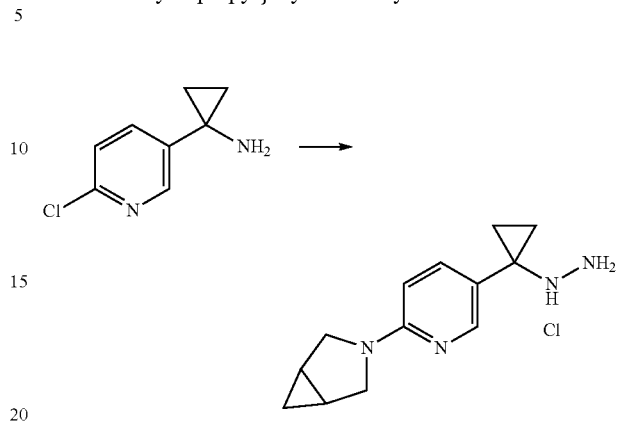

N-Boc-3-(4-cyanophenyl)oxaziridine (365 mg, 1.48 mmol) is added to a stirred solution of 1-(6-chloropyridin-3-yl)cyclopropanamine (250 mg, 1.48 mmol) dissolved in 10 mL of anhydrous DMF under nitrogen atmosphere and the reaction mixture is stirred 1.5 hours at room temperature. After cooling with an ice/water bath, water is added and the mixture is extracted with Et$_2$O. The organic layer is separated and concentrated under reduced pressure. The residue is dissolved in 15 mL of dioxane, HCl (4 M dioxane solution, 5 ml, 20 mmol) is added and the reaction mixture is stirred overnight. The crude solid product (yield 200 mg) is filtered and used without further purification for the next step.

LC (Method 1): $t_R$=0.58 min; Mass spectrum (ES+): m/z=184 [M+H]$^+$.

Intermediate 57

1-{1-[6-(3-Aza-bicyclo[3.1.0]hex-3-yl)-pyridin-3-yl]-cyclopropyl}-1H-pyrazole-4-carboxylic acid ethyl ester

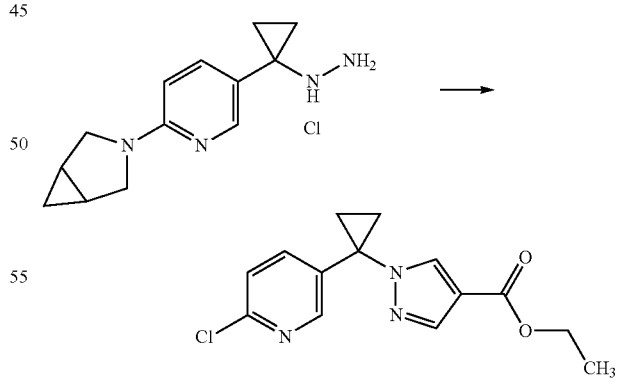

Ethyl-2-formyl-3-oxopropionate (131 mg, 0.91 mmol) is added to a stirred suspension of crude {1-[6-(3-Aza-bicyclo[3.1.0]hex-3-yl)-pyridin-3-yl]-cyclopropyl}-hydrazine hydrochloride (Intermediate 56, 200 mg) in 15 mL of ethanol and the reaction mixture is stirred 7 days at room temperature. The solvent is removed under reduced pressure and the residue is partitioned between EtOAc and 1N HCl aqueous solution. The organic layer is separated and concentrated under reduced pressure. The residue is purified by flash chromatography (20 to 100% EtOAc in cyclohexane) and the impure title product (yield 60 mg) is used without further purification for the next step.

LC (Method 1): $t_R$=1.03 min; Mass spectrum (ES+): m/z=292 [M+H]$^+$.

Intermediate 58

1-{1-[6-(3-Aza-bicyclo[3.1.0]hex-3-yl)-pyridin-3-yl]-cyclopropyl}-1H-pyrazole-4-carboxylic acid ethyl ester

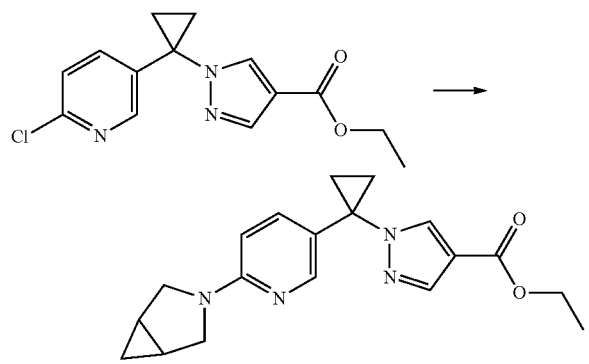

Crude 1-{1-[6-(3-Aza-bicyclo[3.1.0]hex-3-yl)-pyridin-3-yl]-cyclopropyl}-1H-pyrazole-4-carboxylic acid ethyl ester (Intermediate 57, 60 mg), 3-azabicyclo[3.1.0]hexane hydrochloride (37 mg, 0.31 mmol) and cesium carbonate (100 mg, 0.31 mmol) are suspended in 2 mL of anhydrous NMP and the reaction mixture is heated in a microwave reactor at 120° C. for 2 hours then at 140° C. for further 2 hours. Further 3-azabicyclo[3.1.0]hexane hydrochloride (98 mg, 0.82 mmol) and cesium carbonate (100 mg, 0.31 mmol) are added and the reaction mixture is heated in a microwave reactor at 140° C. for 3 hours. Water and EtOAc are added, the organic layer is separated and the aqueous layer is further extracted with EtOAc. The collected organic layers are washed with brine and concentrated under reduced pressure. The residue is purified by flash chromatography (0 to 40% EtOAc in cyclohexane) to obtain the title compound (yield 25 mg).

LC (Method 1): $t_R$=1.15 min; Mass spectrum (ES+): m/z=339 [M+H]$^+$.

Intermediate 59

1-{1-[6-(3-Aza-bicyclo[3.1.0]hex-3-yl)-pyridin-3-yl]-cyclopropyl}-1H-pyrazole-4-carboxylic acid lithium salt

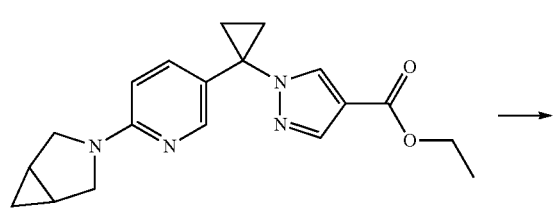

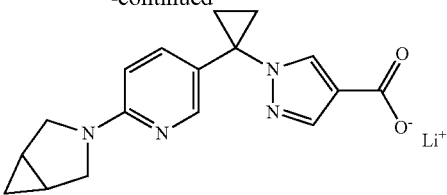

A solution of lithium hydroxide monohydrate (3.5 mg, 0.08 mmol) dissolved in 0.2 mL of water is added to a stirred solution of 1-{1-[6-(3-Aza-bicyclo[3.1.0]hex-3-yl)-pyridin-3-yl]-cyclopropyl}-1H-pyrazole-4-carboxylic acid ethyl ester (Intermediate 58, 25 mg, 0.07 mmol) dissolved in 1 mL of THF. The reaction mixture is stirred overnight at 50° C., 0.5 mL of dioxane are added and the reaction mixture is further stirred overnight at 50° C. The solvent is removed to obtain the crude title compound (yield 26 mg) used without further purification for the next step.

LC (Method 1): $t_R$=0.64 min; Mass spectrum (ES+): m/z acid=311 [M+H]$^+$.

Intermediate 60

1-[6-(3-Aza-bicyclo[3.1.0]hex-3-yl)-2-trifluoromethyl-pyridin-3-ylmethyl]-1H-[1,2,3]triazole-4-carboxylic acid ethyl ester

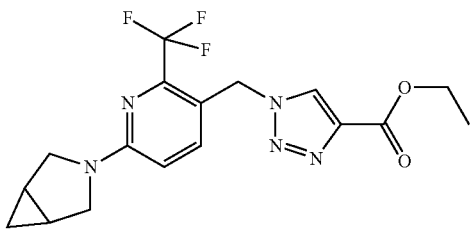 [SMILES: CCOC(=O)c1cn(Cc2ccc(N3CC4CC4C3)nc2C(F)(F)F)nn1]

The title compound is prepared from crude 3-(5-Bromomethyl-6-trifluoromethyl-pyridin-2-yl)-3-aza-bicyclo[3.1.0] hexane (Intermediate 8, 4 g,), in analogy to the method used for the preparation of Intermediate 18 (yield 1.2 g)

LC (Method 2): $t_R$=5.32 min Mass spectrum (ES+): m/z=382 [M+H]$^+$.

Intermediate 61

1-[6-(3-Aza-bicyclo[3.1.0]hex-3-yl)-4-trifluoromethyl-pyridin-3-ylmethyl]-1H-[1,2,3]triazole-4-carboxylic acid ethyl ester

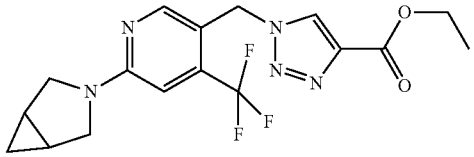 [SMILES: CCOC(=O)c1cn(Cc2cnc(N3CC4CC4C3)cc2C(F)(F)F)nn1]

The title compound is prepared from crude 3-(5-bromomethyl-4-trifluoromethyl-pyridin-2-yl)-3-aza-bicyclo[3.1.0] hexane (Intermediate 9, 2 g,) in analogy to the method used for the preparation of Intermediate 18 (yield 0.80 g)

LC (Method 2): $t_R$=4.67 min Mass spectrum (ES+): m/z=382 [M+H]$^+$.

Intermediate 62

1-[6-(3-Aza-bicyclo[3.1.0]hex-3-yl)-4-methyl-pyridin-3-ylmethyl]-1H-[1,2,3]triazole-4-carboxylic acid ethyl ester

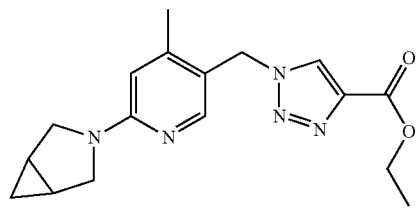 [SMILES: CCOC(=O)c1cn(Cc2cnc(N3CC4CC4C3)cc2C)nn1]

The title compound is prepared from 3-(5-bromomethyl-4-methyl-pyridin-2-yl)-3-aza-bicyclo[3.1.0]hexane (Intermediate 11, 800 mg,) in analogy to the method used for the preparation of Intermediate 18 (yield 0.50 g)

LC (Method 2): $t_R$=4.08 min Mass spectrum (ES+): m/z=328 [M+H]$^+$.

Intermediate 63

1-[4-(Hexahydro-pyrrolo[1,2-a]pyrazin-2-yl)-benzyl]-1H-pyrazole-4-carboxylic acid ethyl ester

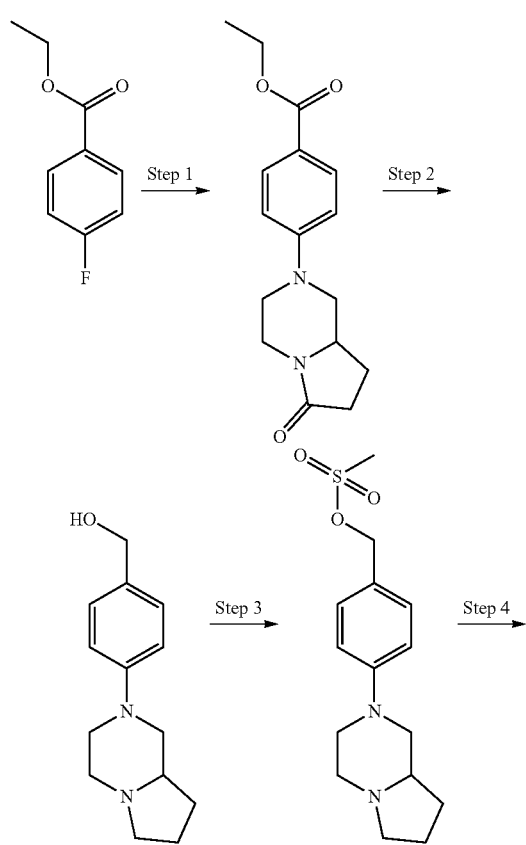

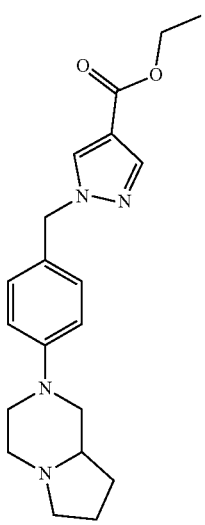

Step 1: 4-(6-Oxo-hexahydro-pyrrolo[1,2-a]pyrazin-2-yl)-benzoic acid ethyl ester

4-Fluoro-benzoic acid ethyl ester (2 g, 11.9 mmol), hexahydro-pyrrolo[1,2-a]pyrazin-6-one hydrochloride (available from JW-Pharmlab 65-0381S, 600 mg, 3.40 mmol) and potassium carbonate (1.17 g, 8.49 mmol) are dissolved in anhydrous DMSO (5 ml). The reaction mixture is stirred at 140° C. for three days. The reaction mixture is diluted with dichloromethane (40 ml), filtered and concentrated under vacuum. The residue obtained is purified by reverse phase flash chromatography (C18, 0-90% acetonitrile in water) to give the title compound (yield 600 mg).

LC (Method 1): $t_R$=0.93 min; Mass spectrum (ES+): m/z=289 [M+H]$^+$.

Step 2: [4-(Hexahydro-pyrrolo[1,2-a]pyrazin-2-yl)-phenyl]-methanol 4-(6-Oxo-hexahydro-pyrrolo[1,2-a]pyrazin-2-yl)-benzoic acid ethyl ester (500 mg, 1.73 mmol) is dissolved in anhydrous tetrahydrofuran (10 ml), the reaction mixture is cooled to 0° C. then lithium aluminumhydride (0.95 mL o a 2 M solution in THF, 1.91 mmol) is added dropwise. The reaction mixture is allowed to reach room temperature and stirred overnight. 1 mL of a 32% aq solution of NaOH (is added, then the reaction mixture is diluted with ethyl acetate and filtered over a Celite pad. The organic phase is concentrated under vacuum to give the title compound. (yield 400 mg)

LC (Method 1): $t_R$=0.55 min; Mass spectrum (ES+): m/z=233 [M+H]$^+$.

Step 3: Methanesulfonic acid 4-(hexahydro-pyrrolo[1,2-a]pyrazin-2-yl)-benzyl ester

[4-(Hexahydro-pyrrolo[1,2-a]pyrazin-2-yl)-phenyl]-methanol (400 mg, 1.69 mmol) and N,N-diisopropylethylamine (0.735 ml, 4.22 mmol) are dissolved in dichloromethane anhydrous (100 ml). the solution is cooled to 0° C. and methanesulfonyl chloride (0.157 ml, 2.02 mmol) is added under stirring. The cooling bath is removed and the solution is stirred at 20° C. for 1 hour. The organic solution is washed with water (50 ml), the organic layer is collected, dried over sodium sulfate and concentrated. The residue is purified by flash chromatography (10-90% ethyl acetate in cyclohexane) to give the title compound. (yield 400 mg).

Step 4: 1-[4-(Hexahydro-pyrrolo[1,2-a]pyrazin-2-yl)-benzyl]-1H-pyrazole-4-carboxylic acid ethyl ester Methanesulfonic acid 4-(hexahydro-pyrrolo[1,2-a]pyrazin-2-yl)-benzyl ester (400 mg, 1.29 mmol), ethyl 4-pyrazolecarboxylate (361 mg, 2.58 mmol) and cesium carbonate (630 mg, 1.93 mmol) are dissolved in DMF (10 ml). the reaction mixture is stirred overnight at room temperature, then dichloromethane (25 ml) is added, the reaction mixture is filtered and the organic solution is concentrated under reduced pressure. The residue obtained is purified by flash chromatography (20-100% ethyl acetate in cyclohexane to give the title compound. (yield 350 mg)

LC (Method 3): $t_R$=0.79 min; Mass spectrum (ES+): m/z=355 [M+H]+

Intermediate 64

Methanesulfonic acid 4-(2-oxo-3-aza-bicyclo[3.1.0]hex-3-ylmethyl)-3-trifluoromethyl-benzyl ester

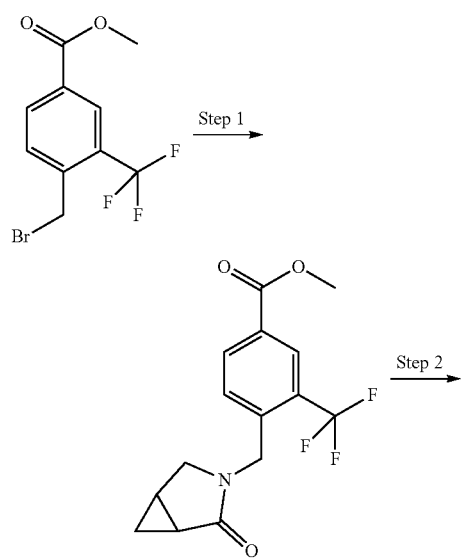

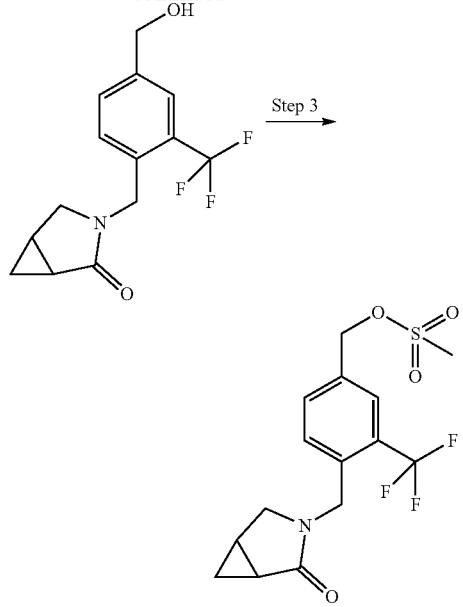

Step 1: 4-(2-Oxo-3-aza-bicyclo[3.1.0]hex-3-ylmethyl)-3-trifluoromethyl-benzoic acid methyl ester 3-Aza-bicyclo[3.1.0]hexan-2-one (available from Diverchim, DIV02536, 1.31 g, 13.5 mmol,) and sodium hydride (592 mg, 60% in oil dispersion, 14.8 mmol) are dissolved in N,N-dimethylformamide (20 ml), the reaction mixture is stirred at 25° C. for 20 minutes, then 4-bromomethyl-3-trifluoromethyl-benzoic acid methyl ester (8.0 g, synthesized as described in Patent: WO2006/79791 A1, 2006; Page 40) is added. The reaction mixture is stirred for 3 hours at 80° C. then it is cooled to room temperature, water is added and the reaction mixture is extracted with dichloromethane. The organic phase is collected and concentrated under vacuum. The residue obtained is purified by flash chromatography (0-70% ethyl acetate in cyclohexane) to give the title compound. (yield 1.50 g)

LC (Method 1): $t_R$=1.05 min; Mass spectrum (ES+): m/z=314 [M+H]+

Step 2: 3-(4-Hydroxymethyl-2-trifluoromethyl-benzyl)-3-aza-bicyclo[3.1.0]hexan-2-one 4-(2-Oxo-3-aza-bicyclo[3.1.0]hex-3-ylmethyl)-3-trifluoromethyl-benzoic acid methyl ester (1.50 g,) is dissolved in anhydrous tetrahydrofuran (30 ml), lithium borohydride (2.39 ml, 2M solution in THF, 4.79 mmol) is added and the reaction mixture is stirred for 10 minutes. Methanol (0.60 ml) is added and the reaction mixture is stirred at room temperature for 5 hours. The reaction mixture is concentrated, water is added and the reaction mixture is extracted with dichloromethane. The organic phase is collected, dried over sodium sulfate and concentrated under vacuum. The residue obtained is purified by flash chromatography (30-100% ethyl acetate in cyclohexane) to give the title compound (yield 1.0 g).

LC (Method 1): $t_R$=0.82 min; Mass spectrum (ES+): m/z=286 [M+H]+.

Step 3: Methanesulfonic acid 4-(2-oxo-3-aza-bicyclo[3.1.0]hex-3-ylmethyl)-3-trifluoromethyl-benzyl ester 3-(4-Hydroxymethyl-2-trifluoromethyl-benzyl)-3-aza-bicyclo[3.1.0]hexan-2-one (550 mg, 1.93 mmol) and triethylamine (0.804 ml, 5.78 mmol) are dissolved in anhydrous dichloromethane (20 ml). The reaction mixture is cooled to 0° C. and methanesulfonyl chloride (0.179 ml, 2.31 mmol) is added under stirring. The reaction mixture is allowed to reach room temperature and stirred for 1 hour. The reaction mixture is washed with water (10 ml), the organic layer is collected, dried over sodium sulfate and concentrated. The crude obtained is used in the next step without further purification (yield 500 mg).

LC (Method 1): $t_R$=0.97 min; Mass spectrum (ES+): m/z=364 [M+H]$^+$.

Intermediate 65

1-(4-Chloromethyl-benzyl)-1H-pyrazole-4-carboxylic acid ethyl ester

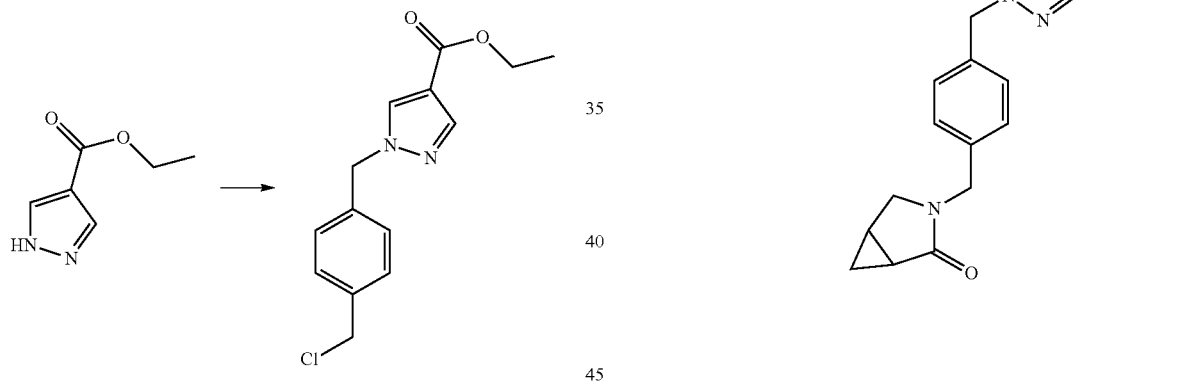

1H-Pyrazole-4-carboxylic acid ethyl ester (2 g, 13.9 mmol), (4-chloromethyl-phenyl)-methanol (2.21 g, 13.9 mmol) and triphenylphosphine (4.49 g, 16.8 mmol) are dissolved in tetrahydrofuran (40 ml). The reaction mixture is cooled to 0° C. then diethylazodicarboxylate (6.47 ml, 16.6 mmol) is added. The reaction mixture is stirred at 0° C. for 2 hours, then 1 hour at room temperature. The solvent is removed under vacuum and the residue is purified by flash chromatography (0-50% ethyl acetate in cyclohexane) to give the title compound (yield 1.72 g).

LC (Method 2): $t_R$=4.40 min; Mass spectrum (ES+): m/z=279 [M+H]+

Intermediate 66

1-[4-(2-Oxo-3-aza-bicyclo[3.1.0]hex-3-ylmethyl)-benzyl]-1H-pyrazole-4-carboxylic acid ethyl ester

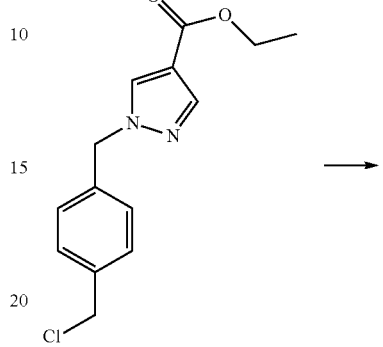

Sodium hydride (271 mg, 60% oil dispersion, 6.78 mmol) is added portionwise to a stirred solution of 3-aza-bicyclo[3.1.0]hexan-2-one (0.60 g, 6.17 mmol) dissolved in N,N-dimethylformamide (10 ml). After stirring 20 minutes at room temperature, 1-(4-Chloromethyl-benzyl)-1H-pyrazole-4-carboxylic acid ethyl ester (Intermediate 65, 1.72 g, 6.17 mmol) is added and the reaction mixture is stirred for 3 hours. The reaction mixture is concentrated, water is added and the mixture is extracted with dichloromethane. The organic phase is collected, dried over sodium sulfate and concentrated under vacuum, The residue obtained is purified by reverse phase flash chromatography (C18, 0-80% acetonitrile in water) to give the title compound (yield 470 mg).

LC (Method 1): $t_R$=0.92 min; Mass spectrum (ES+): m/z=340 [M+H]+

The intermediates in the following table are prepared in analogy to Intermediate 66, from the corresponding starting intermediates:

| Intermediate | Structure | Starting intermediates | Yield | Analysis |
|---|---|---|---|---|
| 67 | 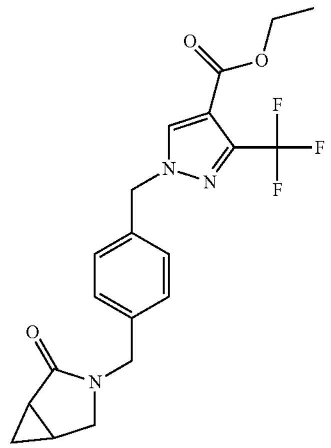 [SMILES: CCOC(=O)c1cn(Cc2ccc(CN3CC4CC4C3=O)cc2)nc1C(F)(F)F] | Intermediate 3 (1.0 g) and 3-aza-bicyclo[3.1.0]hexan-2-one, 140 mg) 3 hours at 25° C. Purified by flash chromatography (0 to 100% EtOAc in cyclohexane) | 320 mg | LC (Method 1): $t_R$ = 1.11 min; Mass spectrum (ES+): m/z = 408 [M + H]$^+$. |
| 68 | 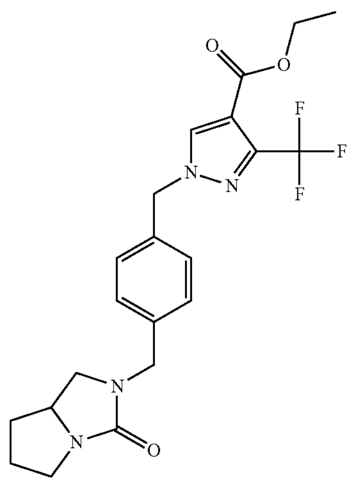 [SMILES: CCOC(=O)c1cn(Cc2ccc(CN3CC4CCCN4C3=O)cc2)nc1C(F)(F)F] | Intermediate 3 (500 mg) and hexahydro-pyrrolo[1,2-c]89midazole-3-one, 146 mg, available from ABBLOCKS C4043306) 1 hour at 25° C. Purified by flash chromatography (0 to 100% EtOAc in cyclohexane) | 330 mg | LC (Method 1): $t_R$ = 1.16 min; Mass spectrum (ES+): m/z = 437 [M + H]$^+$. |

Intermediate 69 and 70

The stereoisomers of Intermediate 66 (1.27 g) prepared as described above are separated by HPLC using a chiral stationary phase to give 620 mg of stereoisomer 1 (Intermediate 69) and 591 mg of stereoisomer 2 (Intermediate 70)

Method for Separation:

HPLC apparatus type: Waters 600 Pump, 2767 Autosampler, UV Detector 2489; column: Daicel Chiralpak AS-H, 5.0 μm, 250 mm×20 mm; method: eluent hexane/EtOH 65:35; flow rate: 15 mL/min, temperature: 25° C.; UV Detection: 230 nm

| Intermediate | Chiral HPLC (Daicel Chiralpak AS-H, hexane/EtOH 65:35, 1 ml/min 25° C.) $R_t$ [min] | HPLC-MS (Method 2): $R_t$ [min] | MS (ESI pos): m/z |
|---|---|---|---|
| 69 | 14.30 | 3.75 | 340 |
| 70 | 17.69 | 3.75 | 340 |

| Intermediate | Chiral HPLC (Daicel Chiralpak AS-H, hexane/EtOH 65:35, 1 ml/min 25° C.) $R_t$ [min] | HPLC-MS (Method 2): $R_t$ [min] | MS (ESI pos): m/z |
|---|---|---|---|
| Intermediate 69: stereoisomer 1 | | | |
| Intermediate 70: stereoisomer 2 | | | |

Intermediate 71 and 72

The stereoisomers of Intermediate 67 (550 mg) prepared as described above are separated by HPLC using a chiral stationary phase to give 230 mg of stereoisomer 1 (intermediate 71) and 230 mg of stereoisomer 2 (intermediate 72).

Method for Separation:

HPLC apparatus type: Waters 600 Pump, 2767 Autosampler, UV Detector 2489; column: Daicel Chiralpak AS-H, 5.0 μm, 250 mm×20 mm; method: eluent hexane/EtOH 65:35; flow rate: 15 mL/min, temperature: 25° C.; UV Detection: 230 nm

| Intermediate | Chiral HPLC (Daicel Chiralpak AS-H, hexane/EtOH 70:30, 1 ml/min 25° C.) $R_t$ [min] | HPLC-MS (Method 3): $R_t$ [min] | MS (ESI pos): m/z |
|---|---|---|---|
| 71 | 21.10 | 1.12 | 408 |
| 72 | 32.12 | 1.12 | 408 |

Intermediate 71: stereoisomer 1

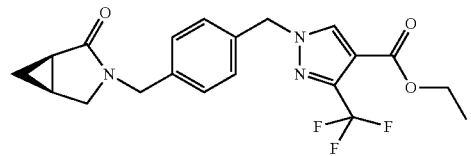 [SMILES: CCOC(=O)c1cn(Cc2ccc(CN3C[C@H]4C[C@H]4C3=O)cc2)nc1C(F)(F)F]

Intermediate 72: stereoisomer 2

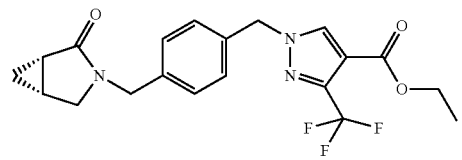 [SMILES: CCOC(=O)c1cn(Cc2ccc(CN3C[C@@H]4C[C@@H]4C3=O)cc2)nc1C(F)(F)F]

Intermediate 73

1-[4-(2-Oxo-3-aza-bicyclo[3.1.0]hex-3-ylmethyl)-3-trifluoromethyl-benzyl]-1H-pyrazole-4-carboxylic acid ethyl ester

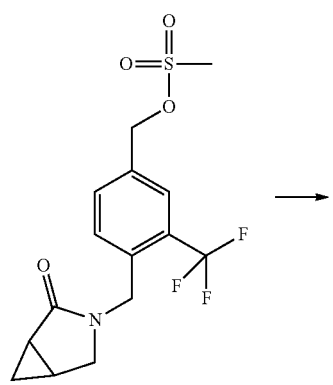

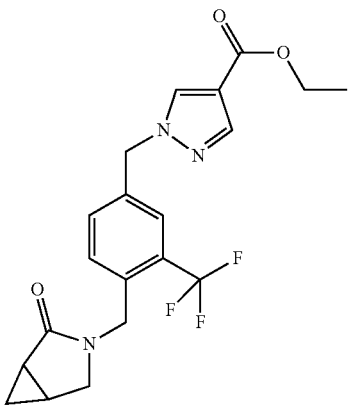

Ethyl 4-pyrazolecarboxylate (389 mg, 2.75 mmol) and potassium carbonate (760 mg, 5.50 mmol) are dissolved in N,N-dimethylformamide (3 ml), the mixture is stirred for 10 minutes at room temperature, then methanesulfonic acid 4-(2-oxo-3-aza-bicyclo[3.1.0]hex-3-ylmethyl)-3-trifluoromethyl-benzyl ester (Intermediate 64, 500 mg, 1.37 mmol) is added. The reaction mixture is heated to 100° C. and stirred overnight. Water is added and the reaction mixture is extracted with dichloromethane. The organic layer is collected and concentrated under reduced pressure. The residue obtained is purified by flash chromatography (10-90% ethyl acetate in cyclohexane to give the title compound. (yield 340 mg)

LC (Method 3): $t_R$=1.06 min; Mass spectrum (ES+): m/z=408 [M+H]+

Intermediate 74

3-Methyl-1-[4-(2-oxo-3-aza-bicyclo[3.1.0]hex-3-ylmethyl)-benzyl]-1H-pyrazole-4-carboxylic acid ethyl ester

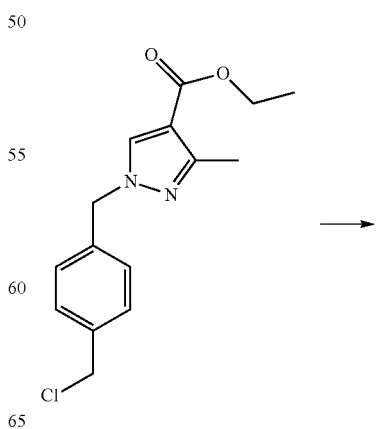

-continued

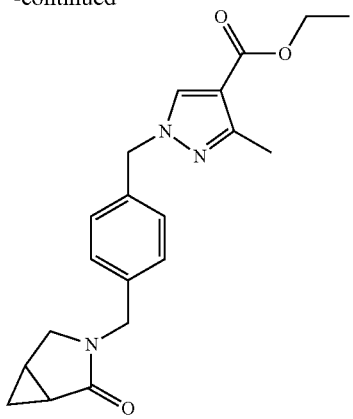

1-(4-Chloromethyl-benzyl)-3-methyl-1H-pyrazole-4-carboxylic acid ethyl ester (Intermediate 4, 600 mg, 1.84 mmol), 3-aza-bicyclo[3.1.0]hexan-2-one (197 mg, 2.03 mmol) and cesium carbonate (1.20 g, 3.69 mmol) are dissolved in N,N-dimethylformamide (15 ml), the reaction mixture is stirred at 90° C. for 1 hour, then dichloromethane (40 ml) is added. The reaction mixture is filtered and concentrated under reduced pressure. The residue obtained is purified by flash chromatography (20-100% ethyl acetate in cyclohexane) to give the title compound. Product obtained as major component in mixture with the regioisomer (yield 300 mg)

LC (Method 1): $t_R$=0.99 min; Mass spectrum (ES+): m/z=354 [M+H]+

Intermediate 75

Step 1: 1-[4-(1-Oxo-octahydro-pyrido[1,2-a]pyrazin-2-yl)-benzyl]-1H-[1,2,3]triazole-4-carboxylic acid ethyl ester

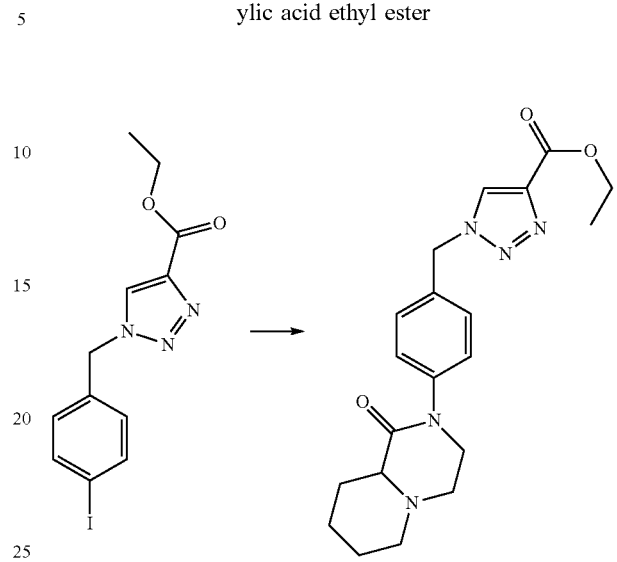

1-(4-Iodo-benzyl)-1H-[1,2,3]triazole-4-carboxylic acid ethyl ester (Intermediate 18, 1.6 g, 4.48 mmol), hexahydro-pyrido[1,2-a]pyrazin-1-one (commercially available from Fluorochem, CN 026340, 829 mg, 5.37 mmol), copper(I) iodide (256 mg, 1.34 mmol) and potassium carbonate (1.24 g, 8.96 mmol) are dissolved in anhydrous DMSO (5 ml), then trans-N,N-dimethylcyclohexane-1,2-diamine (191 mg, 1.34 mmol) is added. The reaction mixture is heated at 110° C. for 1 hour, then the solvent is removed, water is added and the reaction mixture is extracted with dichloromethane. The organic phase is collected, dried over sodium sulfate and concentrated under vacuum. The residue obtained is purified by reverse phase flash chromatography (C18, 0-80% acetonitrile in water) to give the title compound (yield 850 mg). LC (Method 2): $t_R$=3.22 min; Mass spectrum (ES+): m/z=384 [M+H]+.

The following intermediates are prepared in analogy to Intermediate 75, from the corresponding starting intermediates:

| Intermediate | Structure | Starting intermediates | Yield | Analysis |
|---|---|---|---|---|
| 76 | 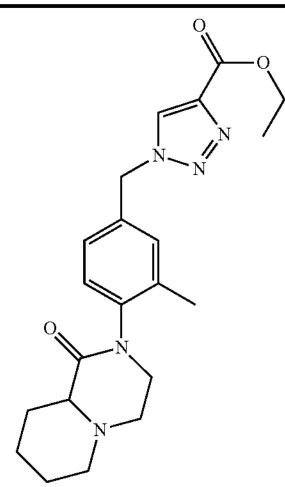 | Intermediate 19 (500 mg) and hexahydro-pyrido[1,2-a]pyrazin-1-one (250 mg, available from Fluorchem, CN 026340) | 200 mg | LC (Method 1): $t_R$ = 0.88 min; Mass spectrum (ES+): m/z = 398 [M + H]+. |

-continued

| Intermediate | Structure | Starting intermediates | Yield | Analysis |
|---|---|---|---|---|
| 77 | 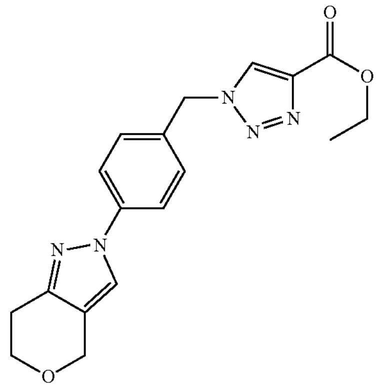 [SMILES: CCOC(=O)c1cn(Cc2ccc(-n3cc4c(n3)CCOC4)cc2)nn1] | Intermediate 18 (400 mg) and 2,4,6,7-tetrahydro-pyrano[4,3-c]pyrazole, (available from Anichem K10970, 417 mg), | 70 mg | LC (Method 1): $t_R$ = 0.87 min; Mass spectrum (ES+): m/z = 354 [M + H]$^+$. |
| 78 | 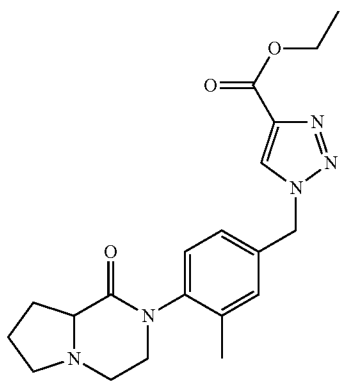 [SMILES: CCOC(=O)c1cn(Cc2ccc(N3CCN4CCCC4C3=O)c(C)c2)nn1] | Intermediate 19 (700 mg) and Hexahydro-pyrrolo[1,2-a]pyrazin-1-one (317 mg, available from Chemcollect, MC006108) | 140 mg | LC (Method 1): $t_R$ = 0.72 min; Mass spectrum (ES+): m/z = 384 [M + H]$^+$. |
| 79 | 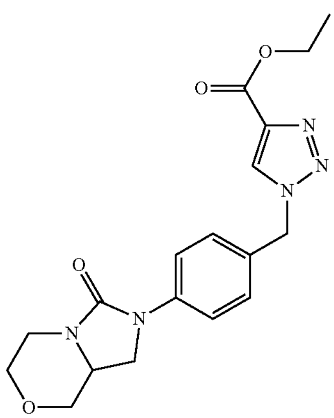 [SMILES: CCOC(=O)c1cn(Cc2ccc(N3CC4COCCN4C3=O)cc2)nn1] | Intermediate 18 (260 mg) and hexahydro-imidazo[5,1-c][1,4]oxazin-3-one, 133 mg), purification by preparative HPLC | 300 mg | LC (Method 6): $t_R$ = 3.59 min; Mass spectrum (ES+): m/z = 372 [M + H]$^+$. |

Intermediate 80

1-[4-(3-Oxo-hexahydro-pyrrolizin-2-yl)-benzyl]-1H-[1,2,3]triazole-4-carboxylic acid ethyl ester

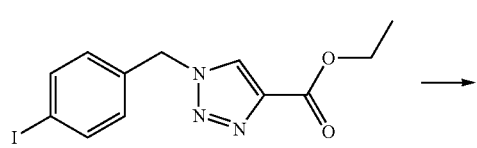

→

-continued

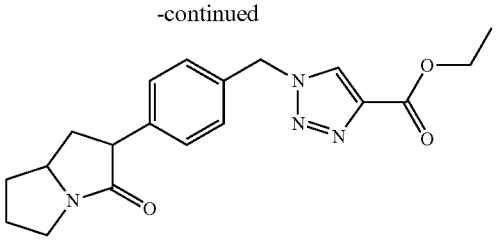

Hexahydro-pyrrolizin-3-one (available from Chess 3410-005, 1 g, 7.99 mmol) is dissolved in tetrahydrofuran (12 ml), the reaction mixture is cooled to 0° C. then sec-butyllithium (6.66 mL of a 1.2 M in cyclohexane, 7.99 mmol) is added. The reaction mixture is stirred at 0° C. for 30 minutes, then a solution of zinc chloride (1.09 g, 7.99 mmol) in tetrahydrofuran (8 ml) is added. After 30 minutes to the reaction mixture a solution of 1-(4-Iodo-benzyl)-1H-[1,2,3]triazole-4-carboxylic acid ethyl ester (Intermediate 18, 1 g, 7.99 mmol), bis(dibenzylideneacetone)palladium(0) (459 mg, 0.799) and 2-dicyclohexylphosphino-2'-(N,N-dimethylamino)biphenyl (629 mg, 1.59 mmol) in tetrahydrofuran (10 ml) is added. The reaction mixture is stirred at 80° C. under nitrogen atmosphere for 24 hours. Na$_2$CO$_3$ (2 g) is added, the reaction mixture is stirred for 1 hour and filtered. The solution obtained is concentrated and diluted with water (50 ml), the aqueous layer is extracted with dichloromethane (100 ml) and the organic phase obtained is collected, dried over sodium sulfate and concentrated under vacuum.

The residue obtained is purified by reverse phase flash chromatography (C18, 0-80% acetonitrile in water). The material obtained is purified again by flash chromatography (20-100% Ethyl acetate in cyclohexane) to give the title compound.

(yield 35 mg)

LC (Method 1): t$_R$=0.88 min; Mass spectrum (ES+): m/z=355 [M+H]$^+$.

Intermediate 81

1-[6-(3-Aza-bicyclo[3.1.0]hex-3-yl)-pyridin-3-ylmethyl]-1H-[1,2,3]triazole-4-carboxylic acid

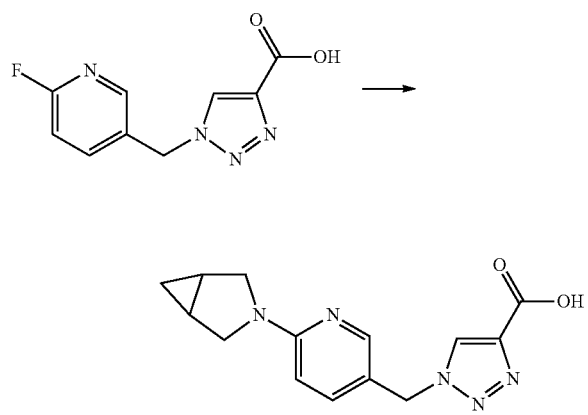

1-(6-Fluoro-pyridin-3-ylmethyl)-1H-[1,2,3]triazole-4-carboxylic acid (Intermediate 17, 800 mg, 3.60 mmol), 3-azabicyclo[3.1.0]hexane hydrochloride (available from Fluorochem CN 223542, 1.29 g, 10.8 mmol) and potassium carbonate (1.74 g, 12.6 mmol) are dissolved in 1-methyl-2-pyrrolidinone (1 ml). The mixture is warmed to 110° C. and stirred overnight. Water (30 ml) and dichloromethane (50 ml) are added, the aqueous layer is collected and acidified to pH 3 with HCl 4 N aqueous solution. The aqueous layer is concentrated and the residue is purified by reverse phase flash chromatography (C18, eluent: 0-30% acetonitrile in water) to give the title compound (yield 300 mg).

LC (Method 6): t$_R$=1.43-1.52 min; Mass spectrum (ES+): m/z=286 [M+H]+

Intermediate 82

1-[6-(3-Aza-bicyclo[3.1.0]hex-3-yl)-pyridin-3-ylmethyl]-1H-[1,2,3]triazole-4-carboxylic acid

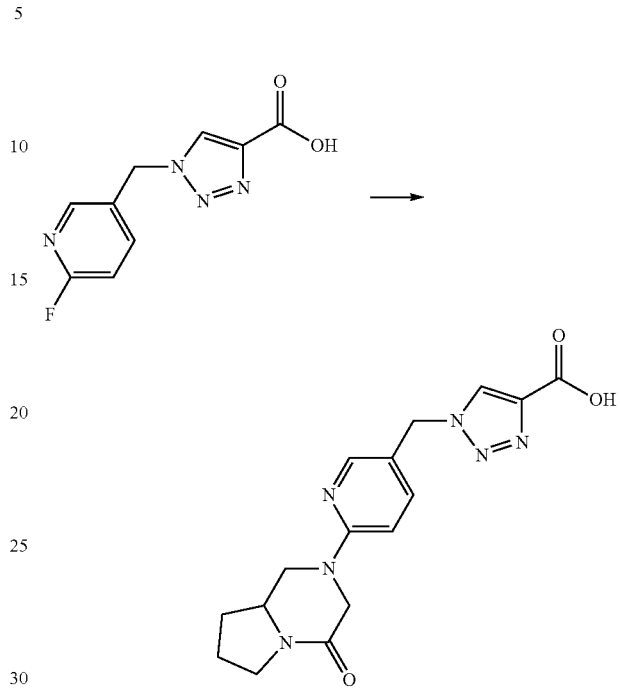

1-(6-Fluoro-pyridin-3-ylmethyl)-1H-[1,2,3]triazole-4-carboxylic acid (Intermediate 17, 150 mg, 0.67 mmol) and hexahydro-pyrrolo[1,2-a]pyrazin-4-one (synthesis described in patent application WO2007/28654 page 41, 189 mg, 1.35 mmol) are dissolved in 1-methyl-2-pyrrolidinone (6 ml). The mixture is warmed to 110° C. and stirred for 3 days. 5% aqueous Na$_2$CO$_3$ solution and dichloromethane are added, the aqueous layer is collected and acidified to pH 3 with HCl 6 N aqueous solution. The aqueous layer is concentrated and the residue is purified by reverse phase flash chromatography (C18, eluent: 0-60% acetonitrile in water) to give the title compound (yield 50 mg).

LC (Method 1): t$_R$=0.56 min; Mass spectrum (ES+): m/z=343 [M+H]+

Intermediate 83

1-[6-(3-Aza-bicyclo[3.1.0]hex-3-yl)-4-trifluoromethyl-pyridin-3-ylmethyl]-1H-[1,2,3]triazole-4-carboxylic acid

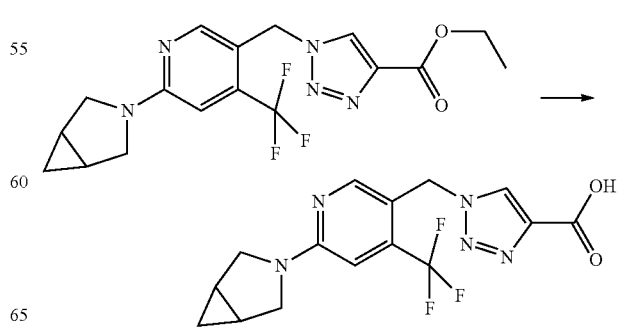

1-[6-(3-Aza-bicyclo[3.1.0]hex-3-yl)-4-trifluoromethyl-pyridin-3-ylmethyl]-1H-[1,2,3]triazole-4-carboxylic acid ethyl ester (Intermediate 61, 300 mg, 0.79 mmol) is dissolved in 1.4-dioxane (2 ml). Under stirring, lithium hydroxide monohydrate (728 mg, 17.3 mmol) is added and the solution is stirred at 70° C. for 4 hours. Triethylamine hydrochloride (300 mg) is added and the mixture is concentrated. The residue is purified by reverse phase flash chromatography (C18, 0-40% acetonitrile in water) to give the title compound (yield 260 mg).

LC (Method 3): $t_R$=0.71 min; Mass spectrum (ES+): m/z=354 [M+H]+

Intermediate 84

1-[6-(4-Oxo-hexahydro-pyrazino[2,1-c][1,4]oxazin-8-yl)-pyridin-3-ylmethyl]-1H-[1,2,3]triazole-4-carboxylic acid

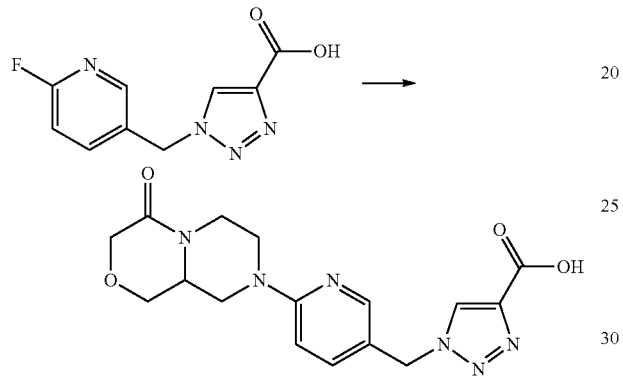

1-(6-Fluoro-pyridin-3-ylmethyl)-1H-[1,2,3]triazole-4-carboxylic acid (Intermediate 17, 300 mg, 1.35 mmol) and hexahydro-pyrazino[2,1-c][1,4]oxazin-4-one (synthesis described in patent application WO2007/37743, 650 mg, 3.38 mmol) are dissolved in 1-methyl-2-pyrrolidinone (1 ml). The mixture is warmed to 110° C. and stirred for 18 hours. % aqueous $Na_2CO_3$ solution and dichloromethane are added, the aqueous layer is collected and acidified to pH 3 with HCl 6 N aqueous solution. The aqueous layer is concentrated and the residue is purified by reverse phase flash chromatography (C18, 0-60% acetonitrile in water) to give the title compound (yield 180 mg).

LC (Method 1): $t_R$=0.28 min; Mass spectrum (ES+): m/z=359 [M+H]+

Intermediate 85

1-(4-Pyrazol-1-ylmethyl-benzyl)-1H-[1,2,3]triazole-4-carboxylic acid hydrochloride

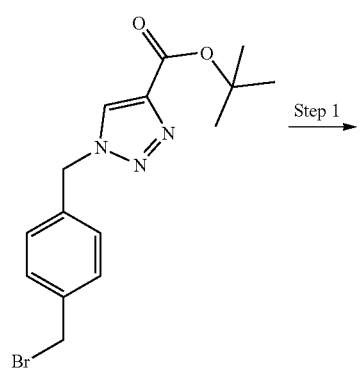

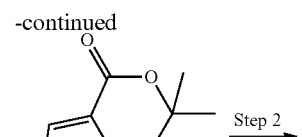

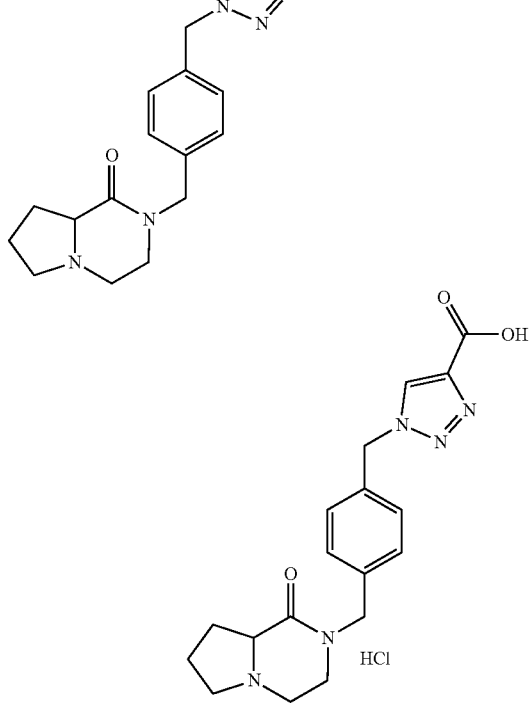

Step 1: 1-[4-(1-Oxo-hexahydro-pyrrolo[1,2-a]pyrazin-2-ylmethyl)-benzyl]-1H-[1,2,3]triazole-4-carboxylic acid tert-butyl ester Hexahydro-pyrrolo[1,2-a]pyrazin-1-one (available from Chemcollect MC006108, 418 mg) is dissolved in anhydrous N,N-dimethylformamide (4 ml), the solution is cooled to 0° C. and sodium hydride (113 mg, 60% dispersion in mineral oil, 2.83 mmol) is added. After 20 minutes, 1-(4-bromomethyl-benzyl)-1H-[1,2,3]triazole-4-carboxylic acid tert-butyl ester (Intermediate 20, 500 mg, 0.93 mmol) is added and the reaction mixture is stirred for 1 hr. The solvent is evaporated, dichloromethane is added and the reaction mixture is washed with water. The organic layer is collected, dried over sodium sulfate, filtered and concentrated under vacuum.

The residue is purified by reverse phase flash chromatography (C18, 0-60% acetonitrile in water) to give the title compound. (yield 198 mg)

LC (Method 1): $t_R$=0.87 min; Mass spectrum (ES+): m/z=412 [M+H]$^+$.

Step 2: 1-[4-(1-Oxo-hexahydro-pyrrolo[1,2-a]pyrazin-2-ylmethyl)-benzyl]-1H-[1,2,3]triazole-4-carboxylic acid hydrochloride 1-[4-(1-Oxo-hexahydro-pyrrolo[1,2-a]pyrazin-2-ylmethyl)-benzyl]-1H-[1,2,3]triazole-4-carboxylic acid tert-butyl ester (198 mg, 0.46 mmol) is dissolved in dichloromethane (2 ml) and trifluoroacetic acid (0.50 ml, 6.52 mmol) is added, the mixture is stirred overnight at room temperature. The solution is concentrated and the residue is evaporated twice from 4M HCl in 1,4-dioxane. The residue is washed with diethyl ether to give the title compound. (yield 210 mg).

LC (Method 1): $t_R$=0.36 min; Mass spectrum (ES+): m/z=356 [M+H]+

Intermediate 86

1-[4-((1R,5S)-2-Oxo-3-aza-bicyclo[3.1.0]hex-3-ylmethyl)-benzyl]-1H-pyrazole-4-carboxylic acid

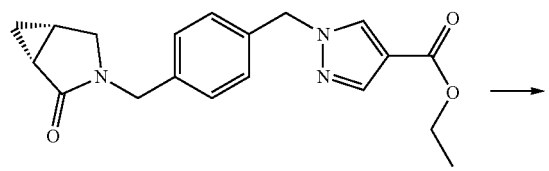

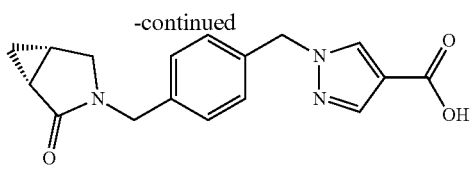

1-[4-((1R,5S)-2-Oxo-3-aza-bicyclo[3.1.0]hex-3-ylmethyl)-benzyl]-1H-pyrazole-4-carboxylic acid ethyl ester (Intermediate 69, 620 mg, 1.73 mmol) is stirred in tetrahydrofuran (10 ml). Lithium hydroxide monohydrate (728 mg, 17.3 mmol) is added and the reaction mixture is stirred at room temperature for 2 days. The mixture is concentrated then resuspended in water (20 ml), citric acid is added until pH 3 is reached, the precipitate is collected, washed with water and dried under vacuum (yield 440 mg).

LC (Method 6): $t_R$=3.10 min; Mass spectrum (ES+): m/z=312 [M+H]+.

The intermediates in the following table are prepared in analogy to Intermediate 86, from the corresponding starting ester intermediates:

| Intermediate | Structure | Starting intermediates | Yield | Analysis |
|---|---|---|---|---|
| 87 | 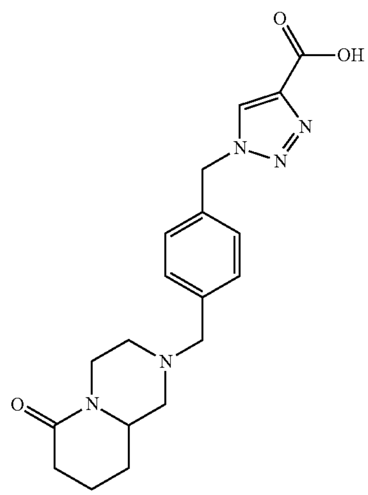 [SMILES: O=C(O)c1cn(Cc2ccc(CN3CCN4C(=O)CCCC4C3)cc2)nn1] | Intermediate 16 (80 mg), overnight 25° C. in 4 ml of THF and 2 ml of water | 80 mg | LC (Method 3): $t_R$ = 0.26 min; Mass spectrum (ES+): m/z = 370 [M + H]+. |
| 88 | 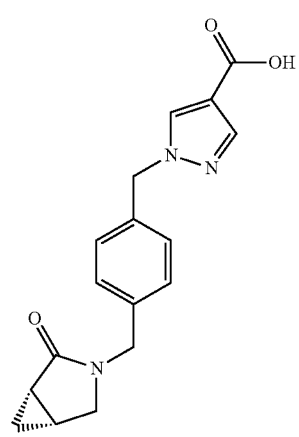 [SMILES: O=C(O)c1cnn(Cc2ccc(CN3C[C@@H]4C[C@@H]4C3=O)cc2)c1] | Intermediate 70 (590 mg), 2 days at 25° C. | 447 mg | LC (Method 6): $t_R$ = 3.11 min; Mass spectrum (ES+): m/z = 312 [M + H]+. |

| Intermediate | Structure | Starting intermediates | Yield | Analysis |
|---|---|---|---|---|
| 89 | 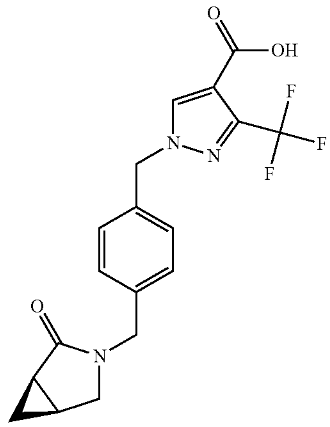 [SMILES: O=C(O)c1cn(Cc2ccc(CN3C[C@H]4C[C@H]4C3=O)cc2)nc1C(F)(F)F] | Intermediate 71 | 110 mg | LC (Method 1): $t_R$ = 0.59 min; Mass spectrum (ES+): m/z = 380 [M + H]⁺. |
| 90 | 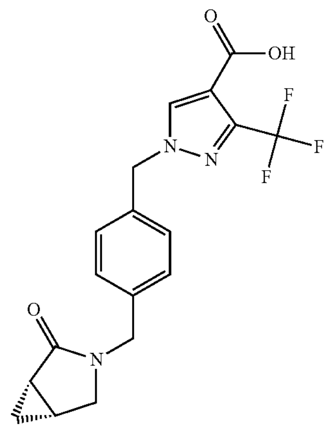 [SMILES: O=C(O)c1cn(Cc2ccc(CN3C[C@@H]4C[C@@H]4C3=O)cc2)nc1C(F)(F)F] | Intermediate 72 (160 mg) | 120 mg | LC (Method 1): $t_R$ = 0.60 min; Mass spectrum (ES+): m/z = 380 [M + H]⁺. |
| 91 | 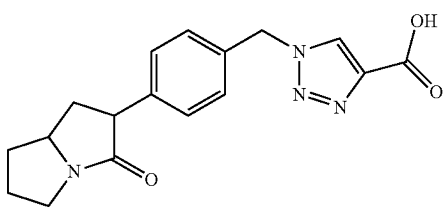 [SMILES: O=C(O)c1cn(Cc2ccc(C3CC4CCCN4C3=O)cc2)nn1] | Intermediate 80 (35 mg) in 4 ml of THF and 2 ml of water | 12 mg | LC (Method 1): $t_R$ = 0.59 min; Mass spectrum (ES+): m/z = 327 [M + H]⁺. |

Intermediate 92

1-[4-(6,7-Dihydro-4H-pyrano[4,3-c]pyrazol-2-ylmethyl)-benzyl]-1H-[1,2,3]triazole-4-carboxylic acid

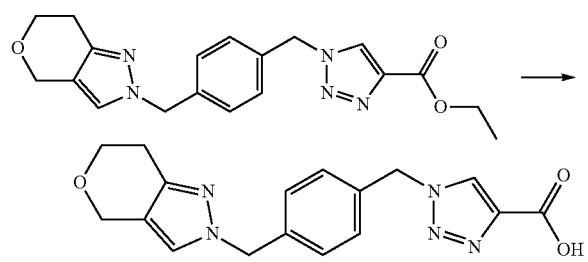

1-[4-(6,7-Dihydro-4H-pyrano[4,3-c]pyrazol-2-ylmethyl)-benzyl]-1H-[1,2,3]triazole-4-carboxylic acid_ethyl ester (Intermediate 15, 130 mg, 0.34 mmol) is dissolved in tetrahydrofuran (2.5 ml) and water (0.050 ml), sodium hydroxide aq. solution 32% (0.200 ml, 2.08 mmol) is added and the reaction mixture is stirred at room temperature for 2 hours. The reaction mixture is concentrated and the residue is purified by reverse phase flash chromatography (C18, 0-50% acetonitrile in water) to give the title compound (yield 53 mg).

LC (Method 3): $t_R$=0.58 min; Mass spectrum (ES+): m/z=340 [M+H]+

The following acid intermediates are prepared in analogy to Intermediate 92, from the corresponding starting ester intermediates:

| Intermediate | Structure | Starting intermediates | Yield | Analysis |
|---|---|---|---|---|
| 93 | (structure) | Intermediate 67 (320 mg), 4 hours at 90° C. | 200 mg | LC (Method 3): $t_R$ = 0.61 min; Mass spectrum (ES+): m/z = 380 [M + H]⁺. |
| 94 | (structure) | Intermediate 68 (330 mg), 4 hours at 90° C. | 276 mg | LC (Method 3): $t_R$ = 0.67 min; Mass spectrum (ES+): m/z = 409 [M + H]⁺. |
| 95 | (structure) | Intermediate 7 (250 mg), 18 hours at 60° C. | 150 mg | LC (Method 3): $t_R$ = 0.60 min; Mass spectrum (ES+): m/z = 326 [M + H]⁺. |
| 96 | (structure) | Intermediate 77 (70 mg), 1 hour at 60° C. | 50 mg | LC (Method 3): $t_R$ = 0.60 min; Mass spectrum (ES+): m/z = 326 [M + H]⁺. |

Intermediate 97

1-[3-Methyl-4-(1-oxo-octahydro-pyrido[1,2-a]pyrazin-2-yl)-benzyl]-1H-[1,2,3]triazole-4-carboxylic acid

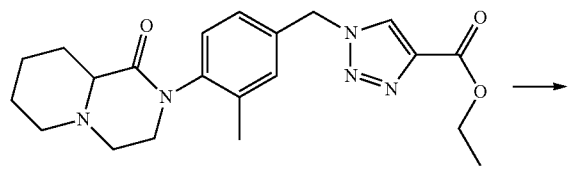

→

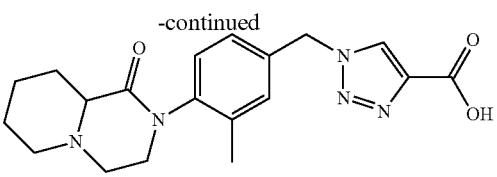

1-[3-Methyl-4-(1-oxo-octahydro-pyrido[1,2-a]pyrazin-2-yl)-benzyl]-1H-[1,2,3]triazole-4-carboxylic acid ethyl ester (Intermediate 76, 200 mg, 0.34 mmol) is dissolved in dioxane (5 ml), sodium hydroxide aq. solution 32% (0.25 ml, 2.6 mmol) is added and the reaction mixture is stirred at room temperature for 10 hours. Hydrochloric acid 2N aq. solution (20 ml) is added and the reaction mixture is concentrated under vacuum to give crude title compound in a mixture with salts (yield 260 mg).

LC (Method 3): $t_R$=0.58 min; Mass spectrum (ES+): m/z=370 [M+H]+

The following acid intermediates are prepared in analogy to Intermediate 97, from the corresponding starting ester intermediates:

| Intermediate | Structure | Starting intermediates | Yield | Analysis |
|---|---|---|---|---|
| 98 | 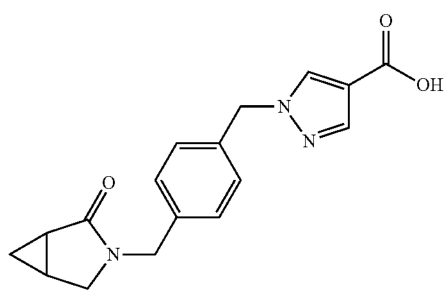 [SMILES: O=C(O)c1cnn(Cc2ccc(CN3CC4CC4C3=O)cc2)c1] | Intermediate 66 (200 mg), 5 hours at 50° C., product extracted with DCM. | 90 mg | LC (Method 3): $t_R$ = 0.62 min; Mass spectrum (ES+): m/z = 312 [M + H]+. |
| 99 | 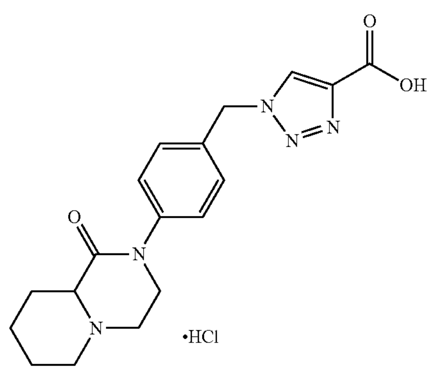 [SMILES: O=C(O)c1cn(Cc2ccc(N3CCN4CCCCC4C3=O)cc2)nn1 ; Cl] | Intermediate 75 (200 mg), 10 hours at 25° C. | 250 mg | LC (Method 2): $t_R$ = 0.28 min; Mass spectrum (ES+): m/z = 356 [M + H]+. |
| 100 | 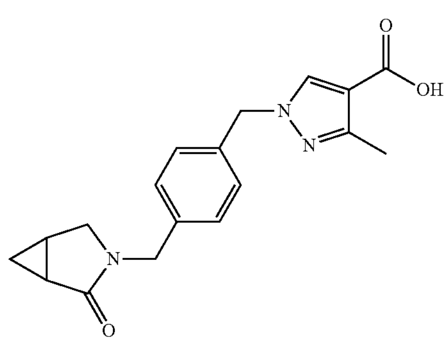 [SMILES: Cc1nn(Cc2ccc(CN3CC4CC4C3=O)cc2)cc1C(=O)O] | Intermediate 74 (350 mg), 10 hours at 25° C., product extracted with DCM. | 220 mg (as major component in mixture with the regioisomer) | LC (Method 3): $t_R$ = 0.70 min; Mass spectrum (ES+): m/z = 326 [M + H]+. |

-continued

| Intermediate | Structure | Starting intermediates | Yield | Analysis |
|---|---|---|---|---|
| 101 | 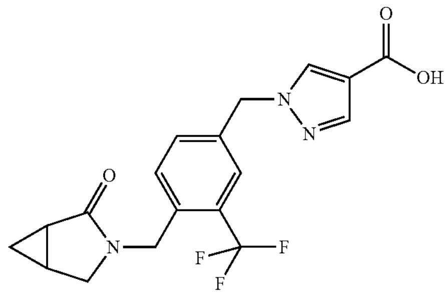 [SMILES: O=C(O)c1cnn(Cc2ccc(CN3CC4CC4C3=O)c(C(F)(F)F)c2)c1] | Intermediate 73 (390 mg), 5 hours at 80° C., product extracted with DCM. | 300 mg | LC (Method 3): $t_R$ = 0.60 min; Mass spectrum (ES+): m/z = 380 [M + H]⁺. |
| 102 | 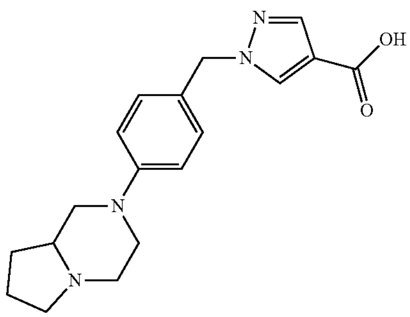 [SMILES: O=C(O)c1cnn(Cc2ccc(N3CCN4CCCC4C3)cc2)c1] | Intermediate 63 (320 mg), 10 hours at 25° C., acidified to pH 4 and product extracted with DCM. | 90 mg | LC (Method 3): $t_R$ = 0.56 min; Mass spectrum (ES+): m/z = 327 [M + H]⁺. |
| 103 | 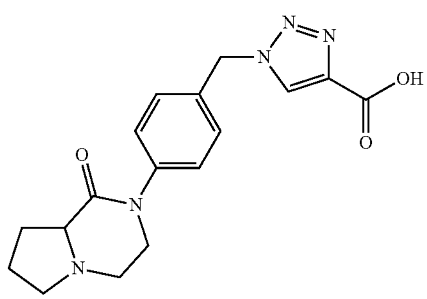 [SMILES: O=C(O)c1cn(Cc2ccc(N3CCN4CCCC4C3=O)cc2)nn1] | Intermediate 78 (155 mg), 4 hours at 60° C. | 55 mg | LC (Method 3): $t_R$ = 0.28 min; Mass spectrum (ES+): m/z = 356 [M + H]⁺. |
| 104 | 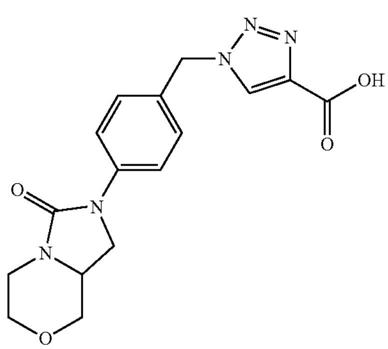 [SMILES: O=C(O)c1cn(Cc2ccc(N3CC4COCCN4C3=O)cc2)nn1] | Intermediate 79 (300 mg), 2 hours at 25° C. Purification on SCX resin eluting with methanolic ammonia | 80 mg | LC (Method 5): $t_R$ = 0.54 min; Mass spectrum (ES−): m/z = 343 [M − H]⁻. |

Intermediate 105

1-(6-Fluoro-pyridin-3-ylmethyl)-1H-pyrazole-4-carboxylic acid

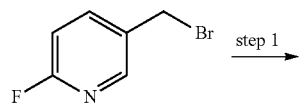

step 1 →

-continued

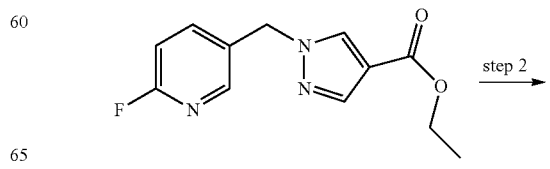

step 2 →

-continued

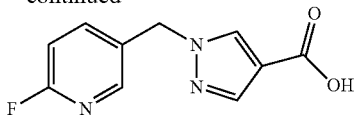

Step 1: 1-(6-Fluoro-pyridin-3-ylmethyl)-1H-pyrazole-4-carboxylic acid ethyl ester 5-(Bromomethyl)-2-fluoropyridine (available from Apollo Scientific, PC5845, 3.0 g, 15.8 mmol) is suspended in DMF (30 mL) and ethyl-4-pyrazole carboxylate (1.77 g, 12.6 mmol) and cesium carbonate (12.86 g, 39.5 mmol) are added. The mixture is stirred at 50° C. for 24 hours then diluted with ethyl acetate, washed with water and brine and the solvent removed under vacuum. The residue is purified by flash chromatography (0-10% EtOAc in cyclohexane) to give the title compound (Yield 2.60 g).

LC (Method 5): $t_R$=0.89 min; Mass spectrum (ES+): m/z=250 [M+H]$^+$.

Step 2: 1-(6-Fluoro-pyridin-3-ylmethyl)-1H-pyrazole-4-carboxylic acid

The material from step 1 is suspended in a mixture of water (5 mL) and THF (45 mL) and lithium hydroxide monohydrate (0.48 g, 11.47 mmol) is added. The mixture is stirred for 24 hours then concentrated under vacuum, diluted with EtOAc and water and the phases separated. The aqueous phase is acidified to pH 2 with the addition of 1M HCl solution then extracted with DCM. The DCM extract is evaporated to give the title compound (Yield 1.80 g).

LC (Method 5): $t_R$=0.30 min; Mass spectrum (ES+): m/z=222 [M+H]$^+$.

Intermediate 106

1-(6-Fluoro-pyridin-3-ylmethyl)-3-trifluoromethyl-1H-pyrazole-4-carboxylic acid

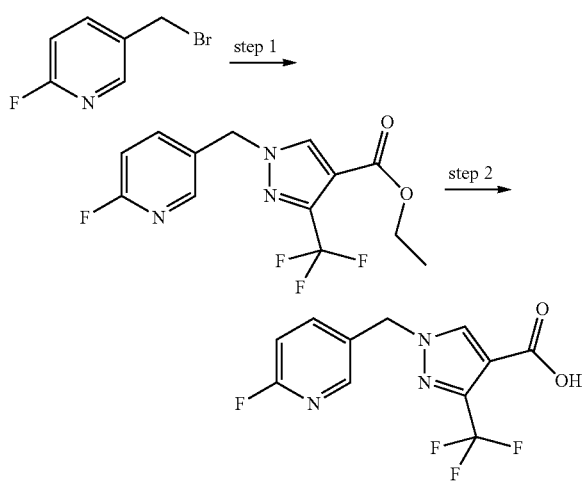

The title compound was prepared from 5-(Bromomethyl)-2-fluoropyridine (available from Apollo Scientific, PC5845, 1.0 g, 5.26 mmol) and ethyl 3-(trifluoromethyl)pyrazole-4-carboxylate (0.88 g, 4.21 mmol) in analogy to the method described for the preparation of Intermediate 105 (Yield 0.80 g).

LC (Method 5): $t_R$=0.54 min; Mass spectrum (ES+): m/z=290 [M+H]$^+$.

Intermediate 107

1-(2-Chloro-pyrimidin-5-ylmethyl)-3-trifluoromethyl-1H-pyrazole-4-carboxylic acid

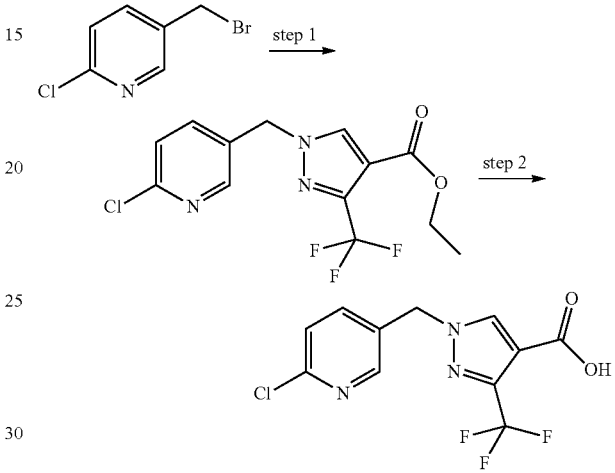

The title compound was prepared from 5-(Bromomethyl)-2-chloropyrimidine (synthesis described in EP2633756, 600 mg, 2.31 mmol) and ethyl 3-(trifluoromethyl)pyrazole-4-carboxylate (0.48 g, 2.31 mmol) in analogy to the method described for the preparation of Intermediate 105 (Yield 204 mg).

$^1$H NMR (500 MHz, DMSO-d6) δ ppm 5.54 (s, 2H) 8.64-8.69 (m, 1H) 8.83 (s, 2H) 13.01 (br s, 1H)

Intermediate 108

1-[6-(3-Aza-bicyclo[3.1.0]hex-3-yl)-pyridin-3-ylmethyl]-1H-pyrazole-4-carboxylic acid, lithium salt

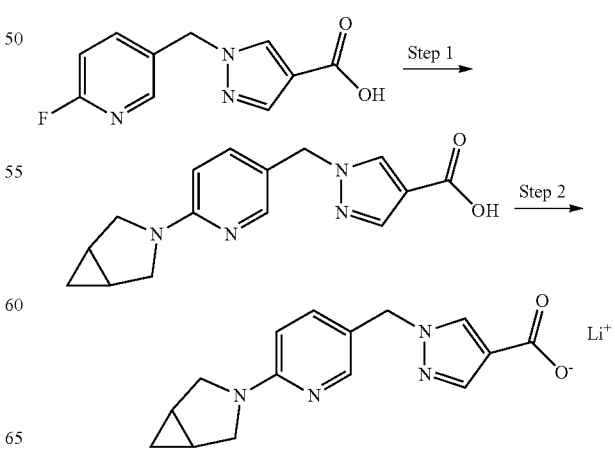

Step 1: 1-[6-(3-Aza-bicyclo[3.1.0]hex-3-yl)-pyridin-3-ylmethyl]-1H-pyrazole-4-carboxylic acid 1-(6-Fluoro-pyridin-3-ylmethyl)-1H-pyrazole-4-carboxylic acid (Intermediate 105, 800 mg, 3.62 mmol) is suspended in 1-methyl-2-pyrrolidinone (6 mL) and 3-azabicyclo[3.1.0]hexane hydrochloride (1.30 g, 10.85 mmol) and potassium carbonate (1.0 g, 7.23 mmol) are added. The mixture is heated under microwave irradiation at 100° C. for 3 hours. The solvent is evaporated and the residue purified by reverse phase flash chromatography (0-100% MeCN in water) to give the title compound (Yield 650 mg).

LC (Method 6): $t_R$=2.41 min; Mass spectrum (ES+): m/z=285 [M+H]$^+$.

Step 2: 1-[6-(3-Aza-bicyclo[3.1.0]hex-3-yl)-pyridin-3-ylmethyl]-1H-pyrazole-4-carboxylic acid lithium salt The material from step 1 (650 mg, 2.29 mmol) and lithium hydroxide (55 mg, 2.29 mmol) are combined in water (5 mL) and stirred for 1 hour. The mixture is evaporated to give the title compound (Yield 631 mg).

$^1$H-NMR (500 MHz, d6-DMSO): 8.02 (dd, J=2.4, 0.7 Hz, 1H), 7.65 (s, 1H), 7.45-7.37 (m, 2H), 6.39 (dd, J=8.7, 0.8 Hz, 1H), 5.05 (s, 2H), 3.60 (d, J=10.1 Hz, 2H), 3.30 (dt, J=10.1, 2.0 Hz, 2H), 1.65 (dddd, J=7.9, 4.0, 2.6, 1.3 Hz, 2H), 0.70 (td, J=7.8, 4.4 Hz, 1H), 0.15 (q, J=4.1 Hz, 1H).

Intermediate 109

1-[3-Aza-bicyclo[3.1.0]hex-3-yl)-pyridin-3-ylmethyl]-3-trifluoromethyl-1H-pyrazole-4-carboxylic acid

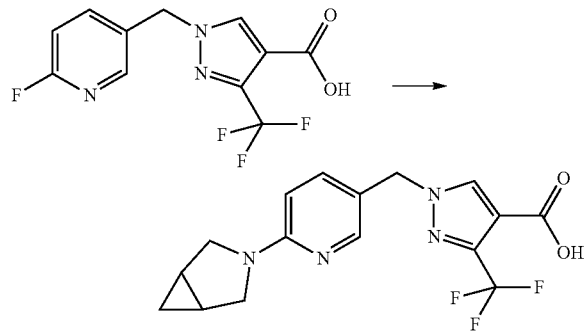

The title compound is prepared from 1-(6-Fluoro-pyridin-3-ylmethyl)-3-trifluoromethyl-1H-pyrazole-4-carboxylic acid (Intermediate 106, 450 mg, 1.57 mmol) in analogy to the method described for the preparation of Intermediate 108 step 1 (Yield 540 mg).

LC (Method 6): $t_R$=3.16 min; Mass spectrum (ES+): m/z=353 [M+H]$^+$.

Intermediate 110

1-[3-Aza-bicyclo[3.1.0]hex-3-yl)-pyrimidin-5-ylmethyl]-3-trifluoromethyl-1H-pyrazole-4-carboxylic acid

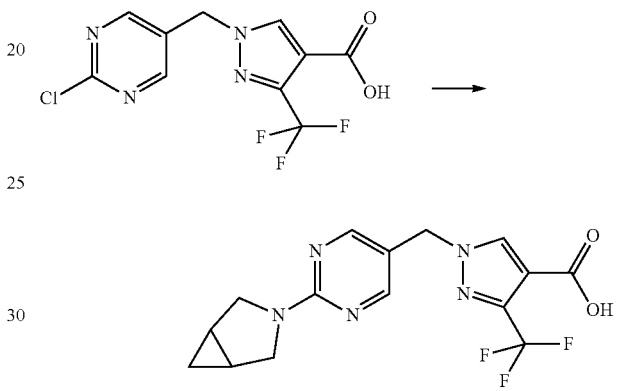

The title compound is prepared from 1-(2-Chloro-pyrimidin-5-ylmethyl)-3-trifluoromethyl-1H-pyrazole-4-carboxylic acid (Intermediate 107, 200 mg, 0.65 mmol) in analogy to the method described for the preparation of Intermediate 108 step 1 (Yield 105 mg).

$^1$H NMR (500 MHz, DMSO-d6) δ ppm 0.13 (q, J=4.16 Hz, 1H) 0.71 (td, J=7.76, 4.52 Hz, 1H) 1.60-1.67 (m, 2H) 3.42-3.47 (m, 2H) 3.74 (d, J=11.00 Hz, 2H) 5.14 (s, 2H) 7.93 (s, 1H) 8.36 (s, 2H)

The compounds in the following table are synthesized in analogy to the method described for Intermediate 108.

| Intermediate | Structure | Starting intermediates | Yield | Analysis |
|---|---|---|---|---|
| 111 | 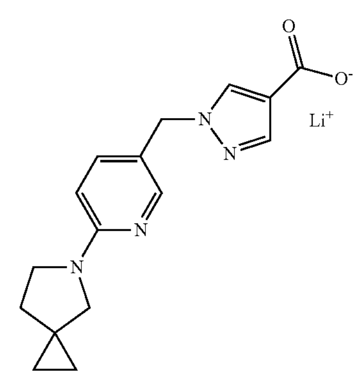 [SMILES: O=C([O-])c1cnn(Cc2ccc(N3CCC4(CC4)C3)nc2)c1 ; [Li+]] | Intermediate 105 (150 mg, 0.68 mmol) and 6-azaspiro[2.4]heptane (commercially available, Enamine EN300-75631, 132 mg, 1.36 mmol) | 100 mg | $^1$H-NMR (500 MHz, d6-DMSO): 8.03 (dd, J = 2.4, 0.8 Hz, 1H), 7.59 (d, J = 0.7 Hz, 1H), 7.41 (dd, J = 8.7, 2.4 Hz, 1H), 7.38 (d, J = 0.7 Hz, 1H), 6.36 (dd, J = 8.7, 0.8 Hz, 1H), 5.04 (s, 2H), 3.50 (t, J = 6.8 Hz, 2H), 3.27 (m, 2H), 1.87 (t, J = 6.8 Hz, 2H), 0.64-0.56 (m, 4H). |

| Intermediate | Structure | Starting intermediates | Yield | Analysis |
|---|---|---|---|---|
| 112 | 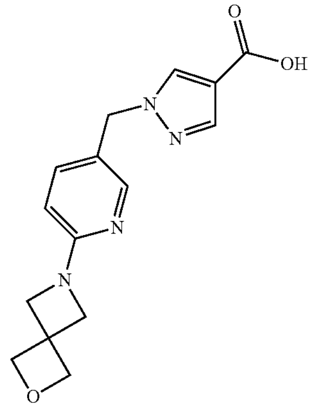 [SMILES: O=C(O)c1cnn(Cc2ccc(N3CC4(COC4)C3)nc2)c1] | Intermediate 105 (150 mg, 0.68 mmol) and 2-Oxa-6-aza-spiro[3.3]heptane hemi-oxalate, 144 mg, 1 mmol) Product isolated as free acid, no treatment with lithium hydroxide | 50 mg | LC (Method 5): $t_R$ = 0.37 min; Mass spectrum (ES+): m/z = 301 [M + H]$^+$. |
| 113 | 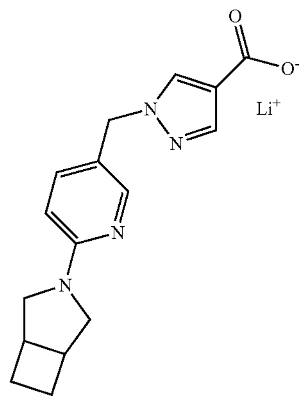 [SMILES: O=C([O-])c1cnn(Cc2ccc(N3CC4CCC4C3)nc2)c1 ; [Li+]] | Intermediate 105 (155 mg, 0.70 mmol) and; 3-azabicyclo[3.2.0]heptane hydrochloride, 93, 0.7 mmol) The intermediate acid is temporarily esterified with excess trimethylsilyldiazomethane in methanol to aid purification. Treatment with lithium hydroxide (1 eq in water/THF) gives the title compound | 18 mg | LC (Method 5): $t_R$ = 0.63 min; Mass spectrum (ES+): m/z = 299 [M + H]$^+$. |

Intermediate 114

1-(6-Fluoro-pyridin-3-ylmethyl)-1H-pyrazole-4-carboxylic acid methyl ester

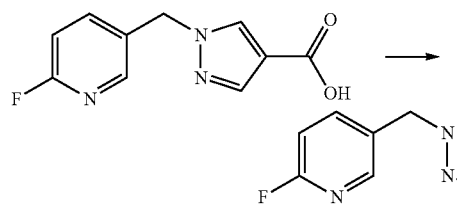

1-(6-Fluoro-pyridin-3-ylmethyl)-1H-pyrazole-4-carboxylic acid (Intermediate 105, 870 mg, 3.94 mmol) is suspended in methanol (15 mL) and cooled to 0° C. Trimethylsilyliazomethane (2M in diethyl ether, 10 mL, 20 mmol) is added, the mixture allowed to warm to room temperature and stirred for 2 hours. The solvent is evaporated, the residue partitioned between dichloromethane and saturated aqueous sodium bicarbonate solution and the phases separated. The organic phase is washed with brine, dried and the solvent removed. The residue is purified by flash chromatography (30% ethyl acetate in cyclohexane) to give the title compound (Yield 400 mg).

LC (Method 5): $t_R$=0.80 min; Mass spectrum (ES+): m/z=236 [M+H]$^+$.

Intermediate 115

1-[6-(6,6-Difluoro-3-aza-bicyclo[3.1.0]hex-3-yl)-pyridin-3-ylmethyl]-1H-pyrazole-4-carboxylic acid methyl ester

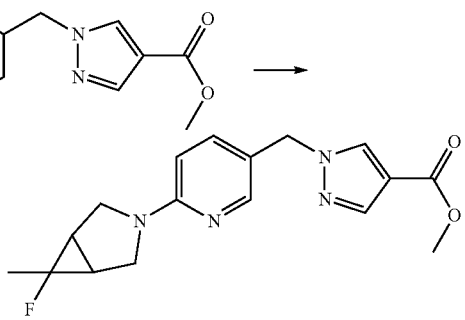

1-(6-Fluoro-pyridin-3-ylmethyl)-1H-pyrazole-4-carboxylic acid methyl ester (Intermediate 114, 75 mg, 0.32 mmol) is suspended in 1-methyl-2-pyrrolidinone (0.5 mL) and 6,6-difluoro-3-azabicyclo[3.1.0]hexane hydrochloride (50 mg, 0.32 mmol) and potassium carbonate (88 mg, 0.64 mmol) are added. The mixture is heated under microwave irradia-

Intermediate 116

1-[6-((1S,5R,6R)-6-Hydroxymethyl-3-aza-bicyclo[3.1.0]hex-3-yl)-pyridin-3-ylmethyl]-1H-pyrazole-4-carboxylic acid methyl ester

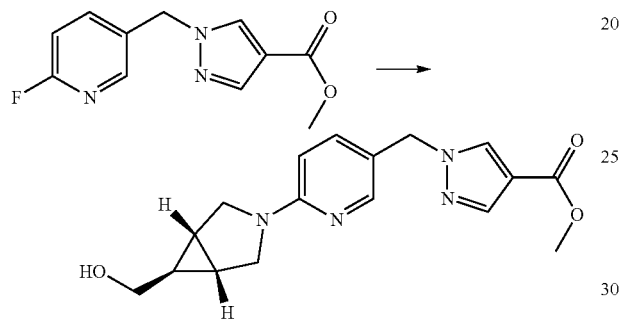

1-(6-Fluoro-pyridin-3-ylmethyl)-1H-pyrazole-4-carboxylic acid methyl ester (Intermediate 114, 100 mg, 0.43 mmol) is suspended in 1-methyl-2-pyrrolidinone (2 mL) and [(1R,5S)-3-azabicyclo[3.1.0]hexan-6-yl]methanol (commercially available from Enamine, EN400-15589, 96 mg, 0.85 mmol) and potassium carbonate (118 mg, 0.85 mmol) are added. The mixture is heated under microwave irradiation at 100° C. for 5 hours. The solvent is evaporated, the residue partitioned between ethyl acetate and 0.1 M NaOH aqueous solution and the phases separated. The organic phase is washed with brine, dried and the solvent removed. The residue is purified by flash chromatography (0-5% methanol in dichloromethane) to give the title compound (Yield 70 mg).

LC (Method 5): $t_R$=0.76 min; Mass spectrum (ES+): m/z=329 [M+H]$^+$.

Intermediate 117

1-[6-((1S,5R,6R)-6-Hydroxymethyl-3-aza-bicyclo[3.1.0]hex-3-yl)-pyridin-3-ylmethyl]-1H-pyrazole-4-carboxylic acid

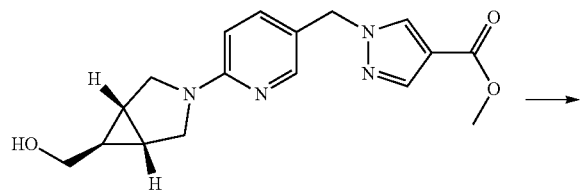

1-[6-((1S,5R,6R)-6-Hydroxymethyl-3-aza-bicyclo[3.1.0]hex-3-yl)-pyridin-3-ylmethyl]-1H-pyrazole-4-carboxylic acid methyl ester (Intermediate 116, 70 mg, 0.21 mmol) is suspended in tetrahydrofuran (10 mL) and water (10 mL) and lithium hydroxide monohydrate (10 mg, 0.23 mmol) is added. The mixture is stirred overnight then he solvent is evaporated, the residue partitioned between ethyl acetate and water and the phases separated. The aqueous phase is acidified with citric acid, loaded onto a prewashed SCX cartridge, washed with water and then eluted with 7M ammonia solution in 1,4-dioxane. The solvent is evaporated to give the crude title compound (Yield 100 mg).

LC (Method 5): $t_R$=0.50 min; Mass spectrum (ES+): m/z=315 [M+H]$^+$.

Intermediate 118

3-(5-Bromomethyl-pyrimidin-2-yl)-3-aza-bicyclo[3.1.0]hexane

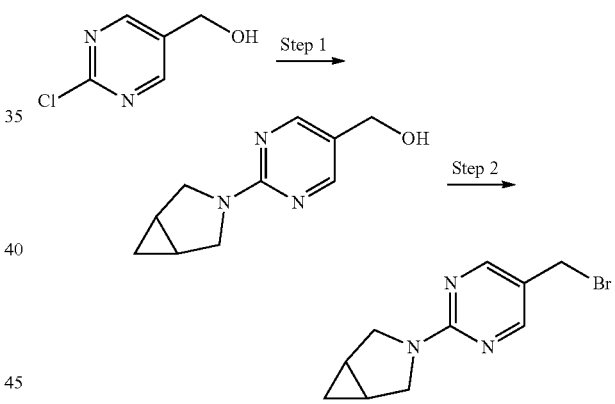

Step 1: [2-(3-Aza-bicyclo[3.1.0]hex-3-yl)-pyrimidin-5-yl]-methanol (2-Chloropyrimidin-5-yl)methanol (500 mg, 3.46 mmol) is suspended in 1-methyl-2-pyrrolidinone (2 mL) and 3-azabicyclo[3.1.0]hexane hydrochloride (414 mg, 3.46 mmol) and potassium carbonate (1.2 g, 8.65 mmol) are added. The mixture is heated under microwave irradiation at 120° C. for 20 minutes. The mixture is diluted with ethyl acetate, filtered to remove undissolved salts and the solvent removed under vacuum to give the crude intermediate (Yield 635 mg).

LC (Method 5): $t_R$=0.67 min; Mass spectrum (ES+): m/z=192 [M+H]$^+$.

Step 2: 3-(5-Bromomethyl-pyrimidin-2-yl)-3-aza-bicyclo[3.1.0]hexane

The material from step 1 (400 mg, 2.09 mmol) is dissolved in anhydrous dichloromethane (10 mL) and cooled to

--- tion at 80° C. for 15 hours. The solvent is evaporated, the residue partitioned between dichloromethane and water and the phases separated. The organic phase is washed with brine, dried and the solvent removed. The residue is purified by flash chromatography (30-100% ethyl acetate in cyclohexane) to give the title compound (Yield 36 mg).

LC (Method 5): $t_R$=0.97 min; Mass spectrum (ES+): m/z=335 [M+H]$^+$.

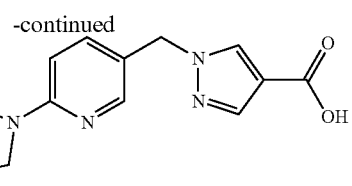

0° C. Phosphorous tribromide solution (1 M in dichloromethane, 3.14 mL, 3.14 mmol) is added dropwise, the mixture allowed to warm to room temperature then stirred for 2 hours. The mixture is diluted with dichloromethane, washed with water, dried over sodium sulfate and the solvent removed to give crude title compound (Yield 260 mg).

GC (Method 9): $t_R$=10.93 min; Mass spectrum (EI+): m/z=253/255 [M]+.

Intermediate 119

1-[2-(3-Aza-bicyclo[3.1.0]hex-3-yl)-pyrimidin-5-ylmethyl]-1H-[1,2,3]triazole-4-carboxylic acid ethyl ester

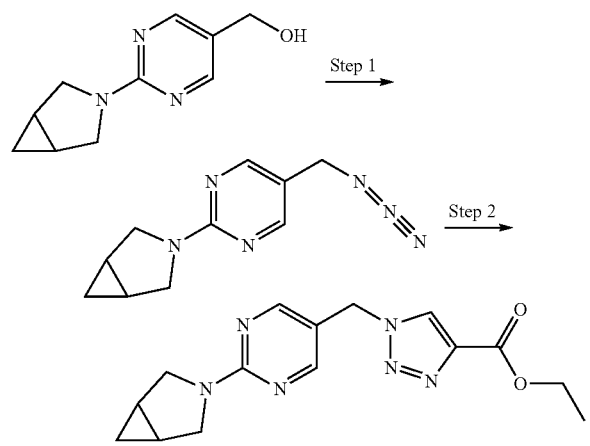

Step 1: 3-(5-Azidomethyl-pyrimidin-2-yl)-3-aza-bicyclo[3.1.0]hexane 2-(3-Aza-bicyclo[3.1.0]hex-3-yl)-pyrimidin-5-yl]-methanol (Intermediate 118 step 1, 225 mg, 1.18 mmol) is suspended in a mixture of anhydrous toluene (5 mL) and anhydrous acetonitrile (5 mL) and cooled to 0° C. under nitrogen. Diphenylphosphoryl azide (0.30 mL, 1.41 mmol) is added followed by 18-diazabicyclo[5.4.0]undec-7-ene and the mixture is stirred for 1 hour at room temperature. The solvent is evaporated, the residue diluted with ethyl acetate, washed with 5% aqueous sodium hydrogen carbonate solution, dried over sodium sulfate and the solvent removed under vacuum to give the crude intermediate (Yield 250 mg).

LC (Method 5): $t_R$=1.01 min; Mass spectrum (ES+): m/z=217 [M+H]+.

Step 2: 1-[2-(3-Aza-bicyclo[3.1.0]hex-3-yl)-pyrimidin-5-ylmethyl]-1H-[1,2,3]triazole-4-carboxylic acid ethyl ester The material from step 1 (250 mg, 1.16 mmol), ethyl propiolate (125 mg, 1.27 mmol), sodium ascorbate (230 mg, 1.16 mmol) and copper (II) sulfate pentahydrate (58 mg, 0.23 mmol) are combined in a mixture of tert-butanol (5 mL) and water (5 mL) and stirred overnight. The solvent is evaporated, the residue diluted with dichloromethane, washed with 10% aqueous ammonium hydroxide solution, the aqueous phase is further extracted with dichloromethane, the combined organic extracts dried over sodium sulfate and the solvent removed under vacuum. The residue is purified by flash chromatography (0-100% ethyl acetate in cyclohexane) to give the title compound (Yield 219 mg).

LC (Method 5): $t_R$=0.91 min; Mass spectrum (ES+): m/z=315 [M+H]+.

Intermediate 120

1-[2-(3-Aza-bicyclo[3.1.0]hex-3-yl)-pyrimidin-5-ylmethyl]-1H-pyrazole-4-carboxylic acid ethyl ester

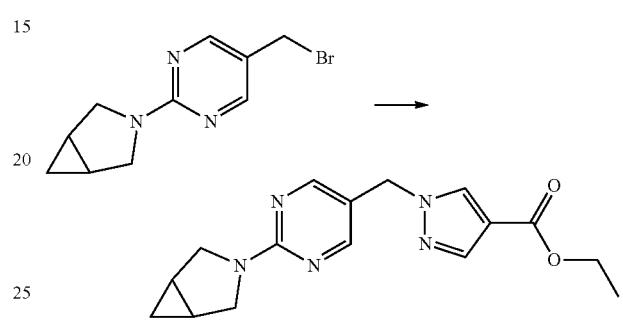

3-(5-Bromomethyl-pyrimidin-2-yl)-3-aza-bicyclo[3.1.0]hexane (Intermediate 118, 260 mg, 1.02 mmol), ethyl 4-pyrazolecarboxylate (143 mg, 1.02 mmol) and potassium carbonate (283 mg, 2.05 mmol) are suspended in anhydrous N,N-dimethylformamide (5 mL) and stirred at 60° C. overnight. The solvent is evaporated and the residue partitioned between ethyl acetate and water and the phases separated. The aqueous phase is further extracted with ethyl acetate, the combined organic extracts dried over sodium sulfate and the solvent removed under vacuum. The residue is purified by flash chromatography (0-60% ethyl acetate in cyclohexane) to give the title compound (Yield 94 mg).

LC (Method 5): $t_R$=1.00 min; Mass spectrum (ES+): m/z=314 [M+H]+.

Intermediate 121

1-[5-(3-Aza-bicyclo[3.1.0]hex-3-yl)-pyrazin-2-ylmethyl]-1H-pyrazole-4-carboxylic acid ethyl ester

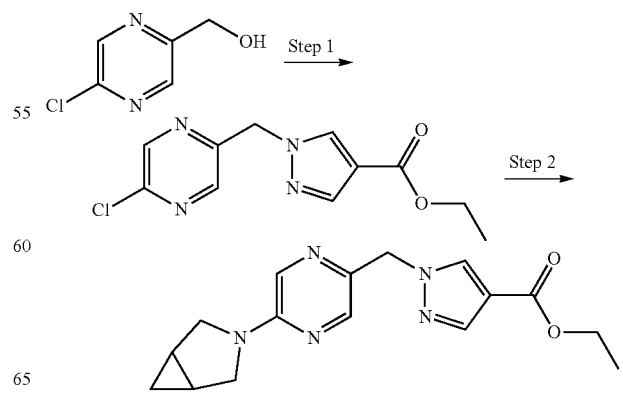

Step 1: 1-(5-Chloro-pyrazin-2-ylmethyl)-1H-pyrazole-4-carboxylic acid ethyl ester (5-chloropyrazin-2-yl)methanol (780 mg, 5.40 mmol), ethyl 4-pyrazolecarboxylate (765 mg, 5.46 mmol) and potassium carbonate (283 mg, 2.05 mmol) and triphenylphosphine (1.57 g, 6.01 mmol) are suspended in anhydrous tetrahydrofuran (20 mL) and cooled to 0° C. Diisopropyldicarboxylate (1.18 mL, 6.01 mmol) is added, the mixture allowed to warm to room temperature and stirred for three hours. The solvent is evaporated and the residue partitioned between dichloromethane and water and the phases separated. The organic extracts are washed with brine, dried over sodium sulfate and the solvent removed under vacuum. The residue is purified by flash chromatography (30-50% ethyl acetate in cyclohexane) to give the desired intermediate as an impure product (Yield 2.12 g).

LC (Method 5): $t_R$=0.95 min; Mass spectrum (ES+): m/z=267 [M+H]$^+$.

Step 2: 1-[5-(3-Aza-bicyclo[3.1.0]hex-3-yl)-pyrazin-2-ylmethyl]-1H-pyrazole-4-carboxylic acid ethyl ester A portion of the material from step 1 (1 g), ethyl 4-pyrazolecarboxylate (765 mg, 5.46 mmol) is suspended in 1-methyl-2-pyrrolidinone (5 mL) and 3-azabicyclo[3.1.0]hexane hydrochloride (300 mg, 2.5 mmol) and potassium carbonate (1.02 g, 7.4 mmol) are added. The mixture is heated under microwave irradiation at 120° C. for 3 hours. The solvent is evaporated, the residue partitioned between dichloromethane and brine, filtered through decalite and the phases separated. The organic phase is dried and the solvent removed. The residue is purified by flash chromatography (30-50% ethyl acetate in cyclohexane) to give the title compound (Yield 382 mg).

LC (Method 5): $t_R$=1.00 min; Mass spectrum (ES+): m/z=314 [M+H]$^+$.

Intermediate 122

1-[6-(6,6-Difluoro-3-aza-bicyclo[3.1.0]hex-3-yl)-pyridin-3-ylmethyl]-1H-pyrazole-4-carboxylic acid lithium salt

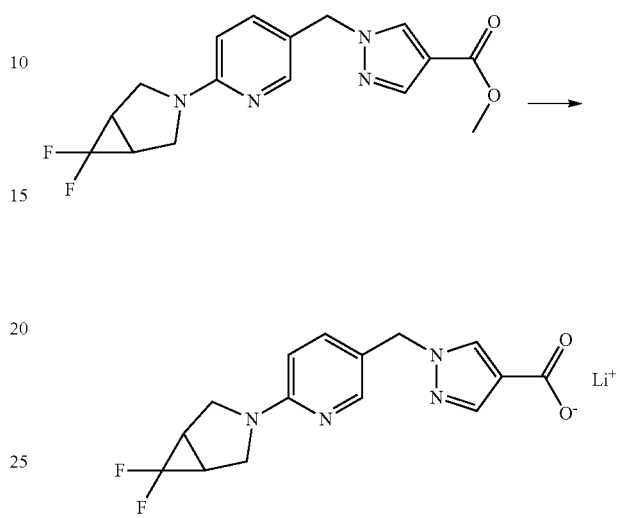

1-[6-(6,6-Difluoro-3-aza-bicyclo[3.1.0]hex-3-yl)-pyridin-3-ylmethyl]-1H-pyrazole-4-carboxylic acid methyl ester (Intermediate 115, 36 mg, 0.11 mmol) is suspended in a mixture of tetrahydrofuran (2 mL) and water (1 mL) and lithium hydroxide monohydrate (5 mg, 0.11 mmol) is added. The mixture is stirred for 3 hours at 50° C. then the solvent is evaporated and the residue dried under vacuum to give the title compound (Yield 31 mg).

LC (Method 5): $t_R$=0.58 min; Mass spectrum (ES−): m/z=319 [M−Li]$^-$.

The compounds in the following table are synthesized in analogy to the method described for Intermediate 122.

| Intermediate | Structure | Starting intermediates | Yield | Analysis |
|---|---|---|---|---|
| 123 | 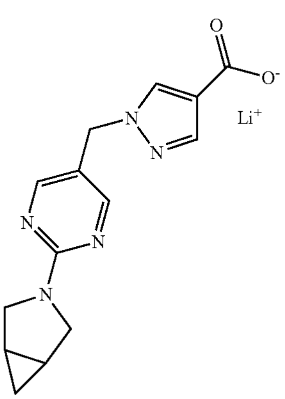 [SMILES: O=C([O-])c1cnn(Cc2cnc(N3CC4CC4C3)nc2)c1 ; [Li+]] | Intermediate 120 (94 mg, 0.30 mmol) 1,4-dioxane (2 mL) and water (1 mL) as solvent 1 hour at 70° C. | 86 mg | LC (Method 5): $t_R$ = 0.58 min; Mass spectrum (ES−): m/z = 284 [M − Li]$^-$. |

-continued

| Intermediate | Structure | Starting intermediates | Yield | Analysis |
|---|---|---|---|---|
| 124 | 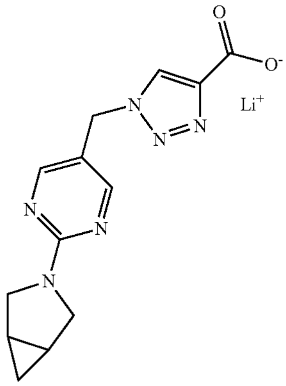 [SMILES: O=C([O-])c1cn(Cc2cnc(N3CC4CC4C3)nc2)nn1 ; [Li+]] | Intermediate 119 (219 mg, 0.70 mmol) 1,4-dioxane (2 mL) and water (1 mL) as solvent 1 hour at 70° C. | 203 mg | LC (Method 5): $t_R$ = 0.56 min; Mass spectrum (ES+): m/z = 287 [M − Li + 2H]$^+$. |
| 125 | 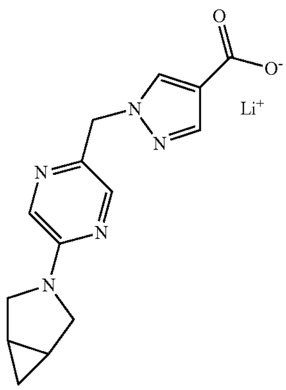 [SMILES: O=C([O-])c1cnn(Cc2cnc(N3CC4CC4C3)cn2)c1 ; [Li+]] | Intermediate 121 (382 mg, 0.70 mmol) 5 hours at 50° C. | 355 mg | LC (Method 5): $t_R$ = 0.54 min; Mass spectrum (ES+): m/z = 286 [M − Li + 2H]$^+$. |
| 126 | 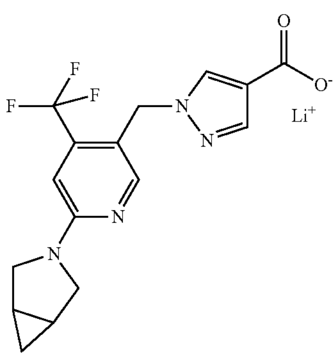 [SMILES: O=C([O-])c1cnn(Cc2cnc(N3CC4CC4C3)cc2C(F)(F)F)c1 ; [Li+]] | Intermediate 13 (2.0 g), 1,4-dioxane (2 mL) and water (1 mL) as solvent 1 hour at 70° C. product triturated with ethyl acetate | 600 mg | LC (Method 1): $t_R$ = 0.80 min; Mass spectrum (ES+): m/z = 353 [M − Li + 2H]$^+$. |
| 127 | 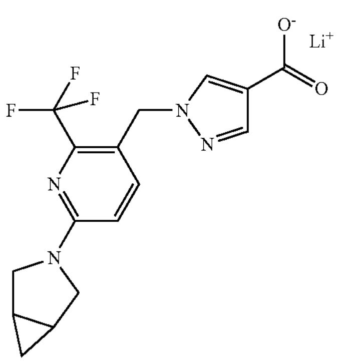 [SMILES: O=C([O-])c1cnn(Cc2ccc(N3CC4CC4C3)nc2C(F)(F)F)c1 ; [Li+]] | Intermediate 60 (1.2 g), 1,4-dioxane (2 mL) and water (1 mL) as solvent 1 hour at 70° C. | 1.0 g | LC (Method 2): $t_R$ = 3.34 min; Mass spectrum (ES+): m/z = 354 [M − Li + 2H]$^+$. |

| Intermediate | Structure | Starting intermediates | Yield | Analysis |
|---|---|---|---|---|
| 128 | 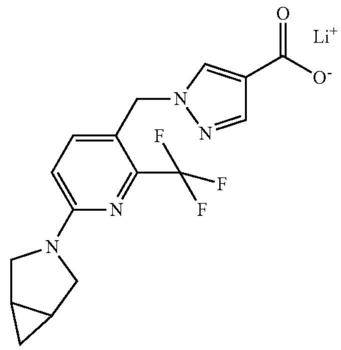 [SMILES: O=C([O-])c1cnn(Cc2ccc(N3CC4CC4C3)nc2C(F)(F)F)c1 ; [Li+]] | Intermediate 12 (1.1 g) 1.4 dioxane (2 mL) and water (1 mL) as solvent 1 hour at 70° C. | 0.95 g | LC (Method 2): $t_R$ = 3.60 min; Mass spectrum (ES+): m/z = 354 [M − Li + 2H]$^+$. |
| 129 | 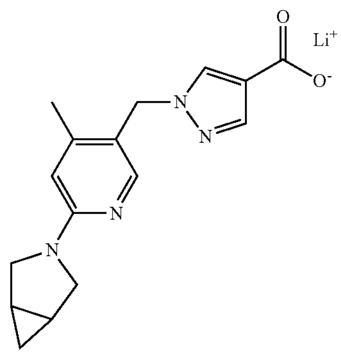 | Intermediate 62 (500 mg), 1,4-dioxane (2 mL) and water (1 mL) as solvent 1 hour at 70° C. Product triturated with diethyl ether | 130 mg | LC (Method 1): $t_R$ = 0.64 min; Mass spectrum (ES+): m/z = 300 [M − Li + 2H]$^+$. |
| 130 | 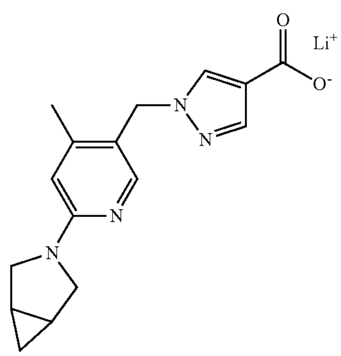 [SMILES: Cc1cc(N2CC3CC3C2)ncc1Cn1cc(C(=O)[O-])cn1 ; [Li+]] | Intermediate 14 (400 mg), 1,4-dioxane (2 mL) and water (1 mL) as solvent 1 hour at 70° C. Product triturated with diethyl ether | 135 mg | LC (Method 1): $t_R$ = 0.63 min; Mass spectrum (ES+): m/z = 299 [M − Li + 2H]$^+$. |

Intermediate 131

(6,7-Dihydro-5H-[2]pyrindin-7-yl)-carbamic acid tert-butyl ester

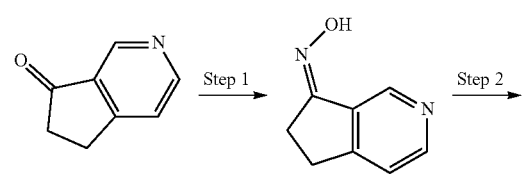

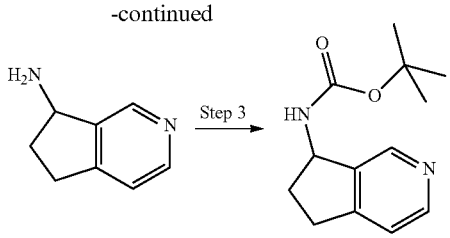

Step 1: 5,6-Dihydro-[2]pyrindin-7-one oxime 5,6-Dihydro-[2]pyrindin-7-one (synthesis described in EP2098513A1, 5 g, 37.5 mmol), hydroxylamine hydrochloride (3.13 g, 45.1 mmol) and sodium acetate (3.70 g, 45.0 mmol) are dissolved in water (8 ml), the mixture is stirred and ethanol (8 ml) is added to the solution. The mixture is stirred under reflux for 2 hours. The mixture is concentrated and ethyl acetate is added, salts are filtered off and the solution is concentrated to give the title compound (Yield 5.5 g)

LC (Method 1): $t_R$=0.61 min; Mass spectrum (ES+): m/z=149 [M+H]$^+$.

Step 2: 6,7-Dihydro-5H-[2]pyrindin-7-ylamine 5,6-Dihydro-[2]pyrindin-7-one oxime (5 g, 33.7 mmol) and zinc (4.41 g, 67.5 mmol) are dissolved in ethanol, the mixture is cooled to 0° C. then HCl aq. solution 37% (5.54 ml, 67.5 mmol) is added. After gas evolution is finished the mixture is heated to 70° C. and stirred for 20 minutes. The mixture is filtered and used in the next step without purification. (Yield 8.0 g)

LC (Method 1): $t_R$=0.32 min; Mass spectrum (ES+): m/z=135 [M+H]$^+$.

Step 3: (6,7-Dihydro-5H-[2]pyrindin-7-yl)-carbamic acid tert-butyl ester

Crude 6,7-Dihydro-5H-[2]pyrindin-7-ylamine (8 g) and di-tert-butyldicarbonate (13.0 g, 59.6 mmol) are dissolved in tetrahydrofuran (30 ml). The mixture is stirred at room temperature for 24 hours. The solution is concentrated and the residue is purified by flash chromatography (0-100% ethyl acetate in cyclohexane) to give the title compound (Yield 6 g).

LC (Method 1): $t_R$=0.91 min; Mass spectrum (ES+): m/z=235 [M+H]$^+$

The compounds in the following table are synthesized in analogy to the method described for Intermediate 131.

| Intermediate | Structure | Starting intermediates | Yield | Analysis |
|---|---|---|---|---|
| 132 | 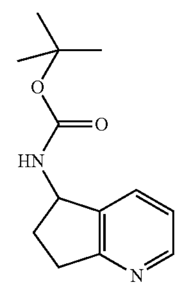 | 6,7-Dihydro-[1]pyrindin-5-one (available from Santailabs ADH-7693, 2.7 g) | 1.2 g | LC (Method 7): $t_R$ = 3.02 min; Mass spectrum (ES+): m/z = 299 [M + H]$^+$. |
| 133 | 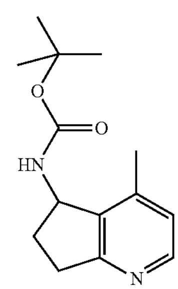 [SMILES: Cc1ccnc2c1C(NC(=O)OC(C)(C)C)CC2] | 4-Methyl-6,7-dihydro-[1]pyrindin-5-one, (synthesis described in *Pharmazie*, 1995, vol. 50, 9 p. 589-592, 2.0 g). | 2.0 g | LC (Method 3): $t_R$ = 0.91 min; Mass spectrum (ES+): m/z = 249 [M + H]$^+$. |
| 134 | 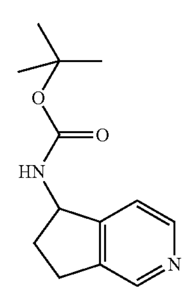 [SMILES: CC(C)(C)OC(=O)NC1CCc2cnccc21] | 6,7-Dihydro-[2]pyrindin-5-one (available from ABCR AB 401490 (1 g) | 1.7 g | LC (Method 3): $t_R$ = 0.86 min; Mass spectrum (ES+): m/z = 235 [M + H]$^+$. |

Intermediate 135

2-((R)-2-Oxy-6,7-dihydro-5H-[2]pyrindin-5-yl)-isoindole-1,3-dione

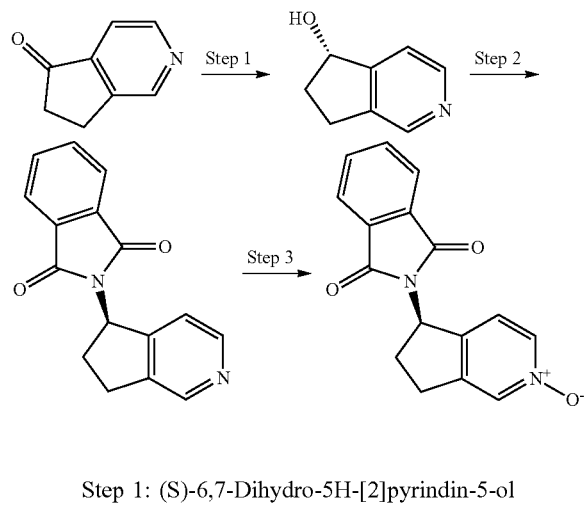

Step 1: (S)-6,7-Dihydro-5H-[2]pyrindin-5-ol

Triethylamine (16.18 ml, 116.1 mmol) is dissolved in dichloromethane (100 ml), the mixture is cooled to 0° C. and formic acid (4.95 ml, 131.4 mmol) is added dropwise, then 6,7-Dihydro-[2]pyrindin-5-one (commercially available from ABCR AB 401490, 5 g, 37.5 mmol) and Chloro[(1S, 2S)-(−)-2-amino-1,2-diphenylethyl](4-toluensulfonyl) amido)(mesitylene) ruthenium(II) (467 mg, 0.75 mmol) is added. The mixture is stirred at room temperature overnight. Dichloromethane (100 ml) is added and the solution is washed with Na$_2$CO$_3$ aq. sat. solution (15 ml), the organic layer is collected, dried over sodium sulfate filtered and concentrated to give the title compound (Yield 5.0 g).

LC (Method 1): t$_R$=0.33 min; Mass spectrum (ES+): m/z=136 [M+H]$^+$ Chiral HPLC (Daicel chiralpak AS-H, Hexane:EtOH 85:15 1 ml/min, 25° C.) T$_R$=5.46 min, 98.0%.

Absolute stereochemistry assigned by analogy with Noyori et. al., J. Am. Chem. Soc., 1995, 117 (28), pp 7562-7563.

Step 2: (R)-2-(6,7-Dihydro-5H-[2]pyrindin-5-yl)-isoindole-1,3-dione (S)-6,7-Dihydro-5H-[2]pyrindin-5-ol (2 g, 13.3 mmol), phthalimide (1.96 g, 13.31 mmol) and triphenylphosphine (3.49 g, 13.3 mmol) are dissolved in tetrahydrofuran (40 ml). The solution is cooled to 0° C. then diisopropylazodicarboxylate (2.64 ml, 13.3 mmol) is added. The mixture is stirred at room temperature for 3 hours. The solvent is removed under vacuum and the residue is purified by flash chromatography (0-80% ethyl acetate in cyclohexane) to give the title compound (Yield 3.5 g).

LC (Method 1): t$_R$=0.92 min; Mass spectrum (ES+): m/z=265 [M+H]$^+$

Step 3: 2-((R)-2-Oxy-6,7-dihydro-5H-[2]pyrindin-5-yl)-isoindole-1,3-dione (R)-2-(6,7-Dihydro-5H-[2]pyrindin-5-yl)-isoindole-1,3-dione (3.5 g, 13.2 mmol) is dissolved in dichloromethane (20 ml), the solution is cooled to 0° C. and 3-chloroperoxybenzoic acid (3.85 g, 17.2 mmol) is added. The mixture is warmed to room temperature and stirred overnight. Dichloromethane (100 ml) is added and the solution is washed twice with Na$_2$CO$_3$ aq. sat. solution (20 ml), the organic layer is collected, dried over sodium sulfate filtered and concentrated to give the title compound. (Yield 3.5 g).

LC (Method 1): t$_R$=0.70 min; Mass spectrum (ES+): m/z=281 [M+H]$^+$

Intermediate 136

2-((R)-1-Oxy-6,7-dihydro-5H-[1]pyrindin-5-yl)-isoindole-1,3-dione

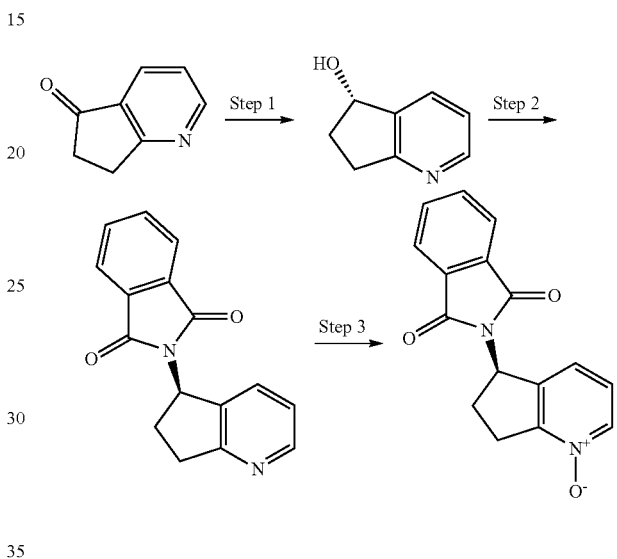

Step 1: (S)-6,7-Dihydro-5H-[1]pyrindin-5-ol

Triethylamine (32.6 ml, 232.8 mmol) is dissolved in dichloromethane (200 ml), the mixture is cooled to 0° C. and formic acid (9.82 ml, 262.8 mmol) is added dropwise, then 6,7-dihydro-[1]pyridin-5-one (available from Santailabs ADH-7693, 10 g, 75.1 mmol) and chloro[(1S,2S)-(−)-2-amino-1,2-diphenylethyl](4-toluensulfonyl) amido) (mesitylene) ruthenium(II) (200 mg, 0.75 mmol) are added. The mixture is stirred at room temperature overnight. Dichloromethane (100 ml) is added and the solution is washed with Na$_2$CO$_3$ aq. sat. solution, the organic layer is collected, dried over sodium sulfate filtered and concentrated to give the title compound. (9.0 g)

LC (Method 1): t$_R$=0.38 min; Mass spectrum (ES+): m/z=136 [M+H]$^+$

Chiral HPLC (Daicel chiralpak AD-H, Hexane:IPA 80:20 1 ml/min, 25° C.) T$_R$=4.78 min, 97.7%.

Absolute stereochemistry assigned by analogy with Noyori et. al., J. Am. Chem. Soc., 1995, 117 (28), pp 7562-7563.

Step 2: (R)-2-(6,7-Dihydro-5H-[1]pyrindin-5-yl) isoindole-1,3-dione (S)-6,7-Dihydro-5H-[1]pyrindin-5-ol (1 g, 7.39 mmol), phthalimide (1.08 g, 7.39 mmol) and triphenylphosphine (1.94 g, 7.39 mmol) are dissolved in tetrahydrofuran (20 ml). The solution is cooled to 0° C. then diisopropylazodicarboxylate (1.46 ml, 7.39 mmol) is added. The mixture is stirred at room temperature for 3 hours. The solvent is removed under vacuum and the residue is purified by flash chromatography (0-80% ethyl acetate in cyclohexane) to give the title compound. (Yield 1.49 g)

LC (Method 1): $t_R$=0.89 min; Mass spectrum (ES+): m/z=265 [M+H]$^+$

Step 3: 2-((R)-1-Oxy-6,7-dihydro-5H-[1]pyrindin-5-yl)-isoindole-1,3-dione (R)-2-(6,7-Dihydro-5H-[1]pyrindin-5-yl)-isoindole-1,3-dione (1.49 g, 4.51 mmol) is dissolved in dichloromethane (20 ml), the solution is cooled to 0° C. and 3-chloroperoxybenzoic acid (1.31 g, 5.86 mmol) is added. The mixture is warmed to room temperature and stirred overnight. Dichloromethane (100 ml) is added and the solution is washed twice with Na$_2$CO$_3$ aq. sat. solution (20 ml), the organic layer is collected, dried over sodium sulfate filtered and concentrated to give the title compound. (Yield 1.6 g).

LC (Method 1): $t_R$=0.68 min; Mass spectrum (ES+): m/z=281 [M+H]$^+$

Intermediate 137

(R)-6,7-Dihydro-5H-[2]pyrindine-1,5-diamine dihydrochloride

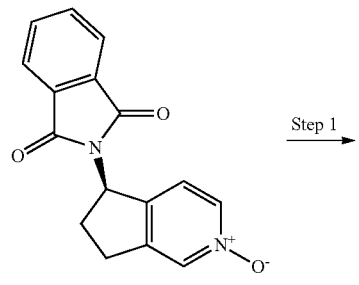

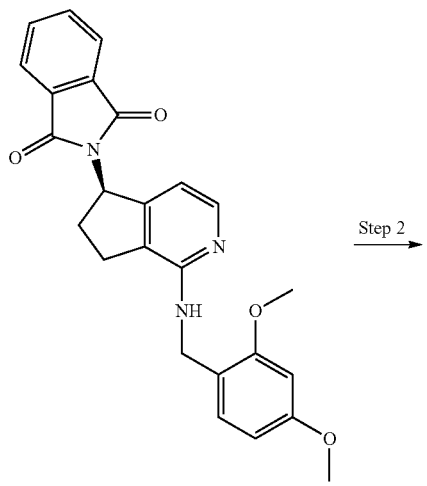

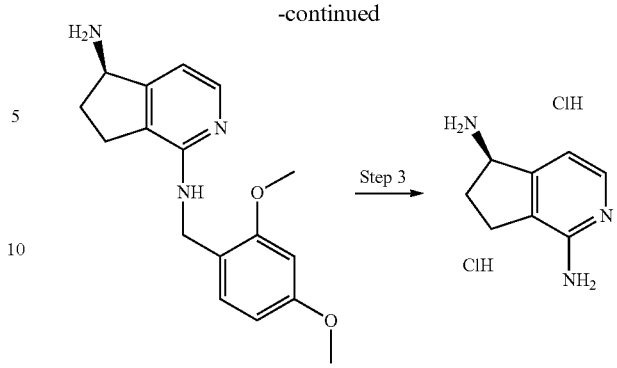

Step 1: 2-[(R)-1-(2,4-Dimethoxy-benzylamino)-6,7-dihydro-5H-[2]pyrindin-5-yl]-isoindole-1,3-dione 2-((R)-2-Oxy-6,7-dihydro-5H-[2]pyrindin-5-yl)-isoindole-1,3-dione (Intermediate 135, 3.5 g, 11.2 mmol) is dissolved in anhydrous dichloromethane (50 ml), then bromotripyrrolidinophosphonium hexafluorophosphate (9.43 g, 20.2 mmol), 2,4-dimethoxybenzylamine (2.19 ml, 14.6 mmol) and N,N-diisopropylethylamine (6.80 ml, 39.3 mmol) are added at 0° C. and the mixture is stirred at room temperature overnight. Dichloromethane (50 ml) is added and the mixture is washed with NaHCO$_3$ aq. sat. solution (50 ml) and brine (50 ml). the organic layer is collected, dried over sodium sulfate filtered and concentrated. The residue is purified by flash chromatography (20-100% ethyl acetate in cyclohexane) to give the title compound (Yield 3.5 g).

LC (Method 1): $t_R$=1.23 min; Mass spectrum (ES+): m/z=430 [M+H]$^+$

Step 2: (R)—N*1*-(2,4-Dimethoxy-benzyl)-6,7-dihydro-5H-[2]pyrindine-1,5-diamine

2-[(R)-1-(2,4-Dimethoxy-benzylamino)-6,7-dihydro-5H-[2]pyrindin-5-yl]-isoindole-1,3-dione (7 g, 15.5 mmol) and hydrazine (50% aq. solution, 2.91 ml, 46.4 mmol) are dissolved in ethanol (20 ml) and tetrahydrofuran (20 ml). The mixture is heated at 70° C. for 3 hours. The solution is concentrated and the residue is purified by flash chromatography (0-30% isopropanol in dichloromethane) to give the title compound (Yield 3.2 g).

LC (Method 2): $t_R$=3.52 min; Mass spectrum (ES+): m/z=300 [M+H]$^+$

Step 3: (R)-6,7-Dihydro-5H-[2]pyrindine-1,5-diamine dihydrochloride (R)—N*1*-(2,4-Dimethoxy-benzyl)-6,7-dihydro-5H-[2]pyrindine-1,5-diamine (3.2 g, 10.6 mmoll) is dissolved in HCl 37% aq. solution (10 ml). The mixture is stirred at 70° C. for 10 minutes. The mixture is concentrated under vacuum and the residue is triturated with diethyl ether to give the title compound (Yield 3 g).

LC (Method 7): $t_R$=0.50 min; Mass spectrum (ES+): m/z=150 [M+H]$^+$

Intermediate 138

(R)-6,7-Dihydro-5H-[2]pyrindine-1,5-diamine dihydrochloride

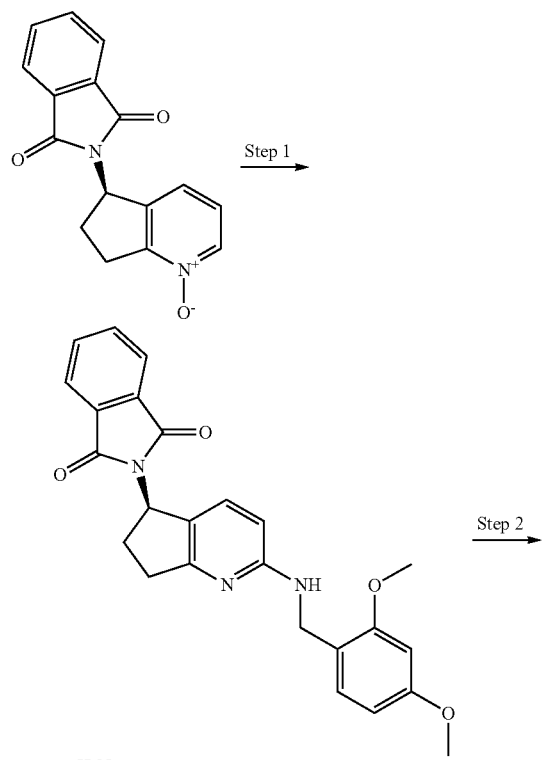

Step 1: 2-[(R)-2-(2,4-Dimethoxy-benzylamino)-6,7-dihydro-5H-[1]pyrindin-5-yl]-isoindole-1,3-dione 2-((R)-1-Oxy-6,7-dihydro-5H-[1]pyrindin-5-yl)-isoindole-1,3-dione (Intermediate 136, 1.6 g, 5.14 mmol) is dissolved in anhydrous dichloromethane (50 ml), then bromotripyrrolidinophosphonium hexafluorophosphate (4.31 g, 9.25 mmol), 2,4-dimethoxybenzylamine (1.03 ml, 6.68 mmol) and N,N-diisopropylethylamine (3.11 ml, 17.9 mmol) are added, the mixture is stirred at room temperature overnight. Dichloromethane (50 ml) is added and the mixture is washed with NaHCO$_3$ aq. sat. solution (50 ml) and brine (50 ml). The organic layer is collected, dried over sodium sulfate filtered and concentrated. The residue is purified by flash chromatography (20-100% ethyl acetate in cyclohexane) to give the title compound (Yield 0.67 g).

LC (Method 1): $t_R$=1.23 min; Mass spectrum (ES+): m/z=430 [M+H]$^+$

Step 2: (R)—N*2*-(2,4-Dimethoxy-benzyl)-6,7-dihydro-5H-[1]pyrindine-2,5-diamine

2-[(R)-2-(2,4-Dimethoxy-benzylamino)-6,7-dihydro-5H-[1]pyrindin-5-yl]-isoindole-1,3-dione (0.67 g, 1.48 mmol) and ethanolamine (0.54 ml, 8.9 mmol) are dissolved in toluene (20 ml). The mixture is heated at 70° C. for 3 hours. The organic layer is washed with water, collected and concentrated. The residue is purified by flash chromatography (20-100% ethyl acetate in cyclohexane) to give the title compound (Yield 220 mg).

LC (Method 1): $t_R$=0.73 min; Mass spectrum (ES+): m/z=300 [M+H]$^+$

Step 3: (R)-6,7-Dihydro-5H-[2]pyrindine-1,5-diamine dihydrochloride (R)—N*2*-(2,4-Dimethoxy-benzyl)-6,7-dihydro-5H-[1]pyrindine-2,5-diamine (220 mg, 0.69 mmol) is dissolved in HCl 37% aq. solution (2 ml) and tetrahydrofuran (2 ml). The mixture is stirred at 70° C. for 1 hour. The mixture is concentrated and the residue is triturated with diethyl ether to give the title compound (Yield 214 mg).

LC (Method 1): $t_R$=0.27 min; Mass spectrum (ES+): m/z=150 [M+H]$^+$

Intermediate 139

6,7-Dihydro-5H-[2]pyrindine-3,7-diamine dihydrochloride

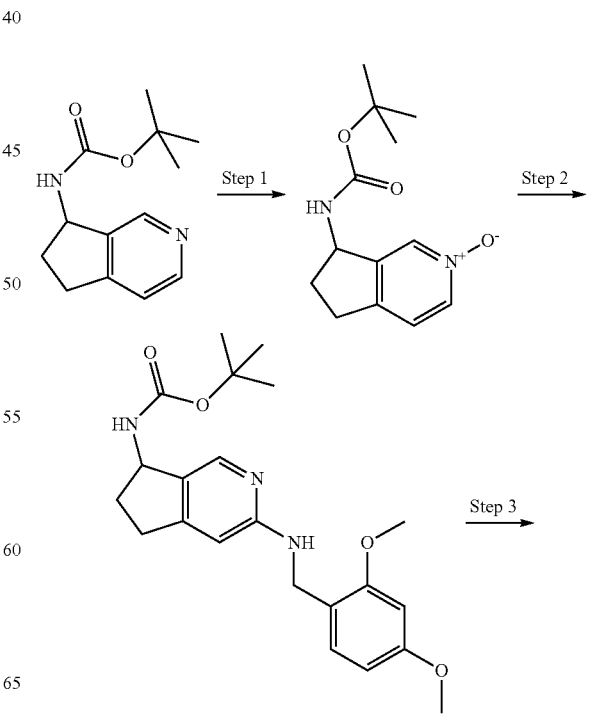

-continued

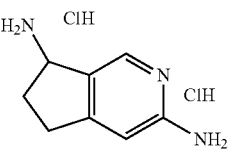

Step 1: (2-Oxy-6,7-dihydro-5H-[2]pyrindin-7-yl)-carbamic acid tert-butyl ester (6,7-Dihydro-5H-[2]pyrindin-7-yl)-carbamic acid tert-butyl ester (Intermediate 131, 6 g, 25.6 mmol) is dissolved in dichloromethane (40 ml), the solution is cooled to 0° C. and 3-chloroperoxybenzoic acid (7.46 g, 33.29 mmol) is added. The mixture is warmed to room temperature and stirred overnight. Dichloromethane (20 ml) is added and the solution is washed twice with Na$_2$CO$_3$ aq. Sat. solution (20 ml) and brine (20 ml), the organic layer is collected, dried over sodium sulfate filtered and concentrated to give the title compound. (Yield 6 g).

LC (Method 1): t$_R$=0.69 min; Mass spectrum (ES+): m/z=251 [M+H]$^+$

Step 2: [3-(2,4-Dimethoxy-benzylamino)-6,7-dihydro-5H-[2]pyrindin-7-yl]-carbamic acid tert-butyl ester (2-Oxy-6,7-dihydro-5H-[2]pyrindin-7-yl)-carbamic acid tert-butyl ester (6 g, 23.97 mmol) is dissolved in anhydrous dichloromethane (40 ml), then bromotripyrrolidinophosphonium hexafluorophosphate (14.53 g, 31.1 mmol), 2,4-dimethoxybenzylamine (3.6 ml, 23.97 mmol) and N,N-diisopropylethylamine (15.6 ml, 91.1 mmol) are added, the mixture is stirred at room temperature overnight. Dichloromethane (40 ml) is added and the mixture is washed with NaHCO$_3$ aq. sat. solution (10 ml) and brine (10 ml). The organic layer is collected, dried over sodium sulfate, filtered and concentrated. The residue is purified by flash chromatography (20-100% ethyl acetate in cyclohexane) to give the title compound (Yield 2 g).

LC (Method 1): t$_R$=1.21 min; Mass spectrum (ES+): m/z=400 [M+H]$^+$

Step 3: 6,7-Dihydro-5H-[2]pyrindine-3,7-diamine dihydrochloride

[3-(2,4-Dimethoxy-benzylamino)-6,7-dihydro-5H-[2]pyrindin-7-yl]-carbamic acid tert-butyl ester (2 g, 5.0 mmol) is dissolved in HCl 37% aq. solution (10 ml). The mixture is stirred at room temperature for 1 h. The mixture is concentrated and the residue is triturated with diethyl ether to give the title compound (Yield 1 g).

LC (Method 1): t$_R$=0.30 min; Mass spectrum (ES+): m/z=150 [M+H]$^+$

Intermediate 140

6,7-Dihydro-5H-[2]pyrindine-1,7-diamine

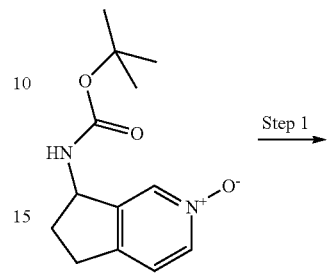

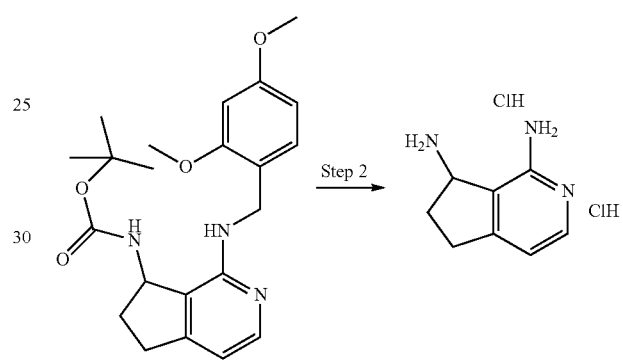

Step 1: [1-(2,4-Dimethoxy-benzylamino)-6,7-dihydro-5H-[2]pyrindin-7-yl]-carbamic acid tert-butyl ester The title compound was isolated as a second product during step 2 of the preparation of Intermediate 139 (Yield 5.0 g).

LC (Method 1): t$_R$=1.29 min; Mass spectrum (ES+): m/z=400 [M+H]$^+$

Step 2: 6,7-Dihydro-5H-[2]pyrindine-1,7-diamine

[1-(2,4-Dimethoxy-benzylamino)-6,7-dihydro-5H-[2]pyrindin-7-yl]-carbamic acid tert-butyl ester (5.0 g, 12.5 mmol) is dissolved in HCl 37% aq. solution. The mixture is stirred at room temperature for 1 hour. The mixture is concentrated and the residue is triturated with diethyl ether. (Yield 2.5 g)

LC (Method 1): t$_R$=0.30 min; Mass spectrum (ES+): m/z=150 [M+H]+

The compounds in the following table are synthesized in analogy to the method described for Intermediate 139.

| Intermediate | Structure | Starting intermediates | Yield | Analysis |
|---|---|---|---|---|
| 141 | 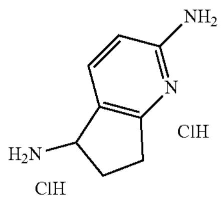 [SMILES: Nc1ccc2c(n1)CCC2N ; Cl ; Cl] | (6,7-Dihydro-5H-[1]pyrindin-5-yl)-carbamic acid tert-butyl ester (Intermediate 132, 1.0 g) | 1.2 g | LC (Method 8): $t_R$ = 0.37 min; Mass spectrum (ES+): m/z = 150 [M + H]+. |
| 142 | 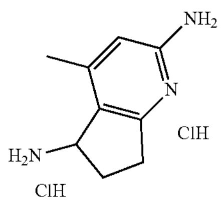 | (4-Methyl-6,7-dihydro-5H-[1]pyrindin-5-yl)-carbamic acid tert-butyl ester (Intermediate 133, 2.0 g) | 700 mg | LC (Method 3): $t_R$ = 0.26 min; Mass spectrum (ES+): m/z = 164 [M + H]+. |
| 143 | 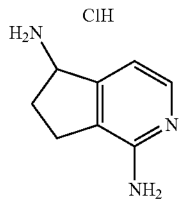 [SMILES: Cl ; Nc1nccc2c1CCC2N] | Intermediate 134 (1.7 g) | 250 mg | LC (Method 1): $t_R$ = 0.25 min; Mass spectrum (ES+): m/z = 150 [M + H]+. |
| 144 | 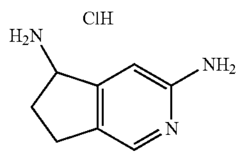 [SMILES: Cl ; Nc1cc2c(cn1)CCC2N] | Intermediate 134 (1.7 g) Isolated as a second product during the preparation of Intermediate 143, seperation of the isomers in step 2. | 20 mg | LC (Method 1): $t_R$ = 0.25 min; Mass spectrum (ES+): m/z = 150 [M + H]+. |

Intermediate 145

4-Trifluoromethyl-6,7-dihydro-5H-[1]pyrindine-2,5-diamine hydrochloride

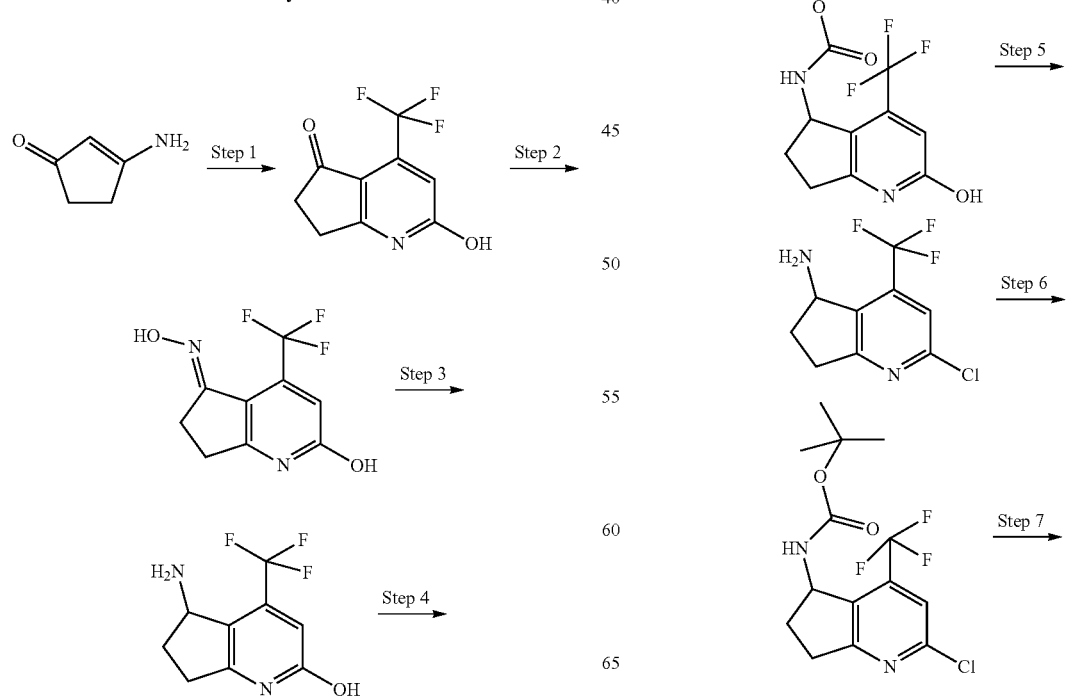

-continued

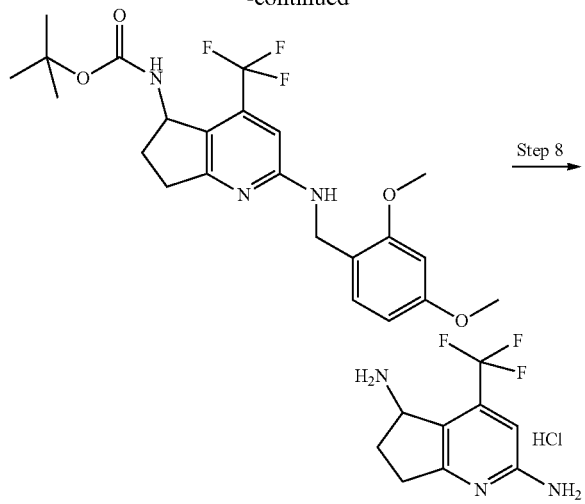

Step 1: 2-Hydroxy-4-trifluoromethyl-6,7-dihydro-[1]pyrindin-5-one

3-Amino-cyclopent-2-enone (available from Astatech CN 90005, 10 g, 102.9 mmol) and ethyl 4,4,4-trifluoroacetoacetate (20.8 g, 113.2 mmol) are dissolved in cyclohexanol (20 ml), the solution is warmed to 140° C. and stirred for 2 hours. The reaction mixture is concentrated then $H_2O$ (100 ml) and dichloromethane (300 ml) are added. The organic layer is collected, filtered on a Celite pad and concentrated. The residue is purified by flash chromatography (0-30% methanol in dichloromethane) to give the title compound (yield 5.8 g).

LC (Method 1): $t_R$=0.73 min; Mass spectrum (ES+): m/z=218 [M+H]$^+$

Step 2: 2-Hydroxy-4-trifluoromethyl-6,7-dihydro-[1]pyrindin-5-one oxime

2-Hydroxy-4-trifluoromethyl-6,7-dihydro-[1]pyrindin-5-one (3.50 g, 16.1 mmol), sodium acetate (1.58 g, 19.3 mmol) and hydroxylamine hydrochloride (1.34 g, 19.3 mmol) are dissolved in ethanol (15 ml) and water (15 ml). The solution is stirred under reflux for 2 hours, then the reaction mixture is concentrated and water (10 ml) is added. The precipitate formed is collected and dried under vacuum to give the title compound (yield 3.0 g).

LC-MS (Method 1): $t_R$=0.57 min; Mass spectrum (ES+): m/z=233 [M+H]$^+$.

Step 3: 5-Amino-4-trifluoromethyl-6,7-dihydro-5H-[1]pyrindin-2-ol

2-Hydroxy-4-trifluoromethyl-6,7-dihydro-[1]pyrindin-5-one oxime (3.0 g, 12.9 mmol) and zinc (4.22 g, 64.6 mmol) are dissolved in ethanol (30 ml), the reaction mixture is cooled to 0° C. then hydrochloric acid (37% aq. solution, 4.24 ml, 51.7 mmol) is added. After gas evolution is finished, the reaction mixture is heated to 70° C. and stirred for 20 minutes. The reaction mixture is filtered and used in the next step without purification.

LC (Method 1): $t_R$=0.34 min; Mass spectrum (ES+): m/z=219 [M+H]$^+$.

Step 4: (2-Hydroxy-4-trifluoromethyl-6,7-dihydro-5H-[1]pyrindin-5-yl)-carbamic acid tert-butyl ester Crude 5-Amino-4-trifluoromethyl-6,7-dihydro-5H-[1]pyrindin-2-ol (1 g) and di-tert-butyldicarbonate (0.77 g, 3.52 mmol) are dissolved in tetrahydrofuran (20 ml). The mixture is stirred at room temperature for 24 hours. The solution is concentrated and the residue is partitioned between ethyl acetate and $NH_4Cl$ saturated water solution. The organic layer is collected and concentrated under vacuum to give the title compound (yield 100 mg).

LC (Method 1): $t_R$=0.89 min; Mass spectrum (ES+): m/z=319 [M+H]$^+$.

Step 5: 2-Chloro-4-trifluoromethyl-6,7-dihydro-5H-[1]pyrindin-5-ylamine (2-Hydroxy-4-trifluoromethyl-6,7-dihydro-5H-[1]pyrindin-5-yl)-carbamic acid tert-butyl ester (100 mg, 0.31 mmol) is dissolved in pyridine (1 ml), then phosphorus oxychloride (96 mg, 0.63 mmol) is added and the reaction mixture is heated to 80° C. and stirred for 2 hours. The reaction mixture is concentrated and the crude obtained is used in the next step without purification (yield 74 mg).

LC (Method 1): $t_R$=0.76 min; Mass spectrum (ES+): m/z=237 [M+H]$^+$.

Step 6: (2-Chloro-4-trifluoromethyl-6,7-dihydro-5H-[1]pyrindin-5-yl)-carbamic acid tert-butyl ester 2-Chloro-4-trifluoromethyl-6,7-dihydro-5H-[1]pyrindin-5-ylamine (74 mg, 0.31 mmol) and di-tert-butyldicarbonate (75 mg, 0.34 mmol) are dissolved in tetrahydrofuran (5 ml). The reaction mixture is stirred at room temperature for 24 hours. The solution is concentrated and the residue is partitioned between ethyl acetate and $NH_4Cl$ saturated water solution, the organic layer is collected and concentrated under vacuum to give the title compound (yield 90 mg).

LC (Method 1): $t_R$=1.27 min; Mass spectrum (ES+): m/z=337 [M+H]$^+$.

Step 7: [2-(2,4-Dimethoxy-benzylamino)-4-trifluoromethyl-6,7-dihydro-5H-[1]pyrindin-5-yl]-carbamic acid tert-butyl ester (2-Chloro-4-trifluoromethyl-6,7-dihydro-5H-[1]pyrindin-5-yl)-carbamic acid tert-butyl ester (75 mg, 0.218 mmol) and 2,4-dimethoxybenzylamine (146 mg, 0.873 mmol) are dissolved in anhydrous N,N-dimethylacetamide (1 ml). The reaction mixture is heated under microwave irradiation (140° C., 30 W) for 1 hour. The reaction mixture is purified by reverse phase flash chromatography (C18, 40-100% acetonitrile in water) to give the title compound (yield 20 mg).

LC (Method 1): $t_R$=1.37 min; Mass spectrum (ES+): m/z=468 [M+H]+

Step 8: 4-Trifluoromethyl-6,7-dihydro-5H-[1]pyrindine-2,5-diamine hydrochloride

[2-(2,4-Dimethoxy-benzylamino)-4-trifluoromethyl-6,7-dihydro-5H-[1]pyrindin-5-yl]-carbamic acid tert-butyl ester (20 mg, 0.043 mmol) is dissolved in 0.2 mL of a 37% aq. solution of hydrochloric acid. The reaction mixture is stirred at 80° C. for 30 minutes. then it is concentrated under vacuum. The crude obtained is triturated with diethyl ether to give the title compound (yield 14 mg).

LC (Method 1): $t_R$=0.42 min; Mass spectrum (ES+): m/z=201 [M-NH$_3$+H]+

SYNTHESIS OF EXAMPLES

Example 1

1-[4-((1R,5S)-2-Oxo-3-aza-bicyclo[3.1.0]hex-3-ylmethyl)-benzyl]-1H-pyrazole-4-carboxylic acid ((R)-2-amino-6,7-dihydro-5H-[1]pyrindin-5-yl)-amide

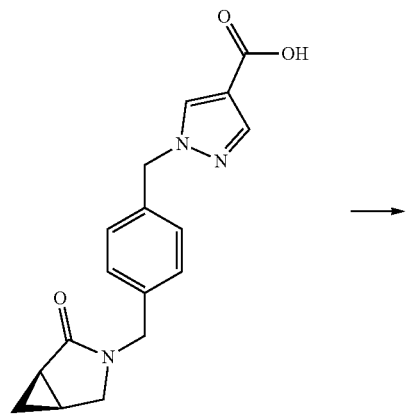

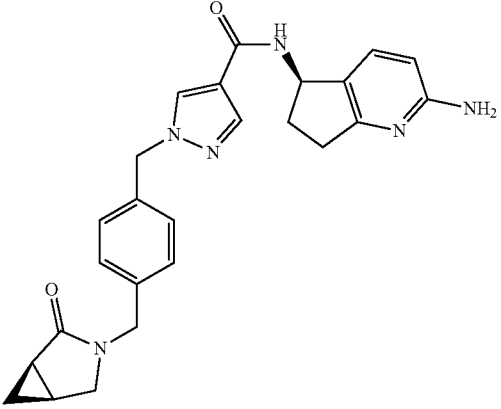

1-[4-((1R,5S)-2-Oxo-3-aza-bicyclo[3.1.0]hex-3-ylmethyl)-benzyl]-1H-pyrazole-4-carboxylic acid (Intermediate 86, 90 mg, 0.27 mmol) and N,N-diisopropylethylamine (0.118 ml, 0.69 mmol) are dissolved in N,N-dimethylformamide (4 ml), then HATU (125 mg, 0.33 mmol) is added. The reaction mixture is stirred for 5 minutes, then 6,7-dihydro-5H-[2]pyrindine-3,7-diamine dihydrochloride (Intermediate 138, 70 mg, 0.30 mmol) is added. The reaction mixture is stirred at room temperature overnight. Then it is purified by reverse phase flash chromatography (C18, 0-50% acetonitrile in water) to give the title compound (yield 44 mg).

LC (Method 2): $t_R$=2.93 min; Mass spectrum (ES+): m/z=443 [M+H]+

The following examples are prepared in analogy to Example 1, starting from the corresponding Acid and Amine Intermediates:

| Example | Structure | Starting intermediates | Yield | Analysis |
|---|---|---|---|---|
| 2 | 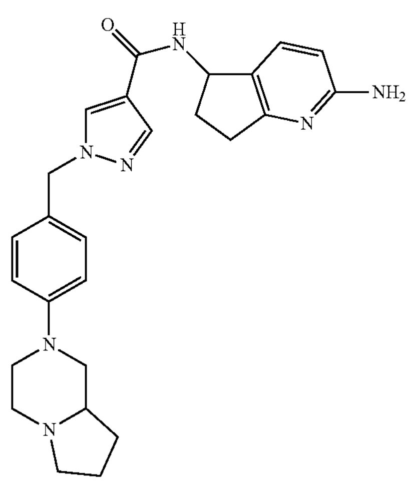 [SMILES: Nc1ccc2c(n1)CCC2NC(=O)c1cnn(Cc2ccc(N3CCN4CCCC4C3)cc2)c1] | Acid: Intermediate 102 (90 mg) Amine: Intermediate 141 (64 mg) | 56 mg | LC (Method 2): $t_R$ = 2.98 min; Mass spectrum (ES+): m/z = 458 [M + H]+. |

-continued

| Example | Structure | Starting intermediates | Yield | Analysis |
|---------|-----------|------------------------|-------|----------|
| 3 | 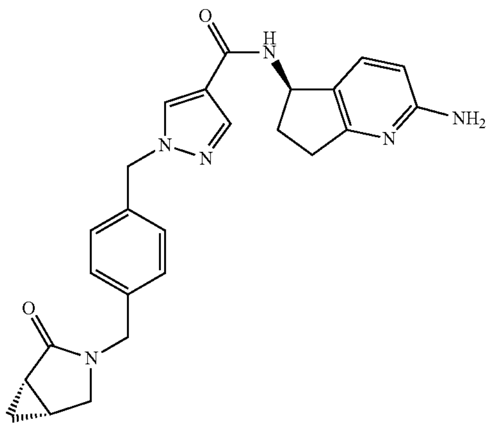 [SMILES: Nc1ccc2c(n1)CC[C@H]2NC(=O)c1cnn(Cc2ccc(CN3C[C@@H]4C[C@@H]4C3=O)cc2)c1] | Acid: Intermediate 88 (90 mg) Amine: Intermediate 138 (64 mg) | 54 mg | LC (Method 2): $t_R$ = 2.97 min; Mass spectrum (ES+): m/z = 443 [M + H]$^+$. |
| 4 | 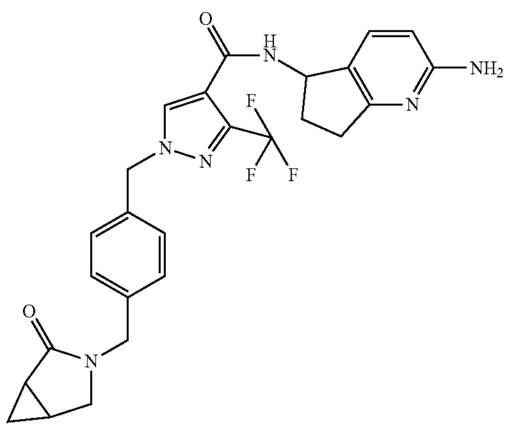 [SMILES: Nc1ccc2c(n1)CCC2NC(=O)c1cn(Cc2ccc(CN3CC4CC4C3=O)cc2)nc1C(F)(F)F] | Acid: Intermediate 93 (200 mg) Amine: Intermediate 141 (144 mg) | 101 mg | LC (Method 2): $t_R$ = 3.52 min; Mass spectrum (ES+): m/z = 511 [M + H]$^+$. |
| 5 | 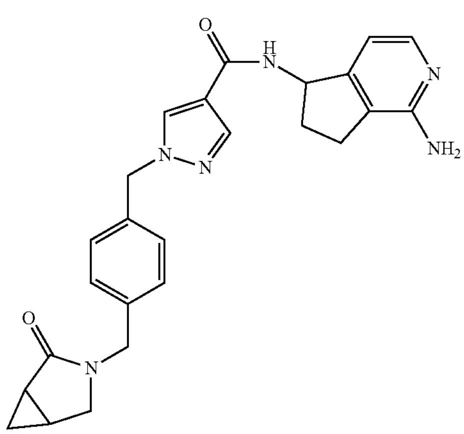 [SMILES: Nc1nccc2c1CCC2NC(=O)c1cnn(Cc2ccc(CN3CC4CC4C3=O)cc2)c1] | Acid: Intermediate 98 (70 mg) Amine: Intermediate 143 (51 mg) | 42 mg | LC (Method 2): $t_R$ = 2.90 min; Mass spectrum (ES+): m/z = 443 [M + H]$^+$. |

-continued

| Example | Structure | Starting intermediates | Yield | Analysis |
|---|---|---|---|---|
| 6 | 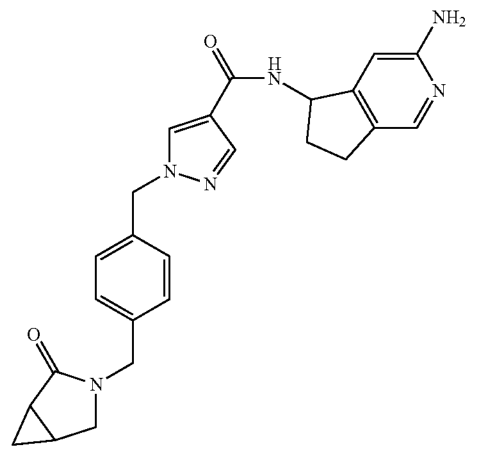 [SMILES: Nc1cc2c(cn1)CCC2NC(=O)c1cnn(Cc2ccc(CN3CC4CC4C3=O)cc2)c1] | Acid: Intermediate 98 (45 mg) Amine: Intermediate 144 (33 mg) | 35 mg | LC (Method 2): $t_R$ = 2.95 min; Mass spectrum (ES+): m/z = 443 [M + H]$^+$. |
| 7 | 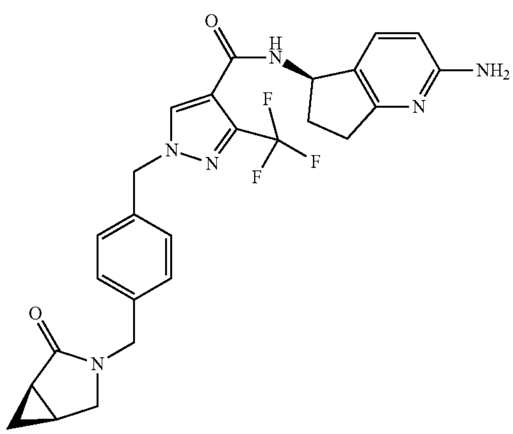 [SMILES: Nc1ccc2c(n1)CC[C@H]2NC(=O)c1cn(Cc2ccc(CN3C[C@H]4C[C@H]4C3=O)cc2)nc1C(F)(F)F] | Acid: Intermediate 89 (100 mg) Amine: Intermediate 138 (63 mg) | 45 mg | LC (Method 2): $t_R$ = 3.55 min; Mass spectrum (ES+): m/z = 511 [M + H]$^+$. |
| 8 | 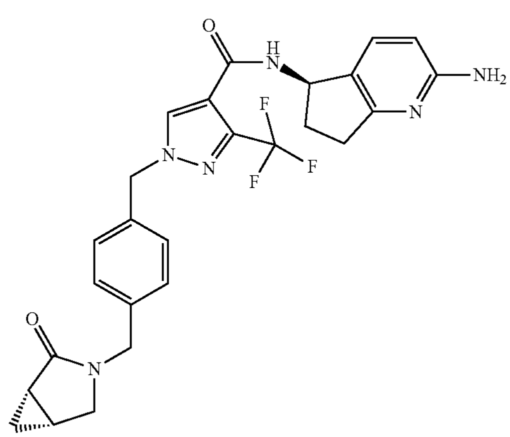 [SMILES: Nc1ccc2c(n1)CC[C@H]2NC(=O)c1cn(Cc2ccc(CN3C[C@@H]4C[C@@H]4C3=O)cc2)nc1C(F)(F)F] | Acid: Intermediate 90 (100 mg) Amine: Intermediate 138 (63 mg) | 61 mg | LC (Method 2): $t_R$ = 3.52 min; Mass spectrum (ES+): m/z = 511 [M + H]$^+$. |

-continued

| Example | Structure | Starting intermediates | Yield | Analysis |
|---|---|---|---|---|
| 9 | 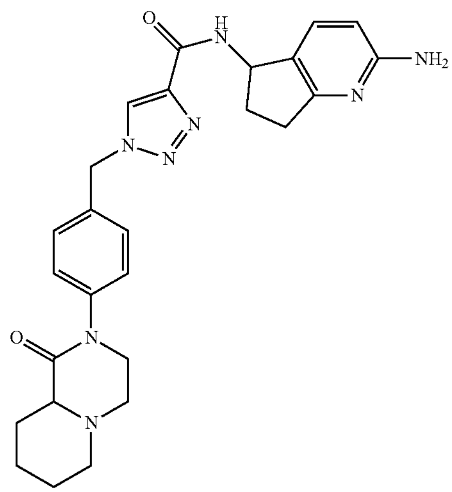 [SMILES: Nc1ccc2c(n1)CCC2NC(=O)c1cn(Cc2ccc(N3CCN4CCCCC4C3=O)cc2)nn1] | Acid: Intermediate 99 (20 mg) Amine: Intermediate 141 (8.4 mg) | 6 mg | LC (Method 2): $t_R$ = 3.17 min; Mass spectrum (ES+): m/z = 487 [M + H]$^+$. |
| 10 | 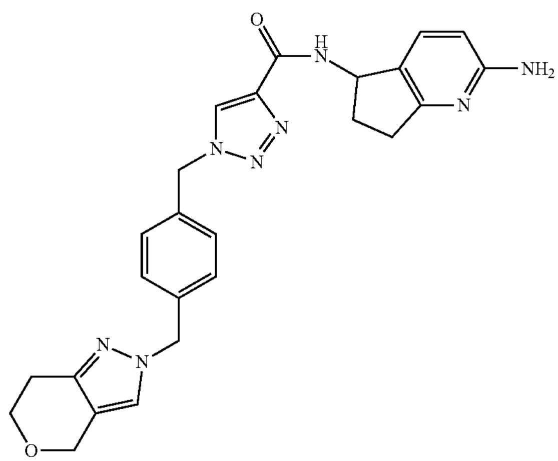 [SMILES: Nc1ccc2c(n1)CCC2NC(=O)c1cn(Cc2ccc(Cn3cc4c(n3)CCOC4)cc2)nn1] | Acid: Intermediate 92 (53 mg) Amine: Intermediate 141 (36 mg) | 14 mg | LC (Method 2): $t_R$ = 3.13 min; Mass spectrum (ES+): m/z = 471 [M + H]$^+$. |
| 11 | 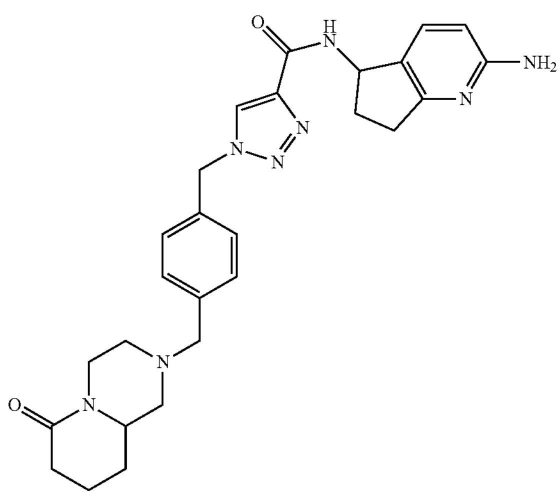 [SMILES: Nc1ccc2c(n1)CCC2NC(=O)c1cn(Cc2ccc(CN3CCN4C(=O)CCCC4C3)cc2)nn1] | Acid: Intermediate 87 (80 mg) Amine: Intermediate 141 (26 mg) | 6 mg | LC (Method 2): $t_R$ = 3.22 min; Mass spectrum (ES+): m/z = 501 [M + H]$^+$. |

-continued

| Example | Structure | Starting intermediates | Yield | Analysis |
|---|---|---|---|---|
| 12 | 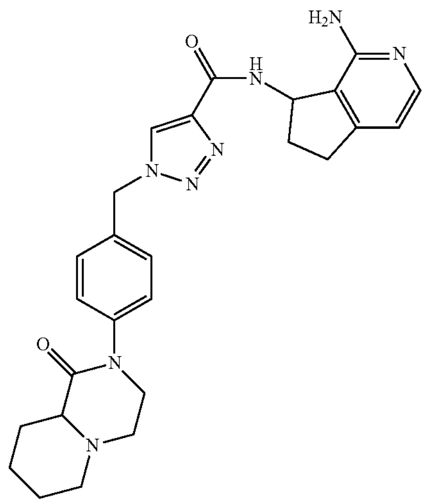 [SMILES: Nc1nccc2c1C(NC(=O)c1cn(Cc3ccc(N4CCN5CCCCC5C4=O)cc3)nn1)CC2] | Acid: Intermediate 99 (40 mg) Amine: Intermediate 140 (23 mg) | 40 mg | LC (Method 2): $t_R$ = 3.47 min; Mass spectrum (ES+): m/z = 487 [M + H]$^+$. |
| 13 | 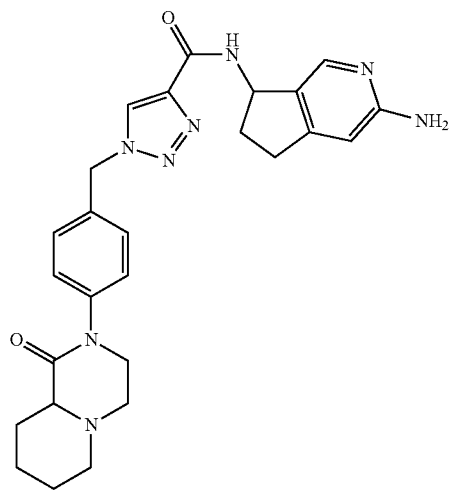 [SMILES: Nc1cc2c(cn1)C(NC(=O)c1cn(Cc3ccc(N4CCN5CCCCC5C4=O)cc3)nn1)CC2] | Acid: Intermediate 99 (20 mg) Amine: Intermediate 139 (12 mg) | 16 mg | LC (Method 2): $t_R$ = 3.17 min; Mass spectrum (ES+): m/z = 487 [M + H]$^+$. |
| 14 | 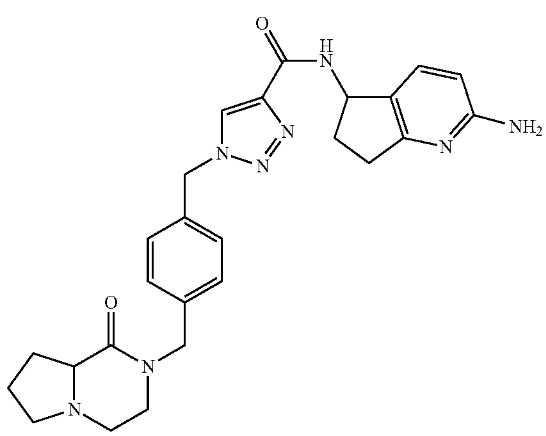 [SMILES: Nc1ccc2c(n1)CCC2NC(=O)c1cn(Cc2ccc(CN3CCN4CCCC4C3=O)cc2)nn1] | Acid: Intermediate 85 (130 mg) Amine: Intermediate 141 (96 mg) | 32 mg | LC (Method 2): $t_R$ = 2.72 min; Mass spectrum (ES+): m/z = 487 [M + H]$^+$. |

-continued

| Example | Structure | Starting intermediates | Yield | Analysis |
|---|---|---|---|---|
| 15 | 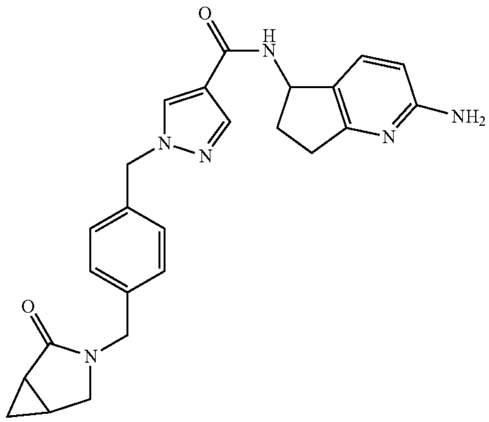 [SMILES: Nc1ccc2c(n1)CCC2NC(=O)c1cnn(Cc2ccc(CN3CC4CC4C3=O)cc2)c1] | Acid: Intermediate 98 (50 mg) Amine: Intermediate 141 (36 mg) | 32 mg | LC (Method 2): $t_R$ = 2.74 min; Mass spectrum (ES+): m/z = 443 [M + H]$^+$. |
| 16 | 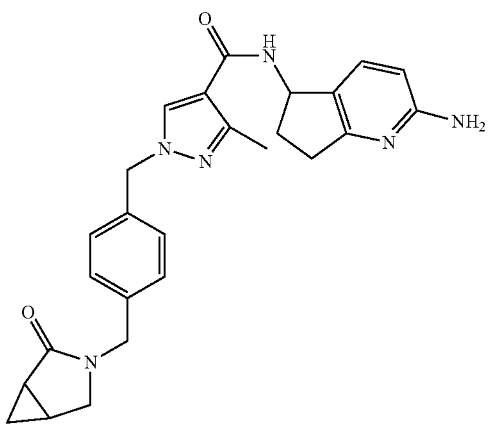 [SMILES: Cc1nn(Cc2ccc(CN3CC4CC4C3=O)cc2)cc1C(=O)NC1CCc2nc(N)ccc21] | Acid: Intermediate 100 (100 mg) Amine: Intermediate 141 (69 mg) | 43 mg major component in mixture with the regioisomer | LC (Method 2): $t_R$ = 2.93 min; Mass spectrum (ES+): m/z = 457 [M + H]$^+$. |
| 17 | 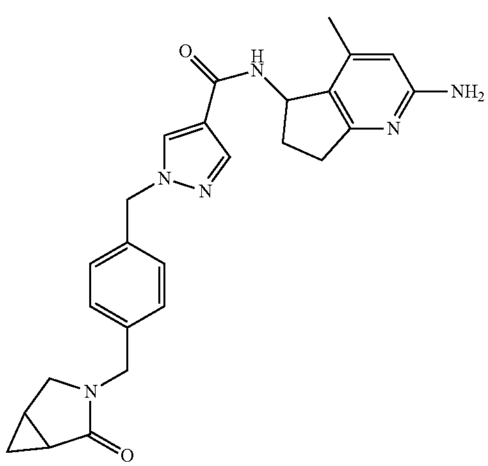 [SMILES: Cc1cc(N)nc2c1C(NC(=O)c1cnn(Cc3ccc(CN4CC5CC5C4=O)cc3)c1)CC2] | Acid: Intermediate 98 (90 mg) Amine: Intermediate 142 (71 mg) | 55 mg | LC (Method 2): $t_R$ = 2.90 min; Mass spectrum (ES+): m/z = 457 [M + H]$^+$. |

-continued

| Example | Structure | Starting intermediates | Yield | Analysis |
|---|---|---|---|---|
| 18 | 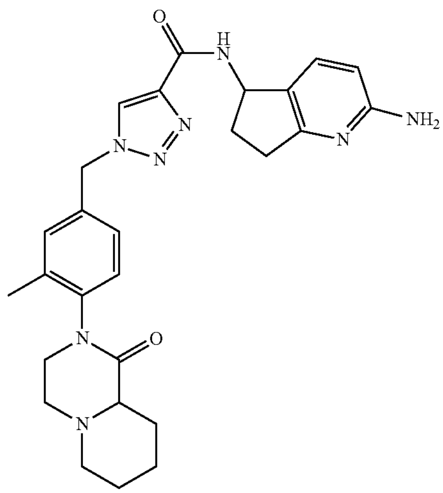 [SMILES: Cc1cc(Cn2cc(C(=O)NC3CCc4nc(N)ccc43)nn2)ccc1N1CCN2CCCCC2C1=O] | Acid: Intermediate 97 (20 mg) Amine: Intermediate 141 (9 mg) | 14 mg | LC (Method 2): $t_R$ = 3.22 min; Mass spectrum (ES+): m/z = 501 [M + H]+. |
| 19 | 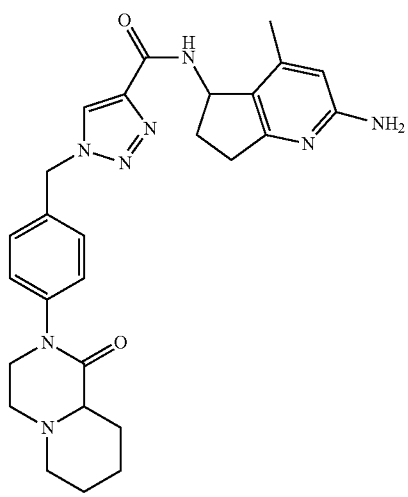 [SMILES: Cc1cc(N)nc2c1C(NC(=O)c1cn(Cc3ccc(N4CCN5CCCCC5C4=O)cc3)nn1)CC2] | Acid: Intermediate 99 (30 mg) Amine: Intermediate 142 (20 mg) | 25 mg | LC (Method 2): $t_R$ = 3.18 min; Mass spectrum (ES+): m/z = 501 [M + H]+. |
| 20 | 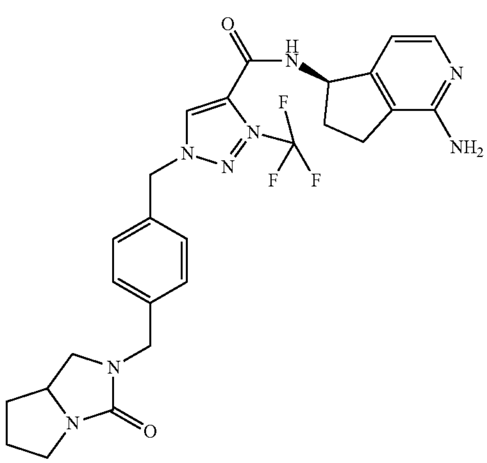 | Acid: Intermediate 94 (80 mg) Amine: Intermediate 137 (95 mg) | 33.5 mg | LC (Method 6): $t_R$ = 3.53 min; Mass spectrum (ES+): m/z = 540 [M + H]+. |

-continued
| Example | Structure | Starting intermediates | Yield | Analysis |
|---|---|---|---|---|
| 21 | 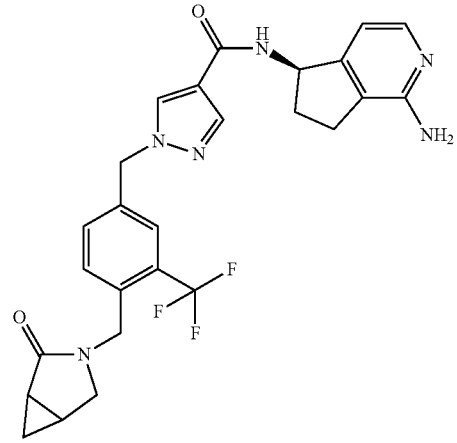 [SMILES: Nc1nccc2c1CC[C@H]2NC(=O)c1cnn(Cc2ccc(CN3CC4CC4C3=O)c(C(F)(F)F)c2)c1] | Acid: Intermediate 101 (100 mg) Amine: Intermediate 137 (98 mg) | 85 mg | LC (Method 6): $t_R$ = 3.32 min; Mass spectrum (ES+): m/z = 511 [M + H]+. |
| 22 | 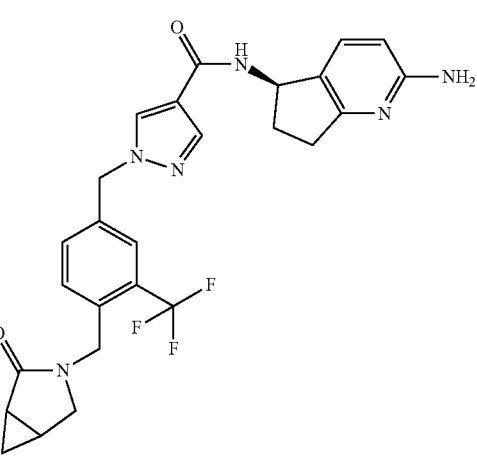 | Acid: Intermediate 101 (50 mg) Amine: Intermediate 138 (28 mg) | 49 mg | LC (Method 6): $t_R$ = 3.30 min; Mass spectrum (ES+): m/z = 511 [M + H]+. |
| 23 | 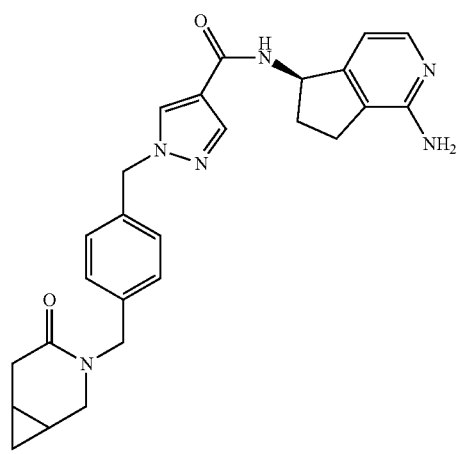 [SMILES: Nc1nccc2c1CC[C@H]2NC(=O)c1cnn(Cc2ccc(CN3CC4CC4CC3=O)cc2)c1] | Acid: Intermediate 95 (40 mg) Amine: Intermediate 137 (45 mg) | 18 mg | LC (Method 7): $t_R$ = 2.48 min; Mass spectrum (ES+): m/z = 457 [M + H]+. |

-continued

| Example | Structure | Starting intermediates | Yield | Analysis |
|---|---|---|---|---|
| 24 | 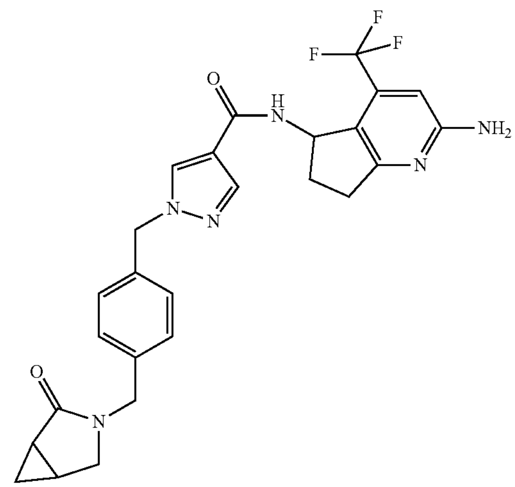 [SMILES: Nc1cc(C(F)(F)F)c2c(n1)CCC2NC(=O)c1cnn(Cc2ccc(CN3CC4CC4C3=O)cc2)c1] | Acid: Intermediate 98 (20 mg) Amine: Intermediate 145 (15 mg) | 8 mg | LC (Method 2): $t_R$ = 3.28 min; Mass spectrum (ES+): m/z = 511 [M + H]$^+$. |
| 25 | 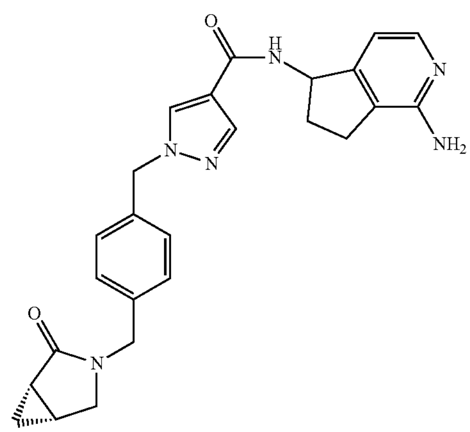 [SMILES: Nc1nccc2c1CCC2NC(=O)c1cnn(Cc2ccc(CN3C[C@@H]4C[C@@H]4C3=O)cc2)c1] | Acid: Intermediate 88 (20 mg) Amine: Intermediate 143 (15 mg) | 16 mg | LC (Method 2): $t_R$ = 2.83 min; Mass spectrum (ES+): m/z = 443 [M + H]$^+$. |
| 26 | 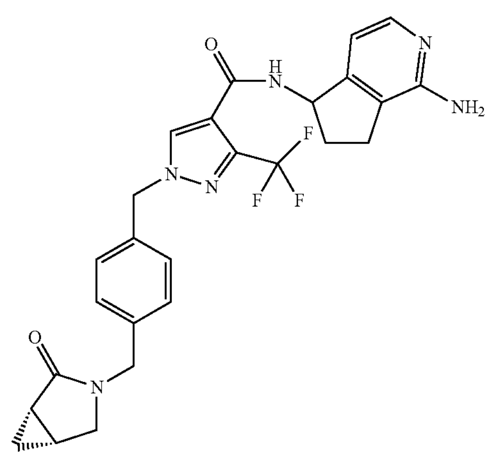 [SMILES: Nc1nccc2c1CCC2NC(=O)c1cn(Cc2ccc(CN3C[C@@H]4C[C@@H]4C3=O)cc2)nc1C(F)(F)F] | Acid: Intermediate 90 (11 mg) Amine: Intermediate 143 (7 mg) | 7 mg | LC (Method 1): $t_R$ = 0.84 min; Mass spectrum (ES+): m/z = 511 [M + H]$^+$. |

-continued

| Example | Structure | Starting intermediates | Yield | Analysis |
|---------|-----------|------------------------|-------|----------|
| 27 | 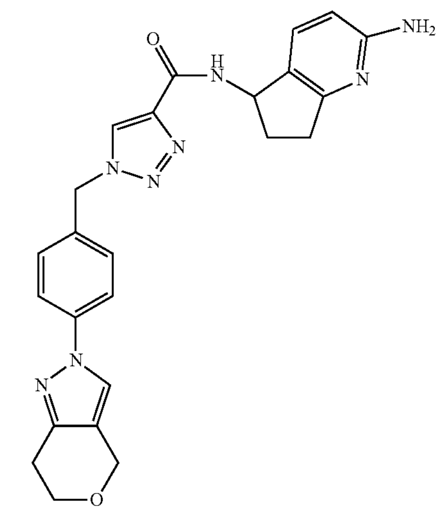 [SMILES: Nc1ccc2c(n1)CCC2NC(=O)c1cn(Cc2ccc(-n3cc4c(n3)CCOC4)cc2)nn1] | Acid: Intermediate 96 (50 mg) Amine: Intermediate 141 (44 mg) | 7 mg | LC (Method 2): $t_R$ = 3.10 min; Mass spectrum (ES+): m/z = 457 [M + H]$^+$. |
| 28 | 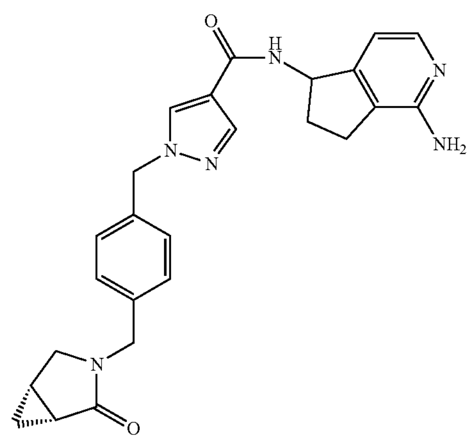 [SMILES: Nc1nccc2c1CCC2NC(=O)c1cnn(Cc2ccc(CN3C[C@H]4C[C@H]4C3=O)cc2)c1] | Acid: Intermediate 86 (180 mg) Amine: Intermediate 143 (140 mg) | 160 mg | LC (Method 1): $t_R$ = 0.63 min; Mass spectrum (ES+): m/z = 443 [M + H]$^+$. |
| 29 | 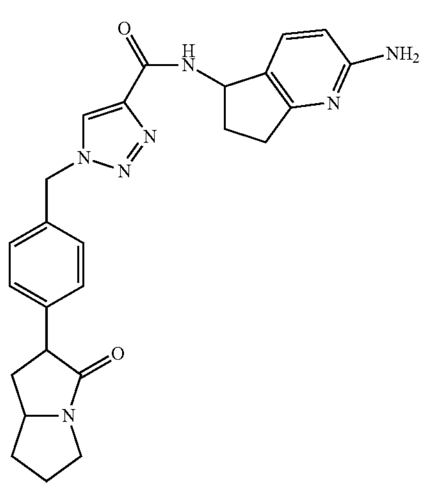 [SMILES: Nc1ccc2c(n1)CCC2NC(=O)c1cn(Cc2ccc(C3CC4CCCN4C3=O)cc2)nn1] | Acid: Intermediate 91 (12 mg) Amine: Intermediate 141 (9 mg) | 9 mg | LC (Method 2): $t_R$ = 3.10 min; Mass spectrum (ES+): m/z = 458 [M + H]$^+$. |

-continued

| Example | Structure | Starting intermediates | Yield | Analysis |
|---|---|---|---|---|
| 30 | 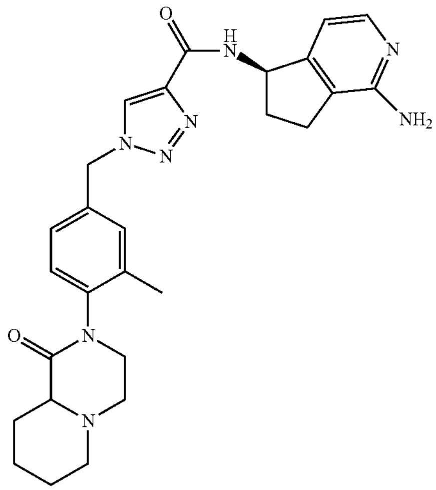 [SMILES: Cc1cc(Cn2cc(C(=O)N[C@@H]3CCc4c3ccnc4N)nn2)ccc1N1CCN2CCCCC2C1=O] | Acid: Intermediate 97 (55 mg) Amine: Intermediate 137 (51 mg) | 28 mg | LC (Method 2): $t_R$ = 3.25 min; Mass spectrum (ES+): m/z = 501 [M + H]$^+$. |
| 31 | 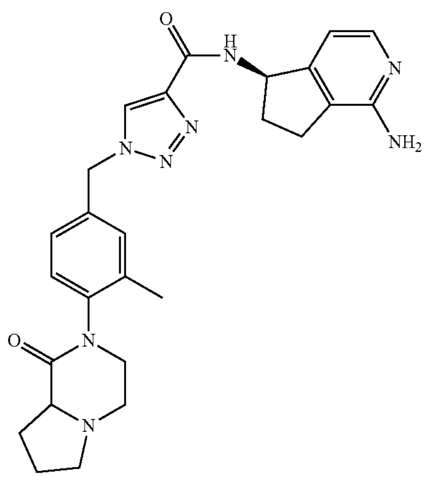 [SMILES: Cc1cc(Cn2cc(C(=O)N[C@@H]3CCc4c3ccnc4N)nn2)ccc1N1CCN2CCCC2C1=O] | Acid: Intermediate 103 (55 mg) Amine: Intermediate 137 (53 mg) | 30 mg | LC (Method 2): $t_R$ = 3.13 min; Mass spectrum (ES+): m/z = 487 [M + H]$^+$. |
| 32 | 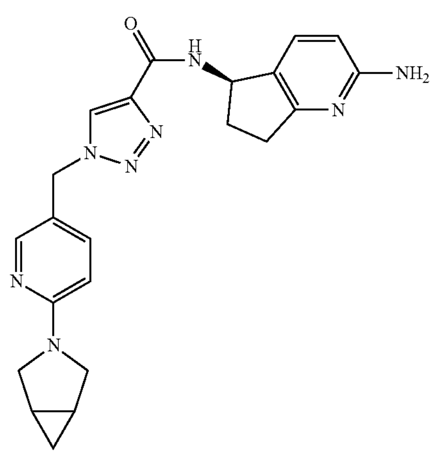 [SMILES: Nc1ccc2c(n1)CC[C@H]2NC(=O)c1cn(Cc2ccc(N3CC4CC4C3)nc2)nn1] | Acid: Intermediate 81 (100 mg) Amine: Intermediate 138 (85 mg) | 6 mg | LC (Method 2): $t_R$ = 3.50 min; Mass spectrum (ES+): m/z = 417 [M + H]$^+$. |

-continued

| Example | Structure | Starting intermediates | Yield | Analysis |
|---|---|---|---|---|
| 33 | 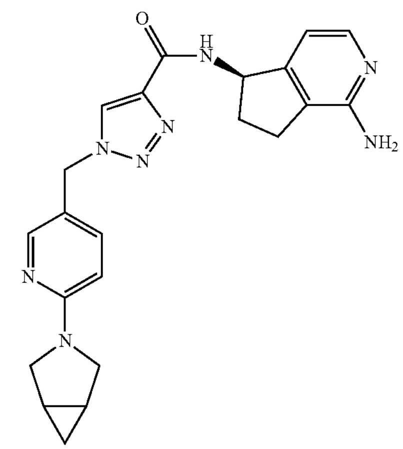 [SMILES: Nc1nccc2c1CC[C@H]2NC(=O)c1cn(Cc2ccc(N3CC4CC4C3)nc2)nn1] | Acid: Intermediate 81 (300 mg) Amine: Intermediate 137 (190 mg) | 19 mg | LC (Method 2): t$_R$ = 3.62 min; Mass spectrum (ES+): m/z = 417 [M + H]$^+$. |
| 34 | 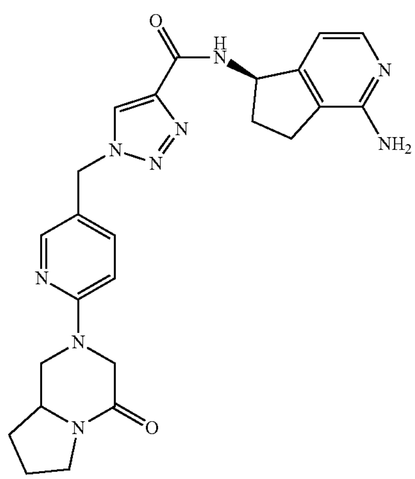 [SMILES: Nc1nccc2c1CC[C@H]2NC(=O)c1cn(Cc2ccc(N3CC(=O)N4CCCC4C3)nc2)nn1] | Acid: Intermediate 82 (50 mg) Amine: Intermediate 137 (42 mg) | 6 mg | LC (Method 2): t$_R$ = 3.07 min; Mass spectrum (ES+): m/z = 474 [M + H]$^+$. |
| 35 | 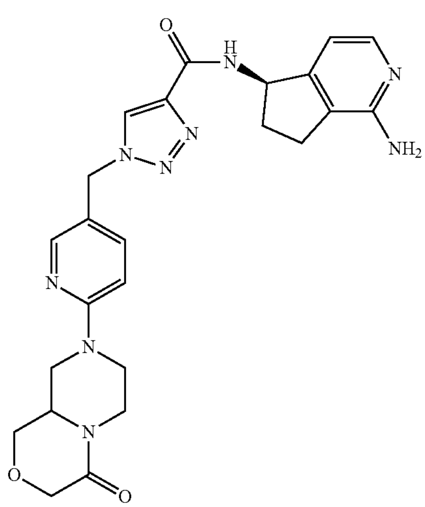 [SMILES: Nc1nccc2c1CC[C@H]2NC(=O)c1cn(Cc2ccc(N3CCN4C(=O)COCC4C3)nc2)nn1] | Acid: Intermediate 84 (30 mg) Amine: Intermediate 137 (24 mg) | 7 mg | LC (Method 2): t$_R$ = 2.82 min; Mass spectrum (ES+): m/z = 490 [M + H]$^+$. |

| Example | Structure | Starting intermediates | Yield | Analysis |
|---------|-----------|------------------------|-------|----------|
| 36 | 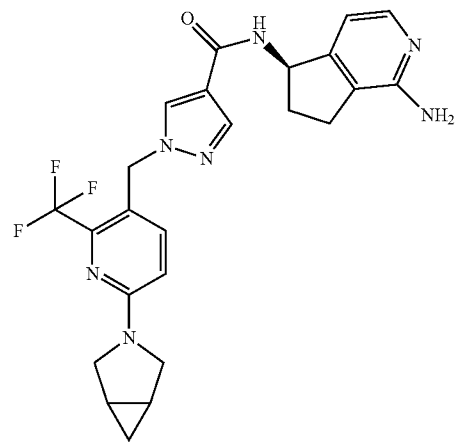 [SMILES: Nc1nccc2c1CC[C@H]2NC(=O)c1cnn(Cc2ccc(N3CC4CC4C3)nc2C(F)(F)F)c1] | Acid: Intermediate 128 (100 mg) Amine: Intermediate 137 (100 mg) | 111 mg | LC (Method 2): $t_R$ = 4.35 min; Mass spectrum (ES+): m/z = 484 [M + H]$^+$. |
| 37 | 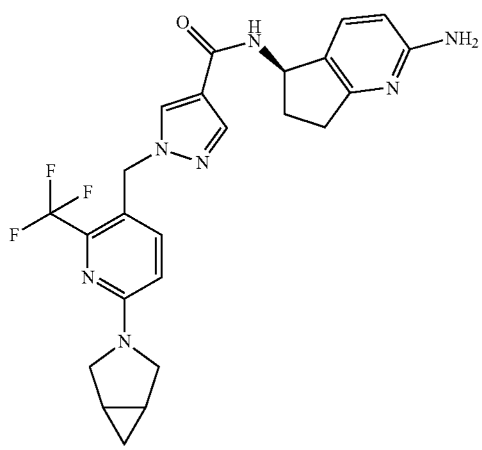 [SMILES: Nc1ccc2c(n1)CC[C@H]2NC(=O)c1cnn(Cc2ccc(N3CC4CC4C3)nc2C(F)(F)F)c1] | Acid: Intermediate 128 (100 mg) Amine: Intermediate 138 (100 mg) | 104 mg | LC (Method 2): $t_R$ = 4.47 min; Mass spectrum (ES+): m/z = 484 [M + H]$^+$. |
| 38 | 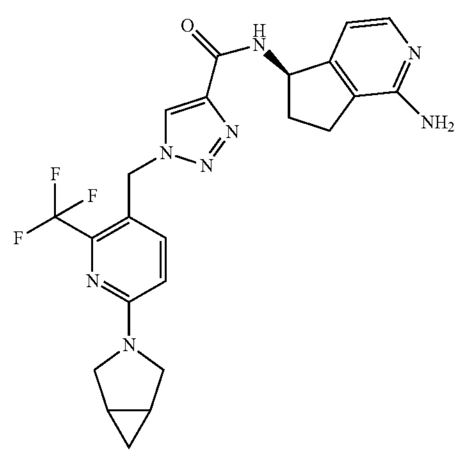 [SMILES: Nc1nccc2c1CC[C@H]2NC(=O)c1cn(Cc2ccc(N3CC4CC4C3)nc2C(F)(F)F)nn1] | Acid: Intermediate 127 (100 mg) Amine: Intermediate 137 (100 mg) | 53 mg | LC (Method 3): $t_R$ = 2.41-2.45 min; Mass spectrum (ES+): m/z = 485 [M + H]$^+$. |

| Example | Structure | Starting intermediates | Yield | Analysis |
|---|---|---|---|---|
| 39 | 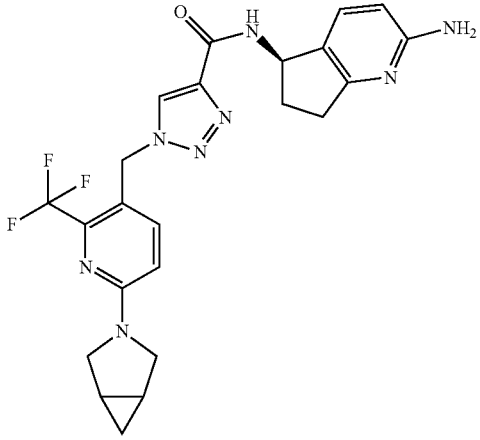 | Acid: Intermediate 127 (100 mg) Amine: Intermediate 138 (100 mg) | 55 mg | LC (Method 2): $t_R$ = 4.57 min; Mass spectrum (ES+): m/z = 485 [M + H]$^+$. |
| 40 | 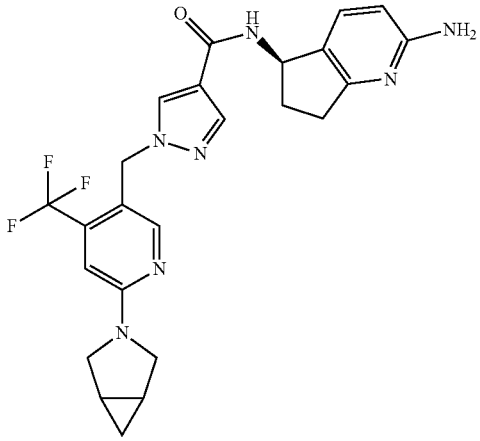 [SMILES: Nc1ccc2c(n1)CC[C@H]2NC(=O)c1cnn(Cc2cnc(N3CC4CC4C3)cc2C(F)(F)F)c1] | Acid: Intermediate 126 (80 mg) Amine: Intermediate 138 (80 mg) | 61 mg | LC (Method 6): $t_R$ = 3.42 min; Mass spectrum (ES+): m/z = 484 [M + H]$^+$. |
| 41 | 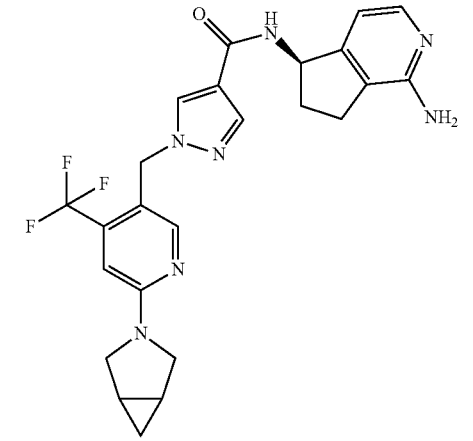 [SMILES: Nc1nccc2c1CC[C@H]2NC(=O)c1cnn(Cc2cnc(N3CC4CC4C3)cc2C(F)(F)F)c1] | Acid: Intermediate 126 (100 mg) Amine: Intermediate 137 (100 mg) | 38 mg | LC (Method 6): $t_R$ = 3.40 min; Mass spectrum (ES+): m/z = 484 [M + H]$^+$. |

-continued

| Example | Structure | Starting intermediates | Yield | Analysis |
|---|---|---|---|---|
| 42 | 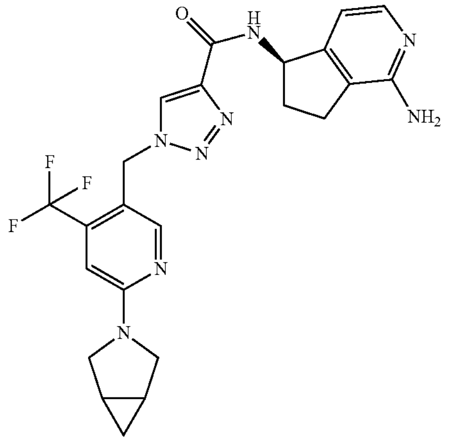 [SMILES: Nc1nccc2c1CC[C@H]2NC(=O)c1cn(Cc2cnc(N3CC4CC4C3)cc2C(F)(F)F)nn1] | Acid: Intermediate 83 (100 mg) Amine: Intermediate 137 (102 mg) | 55 mg | LC (Method 6): $t_R$ = 3.52 min; Mass spectrum (ES+): m/z = 485 [M + H]+. |
| 43 | 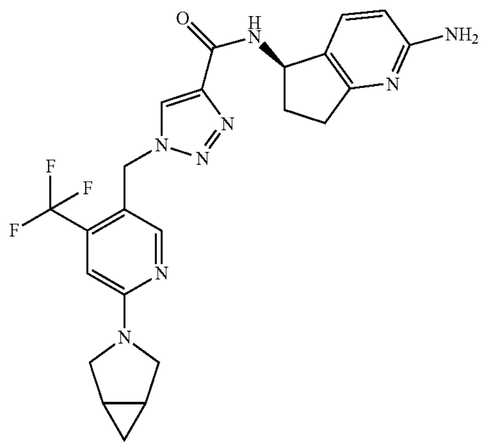 [SMILES: Nc1ccc2c(n1)CC[C@H]2NC(=O)c1cn(Cc2cnc(N3CC4CC4C3)cc2C(F)(F)F)nn1] | Acid: Intermediate 83 (80 mg) Amine: Intermediate 138 (80 mg) | 44 mg | LC (Method 6): $t_R$ = 3.53 min; Mass spectrum (ES+): m/z = 485 [M + H]+. |
| 44 | 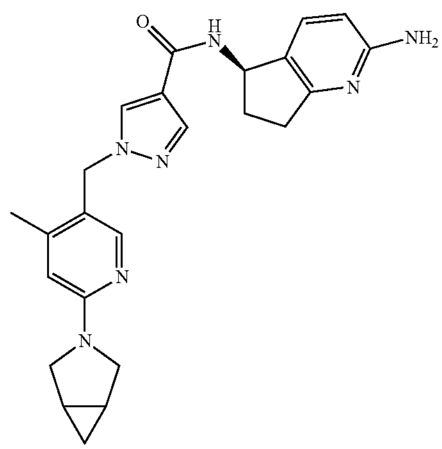 [SMILES: Cc1cc(N2CC3CC3C2)ncc1Cn1cc(C(=O)N[C@@H]2CCc3nc(N)ccc32)cn1] | Acid: Intermediate 130 (50 mg) Amine: Intermediate 138 (59 mg) | 8 mg | LC (Method 2): $t_R$ = 3.50 min; Mass spectrum (ES+): m/z = 430 [M + H]+. |

-continued

| Example | Structure | Starting intermediates | Yield | Analysis |
|---|---|---|---|---|
| 45 | 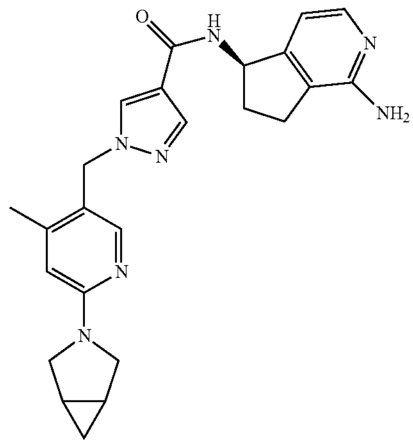 [SMILES: Cc1cc(N2CC3CC3C2)ncc1Cn1cc(C(=O)N[C@@H]2CCc3c2ccnc3N)cn1] | Acid: Intermediate 130 (50 mg) Amine: Intermediate 137 (59 mg) | 11 mg | LC (Method 2): $t_R$ = 3.58 min; Mass spectrum (ES+): m/z = 430 [M + H]$^+$. |
| 46 | 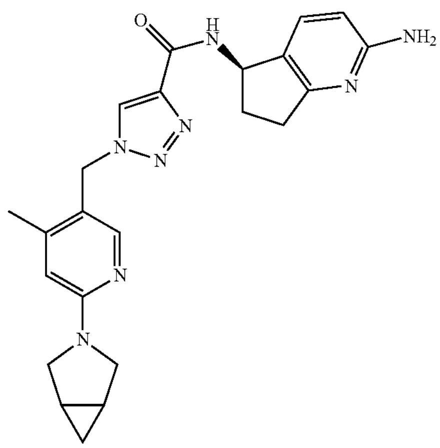 [SMILES: Cc1cc(N2CC3CC3C2)ncc1Cn1cc(C(=O)N[C@@H]2CCc3nc(N)ccc32)nn1] | Acid: Intermediate 129 (50 mg) Amine: Intermediate 138 (59 mg) | 26 mg | LC (Method 2): $t_R$ = 3.61 min; Mass spectrum (ES+): m/z = 431 [M + H]$^+$. |
| 47 | 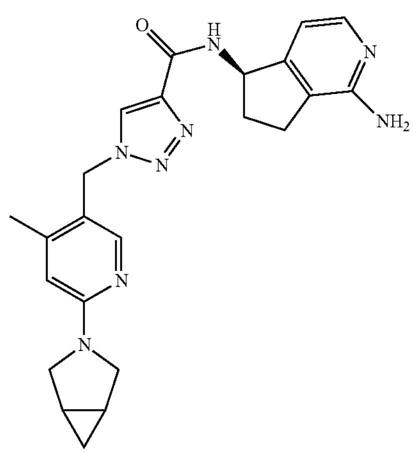 [SMILES: Cc1cc(N2CC3CC3C2)ncc1Cn1cc(C(=O)N[C@@H]2CCc3c2ccnc3N)nn1] | Acid: Intermediate 129 (50 mg) Amine: Intermediate 138 (59 mg) | 23 mg | LC (Method 2): $t_R$ = 3.65 min; Mass spectrum (ES+): m/z = 431 [M + H]$^+$. |

The stereoisomers of Example 25 (16 mg) are separated by HPLC using a chiral stationary phase to give Example 48 (4 mg) and Example 49 (4 mg).

Method for Separation:

HPLC apparatus type: Waters 600 Pump, 2767 Autosampler, UV Detector 2489; column: Daicel Chiralpak AD-H, 5.0 μm, 250 mm×20 mm; method: eluent ACN/MeOH 85:15; flow rate: 15 mL/min, temperature: 25° C.; UV Detection: 230 nm Example 48: stereoisomer 1

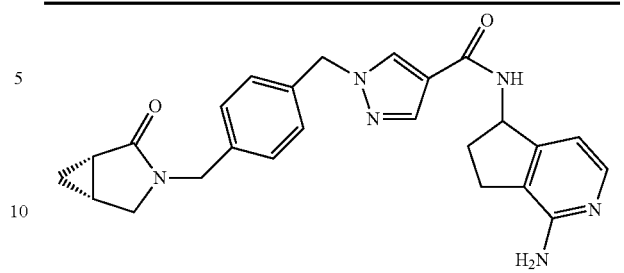

Example 49: stereoisomer 2

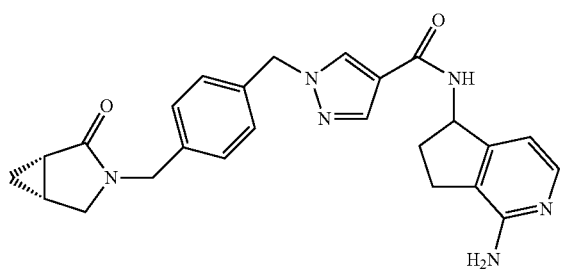 [SMILES: Nc1nccc2c1CCC2NC(=O)c1cnn(Cc2ccc(CN3C[C@@H]4C[C@@H]4C3=O)cc2)c1]

| Example | Chiral HPLC (Column Daicel Chiralpak AS-H, eluent Hexane-Ethanol 70:30, 1 ml/min, 25° C.) $R_t$ [min] | HPLC-MS (Method 2): $R_t$ [min] | MS (ESI pos): m/z |
|---|---|---|---|
| 48 | 43.18 | 2.87 | 443 |
| 49 | 31.93 | 2.87 | 443 |

The stereoisomers of Example 26 (7 mg) are separated by HPLC using a chiral stationary phase to give Example 50 (3 mg) and Example 51 (3 mg).

Method for Separation:

HPLC apparatus type: Waters 600 Pump, 2767 Autosampler, UV Detector 2489; column: Daicel Chiralpak AD-H, 5.0 μm, 250 mm×20 mm; method: eluent ACN/MeOH 85:15; flow rate: 15 mL/min, temperature: 25° C.; UV Detection: 230 nm Example 50: stereoisomer 1

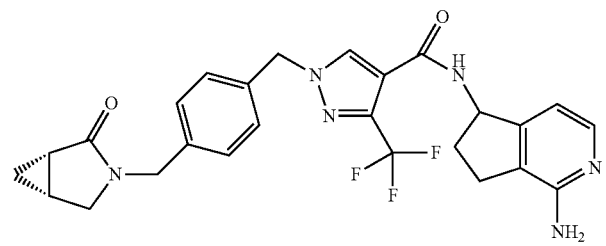 [SMILES: Nc1nccc2c1CCC2NC(=O)c1cn(Cc2ccc(CN3C[C@@H]4C[C@@H]4C3=O)cc2)nc1C(F)(F)F]

Example 51: stereoisomer 2

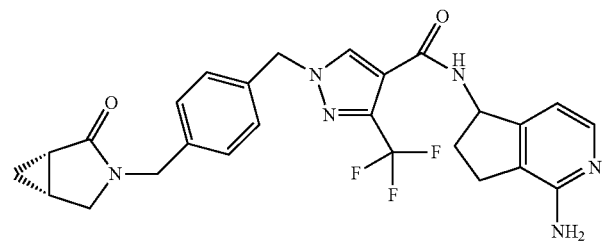 [SMILES: Nc1nccc2c1CCC2NC(=O)c1cn(Cc2ccc(CN3C[C@@H]4C[C@@H]4C3=O)cc2)nc1C(F)(F)F]

| Example | Chiral HPLC (Column Daicel Chiralpak AS-H, eluent Hexane-Ethanol 70:30, 1 ml/min, 25° C.) $R_t$ [min] | HPLC-MS (Method 2): $R_t$ [min] | MS (ESI pos): m/z |
|---|---|---|---|
| 50 | 23.9 | 3.55 | 511 |
| 51 | 32.7 | 3.55 | 511 |

The stereoisomers of Example 21 (80 mg) are separated by HPLC using a chiral stationary phase to give Example 52 (30 mg) and Example 53 (30 mg).

Method for Separation:

HPLC apparatus type: Waters 600 Pump, 2767 Autosampler, UV Detector 2489; column: Daicel Chiralcel OJ-H, 5.0 µm, 250 mm×20 mm; method: eluent Hexane/EtOH 75:25; flow rate: 15 mL/min, temperature: 25° C.; UV Detection: 230 nm 52: stereoisomer 1

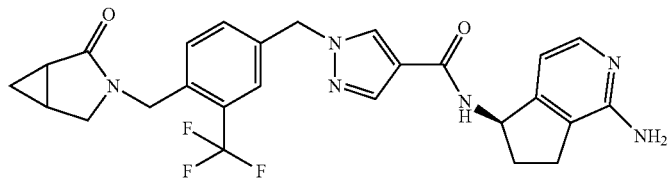 [SMILES: Nc1nccc2c1CC[C@H]2NC(=O)c1cnn(Cc2ccc(CN3CC4CC4C3=O)c(C(F)(F)F)c2)c1]

53: stereoisomer 2

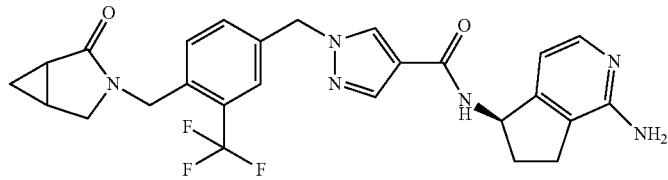 [SMILES: Nc1nccc2c1CC[C@H]2NC(=O)c1cnn(Cc2ccc(CN3CC4CC4C3=O)c(C(F)(F)F)c2)c1]

| Example | Chiral HPLC (Column Daicel Chiralcel OJ-H, eluent Hexane-Ethanol 70:30, 1 ml/min, 25° C.) $R_t$ [min] | HPLC-MS (Method 6): $R_t$ [min] | MS (ESI pos): m/z |
|---|---|---|---|
| 52 | 15.07 | 3.27 | 511 |
| 53 | 17.94 | 3.27 | 511 |

The stereoisomers of Example 28 (80 mg) are separated by HPLC using a chiral stationary phase to give Example 54 (35 mg) and Example 55 (24 mg).

Method for Separation:

HPLC apparatus type: Waters 600 Pump, 2767 Autosampler, UV Detector 2489; column: Daicel Chiralcel AS-H, 5.0 µm, 250 mm×20 mm; method: eluent Exane/EtOH 70:30; flow rate: 15 mL/min, temperature: 25° C.; UV Detection: 230 nm Example 54: stereoisomer 1

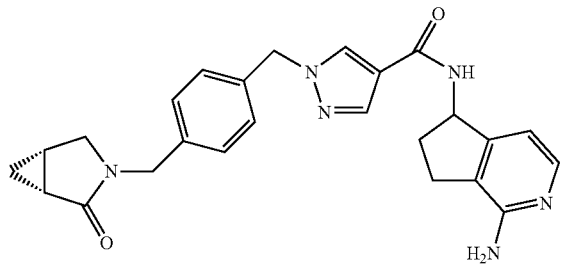 [SMILES: Nc1nccc2c1CCC2NC(=O)c1cnn(Cc2ccc(CN3C[C@H]4C[C@H]4C3=O)cc2)c1]

Example 55: stereoisomer 2

-continued

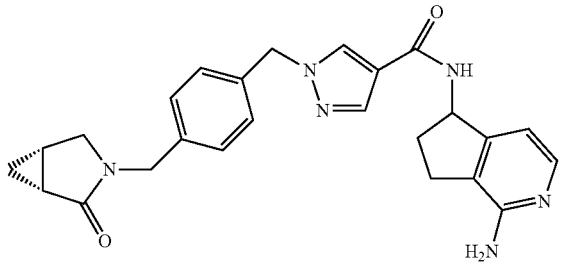 [SMILES: Nc1nccc2c1CCC2NC(=O)c1cnn(Cc2ccc(CN3C[C@H]4C[C@H]4C3=O)cc2)c1]

| Example | Chiral HPLC (Column Daicel Chiralpak AS-H, eluent Hexane-Ethanol 70:30, 1 ml/min, 25° C.) $R_t$ [min] | HPLC-MS (Method 2): $R_t$ [min] | MS (ESI pos): m/z |
|---|---|---|---|
| 54 | 28.8 | 2.83 | 443 |
| 55 | 35.7 | 2.78 | 443 |

The stereoisomers of Example 30 (28 mg) are separated by HPLC using a chiral stationary phase to give Example 56 (9 mg) and Example 57 (9 mg).

Method for Separation:

HPLC apparatus type: Waters 600 Pump, 2767 Autosampler, UV Detector 2489; column: Daicel Chiralpak AD-H, 5.0 μm, 250 mm×20 mm; method: eluent Exane/IPA 60:40; flow rate: 15 mL/min, temperature: 25° C.; UV Detection: 230 nm Example 56: stereoisomer 1

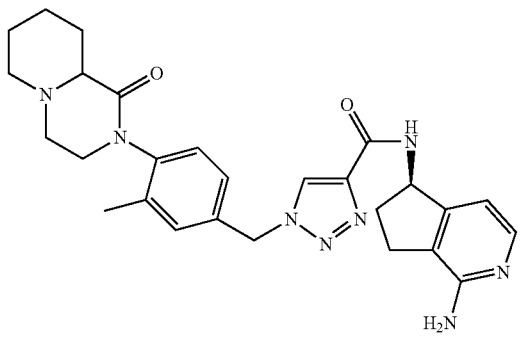 [SMILES: Cc1cc(Cn2cc(C(=O)N[C@@H]3CCc4c3ccnc4N)nn2)ccc1N1CCN2CCCCC2C1=O]

Example 57: stereoisomer 2

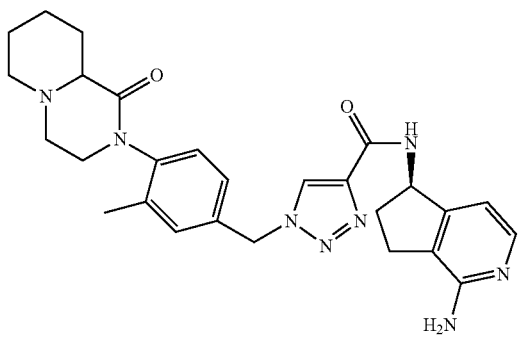 [SMILES: Cc1cc(Cn2cc(C(=O)N[C@@H]3CCc4c3ccnc4N)nn2)ccc1N1CCN2CCCCC2C1=O]

| Example | Chiral HPLC (Column Daicel Chiralpak AD-H, eluent Hexane-IPA 60:40, 1 ml/min, 25° C.) R$_t$ [min] | HPLC-MS (Method 7): R$_t$ [min] | MS (ESI pos): m/z |
|---|---|---|---|
| 56 | 33.5 | 2.44 | 501 |
| 57 | 63.3 | 2.44 | 501 |

The stereoisomers of Example 31 (30 mg) are separated by HPLC using a chiral stationary phase to give Example 58 (7 mg) and Example 59 (7 mg).

Method for Separation:

HPLC apparatus type: Waters 600 Pump, 2767 Autosampler, UV Detector 2489; column: Daicel Chirapak AD-H, 5.0 μm, 250 mm×20 mm; method: eluent Exane/IPA 60:40; flow rate: 15 mL/min, temperature: 25° C.; UV Detection: 230 nm Example 58: stereoisomer 1

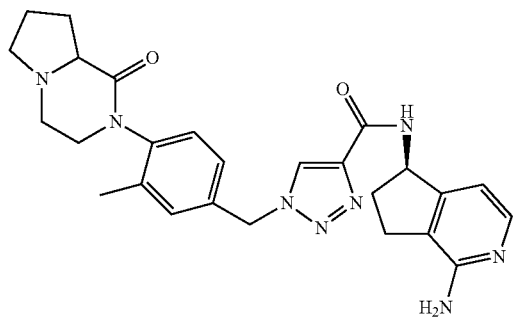 [SMILES: Cc1cc(Cn2cc(C(=O)N[C@@H]3CCc4c3ccnc4N)nn2)ccc1N1CCN2CCCC2C1=O]

Example 59: stereoisomer 2

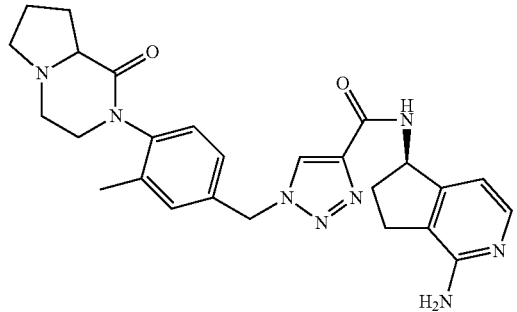 [SMILES: Cc1cc(Cn2cc(C(=O)N[C@@H]3CCc4c3ccnc4N)nn2)ccc1N1CCN2CCCC2C1=O]

| Example | Chiral HPLC (Column Daicel Chiralpak AD-H, eluent Hexane-IPA 60:40, 1 ml/min, 25° C.) R$_t$ [min] | HPLC-MS (Method 2): R$_t$ [min] | MS (ESI pos): m/z |
|---|---|---|---|
| 58 | 36.6 | 3.08 | 487 |
| 59 | 43.4 | 3.17 | 487 |

Example 60

1-[4-(3-Aza-bicyclo[3.1.0]hex-3-ylmethyl)-benzyl]-1H-[1,2,3]triazole-4-carboxylic acid(2-amino-6,7-dihydro-5H-[1]pyrindin-5-yl)-amide

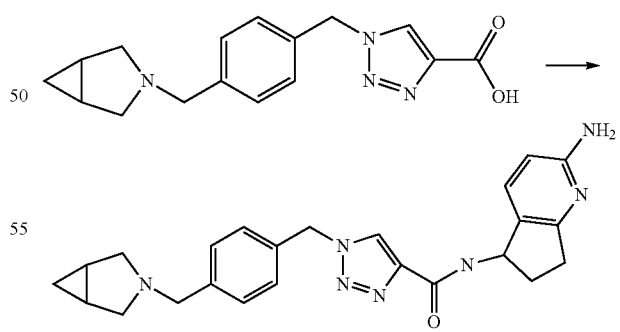

Triethylamine (300 μL, 2.16 mmol) is added to a stirred suspension of 1-[4-(3-Aza-bicyclo[3.1.0]hex-3-ylmethyl)-benzyl]-1H-[1,2,3]triazole-4-carboxylic acid (Intermediate 22, 72.0 mg, 0.19 mmol), 6,7-Dihydro-5H-[1]pyrindine-2, 5-diamine di-hydrochloride (Intermediate 141, 50.7 mg, 0.19 mmol) and benzotriazol-1-yloxytris(pyrrolidino)phosphonium hexafluorophosphate (100.9 mg, 0.19 mmol) in 3 mL of dry DCM. The reaction mixture is stirred at room temperature overnight. Water is added, the organic layer is separated, dried over anhydrous sodium sulfate, filtered and concentrated under reduced pressure. The crude is purified by flash chromatography (75-100% EtOAc in cyclohexane) to give the title compound (yield 3.4 mg).

LC (Method 8): $t_R$=2.53 min; Mass spectrum (ES+): m/z=430 [M+H]$^+$.

Example 61

1-[4-(3-Oxo-tetrahydro-pyrrolo[1,2-c]imidazol-2-ylmethyl)-benzyl]-1H-[1,2,3]triazole-4-carboxylic acid (2-amino-6,7-dihydro-5H-[1]pyrindin-5-yl)-amide

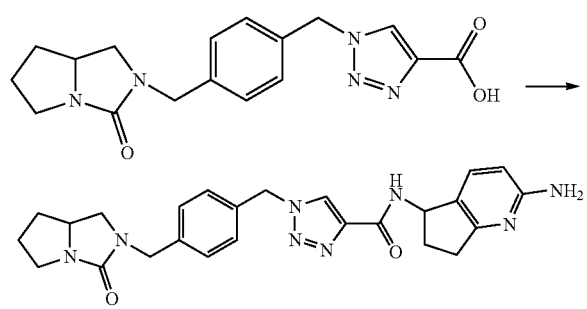

Triethylamine (300 µL, 2.16 mmol) is added to a stirred suspension of 1-[4-(3-Oxo-tetrahydro-pyrrolo[1,2-c]imidazol-2-ylmethyl)-benzyl]-1H-[1,2,3]triazole-4-carboxylic acid (Intermediate 25, 170 mg, 0.47 mmol), 6,7-Dihydro-5H-[1]pyrindine-2,5-diamine di-hydrochloride (Intermediate 141, 124 mg, 0.47 mmol) and benzotriazol-1-yloxytris(pyrrolidino)phosphonium hexafluorophosphate (246 mg, 0.47 mmol) in 3 mL of dry DCM. The reaction mixture is stirred at room temperature overnight. 1N NaOH solution is added, the organic layer is separated, dried over anhydrous sodium sulfate, filtered and concentrated under reduced pressure. The crude is purified by flash chromatography (5% Methanol in EtOAc) to give the title compound (yield 48 mg).

LC (Method 8): $t_R$=2.08 min; Mass spectrum (ES+): m/z=473 [M+H]$^+$.

Example 62

1-[4-(2-Oxo-3-aza-bicyclo[3.1.0]hex-3-ylmethyl)-benzyl]-1H-[1,2,3]triazole-4-carboxylicacid (2-amino-6,7-dihydro-5H-[1]pyrindin-5-yl)-amide

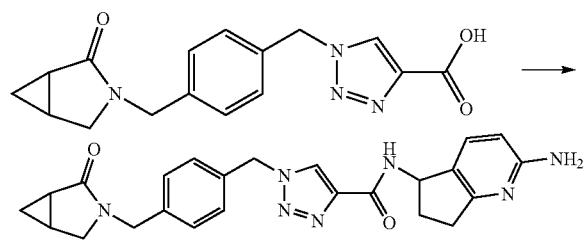

The title compound is prepared from 1-[4-(2-Oxo-3-aza-bicyclo[3.1.0]hex-3-ylmethyl)-benzyl]-1H-[1,2,3]triazole-4-carboxylic acid (Intermediate 27, 72 mg, 0.23 mmol) in a manner analogous to that described for Example 61 (yield 23 mg).

LC (Method 8): $t_R$=1.97 min; Mass spectrum (ES+): m/z=444 [M+H]$^+$.

Example 63

1-[4-(3-Oxo-tetrahydro-pyrrolo[1,2-c]imidazol-2-yl)-benzyl]-1H-[1,2,3]triazole-4-carboxylic acid (2-amino-6,7-dihydro-5H-[1]pyrindin-5-yl)-amide

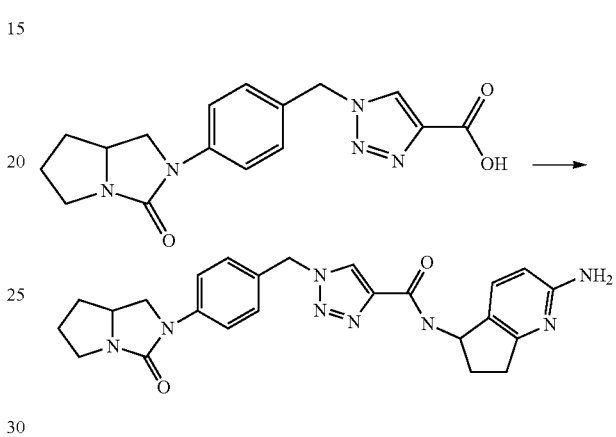

The title compound is prepared from 1-[4-(3-Oxo-tetrahydro-pyrrolo[1,2-c]imidazol-2-yl)-benzyl]-1H-[1,2,3]triazole-4-carboxylic acid (Intermediate 29, 111 mg, 0.32 mmol) in a manner analogous to that described for Example 61 (yield 12 mg).

LC (Method 8): $t_R$=2.17 min; Mass spectrum (ES+): m/z=459 [M+H]$^+$.

Example 64

1-[4-(4-Oxo-5-aza-spiro[2.4]hept-5-ylmethyl)-benzyl]-1H-[1,2,3]triazole-4-carboxylic acid (2-amino-6,7-dihydro-5H-[1]pyrindin-5-yl)-amide

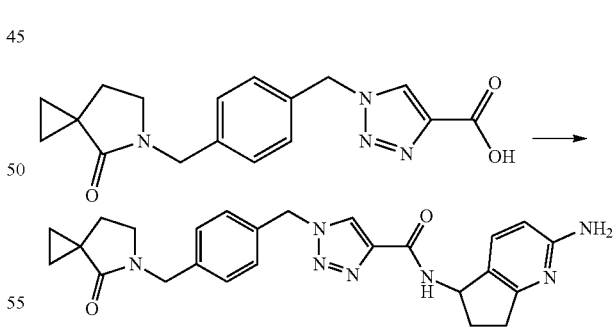

Triethylamine (300 µL, 2.16 mmol) is added to a stirred suspension of 1-[4-(4-Oxo-5-aza-spiro[2.4]hept-5-ylmethyl)-benzyl]-1H-[1,2,3]triazole-4-carboxylic acid (Intermediate 31, 87 mg), 6,7-Dihydro-5H-[1]pyrindine-2,5-diamine di-hydrochloride (Intermediate 141, 66 mg, 0.25 mmol) and benzotriazol-1-yloxytris(pyrrolidino)phosphonium hexafluorophosphate (132 mg, 0.25 mmol) in 3 mL of dry DCM. The reaction mixture is stirred at room temperature overnight. Water is added, the organic layer is separated, dried over anhydrous sodium sulfate, filtered and concentrated under reduced pressure. The crude is purified by flash chromatography (75-100% EtOAc in cyclohexane then EtOAc/MeOH 8:2) to give the title compound (yield 22 mg).

LC (Method 2): $t_R$=3.17 min; Mass spectrum (ES+): m/z=458 [M+H]+.

Example 65

1-[4-(2-Oxo-3-aza-bicyclo[3.1.0]hex-3-yl)-benzyl]-1H-[1,2,3]triazole-4-carboxylic acid (2-amino-6,7-dihydro-5H-[1]pyrindin-5-yl)-amide

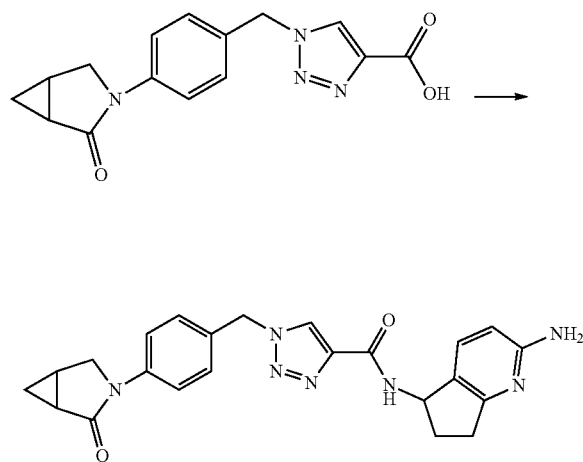

Triethylamine (300 μL, 2.16 mmol) is added to a stirred suspension of 1-[4-(2-Oxo-3-aza-bicyclo[3.1.0]hex-3-yl)-benzyl]-1H-[1,2,3]triazole-4-carboxylic acid (Intermediate 33, 43 mg, 0.20 mmol), 6,7-Dihydro-5H-[1]pyrindine-2,5-diamine di-hydrochloride (Intermediate 141, 44 mg, 0.17 mmol) and benzotriazol-1-yloxytris(pyrrolidino)phosphonium hexafluorophosphate (87 mg, 0.17 mmol) in 3 mL of dry DCM. The reaction mixture is stirred at room temperature overnight. Water is added, the organic layer is separated, dried over anhydrous sodium sulfate, filtered and concentrated under reduced pressure. The crude is purified by flash chromatography (20% Methanol in EtOAc) then by preparative HPLC system to give the title compound (yield 23 mg).

LC (Method 2): $t_R$=3.04 min; Mass spectrum (ES+): m/z=430 [M+H]+.

Example 66

1-[3-Methyl-4-(2-oxo-3-aza-bicyclo[3.1.0]hex-3-ylmethyl)-benzyl]-1H-pyrazole-4-carboxylic acid ((R)-2-amino-6,7-dihydro-5H-[1]pyrindin-5-yl)-amide Triethylamine (300 μL, 2.16 mmol) is added to a stirred suspension of 1-[3-Methyl-4-(2-oxo-3-aza-bicyclo[3.1.0]hex-3-ylmethyl)-benzyl]-1H-pyrazole-4-carboxylic acid (Intermediate 41, 67 mg, 0.20 mmol), (R)-6,7-Dihydro-5H-[1]pyrindine-2,5-diamine hydrochloride salt (Intermediate 138, 43 mg, 0.17 mmol) and benzotriazol-1-yloxytris(pyrrolidino)phosphonium hexafluorophosphate (102 mg, 0.20 mmol) in 3 mL of dry DCM. The reaction mixture is stirred at room temperature overnight. Water is added, the organic layer is separated, dried over anhydrous sodium sulfate, filtered and concentrated under reduced pressure. The crude is purified by flash chromatography (20% Methanol in EtOAc) to give the title compound (yield 18 mg).

LC (Method 6): $t_R$=3.11 min; Mass spectrum (ES+): m/z=457 [M+H]+.

Example 67 and Example 68

The stereoisomers of Example 66 (109 mg) prepared as described above are separated by HPLC using a chiral stationary phase to give 12.4 mg of stereoisomer 1 (Example 67) and 12.6 mg of stereoisomer 2 (Example 68).

Method for Separation:

HPLC apparatus type: Waters 600 Pump, 2767 Autosampler, UV Detector 2489; column: Daicel Chiralpak AS-H, 5.0 μm, 250 mm×20 mm; method: eluent hexane/ethanol 65:35; flow rate: 15 mL/min, temperature: 25° C.; UV Detection: 230 nm Example 67: stereoisomer 1

Chiral

Example 68: stereoisomer 2

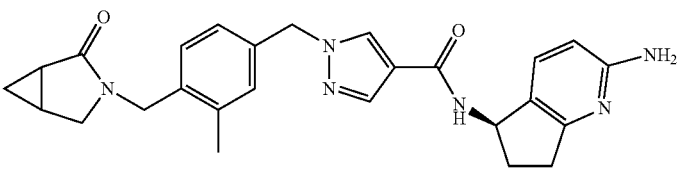

Chiral

| Example | Chiral HPLC (Column Daicel Chiralpak AS-H, eluent: hexane-ethanol 70:30, 1 ml/min, 25° C.) $R_t$ [min] | HPLC-MS (MIL-01_007): $R_t$ [min] | MS (ESI pos): m/z |
| --- | --- | --- | --- |
| 67 | 14.55 | 3.00 | 457 |
| 68 | 21.35 | 2.98 | 457 |

Example 69

1-[2-Methyl-4-(2-oxo-3-aza-bicyclo[3.1.0]hex-3-ylmethyl)-benzyl]-1H-pyrazole-4-carboxylic acid ((R)-2-amino-6,7-dihydro-5H-[1]pyrindin-5-yl)-amide

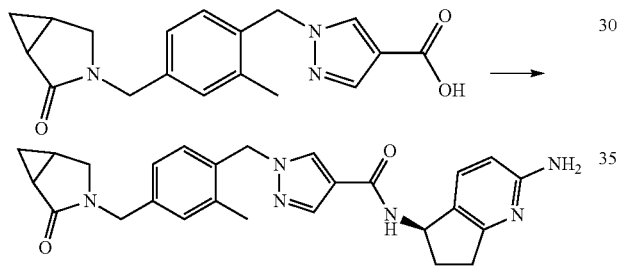

The title compound is prepared from 1-[2-Methyl-4-(2-oxo-3-aza-bicyclo[3.1.0]hex-3-ylmethyl)-benzyl]-1H-pyrazole-4-carboxylic acid (Intermediate 47, 70 mg, 0.19 mmol) in a manner analogous to that described for Example 66 (yield 22 mg).

LC (Method 6): $t_R$=3.13 min; Mass spectrum (ES+): m/z=457 [M+H]$^+$.

Example 70

1-[3-(1-Oxo-octahydro-pyrido[1,2-a]pyrazin-2-yl)-benzyl]-1H-[1,2,3]triazole-4-carboxylic acid (2-amino-6,7-dihydro-5H-[1]pyrindin-5-yl)-amide

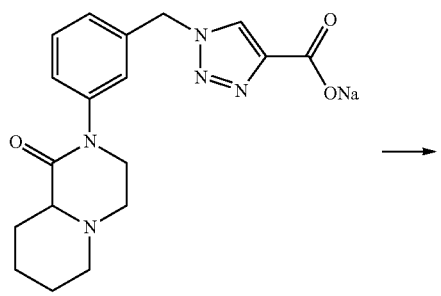

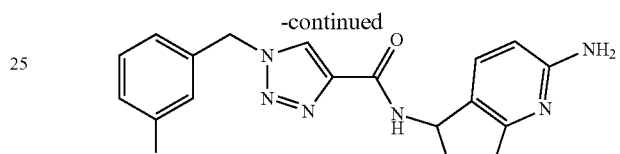

Triethylamine (44.8 μL, 0.312 mmol) is added to a stirred suspension of 1-[3-(1-Oxo-octahydro-pyrido[1,2-a]pyrazin-2-yl)-benzyl]-1H-[1,2,3]triazole-4-carboxylic acid sodium salt (Intermediate 50, 44 mg, 0.10 mmol) and HATU (47.9 mg, 0.13 mmol) in 5 mL of anhydrous DCM. After 30 minutes stirring, 6,7-Dihydro-5H-[1]pyrindine-2,5-diamine di-hydrochloride (Intermediate 141, 26 mg, 0.11 mmol) is added and the reaction mixture is stirred for 2 hours. Further 6,7-Dihydro-5H-[1]pyrindine-2,5-diamine di-hydrochloride (Intermediate 141, 9 mg, 0.04 mmol) and HATU (14 mg, 0.04 mmol) are added and the reaction mixture is stirred for 2 hours. Water is added and the organic layer is separated, washed with brine and dried over anhydrous sodium sulfate. The solvent is removed and the crude is purified by flash chromatography (0-25% methanol in DCM) then by preparative HPLC to obtain the title compound (yield 5 mg).

LC (Method 2): $t_R$=3.12 min; Mass spectrum (ES+): m/z=487 [M+H]$^+$.

Example 71

1-{1-[6-(3-Aza-bicyclo[3.1.0]hex-3-yl)-pyridin-3-yl]-ethyl}-1H-pyrazole-4-carboxylic acid ((R)-1-amino-6,7-dihydro-5H-[2]pyrindin-5-yl)amide

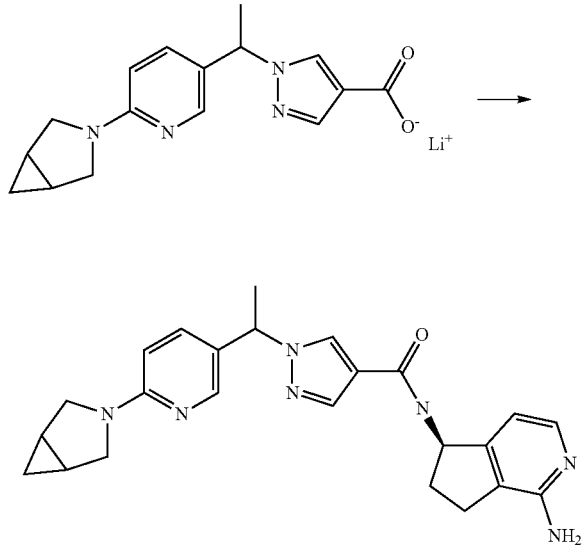

Triethylamine (298 µL, 2.15 mmol) is added to a stirred suspension of 1-{1-[6-(3-Aza-bicyclo[3.1.0]hex-3-yl)-pyridin-3-yl]-ethyl}-1H-pyrazole-4-carboxylic acid lithium salt (Intermediate 55, 157 mg), (R)-6,7-Dihydro-5H-[1]pyrindine-2,5-diamine hydrochloride salt (Intermediate 137, 120 mg, 0.43 mmol) and benzotriazol-1-yloxytris(pyrrolidino)phosphonium hexafluorophosphate (335 mg, 0.65 mmol) in 5 mL of dry DMF. The reaction mixture is stirred at room temperature for 1.5 hours. Water is added, and the mixture is extracted with EtOAc. The organic layer is separated, washed with saturated NaHCO$_3$ aqueous solution, dried over anhydrous sodium sulfate and concentrated under reduced pressure. The crude is purified by flash chromatography (0 to 10% Methanol in DCM) to give the title compound (yield 120 mg).

LC (Method 6): $t_R$=2.67 min; Mass spectrum (ES+): m/z=430 [M+H]$^+$.

Example 72 and Example 73

The stereoisomers of Example 71 (51 mg) prepared as described above are separated by HPLC using a chiral stationary phase to give 16.5 mg of stereoisomer 1 (Example 72) and 16.4 mg of stereoisomer 2 (Example 73).

Method for Separation:

HPLC apparatus type: Waters 600 Pump, 2767 Autosampler, UV Detector 2489; column: Daicel Chiralpak AS-H, 5.0 µm, 250 mm×20 mm; method: eluent hexane/ethanol 90:10; flow rate: 15 mL/min, temperature: 25° C.; UV Detection: 230 nm Example 72: stereoisomer 1

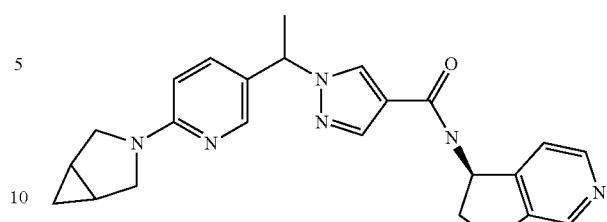

Example 73: stereoisomer 2

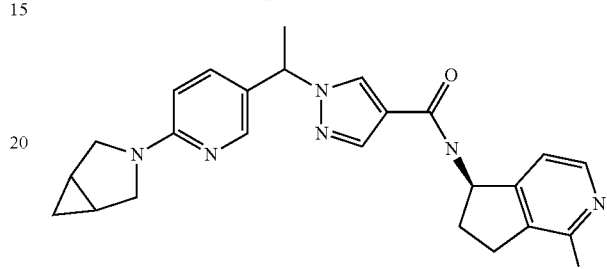

| Example | Chiral HPLC (Column Daicel Chiralpak AS-H, eluent hexane-ethanol 90:10, 1 ml/min, 25° C.) $R_t$ [min] | HPLC-MS (MIL-01_007): $R_t$ [min] | MS (ESI pos): m/z |
|---|---|---|---|
| 72 | 30.3 | 3.37 | 430 |
| 73 | 34.0 | 3.37 | 430 |

Example 74

1-{1-[6-(3-Aza-bicyclo[3.1.0]hex-3-yl)-pyridin-3-yl]-cyclopropyl}-1H-pyrazole-4-carboxylic acid ((R)-1-amino-6,7-dihydro-5H-[2]pyrindin-5-yl) amide

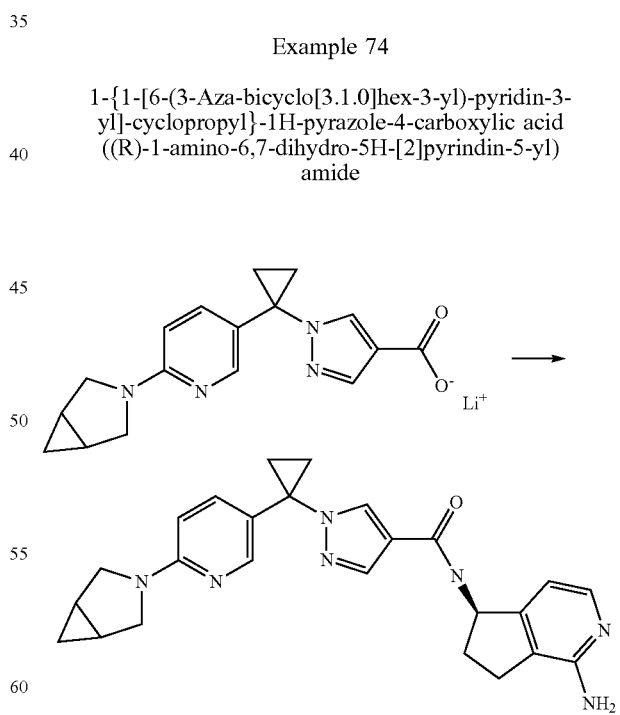

Triethylamine (55 µL, 0.35 mmol) is added to a stirred suspension of 1-{1-[6-(3-Aza-bicyclo[3.1.0]hex-3-yl)-pyridin-3-yl]-cyclopropyl}-1H-pyrazole-4-carboxylic acid lithium salt (Intermediate 59, 26 mg), (R)-6,7-Dihydro-5H-[1]pyrindine-2,5-diamine hydrochloride salt (Intermediate 137, 19 mg, 0.07 mmol) and benzotriazol-1-yloxytris(pyrrolidino)phosphonium hexafluorophosphate (47 mg, 0.09 mmol) in 1 mL of dry DMF. The reaction mixture is stirred at room temperature for 1.5 hours. Diluted aqueous NaOH solution is added and the mixture is extracted with EtOAc. The organic layer is separated, filtered and concentrated under reduced pressure. The crude is purified by flash chromatography (0 to 10% Methanol in DCM) to give the impure product that is further purified by reverse phase flash chromatography (5 to 100% ACN in water) to obtain the title compound (yield 12 mg).

LC (Method 2): $t_R$=3.53 min; Mass spectrum (ES+): m/z=442 [M+H]$^+$.

Example 75

1-[6-(3-Aza-bicyclo[3.1.0]hex-3-yl)-pyridin-3-ylmethyl]-1H-pyrazole-4-carboxylic acid ((R)-1-amino-6,7-dihydro-5H-[2]pyrindin-5-yl)amide

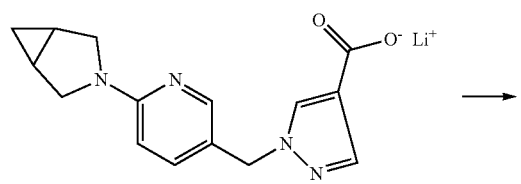

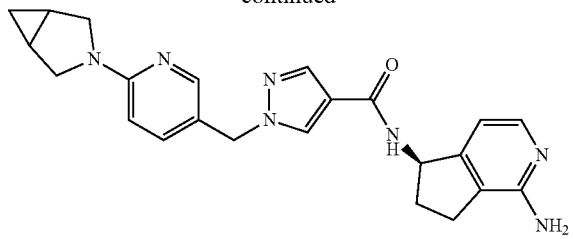

1-[6-(3-Aza-bicyclo[3.1.0]hex-3-yl)-pyridin-3-ylmethyl]-1H-pyrazole-4-carboxylic acid, lithium salt (Intermediate 108, 209 mg, 0.72 mmol), (R)-6,7-Dihydro-5H-[2]pyrindine-1,5-diamine dihydrochloride (Intermediate 137, 200 mg), PyBop (526 mg, 1.08 mmol) and triethylamine (500 μL, 3.60 mmol) are combined in DMF (5 mL) and stirred overnight. The solvent is removed, the residue suspended in DCM and washed with 0.2 M aqueous NaOH solution, dried and the solvent removed. The residue is purified by flash chromatography (0-10% MeOH in DCM) to give the title compound which is triturated with diethyl ether (Yield 61 mg).

LC (Method 7): $t_R$=2.51 min; Mass spectrum (ES+): m/z=416 [M+H]$^+$.

The examples in the following table are synthesized in analogy to the method described for Example 75.

| Example | Structure | Starting intermediates, Conditions | Yield | Analysis |
|---|---|---|---|---|
| 76 | 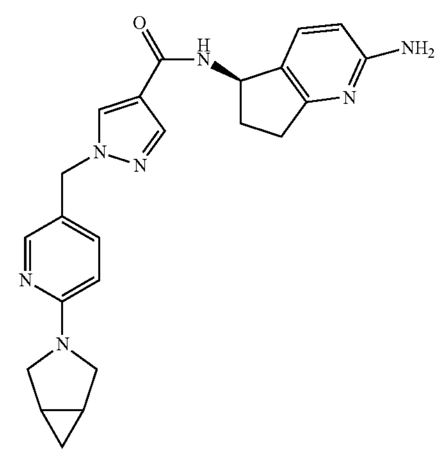 [SMILES: Nc1ccc2c(n1)CC[C@H]2NC(=O)c1cnn(Cc2ccc(N3CC4CC4C3)nc2)c1] | Acid: Intermediate 108 (250 mg) Amine: Intermediate 138 (200 mg) | 87 mg | LC (Method 7): $t_R$ = 2.63 min; Mass spectrum (ES+): m/z = 416 [M + H]$^+$. |

-continued

| Example | Structure | Starting intermediates, Conditions | Yield | Analysis |
|---|---|---|---|---|
| 77 | 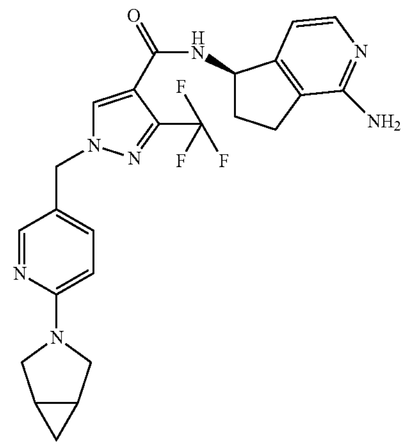 [SMILES: Nc1nccc2c1CC[C@H]2NC(=O)c1cn(Cc2ccc(N3CC4CC4C3)nc2)nc1C(F)(F)F] | Acid: Intermediate 109 (200 mg) Amine: Intermediate 137 (221 mg) | 160 mg | LC (Method 6): $t_R$ = 2.94 min; Mass spectrum (ES+): m/z = 484 [M + H]$^+$. |
| 78 | 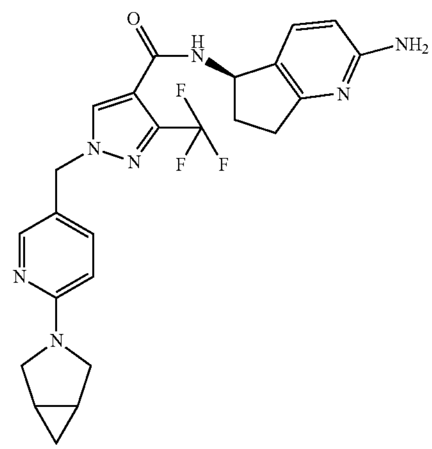 [SMILES: Nc1ccc2c(n1)CC[C@H]2NC(=O)c1cn(Cc2ccc(N3CC4CC4C3)nc2)nc1C(F)(F)F] | Acid: Intermediate 109 (50 mg) Amine: Intermediate 138 (49 mg) No trituration | 17 mg | LC (Method 2): $t_R$ = 4.10 min; Mass spectrum (ES+): m/z = 484 [M + H]$^+$. |
| 79 | 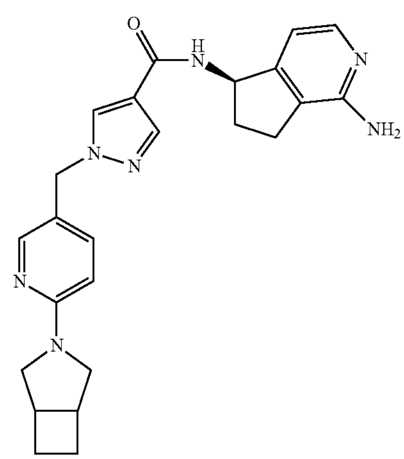 [SMILES: Nc1nccc2c1CC[C@H]2NC(=O)c1cnn(Cc2ccc(N3CC4CCC4C3)nc2)c1] | Acid: Intermediate 113 (18 mg) Amine: Intermediate 137 (17 mg) Product further purified using an SCX cartridge instead of trituration | 9 mg | LC (Method 2): $t_R$ = 3.48 min; Mass spectrum (ES+): m/z = 430 [M + H]$^+$. |

-continued

| Example | Structure | Starting intermediates, Conditions | Yield | Analysis |
|---|---|---|---|---|
| 80 | 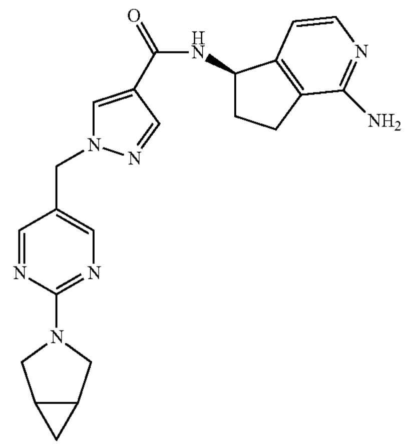 [SMILES: Nc1nccc2c1CC[C@H]2NC(=O)c1cnn(Cc2cnc(N3CC4CC4C3)nc2)c1] | Acid: Intermediate 123 (43 mg) Amine: Intermediate 137 (33 mg) 1 h reaction at 50° C., no trituration | 26 mg | LC (Method 2): $t_R$ = 3.02 min; Mass spectrum (ES+): m/z = 417 [M + H]⁺. |
| 81 | 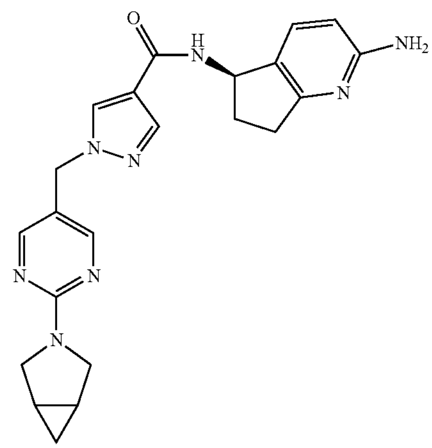 [SMILES: Nc1ccc2c(n1)CC[C@H]2NC(=O)c1cnn(Cc2cnc(N3CC4CC4C3)nc2)c1] | Acid: Intermediate 123 (43 mg) Amine: Intermediate 138 (33 mg) 1 h reaction at 50° C., no trituration | 22 mg | LC (Method 2): $t_R$ = 3.08 min; Mass spectrum (ES+): m/z = 417 [M + H]⁺. |
| 82 | 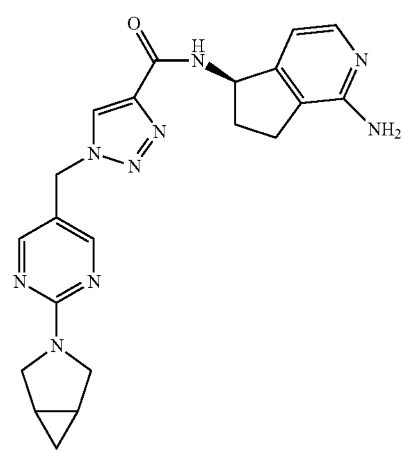 [SMILES: Nc1nccc2c1CC[C@H]2NC(=O)c1cn(Cc2cnc(N3CC4CC4C3)nc2)nn1] | Acid: Intermediate 124 (60 mg) Amine: Intermediate 137 (46 mg) 1 h reaction at 50° C., no trituration | 45 mg | LC (Method 2): $t_R$ = 3.08 min; Mass spectrum (ES+): m/z = 418 [M + H]⁺. |

-continued

| Example | Structure | Starting intermediates, Conditions | Yield | Analysis |
|---------|-----------|-----------------------------------|-------|----------|
| 83 | 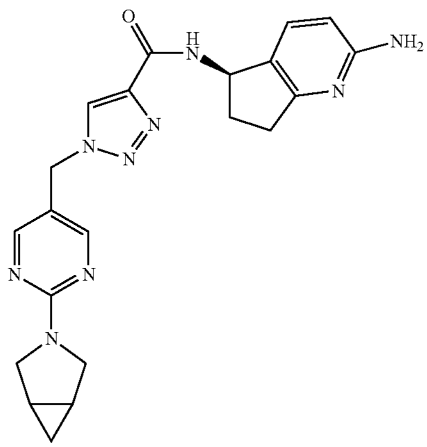 [SMILES: Nc1ccc2c(n1)CC[C@H]2NC(=O)c1cn(Cc2cnc(N3CC4CC4C3)nc2)nn1] | Acid: Intermediate 124 (60 mg) Amine: Intermediate 138 (65 mg) 1 h reaction at 50° C., no trituration | 42 mg | LC (Method 2): $t_R$ = 4.42 min; Mass spectrum (ES+): m/z = 418 $[M + H]^+$. |
| 84 | 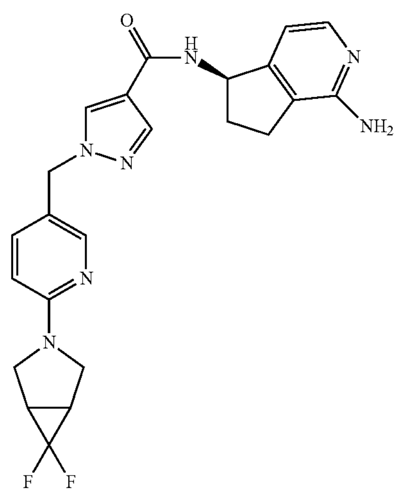 [SMILES: Nc1nccc2c1CC[C@H]2NC(=O)c1cnn(Cc2ccc(N3CC4C(C3)C4(F)F)nc2)c1] | Acid: Intermediate 122 (31 mg) Amine: Intermediate 137 (28 mg) 2 h reaction, product purified using RP-HPLC/MS | 12 mg | LC (Method 2): $t_R$ = 3.27 min; Mass spectrum (ES+): m/z = 452 $[M + H]^+$. |
| 85 | 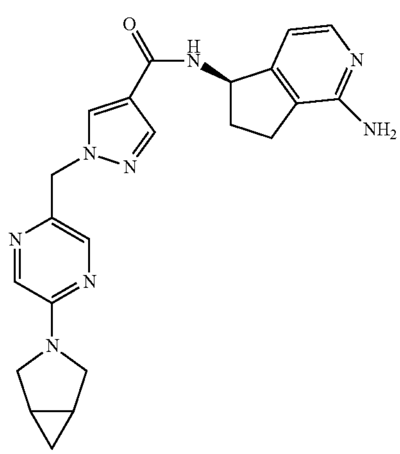 [SMILES: Nc1nccc2c1CC[C@H]2NC(=O)c1cnn(Cc2cnc(N3CC4CC4C3)cn2)c1] | Acid: Intermediate 125 (52 mg) Amine: Intermediate 137 (50 mg) 3 h reaction, product further purified using an SCX cartridge instead of trituration | 35 mg | LC (Method 2): $t_R$ = 3.15 min; Mass spectrum (ES+): m/z = 417 $[M + H]^+$. |

| Example | Structure | Starting intermediates, Conditions | Yield | Analysis |
|---|---|---|---|---|
| 86 | 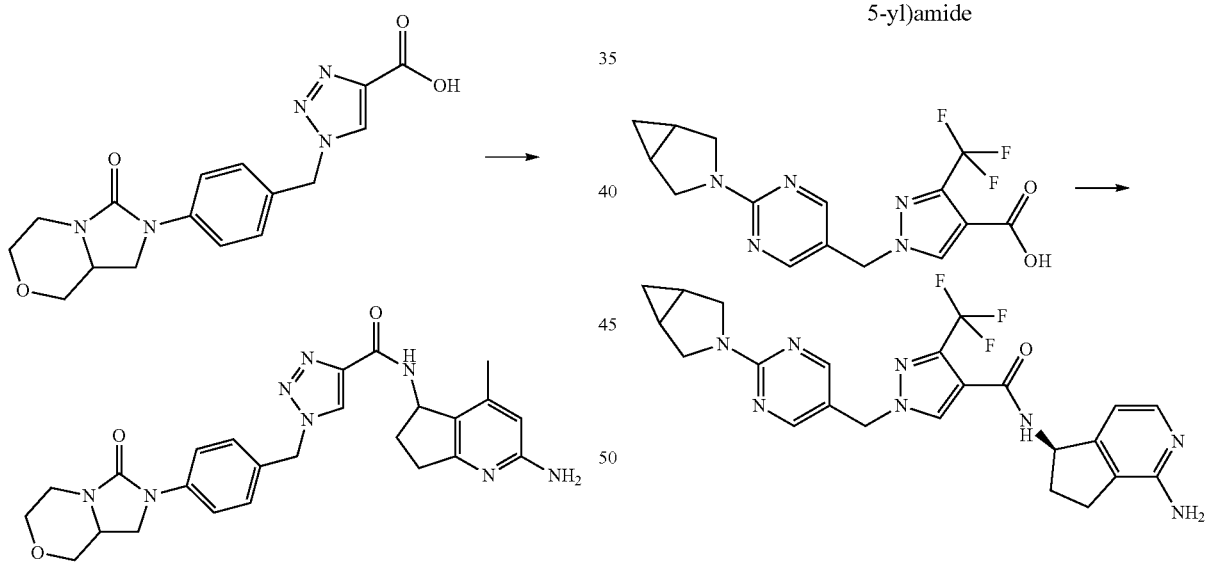 | Acid: Intermediate 125 (93 mg) Amine: Intermediate 138 (100 mg) 3 h reaction, product further purified using an SCX cartridge instead of trituration | 60 mg | LC (Method 2): $t_R$ = 3.11 min; Mass spectrum (ES+): m/z = 417 [M + H]$^+$. |

Example 87

1-[4-(3-Oxo-tetrahydro-imidazo[5,1-c][1,4]oxazin-2-yl)-benzyl]-1H-[1,2,3]triazole-4-carboxylic acid (2-amino-4-methyl-6,7-dihydro-5H-[1]pyrindin-5-yl)-amide 1-[4-(3-Oxo-tetrahydro-imidazo[5,1-c][1,4]oxazin-2-yl)-benzyl]-1H-[1,2,3]triazole-4-carboxylic acid (Intermediate 104, 87 mg), 4-Methyl-6,7-dihydro-5H-[1]pyrindine-2,5-diamine dihydrochloride (Intermediate 142, 30 mg), PyBop (72 mg, 0.14 mmol) and triethylamine (90 µL, 0.64 mmol) are combined in DCM (5 mL) and stirred overnight. The mixture is washed with water and the phases separated. The organic phase is dried over sodium sulfate and concentrated under vacuum The residue is purified by flash chromatography (0-20% MeOH in ethyl acetate) followed by loading onto an SCX cartridge and eluting with 7M ammonia in methanol to give the title compound (Yield 20 mg).

LC (Method 2): $t_R$=3.11 min; Mass spectrum (ES+): m/z=489 [M+H]$^+$.

Example 88

1-[6-(3-Aza-bicyclo[3.1.0]hex-3-yl)-pyrimidin-5-ylmethyl]-3-trifluoromethyl-1H-pyrazole-4-carboxylic acid ((R)-1-amino-6,7-dihydro-5H-[2]pyrindin-5-yl)amide 1-[6-(3-Aza-bicyclo[3.1.0]hex-3-yl)-pyrimidin-5-ylmethyl]-3-trifluoromethyl-1H-pyrazole-4-carboxylic acid (Intermediate 110, 105 mg, 0.30 mmol), (R)-6,7-Dihydro-5H-[2]pyrindine-1,5-diamine dihydrochloride (Intermediate 137, 99 mg), PyBop (232 mg, 0.45 mmol) and triethylamine (206 µL, 1.49 mmol) are combined in DMF (5 mL) and stirred overnight. The solvent is removed, the residue suspended in DCM, shaken with 1 M HCl solution and the phases separated. The aqueous phase is basified and extracted with DCM. The organic extracts are concentrated under vacuum and the residue is purified by flash chromatography (0-5% MeOH in DCM) to give the title compound (Yield 20 mg).

LC (Method 6): t_R=3.41 min; Mass spectrum (ES+): m/z=485 [M+H]+.

The examples in the following table are synthesized in analogy to the method described for Example 88.

| Example | Structure | Starting intermediates, Conditions | Yield | Analysis |
|---|---|---|---|---|
| 89 | 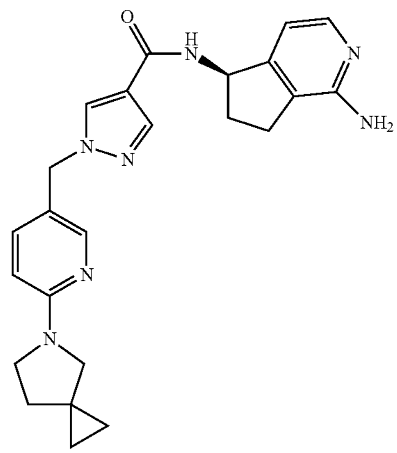 [SMILES: Nc1nccc2c1CC[C@H]2NC(=O)c1cnn(Cc2ccc(N3CCC4(CC4)C3)nc2)c1] | Acid: Intermediate 111 (100 mg) Amine: Intermediate 137 (109 mg) | 22 mg | LC (Method 7): $t_R$ = 2.78 min; Mass spectrum (ES+): m/z = 430 [M + H]+. |
| 90 | 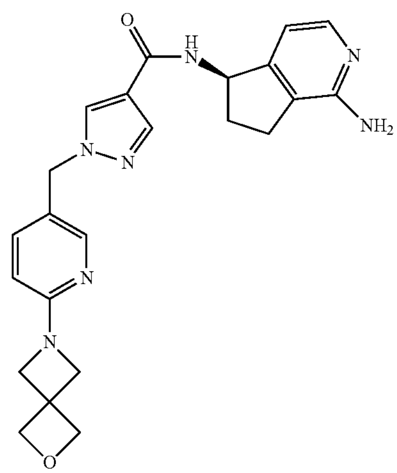 [SMILES: Nc1nccc2c1CC[C@H]2NC(=O)c1cnn(Cc2ccc(N3CC4(COC4)C3)nc2)c1] | Acid: Intermediate 112 (50 mg) Amine: Intermediate 137 (55 mg) | 36 mg | LC (Method 2): $t_R$ = 2.53 min; Mass spectrum (ES+): m/z = 432 [M + H]+. |
| 91 | 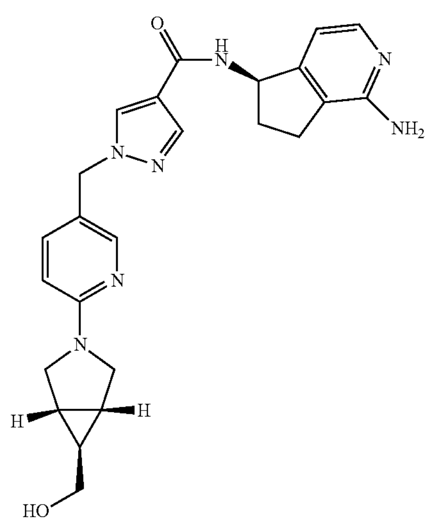 [SMILES: Nc1nccc2c1CC[C@H]2NC(=O)c1cnn(Cc2ccc(N3C[C@@H]4[C@@H](CO)[C@@H]4C3)nc2)c1] | Acid: Intermediate 117 (50 mg) Amine: Intermediate 137 (53 mg) | 22 mg | LC (Method 2): $t_R$ = 2.67 min; Mass spectrum (ES+): m/z = 446 [M + H]+. |

| Example | Structure | Starting intermediates, Conditions | Yield | Analysis |
|---|---|---|---|---|
| 92 | 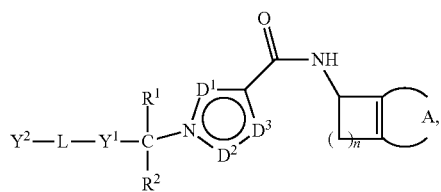 | Acid: Intermediate 110 (63 mg) Amine: Intermediate 138 (50 mg) | 29 mg | LC (Method 2): $t_R$ = 3.71 min; Mass spectrum (ES+): m/z = 485 $[M + H]^+$. |

The invention claimed is:

1. A compound of formula (I)

wherein
of $D^1$ to $D^3$
(i) each denote N, or
(ii) 2 denote N and 1 denotes CH, or
(iii) 1 denotes N, 2 denote CH, or
(iv) each denote CH
and one or two H-atoms attached to C optionally are replaced by a substituent selected from the group consisting of $C_{1-4}$-alkyl, —$CF_3$, —$CHF_2$, —CN and —$OCH_3$;
n is 1, 2 or 3;

[A ring depicted]

denotes a 4-membered bridge composed of a —C(NH$_2$)=N— unit and a second unit of —CH=CH—, including both orientations for unsymmetric units, wherein a H-atom attached to a C-atom optionally is replaced by a substituent selected from the group consisting of F, Cl, $CH_3$, $CF_3$ and $CHF_2$;
$R^1$ denotes H, F, CN, $C_{1-3}$-alkyl, $CF_3$, OH, or —$OCH_3$;
$R^2$ denotes H, F, CN, $CF_3$, $CHF_2$, —$OCH_3$ or a $C_{1-3}$-alkyl group optionally substituted by —OH;
or $R^1$ and $R^2$ together denote =O or together with the carbon atom they are attached to form a 3-7 membered saturated ring system wherein 1 —$CH_2$— group optionally is replaced by O, S or NH;

$Y^1$ denotes a divalent phenyl ring or a divalent 6-membered heteroaromatic ring containing 1 or 2 =N— ring members, wherein both ring systems are optionally substituted at one or two carbon atoms by a halogen atom, $C_{1-3}$-alkyl, —$C_{1-4}$-cycloalkyl, —$CF_3$, —CN, —OH, HO—$C_{1-3}$-alkyl- or $C_{1-3}$-alkyloxy-;
L denotes a bond or a linker selected from —C($R_3R_4$)— and —O—, wherein
$R^3$ denotes H, F, CN, $C_{1-3}$-alkyl, $CF_3$, $CHF_2$, —OH, —$CH_2$—OH or —$OCH_3$,
$R^4$ denotes H, F, CN, $C_{1-3}$-alkyl, $CF_3$, $CHF_2$, —$CH_2$—OH or —$OCH_3$; and
$Y^2$ denotes a fused or spiro polycyclic ring system attached to L via a C-atom or, where applicable, via a N-atom, containing 6 to 12 ring members in total, wherein
0 to 3 ring members are heteroatoms selected from —N<, —NH—, —N=, —O—, —S— with the proviso that one ring does not contain more than one heteroatom selected from —O— and —S—,
the polycyclic ring system is saturated, or
one ring is saturated and a second ring is partially unsaturated, or
one ring is saturated and a second ring is aromatic or heteroaromatic, or
one ring is partially unsaturated and a second ring is aromatic or heteroaromatic, or
a first and a second ring of the polycyclic ring system are partially unsaturated
one —$CH_2$— ring member linked to a N-atom optionally is replaced by —C(O)—,
and wherein the polycyclic ring system is optionally substituted at one or two carbon atoms by one or two groups independently selected from halogen atoms, $C_{1-3}$-alkyl, —$CF_3$, —CN, —OH, HO—$C_{1-3}$-alkyl- and $C_{1-3}$-alkyloxy-, with the proviso that two substituents containing an O-atom cannot be attached to the same carbon atom, and wherein the H atom in one or more NH groups present in $Y^2$ optionally is replaced by $C_{1-4}$-alkyl or -$CH_2$-$C_{1-4}$-cycloalkyl;
wherein in any definition mentioned hereinbefore and if not specified otherwise, any alkyl group or sub-group may be straight-chained or branched,
or a salt thereof.

2. The compound according to claim 1, wherein
R¹ and R² together with the carbon atom they are attached to form a 3-5 membered saturated ring system,
or a salt thereof.

3. The compound according to claim 1, wherein
Y¹ denotes a divalent phenyl ring, optionally mono- or disubstituted independently by a F or Cl atom, by $C_{1-3}$-alkyl or —$CF_3$,
or a salt thereof.

4. The compound according to claim 1, wherein
Y¹ denotes a divalent 6-membered heteroaromatic ring containing 1 or 2 =N— ring members, optionally substituted by a F or Cl atom, by $C_{1-3}$-alkyl or —$CF_3$,
or a salt thereof.

5. The compound according to claim 1, wherein
L denotes a bond,
or a salt thereof.

6. The compound according to claim 1, wherein
L denotes a —$C(R_3R_4)$— linker, wherein
R³ denotes H, F, $CH_3$ or $CF_3$, and
R⁴ denotes H.

7. The compound according to claim 1, wherein L denotes —O—.

8. The compound according to claim 1, with the stereochemistry shown in formula I.1

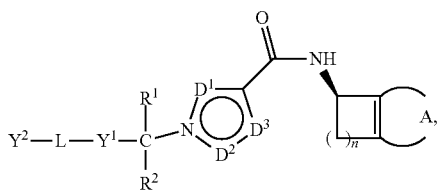

I.1 or a salt thereof.

9. The compound according to claim 1, with the stereochemistry shown in formula I.2

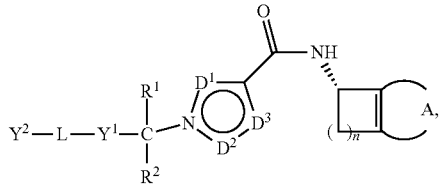

I.2 or a salt thereof.

10. A pharmaceutically acceptable salt of a compound according to claim 1.

11. A pharmaceutical composition comprising one or more compounds according to claim 1 or one or more pharmaceutically acceptable salts thereof, optionally together with one or more inert carriers and/or diluents.

12. A pharmaceutical composition comprising one or more compounds according to claim 1 or one or more pharmaceutically acceptable salts thereof and one or more additional therapeutic agents, optionally together with one or more inert carriers and/or diluents.

13. The pharmaceutical composition according to claim 12 wherein the additional therapeutic agents are selected from the group consisting of antidiabetic agents, agents for the treatment of overweight and/or obesity, agents for the treatment of high blood pressure, heart failure and/or atherosclerosis and agents for the treatment of ocular diseases.

* * * * *